United States Patent
Deng et al.

(10) Patent No.: US 11,292,787 B2
(45) Date of Patent: Apr. 5, 2022

(54) FIVE-MEMBERED-FUSED-SIX-MEMBERED AZA-AROMATIC RING COMPOUND, PREPARATION METHOD THEREOF, PHARMACEUTICAL COMPOSITION AND APPLICATION THEREOF

(71) Applicant: XIAMEN UNIVERSITY, Xiamen (CN)

(72) Inventors: Xianming Deng, Xiamen (CN); Hongrui Wang, Xiamen (CN); Taoling Zeng, Xiamen (CN); Ting Zhang, Xiamen (CN); Tingting Jiang, Xiamen (CN)

(73) Assignee: Xiamen University, Xiamen (CN)

( * ) Notice: Subject to any disclaimer, the term of this patent is extended or adjusted under 35 U.S.C. 154(b) by 0 days.

(21) Appl. No.: 16/614,716

(22) PCT Filed: May 17, 2018

(86) PCT No.: PCT/CN2018/087336
§ 371 (c)(1),
(2) Date: Nov. 18, 2019

(87) PCT Pub. No.: WO2018/210314
PCT Pub. Date: Nov. 22, 2018

(65) Prior Publication Data
US 2020/0172521 A1 Jun. 4, 2020

(30) Foreign Application Priority Data
May 19, 2017 (CN) .......................... 201710357938.2

(51) Int. Cl.
| | |
|---|---|
| *C07D 409/04* | (2006.01) |
| *C07D 403/04* | (2006.01) |
| *C07D 405/04* | (2006.01) |
| *C07D 409/14* | (2006.01) |
| *C07D 209/18* | (2006.01) |
| *C07D 231/56* | (2006.01) |
| *C07D 413/14* | (2006.01) |
| *C07D 471/04* | (2006.01) |
| *C07D 487/04* | (2006.01) |

(52) U.S. Cl.
CPC ......... *C07D 409/04* (2013.01); *C07D 209/18* (2013.01); *C07D 231/56* (2013.01); *C07D 403/04* (2013.01); *C07D 405/04* (2013.01); *C07D 409/14* (2013.01); *C07D 413/14* (2013.01); *C07D 471/04* (2013.01); *C07D 487/04* (2013.01)

(58) Field of Classification Search
CPC .. C07D 403/04; C07D 405/04; C07D 409/04; C07D 409/14
See application file for complete search history.

(56) References Cited

U.S. PATENT DOCUMENTS 6,162,819 A * 12/2000 Schindler .................. A61P 9/10
514/405

FOREIGN PATENT DOCUMENTS

| CN | 101014597 A | 8/2017 |
|---|---|---|
| EP | 2818471 A1 | 12/2014 |
| WO | 2004014368 A1 | 2/2004 |
| WO | 2005103050 | 11/2005 |
| WO | 2006058120 A1 | 6/2006 |
| WO | 2007076423 A2 | 7/2007 |
| WO | 2010126002 A1 | 11/2010 |
| WO | 2017025868 A1 | 2/2017 |
| WO | 2018011227 A1 | 1/2018 |
| WO | 2019206203 A1 | 10/2019 |

OTHER PUBLICATIONS

Stella (J. Pharmaceutical Sciences, 2010, 99(12), pp. 4755-4765).*
STNEXT database (Registry No. 2126984-49-2, downloaded Jan. 30, 2021, pp. 1-2).*
PCT/CN2018/087336 International Search Report dated Aug. 22, 2018.
"2127019-23-0" STN: Registry, Sep. 13, 2017.
"2125563-43-9" STN: Registry, Sep. 6, 2017.
"2126984-49-2" STN: Registry, Sep. 13, 2017.
"1349151-67-2" STN: Registry, Dec. 5, 2011.
"1347830-29-8" STN: Registry, Dec. 4, 2011.
"1125428-61-6" STN: Registry, Mar. 23, 2009.
"918516-05-9" STN: Registry, Jun. 26, 2007.
"918513-25-4" STN: Registry, Jun. 26, 2007.
"918512-48-8" STN: Registry, Jun. 26, 2007.

(Continued)

*Primary Examiner* — Susanna Moore
(74) *Attorney, Agent, or Firm* — Honigman LLP; Thomas A. Wootton, Esq.; Jonathan P. O'Brien

(57) ABSTRACT

The invention relates to the field of medicinal chemistry, and to five-membered-fused-six-membered aza-aromatic ring compound, preparation method thereof, pharmaceutical composition and application thereof. In particular, the invention relates to a type of compounds capable of specifically enhancing ubiquitination degradation of Ras proteins, a method for the preparation thereof, a pharmaceutical composition comprising the same, and use of these compounds in the manufacture of a medicament for preventing or treating a disease associated with Ras activity in vivo, in particular in the manufacture of a medicament for preventing or treating tumor growth and metastasis.

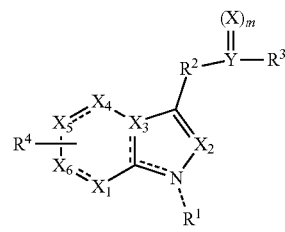

4 Claims, 3 Drawing Sheets

(56) References Cited

OTHER PUBLICATIONS

Bashandy, M.S. 1-(4-(Pyrrolidin-1-ylsulfonyl)phenyl)ethanone in Heterocyclic Synthesis: Synthesis, Molecular Docking and Anti-Human Liver Cancer Evaluation of Novel Sulfonamides Incorporating Thiazole, Imidazo[1,2-a] pyridine, Imidazo[2,1-c][1,2,4]triazole, Imidazo[2,1-b][b]thiazole,1,3,4-Thiadiazine and 1,4-Thiazine Moieties, vol. 5, No. (3), Sep. 8, 2015, ISSN: 2161-4695, pp. 166-190, especially pp. 170 and 175.

\* cited by examiner a b a b

FIVE-MEMBERED-FUSED-SIX-MEMBERED AZA-AROMATIC RING COMPOUND, PREPARATION METHOD THEREOF, PHARMACEUTICAL COMPOSITION AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2018/087336, filed May 17, 2018, which claims the benefit of Chinese Patent Application No. 201710357938.2, filed May 19, 2017, priority is claimed to both of these applications and the disclosures of these prior applications are considered part of the disclosure of this application and to the extent allowed the entire contents of the aforementioned applications are incorporated herein.

TECHNICAL FIELD

The invention relates to the field of medicinal chemistry, and in particular to a type of compounds capable of specifically enhancing ubiquitination degradation of Ras proteins, a method for the preparation thereof, a pharmaceutical composition comprising the same, and use of these compounds in the manufacture of a medicament for preventing or treating a disease associated with Ras activity in vivo, in particular in the manufacture of a medicament for preventing or treating tumor growth and metastasis.

BACKGROUND ART

Ras protein, as a molecular switch in cells, plays a key role in numerous physiological and biochemical regulation processes in cells, including gene expression, cell growth and differentiation, cell cycle, cytoskeleton and cell migration, membrane vesicle transport, transport between nucleus and cytoplasm and the like. Meanwhile, Ras proteins (including H-Ras, K-Ras and N-Ras) are also the most common protooncoproteins in humans, closely related to tumor growth and transformation activity. RAS gene mutations are found in 20%-30% of all human tumors. Specifically, point mutation of RAS gene was found in 90% of pancreatic cancer, 50% of colon cancer, 30% of lung cancer, 50% of thyroid cancer and 30% of myelogenous leukemia (Nat Rev Cancer 2003, 3, 459-465; Nat Rev Cancer 2011, 11, 761-774). Therefore, studies on Ras family proteins have received a great deal of attention from researchers all the time (Nat Rev Cancer 2003, 3, 11-22; Nature reviews. Drug discovery 2014, 13, 928-942).

Ubiquitination of protein molecules is an important covalent modification of intracellular proteins after translation, which regulates many important biological functions including degradation of protein molecules, DNA repair, gene transcription, cell cycle, endocytosis and the like (1). Ubiquitination-mediated protein degradation plays an extremely important role in maintaining normal biological functions of cells, and abnormal protein degradation can cause many diseases including cancer (Biochim Biophys Acta 2004, 1695, 3-17). The results of recent studies have shown that the inhibition of activity of protease complex has a certain therapeutic effect on diseases such as cancer, autoimmune diseases, inflammation, and cardiovascular diseases. Proteasome inhibitors such as Bortezomib are currently approved by the FDA in the United States for clinical tumor treatment, and are used for treating malignant tumors such as multiple myeloma (Chemistry & biology 2012, 19, 99-115). However, since protease complex inhibitors non-specifically affect the degradation of almost all proteins, they inevitably cause strong toxic side effects, so that their use is greatly restricted (Cancer Biol Ther 2003, 2, 623-629). Therefore, the specific ubiquitination control of proteins that play an important role in cancer development is currently a focus of research in the biomedical field.

We have recently found that E3 ubiquitin ligase Nedd4-1 can ubiquitously degrade three major types of Ras proteins, H-Ras, K-Ras and N-Ras, to maintain the homeostasis of Ras signals in cells, and that disorder of this regulatory mechanism may enhance the development of tumors (Cell Rep 2014, 7, 871-882). In this study, we found that when Ras is continuously activated due to mutation or stimulation of upstream signals, it can resist ubiquitination regulation by Nedd4-1, thereby maintaining relatively high Ras activity and level, and further enhancing tumor development.

Therefore, the development of small molecular compounds capable of enhancing ubiquitination degradation of Ras, which can be used for preventing and treating cancers and other diseases caused by Ras overactivation, has higher economic and social values.

SUMMARY OF INVENTION

In order to find compounds capable of enhancing ubiquitination degradation of Ras in active form by Nedd4-1, the inventors of the present invention have obtained a series of five-membered-fused-six-membered aza-aromatic ring compounds through extensive large-scale screening, and have designed and synthesized after in-depth research a series of derivatives having novel structures, high safety and capable of enhancing ubiquitination degradation of Ras in active form by Nedd4-1, and have studied antitumor activity of this novel type of derivatives.

Accordingly, the present invention provides a compound having the general formula:

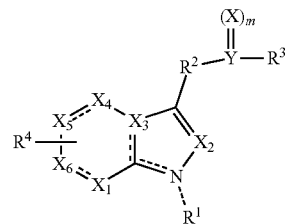

or a stereoisomer thereof, a prodrug thereof, a pharmaceutically acceptable salt thereof or a pharmaceutically acceptable solvate thereof.

More specifically, the present invention provides a compound having the general formula:

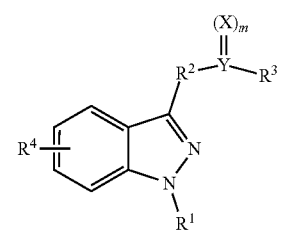

I

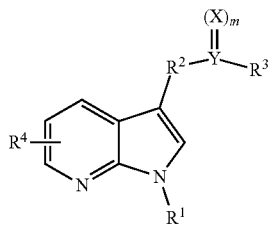

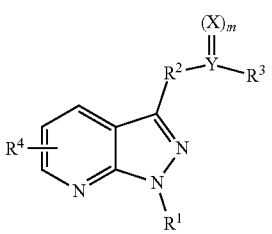

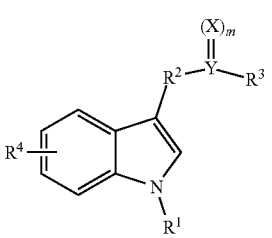

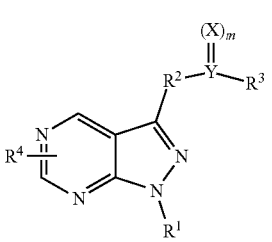

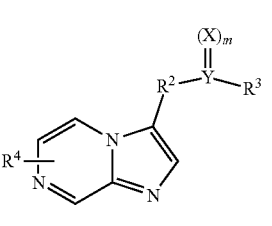

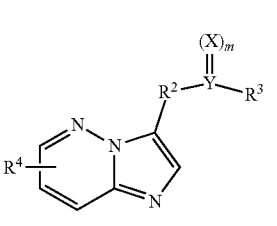

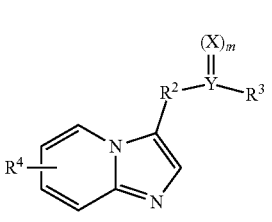

II

III

IV

VI

VII

VIII

IX

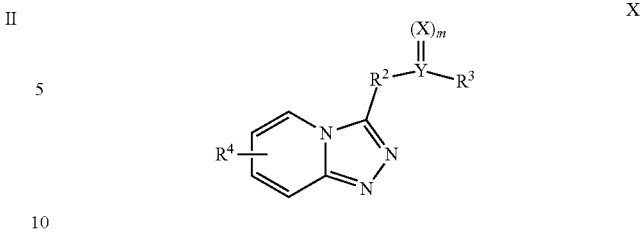

X or a stereoisomer thereof, a prodrug thereof, a pharmaceutically acceptable salt thereof or a pharmaceutically acceptable solvate thereof.

The definitions of substituents and symbols are described in detail below.

One object of the present invention is to provide a compound having Ras inhibitory activity, and a stereoisomer thereof, a prodrug thereof, a pharmaceutically acceptable salt thereof or a pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound and a pharmaceutical composition comprising the above compound in the manufacture of a medicament for preventing or treating cancers and other diseases caused by Ras overactivation.

a) 293T cells overexpress K-RAS-G12V proteins, and compound I-a-1 can effectively enhance the degradation of exogenous overexpressed RAS proteins and has good concentration dependence; b) in SW620 cells, compound I-a-1 can effectively enhance the degradation of endogenous K-RAS-G12V proteins and has good concentration dependence.

Figure 2:
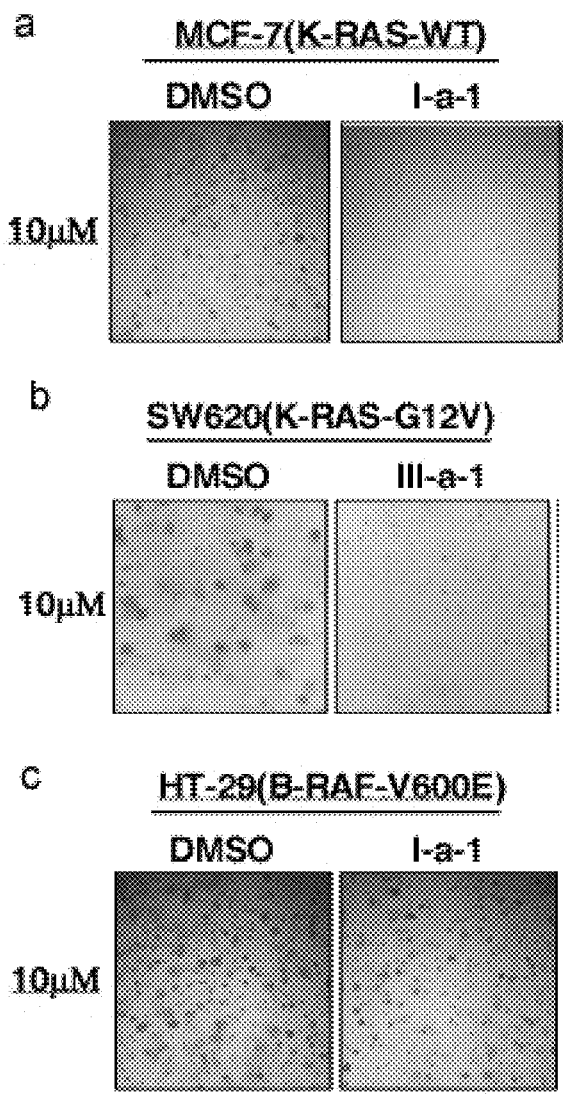

FIG. 2 shows that representative compounds are effective in inhibiting colony formation of RAS positive tumor cells on soft agar.

a) In MCF-7 cells with a K-RAS-WT genetic background, compound I-a-1 can effectively inhibit colony formation of the cells; b) in SW620 cells with a K-RAS-G12V genetic background, compound III-a-1 can effectively inhibit colony formation of the cells; c) in HT-29 cells with a genetic background of RAF mutation, compound I-a-1 does not inhibit colony formation of the cells.

Figure 3:
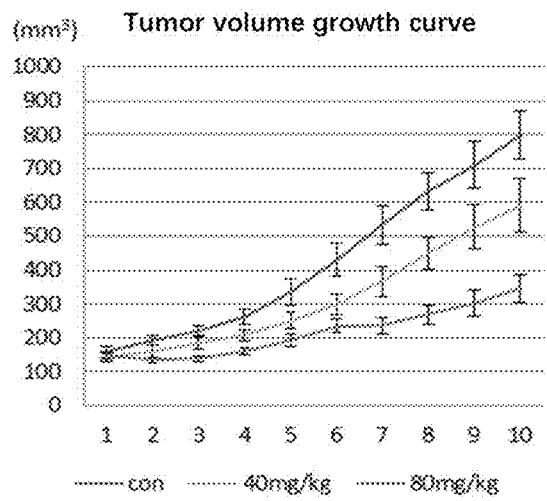
Figure 3:
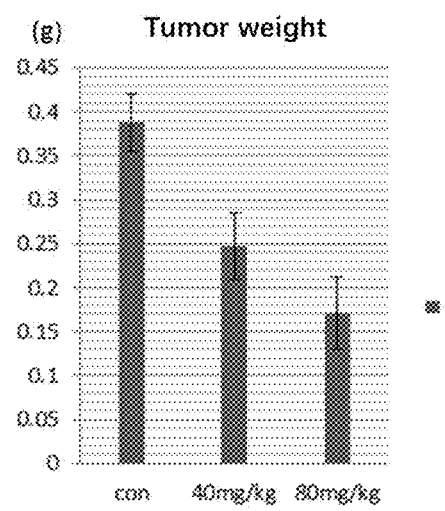

FIG. 3 shows that the representative compound I-a-1 is effective in inhibiting tumor growth in a xenograft model of RAS-positive tumor cells (SW620). In the constructed SW620 xenograft mouse model, the administration is carried out via tail vein at a dose of 40 mg/kg, 80 mg/kg per day. a) In the administration group, the compound can effectively inhibit the increase of tumor volume and has good dose dependence; b) the final tumor weight of the administration group is obviously smaller than that of the control group, and the administration group has good dose dependence.

SPECIFIC MODES FOR CARRYING OUT THE INVENTION

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In one aspect, the present invention provides a compound having the general formula:

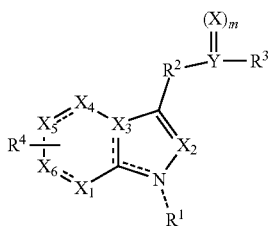

wherein, $X_1$, $X_2$, $X_3$, $X_4$, $X_5$, $X_6$ may comprise a combination of:

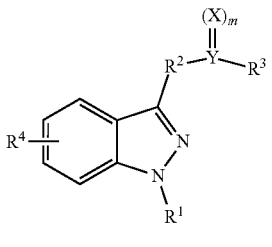

I

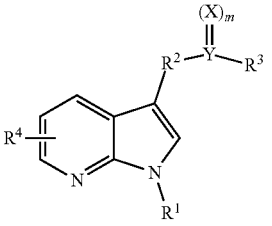

II

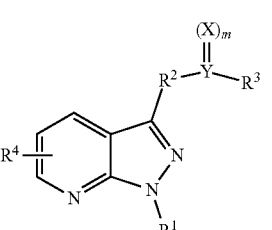

III

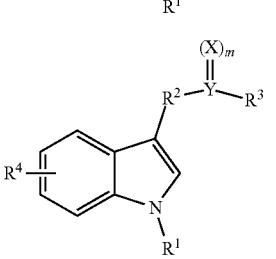

IV

VI

VII

VIII

IX

X

X is selected from O, S, NH;
preferably, X is selected from O, S;
Y is selected from C, S, P; preferably, Y is selected from C, S;
m=1 or 2;
$R^1$ is selected from H, C1-C6 alkyl, C3-C6 cycloalkyl;
preferably, $R^1$ is selected from H, C1-C6 alkyl;
$R^2$ is selected from:
1)

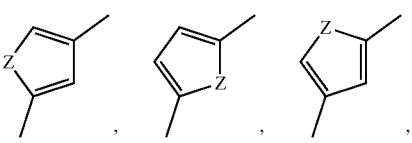

wherein Z is selected from S, O, NH;

2)

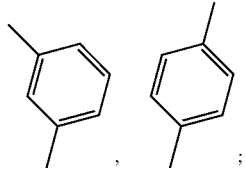

preferably, R² is selected from:

1)

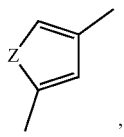

wherein Z is selected from S, O, NH;

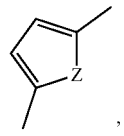

wherein Z is S, NH;

2)

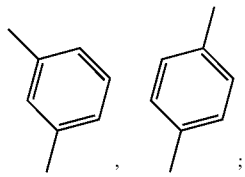

R³ is selected from:

1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:

1)

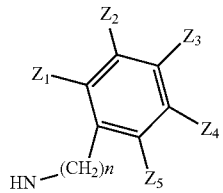

wherein, n=0 or 1, when n=0, any one of $Z_1$, $Z_2$, $Z_3$, $Z_4$, $Z_5$ is selected from halogen, C1-C3 fluorine-containing alkyl, C1-C3 fluorine-containing alkoxy, C1-C6 alkyl, C1-C6 alkoxy, di(C1-C6 alkyl)amino, C1-C6 alkoxycarbonyl, the rest being H; or, any two of $Z_1$, $Z_2$, $Z_3$, $Z_4$, $Z_5$ each are independently selected from halogen, C1-C3 fluorine-containing alkyl, optionally substituted heterocyclyl, said heterocyclyl being selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl, the rest being H; or, $Z_2$, $Z_3$, $Z_4$, $Z_5$ are all H;

when n=1, any two of $Z_1$, $Z_2$, $Z_3$, $Z_4$, $Z_5$ each are independently selected from halogen, C1-C6 alkyl, C1-C6 alkoxy, C1-C3 fluorine-containing alkyl, the rest being H; or, any one of $Z_1$, $Z_2$, $Z_3$, $Z_4$, $Z_5$ is selected from halogen, C1-C3 fluorine-containing alkyl, the rest being H; or, $Z_2$, $Z_3$, $Z_4$, $Z_5$ are all H;

2) C3-C6 cycloalkylamino;

3) HN-heteroaryl, wherein said heteroaryl is selected from pyridyl, pyrazinyl, pyrimidinyl, pyrrolyl, phenyl-pyrrolyl, furyl, phenyl-furyl, oxazolyl, isoxazolyl, pyrazolyl, thienyl, benzothienyl;

4) heterocyclyl, wherein said heterocyclyl is selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl;

5) —NH—$C_2H_4$—$R_6$, wherein $R_6$ is selected from hydroxy, phenyl, halo-substituted phenyl;

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, halogen, amino, hydroxy.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

However, the compound of the general formula excludes the following compounds:

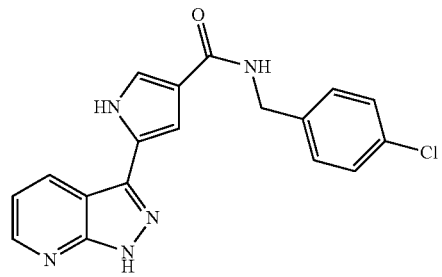

III-f-6

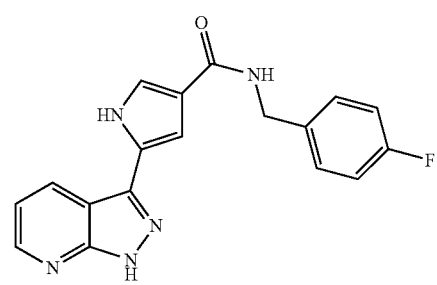

III-f-7

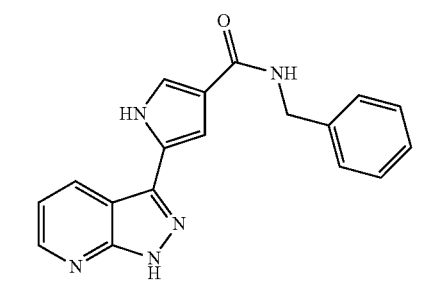

III-f-9

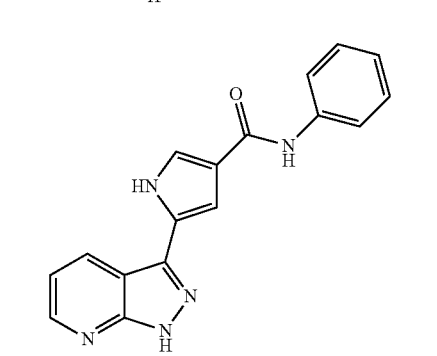

III-f-10

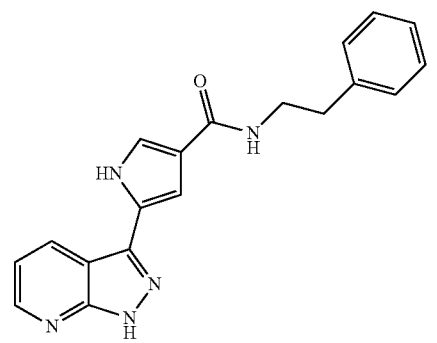

III-f-24

-continued

III-g-2
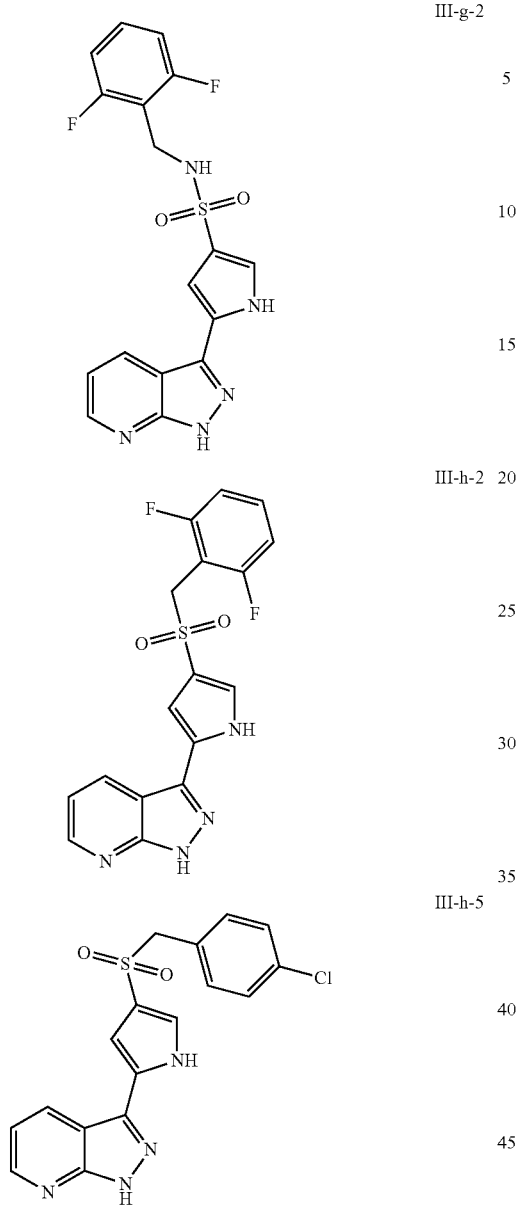

III-h-2

III-h-5

In one aspect, according to a specific embodiment of the present invention, the compound, or a stereoisomer thereof, a prodrug thereof, a pharmaceutically acceptable salt thereof or a pharmaceutically acceptable solvate thereof has the following structure:

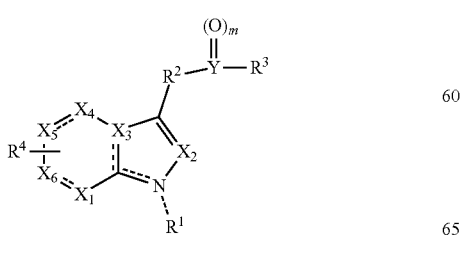

wherein, $X_1$, $X_2$, $X_3$, $X_4$, $X_5$, $X_6$ may comprise a combination of:

I
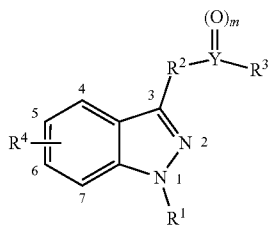

II
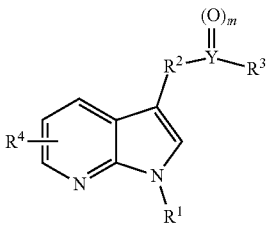

III
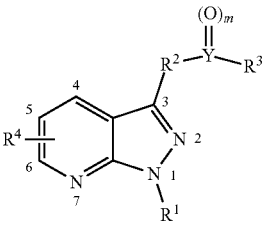

IV
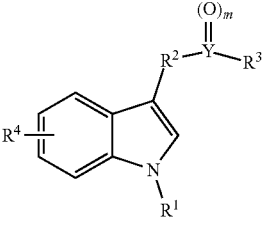

VI
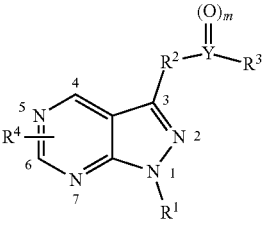

VII
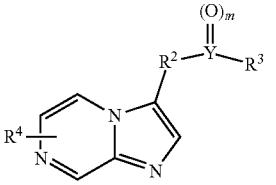

VIII
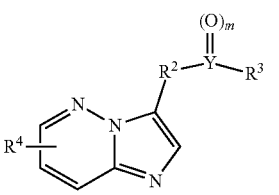

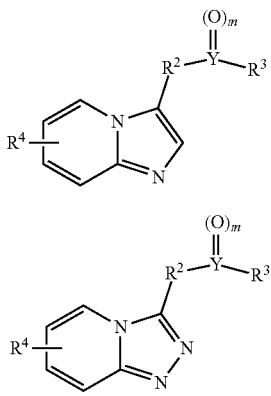

for some of the parent nuclei of the general formulas, the positions in the rings are numbered, so as to indicate the position of the most preferred group of R⁴;

R$^1$ is selected from H, C1-C6 alkyl, C3-C6 cycloalkyl;
R$^2$ is selected from:
1)

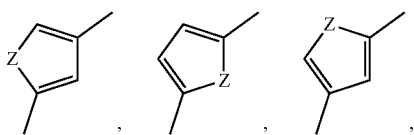

wherein Z is selected from S, O, NH;
2)

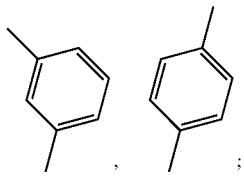

Y is selected from C, S, P;
m=1 or 2;
R$^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;
2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;
6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;
R$^4$ is selected from H, C1-C3 alkyl, C1-C3 alkoxy, C1-C3 oxygen-containing alkyl, C1-C3 fluorine-containing alkyl, halogen, nitro, cyano, amino, hydroxy.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a first aspect, according to a specific embodiment of the present invention, the compound, or a stereoisomer thereof, a prodrug thereof, a pharmaceutically acceptable salt thereof or a pharmaceutically acceptable solvate thereof has the following structure:

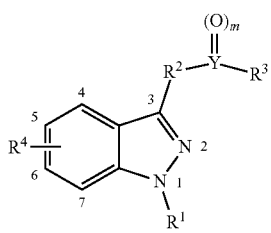

I wherein,
$R^1$ is selected from H, C1-C6 alkyl, C3-C6 cycloalkyl; preferably, $R^1$ is selected from H, C1-C6 alkyl; most preferably, $R^1$ is selected from H, methyl;
$R^2$ is selected from:
1)

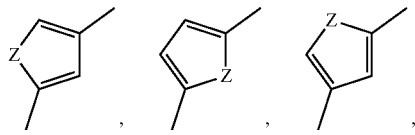

wherein Z is selected from S, O, NH;
2)

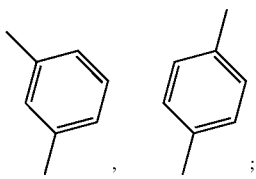

preferably, $R^2$ is selected from:
1)

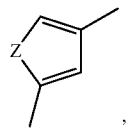

wherein Z is selected from S, O, NH;
2)

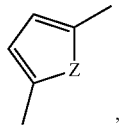

wherein Z is S, NH;
2)

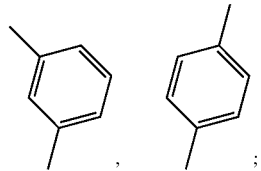

Y is selected from C, S, P; preferably, Y is C;
m=1 or 2; preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;
2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl,
including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)

piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:
1)

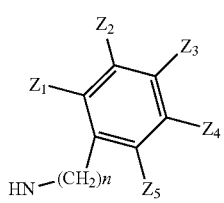

wherein, n=0 or 1, when n=0, any one of $Z_1$, $Z_2$, $Z_3$, $Z_4$, $Z_5$ is selected from halogen, C1-C3 fluorine-containing alkyl, C1-C6 alkyl, C1-C6 alkoxy, di(C1-C6 alkyl)amino, the rest being H; or, $Z_2$, $Z_3$, $Z_4$, $Z_5$ are all H;

when n=1, any two of $Z_1$, $Z_2$, $Z_3$, $Z_4$, $Z_5$ each are independently selected from halogen, C1-C3 fluorine-containing alkyl, C1-C6 alkyl, C1-C6 alkoxy, the rest being H; or, any one of $Z_1$, $Z_2$, $Z_3$, $Z_4$, $Z_5$ is selected from halogen, C1-C3 fluorine-containing alkyl, the rest being H; or, $Z_2$, $Z_3$, $Z_4$, $Z_5$ are all H;

2) C3-C6 cycloalkylamino;

3) HN-heteroaryl, wherein said heteroaryl is selected from pyridyl, pyrazinyl, pyrimidinyl, pyrrolyl, phenyl-pyrrolyl, furyl, phenyl-furyl, oxazolyl, isoxazolyl, pyrazolyl, thienyl, benzothienyl;

4) heterocyclyl, wherein said heterocyclyl is selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl;

5) —NH—$C_2H_4$—$R_6$, wherein $R_6$ is selected from phenyl, halo-substituted phenyl;

more preferably, $R^3$ is selected from:
1)

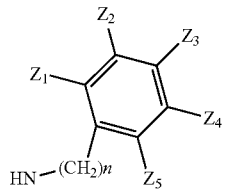

wherein, n=0 or 1, when n=0, $Z_2$ in $Z_1$, $Z_2$, $Z_3$, $Z_4$, $Z_5$ is selected from halogen, C1-C3 fluorine-containing alkyl, the rest being H; or, $Z_3$ in $Z_1$, $Z_2$, $Z_3$, $Z_4$, $Z_5$ is selected from C1-C6 alkyl, C1-C6 alkoxy, halogen, di(C1-C6 alkyl)amino, the rest being H; or, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H; or, $Z_2$, $Z_3$ in $Z_1$, $Z_2$, $Z_3$, $Z_4$, $Z_5$ each are independently selected from halogen, the rest being H; or, $Z_1$, $Z_3$ in $Z_1$, $Z_2$, $Z_3$, $Z_4$, $Z_5$ each are independently selected from C1-C6 alkoxy, the rest being H; or, $Z_1$, $Z_4$ in $Z_1$, $Z_2$, $Z_3$, $Z_4$, $Z_5$ each are independently selected from halogen, C1-C3 fluorine-containing alkyl, the rest being H; or, $Z_1$, $Z_5$ in $Z_1$, $Z_2$, $Z_3$, $Z_4$, $Z_5$ each are independently selected from halogen, C1-C3 fluorine-containing alkyl, the rest being H; or, $Z_3$ in $Z_1$, $Z_2$, $Z_3$, $Z_4$, $Z_5$ is selected from halogen, the rest being H; or, $Z_2$ in $Z_1$, $Z_2$, $Z_3$, $Z_4$, $Z_5$ is selected from C1-C3 fluorine-containing alkyl, the rest being H; or, $Z_2$, $Z_3$, $Z_4$, $Z_5$ are all H;

2) C3-C6 cycloalkylamino;

3) HN-heteroaryl, wherein said heteroaryl is selected from pyridyl, pyrazinyl, pyrimidinyl, pyrrolyl, phenyl-pyrrolyl, furyl, phenyl-furyl, oxazolyl, isoxazolyl, pyrazolyl, thienyl, benzothienyl;

4) heterocyclyl, wherein said heterocyclyl is selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl;

5) —NH—C₂H₄—R₆, wherein R₆ is selected from phenyl, halo-substituted phenyl;
most preferably, R³ is selected from:
1)

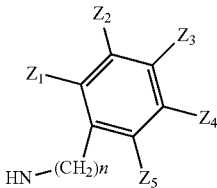

wherein, n=0 or 1,
when n=0, Z₂ in Z₁, Z₂, Z₃, Z₄, Z₅ is selected from fluoro, chloro, trifluoromethyl, the rest being H; or,
Z₃ in Z₁, Z₂, Z₃, Z₄, Z₅ is selected from methyl, methoxy, isopropoxy, fluoro, dimethylamino, the rest being H; or,
Z₂, Z₃, Z₄, Z₅ are all H;
when n=1, Z₁, Z₅ in Z₁, Z₂, Z₃, Z₄, Z₅ each are independently selected from fluoro, chloro, the rest being H; or,
Z₂, Z₃ in Z₁, Z₂, Z₃, Z₄, Z₅ each are independently selected from chloro, the rest being H; or,
Z₁, Z₃ in Z₁, Z₂, Z₃, Z₄, Z₅ each are independently selected from methoxy, the rest being H; or,
Z₁, Z₄ in Z₁, Z₂, Z₃, Z₄, Z₅ each are independently selected from fluoro, trifluoromethyl, the rest being H; or,
Z₁, Z₅ in Z₁, Z₂, Z₃, Z₄, Z₅ each are independently selected from fluoro, trifluoromethyl, the rest being H; or,
Z₃ in Z₁, Z₂, Z₃, Z₄, Z₅ is selected from chloro, fluoro, the rest being H; or, Z₂ in Z₁, Z₂, Z₃, Z₄, Z₅ is selected from trifluoromethyl, the rest being H; or,
Z₂, Z₃, Z₄, Z₅ are all H;
2)

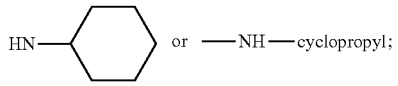

3) HN-heteroaryl, wherein said heteroaryl is selected from 2-methyl-pyrid-5-yl, pyrid-3-yl;
4) heterocyclyl, wherein said heterocyclyl is selected from 4-methylpiperazin-1-yl, morpholin-4-yl;
5) —NH—C₂H₄—R₆, wherein R₆ is selected from phenyl, 4-fluorophenyl; R⁴ is selected from H, C1-C3 alkyl, C1-C3 alkoxy, C1-C3 oxygen-containing alkyl, C1-C3 fluorine-containing alkyl, halogen, nitro, cyano, amino, hydroxy;
more preferably, R⁴ is selected from H, fluoro, chloro, bromo, amino;
most preferably, R⁴ is selected from H, 4-chloro, 6-amino.
preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.
In a second aspect, according to a specific embodiment of the present invention, the compound, or a stereoisomer thereof, a prodrug thereof, a pharmaceutically acceptable salt thereof or a pharmaceutically acceptable solvate thereof has the following structure:

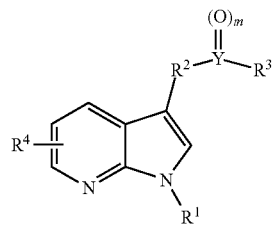

wherein,
R¹ is selected from H, C1-C6 alkyl, C3-C6 cycloalkyl;
preferably, R¹ is selected from H, C1-C3 alkyl;
most preferably, R¹ is selected from H;
R² is selected from:
1)

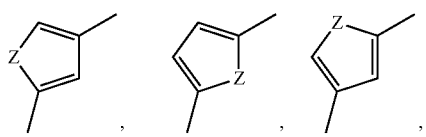

wherein Z is selected from S, O, NH;
2)

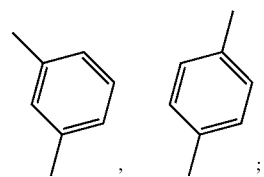

preferably, R² is selected from:
1)

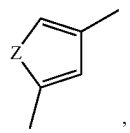

wherein Z is selected from S, O;

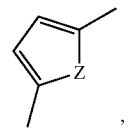

wherein Z is S, NH;

2)

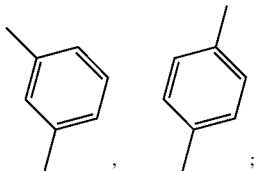

Y is selected from C, S, P; preferably, Y is selected from C;

m=1 or 2; preferably, m=1;

$R^3$ is selected from:

1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:

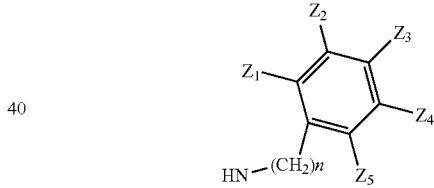

wherein, n=0 or 1;

when n=0, $Z_1$, $Z_2$, $Z_3$, $Z_4$, $Z_5$ are all H;

when n=1, any two of $Z_1$, $Z_2$, $Z_3$, $Z_4$, $Z_5$ each are independently selected from halogen, C1-C6 alkyl, C1-C6 alkoxy, the rest being H; or any one of $Z_1$, $Z_2$, $Z_3$, $Z_4$, $Z_5$ is selected from C1-C3 fluorine-containing alkyl, the rest being H;

more preferably, $R^3$ is selected from:

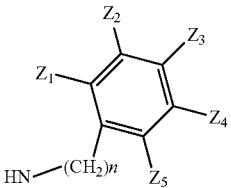

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H; or $Z_2$ in $Z_1, Z_2, Z_3, Z_4, Z_5$ is selected from C1-C3 fluorine-containing alkyl, the rest being H;

most preferably, $R^3$ is selected from:

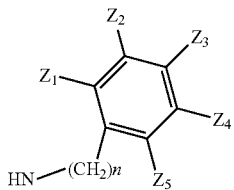

wherein, n=0 or 1;
when n=0, $Z_1, Z_2, Z_3, Z_4, Z_5$ are all H;
when n=1, $Z_1, Z_5$ in $Z_1, Z_2, Z_3, Z_4, Z_5$ each are independently selected from fluoro, chloro, the rest being H; or
$Z_2$ in $Z_1, Z_2, Z_3, Z_4, Z_5$ is selected from trifluoromethyl, the rest being H;

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;
preferably, $R^4$ is selected from H, C1-C3 alkyl, amino, hydroxy;
most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a third aspect, according to a specific embodiment of the present invention, the compound, or a stereoisomer thereof, a prodrug thereof, a pharmaceutically acceptable salt thereof or a pharmaceutically acceptable solvate thereof has the following structure:

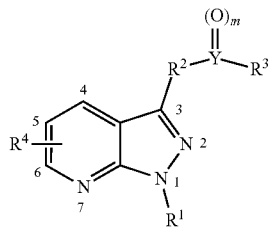

III wherein,
$R^1$ is selected from H, C1-C6 alkyl, C3-C6 cycloalkyl;
preferably, $R^1$ is selected from H, C1-C3 alkyl;
most preferably, $R^1$ is selected from H;
$R^2$ is selected from:
1)

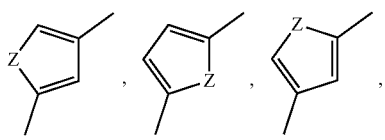

wherein Z is selected from S, O, NH;
2)

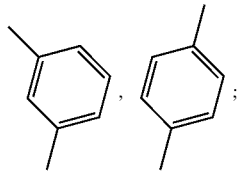

preferably, $R^2$ is selected from:
1)

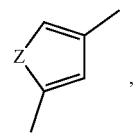

wherein Z is selected from S, O, NH;

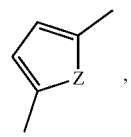

wherein Z is S, NH;
2)

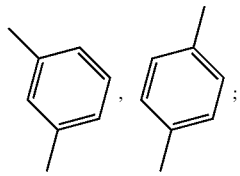

Y is selected from C, S, P; preferably, Y is selected from C, S;
m=1 or 2;
wherein, when Y is C, m=1;
when Y is S, m=2;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;
2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:
1)

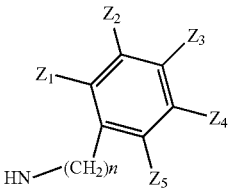

wherein, n=0 or 1 when n=0, any two of $Z_1$, $Z_2$, $Z_3$, $Z_4$, $Z_5$ each are independently selected from halogen, C1-C3 fluorine-containing alkyl, optionally substituted heterocyclyl, said heterocyclyl being selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl, the rest being H; or, any one of $Z_1$, $Z_2$, $Z_3$, $Z_4$, $Z_5$ is selected from halogen, C1-C3 fluorine-containing alkyl, C1-C3 fluorine-containing alkoxy, C1-C6 alkyl, C1-C6 alkoxy, the rest being H; or, $Z_2$, $Z_3$, $Z_4$, $Z_5$ are all H;

when n=1, any two of $Z_1$, $Z_2$, $Z_3$, $Z_4$, $Z_5$ each are independently selected from halogen, C1-C6 alkyl, C1-C6 alkoxy, C1-C3 fluorine-containing alkyl, the rest being H; or, any one of $Z_1$, $Z_2$, $Z_3$, $Z_4$, $Z_5$ is independently selected from halogen, C1-C6 alkyl, C1-C3 fluorine-containing alkyl, C1-C6 alkoxy, C1-C3 fluorine-containing alkoxy, hydroxy, cyano, amino, nitro, the rest being H; or, $Z_1$-$Z_5$ are all H;

2) C3-C6 cycloalkylamino;

3) HN-heteroaryl, wherein said heteroaryl is selected from pyridyl, pyrazinyl, pyrimidinyl, pyrrolyl, phenyl-pyrrolyl, furyl, phenyl-furyl, oxazolyl, isoxazolyl, pyrazolyl, thienyl, benzothienyl;

4) heterocyclyl, wherein said heterocyclyl is selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl;

5) —NH—$C_2H_4$—$R_6$, wherein $R_6$ is selected from hydroxy, halo-substituted phenyl;

more preferably, $R^3$ is selected from:
1)

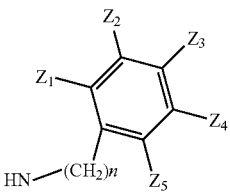

wherein, n=0 or 1 when n=0, $Z_1$, $Z_5$ in $Z_1$, $Z_2$, $Z_3$, $Z_4$, $Z_5$ each are independently selected from halogen, the rest being H; or, $Z_2$ in $Z_1$, $Z_2$, $Z_3$, $Z_4$, $Z_5$ is selected from halogen, C1-C3 fluorine-containing alkyl, the rest being H; or, $Z_2$, $Z_3$ in $Z_1$, $Z_2$, $Z_3$, $Z_4$, $Z_5$ each are independently selected from C1-C3 fluorine-containing alkyl, optionally substituted heterocyclyl, said heterocyclyl being selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl, the rest being H; or, $Z_3$ in $Z_1$, $Z_2$, $Z_3$, $Z_4$, $Z_5$ is selected from C1-C6 alkyl, C1-C6 alkoxy, halogen, C1-C3 fluorine-containing alkoxy, the rest being H; or, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H; or, $Z_1$, $Z_3$ in $Z_1$, $Z_2$, $Z_3$, $Z_4$, $Z_5$ each are independently selected from C1-C6 alkoxy, the rest being H; or, $Z_2$, $Z_3$ in $Z_1$, $Z_2$, $Z_3$, $Z_4$, $Z_5$ each are independently selected from halogen, C1-C3 fluorine-containing alkyl, the rest being H; or, $Z_3$, $Z_4$ in $Z_1$, $Z_2$, $Z_3$, $Z_4$, $Z_5$ each are independently selected from halogen, the rest being H; or, $Z_1$, $Z_4$ in $Z_1$, $Z_2$, $Z_3$, $Z_4$, $Z_5$ each are independently selected from halogen, C1-C3 fluorine-containing alkyl, the rest being H; or, $Z_2$, $Z_4$ in $Z_1$, $Z_2$, $Z_3$, $Z_4$, $Z_5$ each are independently selected from halogen, C1-C3 fluorine-containing alkyl, the rest being H; or, $Z_1$, $Z_2$ in $Z_1$, $Z_2$, $Z_3$, $Z_4$, $Z_5$ each are independently selected from halogen, C1-C3 fluorine-containing alkyl, the rest being H; or, $Z_1$ in $Z_1$, $Z_2$, $Z_3$, $Z_4$, $Z_5$ is selected from halogen, C1-C6 alkyl, C1-C3 fluorine-containing alkyl, C1-C6 alkoxy, C1-C3 fluorine-containing alkoxy, hydroxy, the rest being H; or $Z_2$ in $Z_1$, $Z_2$, $Z_3$, $Z_4$, $Z_5$ is selected from C1-C3 fluorine-containing alkyl, C1-C3 fluorine-containing alkoxy, cyano, halogen, amino, nitro, C1-C6 alkyl, C1-C6 alkoxy, the rest being H; or $Z_3$ in $Z_1$, $Z_2$, $Z_3$, $Z_4$, $Z_5$ is selected from cyano, C1-C6 alkyl, C1-C3 fluorine-containing alkyl, C1-C6 alkoxy, C1-C3 fluorine-containing alkoxy, hydroxy, halogen, the rest being H; or $Z_1$-$Z_5$ are all H;

2) C3-C6 cycloalkylamino;

3) HN-heteroaryl, wherein said heteroaryl is selected from pyridyl, pyrazinyl, pyrimidinyl, pyrrolyl, phenyl-pyrrolyl, furyl, phenyl-furyl, oxazolyl, isoxazolyl, pyrazolyl, thienyl, benzothienyl;

4) heterocyclyl, wherein said heterocyclyl is selected from pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholino, morpholinyl, tetrahydropyrrolyl, thiomorpholinyl;

5) —NH—$C_2H_4$—$R_6$, wherein $R_6$ is selected from hydroxy, halo-substituted phenyl;

most preferably, $R^3$ is selected from:
1)

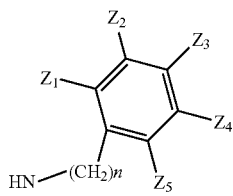

wherein, n=0 or 1 when n=0, $Z_1$, $Z_5$ in $Z_1$, $Z_2$, $Z_3$, $Z_4$, $Z_5$ each are independently selected from fluoro, chloro, the rest being H; or, $Z_2$ in $Z_1$, $Z_2$, $Z_3$, $Z_4$, $Z_5$ is selected from fluoro, chloro, trifluoromethyl, the rest being H; or, $Z_2$, $Z_3$ in $Z_1$, $Z_2$, $Z_3$, $Z_4$, $Z_5$ each are independently selected from trifluoromethyl, 4-methylpiperazin-1-yl-methyl, the rest being H; or, $Z_3$ in $Z_1$, $Z_2$, $Z_3$, $Z_4$, $Z_5$ is selected from methyl, methoxy, isopropoxy, fluoro, trifluoromethoxy, the rest being H; or, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from fluoro, chloro, the rest being H; or, $Z_1$, $Z_3$ in $Z_1$, $Z_2$, $Z_3$, $Z_4$, $Z_5$ each are independently selected from methoxy, the rest being H; or, $Z_2$, $Z_3$ in $Z_1$, $Z_2$, $Z_3$, $Z_4$, $Z_5$ each are independently selected from chloro, fluoro, trifluoromethyl, the rest being H; or, $Z_3$, $Z_4$ in $Z_1$, $Z_2$, $Z_3$, $Z_4$, $Z_5$ each are independently selected from fluoro, the rest being H; or, $Z_1$, $Z_4$ in $Z_1$, $Z_2$, $Z_3$, $Z_4$, $Z_5$ each are independently selected from fluoro, trifluoromethyl, the rest being H; or, $Z_2$, $Z_4$ in $Z_1$, $Z_2$, $Z_3$, $Z_4$, $Z_5$ each are independently selected from fluoro, trifluoromethyl, the rest being H; or, $Z_1$, $Z_2$ in $Z_1$, $Z_2$, $Z_3$, $Z_4$, $Z_5$ each are independently selected from fluoro, trifluoromethyl, the rest being H; or, $Z_1$ in $Z_1$, $Z_2$, $Z_3$, $Z_4$, $Z_5$ is selected from fluoro, chloro, bromo, methyl, trifluoromethyl, methoxy, trifluoromethoxy, hydroxy, the rest being H; or, $Z_2$ in $Z_1$, $Z_2$, $Z_3$, $Z_4$, $Z_5$ is selected from trifluoromethyl, trifluoromethoxy, cyano, fluoro, chloro, bromo, amino, nitro, methyl, methoxy, the rest being H; or, $Z_3$ in $Z_1$, $Z_2$, $Z_3$, $Z_4$, $Z_5$ is selected from cyano, methyl, trifluoromethyl, methoxy, trifluoromethoxy, hydroxy, bromo, the rest being H; or, $Z_2$ in $Z_1$, $Z_2$, $Z_3$, $Z_4$, $Z_5$ is selected from trifluoromethyl, the rest being H; or, $Z_1$-$Z_5$ are all H;

2)

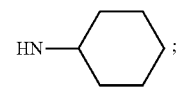

3) HN-heteroaryl, wherein said heteroaryl is selected from 2-methyl-pyrid-5-yl, pyrid-3-yl, pyrid-2-yl;

4) heterocyclyl, wherein said heterocyclyl is selected from 4-methylpiperazin-1-yl, morpholin-4-yl;

5) —NH—$C_2H_4$—$R_6$, wherein $R_6$ is selected from 4-chlorophenyl, 4-fluorophenyl;

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, fluoro, chloro, bromo, amino;

most preferably, $R^4$ is selected from H, 6-chloro.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a fourth aspect, according to a specific embodiment of the present invention, the compound, or a stereoisomer thereof, a prodrug thereof, a pharmaceutically acceptable salt thereof or a pharmaceutically acceptable solvate thereof has the following structure:

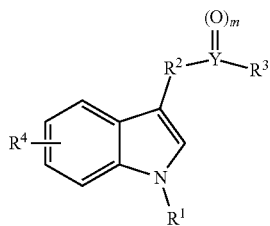

IV wherein,
$R^1$ is H;
$R^2$ is selected from:
1)

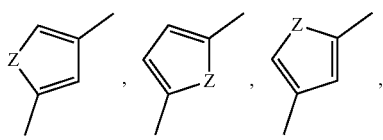

wherein Z is selected from S, O, NH;
2)

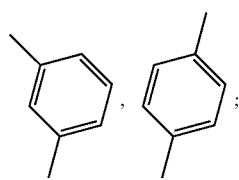

preferably, $R^2$ is selected from:
1)

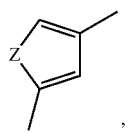

wherein Z is selected from S, O, NH;

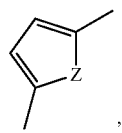

wherein Z is S, NH;
2)

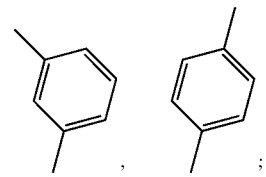

Y is selected from C, S, P;
preferably, Y is C;
m=1 or 2;
preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:

1)

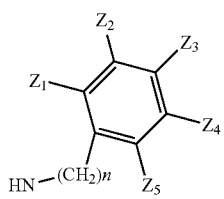

wherein, n=0 or 1;

when n=0, $Z_1$, $Z_2$, $Z_3$, $Z_4$, $Z_5$ are all H;

when n=1, any two of $Z_1$, $Z_2$, $Z_3$, $Z_4$, $Z_5$ each are independently selected from halogen, C1-C6 alkyl, C1-C6 alkoxy, the rest being H;

2) C3-C6 cycloalkylamino;

more preferably, $R^3$ is selected from:

1)

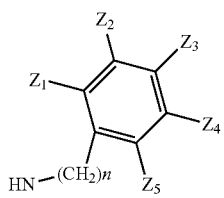

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H;

2) C3-C6 cycloalkylamino;

most preferably, $R^3$ is selected from:

1)

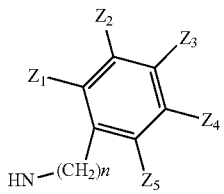

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from fluoro, chloro, the rest being H;

2)

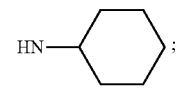

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, C1-C3 alkyl, amino, hydroxy;

most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a fifth aspect, according to a specific embodiment of the present invention, the compound, or a stereoisomer thereof, a prodrug thereof, a pharmaceutically acceptable salt thereof or a pharmaceutically acceptable solvate thereof has the following structure:

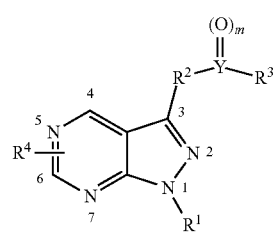

VI wherein,
wherein, $R^1$ is selected from H, C1-C6 alkyl, C3-C6 cycloalkyl;
preferably, $R^1$ is selected from H, t-butyl;
$R^2$ is selected from:
1)

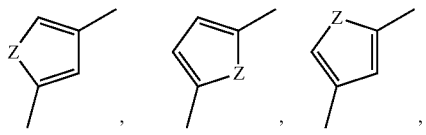

wherein Z is selected from S, O, NH;
2)

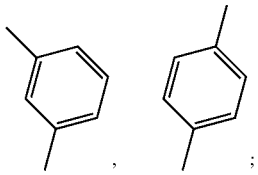

preferably, $R^2$ is selected from:
1)

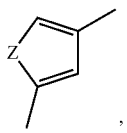

wherein Z is selected from S, O, NH;

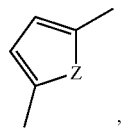

wherein Z is S, NH;
2)

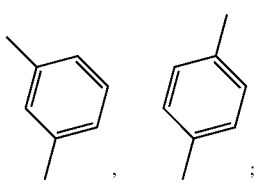

Y is selected from C, S, P;
preferably, Y is C;
m=1 or 2;
preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;
2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl,
including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;
N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;
morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;
6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from: 1)

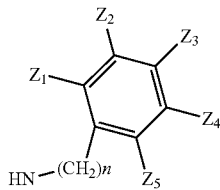

wherein, n=0 or 1;
when n=0, $Z_1$, $Z_2$, $Z_3$, $Z_4$, $Z_5$ are all H;
when n=1, any two of $Z_1$, $Z_2$, $Z_3$, $Z_4$, $Z_5$ each are independently selected from halogen, C1-C6 alkyl, C1-C6 alkoxy, the rest being H;
2) C3-C6 cycloalkylamino;
more preferably, $R^3$ is selected from: 1)

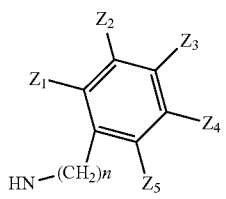

wherein, n=0 or 1;
when n=0, $Z_1$, $Z_2$, $Z_3$, $Z_4$, $Z_5$ are all H;
when n=1, $Z_1$, $Z_5$ in $Z_1$, $Z_2$, $Z_3$, $Z_4$, $Z_5$ each are independently selected from halogen, the rest being H;
2) C3-C6 cycloalkylamino;
most preferably, $R^3$ is selected from:
1)

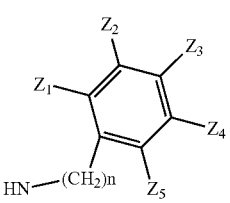

wherein, n=0 or 1;
when n=0, $Z_1$, $Z_2$, $Z_3$, $Z_4$, $Z_5$ are all H;
when n=1, $Z_1$, $Z_5$ in $Z_1$, $Z_2$, $Z_3$, $Z_4$, $Z_5$ each are independently selected from fluoro, chloro, the rest being H;
2)

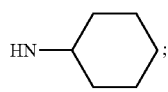

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;
preferably, $R^4$ is selected from H, C1-C3 alkyl, amino, hydroxy;
most preferably, $R^4$ is selected from H, 4-amino.
preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a sixth aspect, according to a specific embodiment of the present invention, the compound, or a stereoisomer thereof, a prodrug thereof, a pharmaceutically acceptable salt thereof or a pharmaceutically acceptable solvate thereof has the following structure:

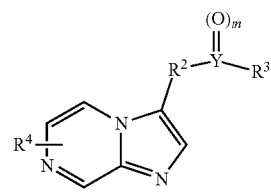

VII wherein,
$R^2$ is selected from:
1)

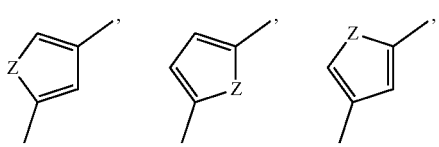

wherein Z is selected from S, O, NH;
2)

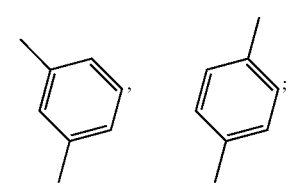

preferably, $R^2$ is selected from:
1)

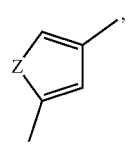

wherein Z is selected from S, O, NH;

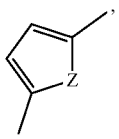

wherein Z is S, NH;
2)

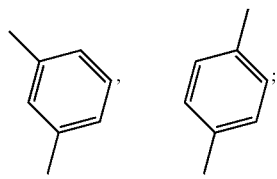

Y is selected from C, S, P;
preferably, Y is C;
m=1 or 2;
preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;
2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;
3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 acyl;
4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 acyl;
5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 acyl, cyano, optionally substituted heterocyclyl,
including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:
1)

wherein, n=0 or 1;
when n=0, $Z_1$, $Z_2$, $Z_3$, $Z_4$, $Z_5$ are all H;
when n=1, any two of $Z_1$, $Z_2$, $Z_3$, $Z_4$, $Z_5$ each are independently selected from halogen, C1-C6 alkyl, C1-C6 alkoxy, the rest being H; or
any one of $Z_1$, $Z_2$, $Z_3$, $Z_4$, $Z_5$ is selected from C1-C3 fluorine-containing alkyl, the rest being H; or any two of $Z_1$, $Z_2$, $Z_3$, $Z_4$, $Z_5$ each are independently selected from halogen, C1-C3 fluorine-containing alkyl, the rest being H;

2) C3-C6 cycloalkylamino;

more preferably, $R^3$ is selected from:

1)

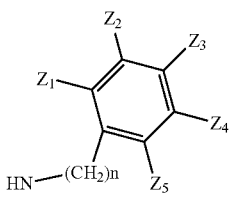

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H; or $Z_2$ in $Z_1$, $Z_2$, $Z_3$, $Z_4$, $Z_5$ is selected from C1-C3 fluorine-containing alkyl, the rest being H; or $Z_3$, $Z_4$ in $Z_1$, $Z_2$, $Z_3$, $Z_4$, $Z_5$ each are independently selected from halogen, C1-C3 fluorine-containing alkyl, the rest being H;

2) C3-C6 cycloalkylamino;

most preferably, $R^3$ is selected from:

1)

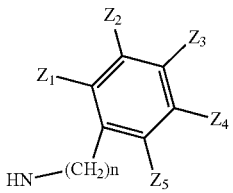

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from fluoro, chloro, the rest being H; or $Z_2$ in $Z_1$, $Z_2$, $Z_3$, $Z_4$, $Z_5$ is selected from trifluoromethyl, the rest being H; or $Z_3$, $Z_4$ in $Z_1$, $Z_2$, $Z_3$, $Z_4$, $Z_5$ each are independently selected from fluoro, trifluoromethyl, the rest being H;

2)

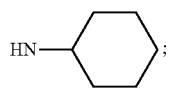

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, C1-C3 alkyl, amino, hydroxy;

most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a seventh aspect, according to a specific embodiment of the present invention, the compound, or a stereoisomer thereof, a prodrug thereof, a pharmaceutically acceptable salt thereof or a pharmaceutically acceptable solvate thereof has the following structure:

VIII

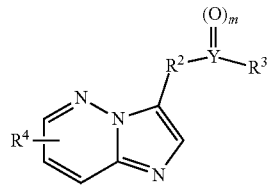

wherein, $R^2$ is selected from:

1)

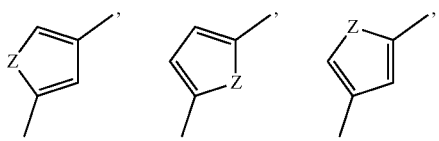

wherein Z is selected from S, O, NH;

2)

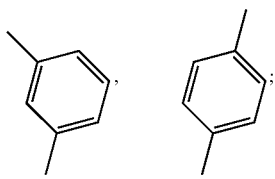

preferably, $R^2$ is selected from:

1)

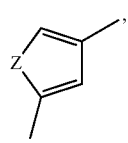

wherein Z is selected from S, O, NH;

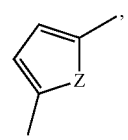

wherein Z is S, NH;
2)

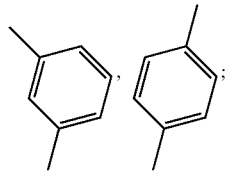

Y is selected from C, S, P;
preferably, Y is C;
m=1 or 2;
preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl,
including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;
morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:
1)

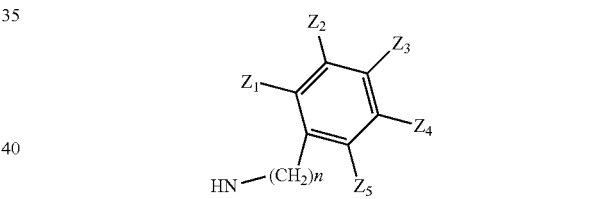

wherein, n=0 or 1;
when n=0, $Z_1$, $Z_2$, $Z_3$, $Z_4$, $Z_5$ are all H;
when n=1, any two of $Z_1$, $Z_2$, $Z_3$, $Z_4$, $Z_5$ each are independently selected from halogen, C1-C6 alkyl, C1-C6 alkoxy, the rest being H; or
any one of $Z_1$, $Z_2$, $Z_3$, $Z_4$, $Z_5$ is selected from C1-C3 fluorine-containing alkyl, the rest being H; or
any two of $Z_1$, $Z_2$, $Z_3$, $Z_4$, $Z_5$ each are independently selected from halogen, C1-C3 fluorine-containing alkyl, the rest being H;
2) C3-C6 cycloalkylamino;
more preferably, $R^3$ is selected from:
1)

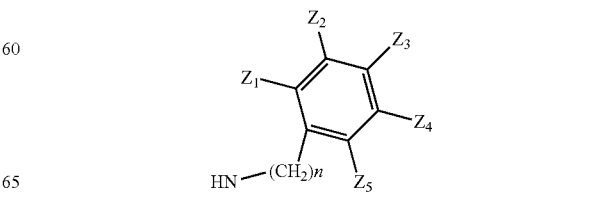

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from halogen, the rest being H; or $Z_2$ in $Z_1$, $Z_2$, $Z_3$, $Z_4$, $Z_5$ is selected from C1-C3 fluorine-containing alkyl, the rest being H; or $Z_3$, $Z_4$ in $Z_1$, $Z_2$, $Z_3$, $Z_4$, $Z_5$ each are independently selected from halogen, C1-C3 fluorine-containing alkyl, the rest being H;

2) C3-C6 cycloalkylamino;

most preferably, $R^3$ is selected from:

1)

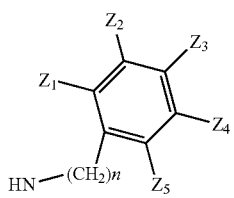

wherein, n=0 or 1;

when n=0, $Z_1$, $Z_2$, $Z_3$, $Z_4$, $Z_5$ are all H;

when n=1, $Z_1$, $Z_5$ in $Z_1$, $Z_2$, $Z_3$, $Z_4$, $Z_5$ each are independently selected from fluoro, chloro, the rest being H; or $Z_2$ in $Z_1$, $Z_2$, $Z_3$, $Z_4$, $Z_5$ is selected from trifluoromethyl, the rest being H; or $Z_3$, $Z_4$ in $Z_1$, $Z_2$, $Z_3$, $Z_4$, $Z_5$ each are independently selected from fluoro, trifluoromethyl, the rest being H;

2)

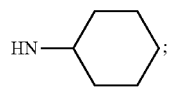

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, C1-C3 alkyl, amino, hydroxy;

most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In an eighth aspect, according to a specific embodiment of the present invention, the compound, or a stereoisomer thereof, a prodrug thereof, a pharmaceutically acceptable salt thereof or a pharmaceutically acceptable solvate thereof has the following structure:

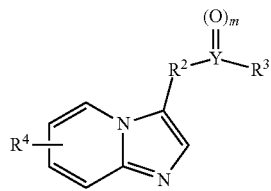

IX wherein, $R^2$ is selected from:

1)

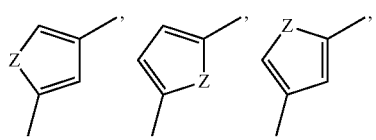

wherein Z is selected from S, O, NH;

2)

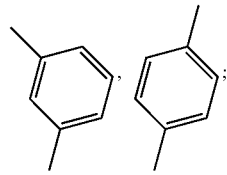

preferably, $R^2$ is selected from:

1)

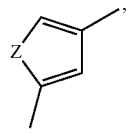

wherein Z is selected from S, O, NH;

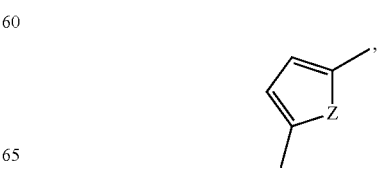

wherein Z is S, NH;

2)

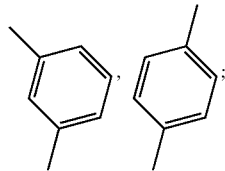

Y is selected from C, S, P;
preferably, Y is C;
m=1 or 2;
preferably, m=1;
R³ is selected from:

1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl,
including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, R³ is selected from:

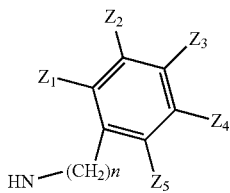

wherein, n=0 or 1;
when n=0, $Z_1$, $Z_2$, $Z_3$, $Z_4$, $Z_5$ are all H;
when n=1, any two of $Z_1$, $Z_2$, $Z_3$, $Z_4$, $Z_5$ each are independently selected from halogen, C1-C6 alkyl, C1-C6 alkoxy, the rest being H;
more preferably, R³ is selected from:

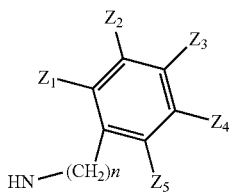

wherein, n=0 or 1;

when n=0, $Z_1, Z_2, Z_3, Z_4, Z_5$ are all H;

when n=1, $Z_1, Z_5$ in $Z_1, Z_2, Z_3, Z_4, Z_5$ each are independently selected from halogen, the rest being H;

most preferably, $R^3$ is selected from:

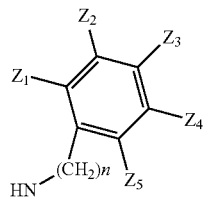

wherein, n=0 or 1;

when n=0, $Z_1, Z_2, Z_3, Z_4, Z_5$ are all H;

when n=1, $Z_1, Z_5$ in $Z_1, Z_2, Z_3, Z_4, Z_5$ each are independently selected from fluoro, chloro, the rest being H;

$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;

preferably, $R^4$ is selected from H, C1-C3 alkyl, amino, hydroxy;

most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

In a ninth aspect, according to a specific embodiment of the present invention, the compound, or a stereoisomer thereof, a prodrug thereof, a pharmaceutically acceptable salt thereof or a pharmaceutically acceptable solvate thereof has the following structure:

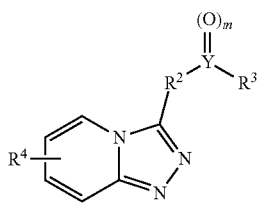

wherein, $R^2$ is selected from:
1)

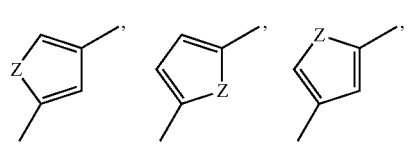

wherein Z is selected from S, O, NH;
2)

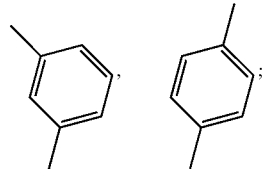

preferably, $R^2$ is selected from:
1)

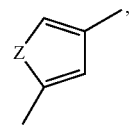

wherein Z is selected from S, O, NH;

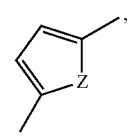

wherein Z is S, NH;
2)

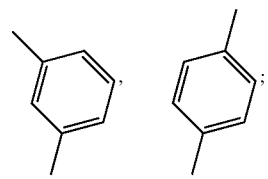

Y is selected from C, S, P;
preferably, Y is C;
m=1 or 2;
preferably, m=1;
$R^3$ is selected from:
1) amino, cyclopropylamino, cyclobutylamino, cyclopentylamino, cyclohexylamino, N,N-dimethylamino, N,N-diethylamino, N,N-diisopropylamino, 2-N,N-dimethylaminoethylamino, 2-hydroxyethylamino, 2-morpholinylethylamino, 2-thiomorpholinylethylamino, 2-(4-N-methylpiperazinyl)ethylamino, 3-N,N-dimethylaminopropylamino, 3-N,N-diethylaminopropylamino, 3-N,N-diisopropylaminopropylamino, 3-hydroxypropylamino, 3-morpholinylpropylamino, 3-thiomorpholinylpropylamino, 3-(4-N-methylpiperazinyl)propylamino, N-methylpiperidinyl-4-amino, N-ethylpiperidinyl-4-amino, N-isopropylpiperidinyl-4-amino, N-acetylpiperidinyl-4-amino;

2) arylamino or heteroarylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

3) phenylmethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

4) phenylethylamino, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

5) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy, amino, C1-C6 alkoxycarbonyl, C1-C6 acyl, cyano, optionally substituted heterocyclyl, including but not limited to: piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl, 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl, 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl)piperidinyl, 4-(3-N,N-dimethyltetrahydropyrrolyl)piperidinyl;

N-methylpiperazinyl, N-ethylpiperazinyl, N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropyl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

morpholinyl, 3,5-dimethylmorpholinyl, thiomorpholinyl, tetrahydropyrrolyl, 3-N,N-dimethyltetrahydropyrrolyl, 3-N,N-diethyltetrahydropyrrolyl;

6) benzyl, which is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, amino, hydroxy, optionally substituted heterocyclyl, C1-C6 alkoxycarbonyl, C1-C6 acyl;

7) hydroxy, 2-N,N-dimethylaminoethoxy, 2-N,N-diethylaminoethoxy, 2-N,N-diisopropylaminoethoxy, 2-(N-methylpiperazinyl)ethoxy, 2-(N-acetylpiperazinyl)ethoxy, 2-morpholinylethoxy, 2-thiomorpholinylethoxy, 2-piperidinylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidinylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy;

preferably, $R^3$ is selected from:

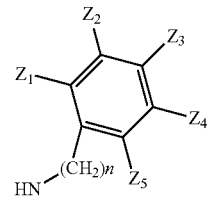

wherein, n=0 or 1;
when n=0, $Z_1$, $Z_2$, $Z_3$, $Z_4$, $Z_5$ are all H;
when n=1, any two of $Z_1$, $Z_2$, $Z_3$, $Z_4$, $Z_5$ each are independently selected from halogen, C1-C6 alkyl, C1-C6 alkoxy, the rest being H;
more preferably, $R^3$ is selected from:

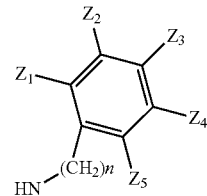

wherein, n=0 or 1;
when n=0, $Z_1$, $Z_2$, $Z_3$, $Z_4$, $Z_5$ are all H;
when n=1, $Z_1$, $Z_5$ in $Z_1$, $Z_2$, $Z_3$, $Z_4$, $Z_5$ each are independently selected from halogen, the rest being H;
most preferably, $R^3$ is selected from:

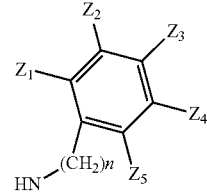

wherein, n=0 or 1;
when n=0, $Z_1$, $Z_2$, $Z_3$, $Z_4$, $Z_5$ are all H;
when n=1, $Z_1$, $Z_5$ in $Z_1$, $Z_2$, $Z_3$, $Z_4$, $Z_5$ each are independently selected from fluoro, chloro, the rest being H;
$R^4$ is selected from H, C1-C3 alkyl, C1-C3 alkoxy, C1-C3 oxygen-containing alkyl, C1-C3 fluorine-containing alkyl, halogen, nitro, cyano, amino, hydroxy;
preferably, $R^4$ is selected from H, C1-C3 alkyl, amino, hydroxy;
most preferably, $R^4$ is H.

preferably, the pharmaceutically acceptable salt is: an inorganic acid salt, selected from hydrochloride, hydrobromide, hydroiodide, nitrate, bicarbonate and carbonate, sulfate or phosphate; or an organic acid salt, selected from formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate and the like.

Unless otherwise indicated, the above groups and substituents have the ordinary meanings in the field of medicinal chemistry.

It should be noted that C1-C6 oxygen-containing alkyl refers to a group in which C1-C6 alkyl skeleton is substituted by one or more C1-C6 alkoxy groups, for example, methoxyethyl, methoxyethoxymethyl and the like.

The term "aryl" refers to a C6-10 mono-, di- or polycarbocyclic hydrocarbon having from 1 to 2 ring systems which are optionally further fused or attached to each other by a single bond, wherein at least one of the carbon rings is "aromatic", and the term "aromatic" refers to a fully conjugated π-electron bond system. The aryl ring may be optionally further fused or attached to aromatic or non-aromatic carbocyclic rings or heterocyclic rings. Non-limiting examples of the aryl group are phenyl, α- or β-naphthyl.

The term "heteroaryl" refers to an aromatic heterocyclic ring, which is usually a 5- to 8-membered heterocyclic ring having from 1 to 3 heteroatoms selected from N, O or S; a heteroaryl ring may be optionally further fused or attached to aromatic or non-aromatic carbocyclic rings or heterocyclic rings. Non-limiting examples of the heteroaryl group are, for example, pyridyl, pyrazinyl, pyrimidinyl, pyridazinyl, indolyl, imidazolyl, thiazolyl, isothiazolyl, thioxazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolyl, isoquinolyl, 1,2,3-triazolyl, 1-phenyl-1,2,3-triazolyl, 2,3-indolinyl, 2,3-dihydrobenzofuryl, 2,3-dihydrobenzothienyl, benzopyranyl, 2,3-dihydrobenzoxazinyl, 2,3-dihydroquinoxalinyl and the like.

The term "heterocyclyl" (also referred to as "heterocycloalkyl") refers to 3-, 4-, 5-, 6- and 7-membered saturated or partially unsaturated carbocyclic rings, wherein one or more carbon atoms are replaced by heteroatoms such as nitrogen, oxygen and sulfur. Non-limiting examples of the heterocyclic group are, for example, pyranyl, pyrrolidinyl, pyrrolinyl, imidazolinyl, imidazolidinyl, pyrazolidinyl, pyrazolinyl, thiazolinyl, thiazolidinyl, dihydrofuryl, tetrahydrofuryl, 1,3-dioxolanyl, piperidinyl, piperazinyl, morpholino, morpholinyl, tetrahydropyrrolyl, thiomorpholinyl and the like.

The term "optionally substituted heterocyclyl" refers to that the above-mentioned "heterocyclyl" is substituted by one or more "C1-C6 alkyl", "C1-C3 alkyl", "C3-C6 cycloalkyl" and the like.

The term "C1-C6 alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "C1-C3 alkyl" refers to any straight-chain or branched-chain group having 1 to 3 carbon atoms, such as methyl, ethyl, n-propyl, isopropyl and the like.

Unless otherwise provided, the term "C3-C6 cycloalkyl" refers to a 3- to 6-membered all-carbon monocyclic ring that may contain one or more double bonds, but does not have a fully conjugated π-electron system. Examples of cycloalkyl include, but are not limited to, cyclopropyl, cyclobutyl, cyclopentyl, cyclopentenyl, cyclohexyl, cyclohexenyl, cyclohexadienyl.

The term "C1-C3 fluorine-containing alkyl" refers to a group in which C1-C3 alkyl skeleton is substituted by one or more fluoro groups, for example, monofluoromethyl, difluoroethyl, trifluoromethyl, and the like.

The term "C1-C6 acyl" refers to —C(═O)—H and —C(═O)—C1-C5 alkyl, for example, formyl, acetyl, propionyl, butyryl, and the like.

The terms "alkoxy", "cycloalkoxy" and derivatives thereof refer to any of the above-mentioned alkyl (for example, C1-C24 alkyl, C1-C6 alkyl, C1-C3 alkyl and the like), cycloalkyl (for example, C3-C6 cycloalkyl), which is attached to the remainder of molecules through oxygen atom (—O—).

From all of the above description, it will be apparent to those skilled in the art that any group whose name is a compound name, for example, "fluorine-containing oxygen-containing alkyl" shall mean to conventionally construct from the moiety that is derived, such as the oxygen-containing alkyl substituted by the fluoro, wherein the alkyl is as defined above. For another example, "arylamino" shall mean to conventionally construct from the moiety that is derived, such as the amino substituted by the aryl, wherein the aryl is as defined above. Similarly, the meaning of "heteroarylamino" can be understood.

Similarly, any term such as alkylthio, alkylamino, dialkylamino, alkoxycarbonyl, alkoxycarbonylamino, heterocyclylcarbonyl, heterocyclyl carbonylamino, cycloalkyloxycarbonyl and the like includes groups, wherein alkyl, alkoxy, aryl, C3-C7 cycloalkyl and heterocyclyl moieties are as defined above.

According to the present invention and unless otherwise provided, any of the above groups may optionally be substituted at any of its free positions by one or more groups, for example by 1 to 6 groups, the groups being independently selected from: halogen atom, nitro, oxo (═O), cyano, C1-C6 alkyl, polyfluorinated alkyl, polyfluorinated alkoxy, alkenyl, alkynyl, hydroxyalkyl, hydroxyalkylamino, hydroxyheterocyclyl, aryl, aryl-alkyl, heteroaryl, heteroarylalkyl, heterocyclyl, heterocyclyl-alkyl, C3-C7 cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkylamino, hydroxy, alkoxy, aryloxy, heterocyclyloxy, alkyl-heterocyclyloxy, methylenedioxy, alkylcarbonyloxy, arylcarbonyloxy, cycloalkenyloxy, heterocyclylcarbonyloxy, alkyleneaminooxy, carboxy, alkoxycarbonyl, aryloxycarbonyl, cycloalkyloxycarbonyl, heterocyclyloxycarbonyl, amino, ureido, alkylamino, aminoalkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, formamido, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxycarbonylheterocyclyl-alkylamino, alkoxy-aryl-alkyl, hydroxyamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

Further, if appropriate, each of the above substituents may be further substituted by one or more of the above-exemplified groups.

In this respect, the term "halogen atom" refers to a fluoro (F), chloro (Cl), bromo (Br) or iodine (I) atom.

The term "cyano" refers to —CN residue.

The term "nitro" refers to —NO₂ group.

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in Burger's Medicinal Chemistry and Drug Discovery (1995) 172-178, 949-982 (Manfred E. Wolff, ed. $5^{th}$ edition).

As used herein, examples of the term "pharmaceutically acceptable salts of the compounds of formula (I)" are organic acid addition salts formed from organic acids that form pharmaceutically acceptable anions, including but not limited to formate, acetate, propionate, benzoate, maleate, fumarate, succinate, tartrate, citrate, ascorbate, α-ketoglutarate, α-glycerophosphate, alkyl sulfonate or aryl sulfonate; preferably, said alkyl sulfonate is methyl sulfonate or ethyl sulfonate; said aryl sulfonate is benzenesulfonate or p-toluenesulfonate. Suitable inorganic acid salts may also be formed, including but not limited to hydrochloride, hydrobromide, hydroiodide, nitrate, bicarbonate and carbonate, sulfate or phosphate and the like.

Pharmaceutically acceptable salts can be obtained using standard procedures well known in the art, for example, by reacting a sufficient amount of an alkaline compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a table. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the composition may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solution or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s). Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles), etc.

In another aspect, the present invention further provides a preparation method of the compounds (I, II, III-a~III-f, IV, VI, VII, VIII, IX, X) according to any of the above embodiments, comprising the following steps:

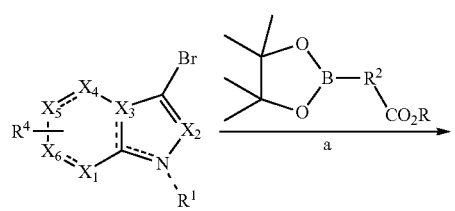

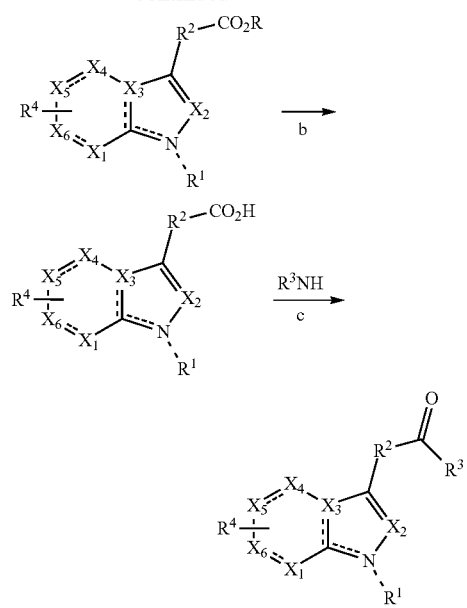

reaction conditions: (a) coupling reaction of carbon-carbon bond formation catalyzed by metal palladium; (b) ester hydrolysis under alkaline condition (LiOH or NaOH, etc.); (c) amide condensation reaction under alkaline condition (HOBT or HATU; triethylamine or diisopropylethylamine, etc.).

A preparation method of the compound (III-g), comprising the following steps:

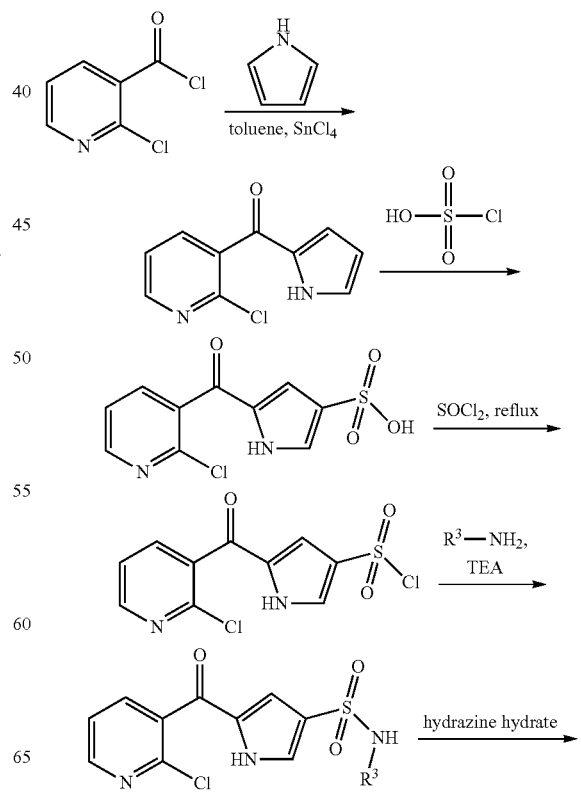

-continued

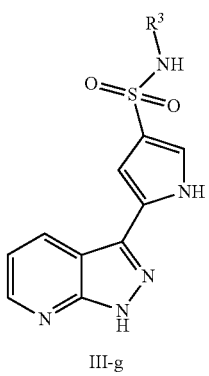

III-g

A preparation method of the compound (III-h), comprising the following steps:

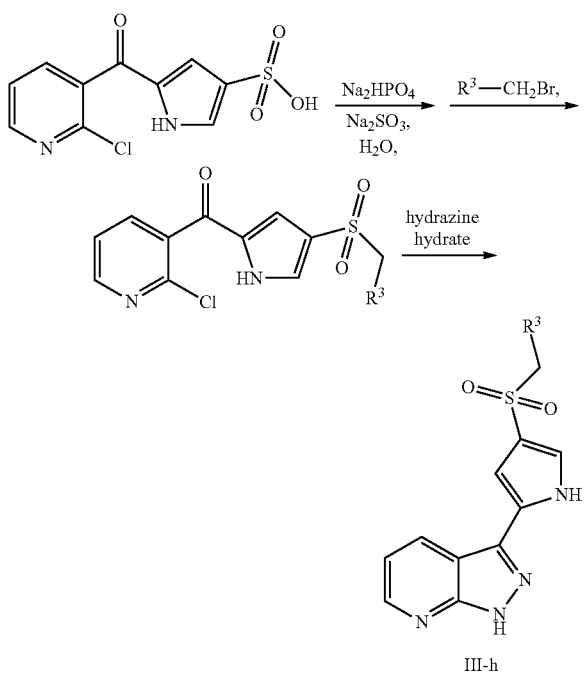

III-h

In another aspect, the present invention further provides use of the compound according to any one of the above embodiments, a stereoisomer thereof, a prodrug thereof, or a pharmaceutically acceptable salt thereof or a pharmaceutically acceptable solvate thereof, and a pharmaceutical composition comprising the compound in the manufacture of a medicament for preventing or treating cancers and other diseases caused by Ras overactivation.

Experimental Section

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhihuangwu Silica Gel Development Reagent Factory) under medium pressure or by a pre-packed silica gel cartridge (ISCO or Welch) with the use of an ISCO Combiflash Rf200 rapid purification system. The ingredient was developed by UV light (λ: 254 nm) or iodine vapor. When necessary, the compound was prepared by preparative HPLC and purified by a Waters Symmetry C18 (19×50 mm, 5 μm) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: MeOH/H$_2$O 95/5. Gradient: proceeding at 10 to 90% B for 8 min, keeping at 90% B for 2 min; flow rate 20 mL/min. Method 2: Phase A: 0.05% NH$_4$OH/MeOH 95/5; Phase B: MeOH/H$_2$O 95/5. Gradient: proceeding at 10 to 100% B for 8 min, keeping at 100% B for 2 min. Flow rate 20 m L/m in.

$^1$H-NMR spectra were recorded via a Bruker Avance 600 spectrometer (for $^1$H) operated at 600 MHz. The tetramethylsilane signal was used as a reference (δ=0 ppm). Chemical shift (δ) was reported in parts per million (ppm) and coupling constant (J) in Hz. The following abbreviations were used for peak splitting: s=single; br. s.=wide signal; d=double; t=triple; m=multiple; dd=double double.

Electrospray (ESI) mass spectra were obtained via Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm). Mobile phase A was ammonium acetate 5 mM buffer (pH 5.5 with acetic acid): acetonitrile 90:10, mobile phase B was ammonium acetate 5 mM buffer (pH 5.5 with acetic acid): acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol, dichloromethane were all analytically pure.

The abbreviations hereinafter have the following meanings:

HPLC: high performance liquid chromatography

TFA: trifluoroacetic acid

DIEA: N, N-diisopropylethylamine

EDCl.HCl: 1-ethyl-(3-dimethylaminopropyl) carbodiimide hydrochloride HOBt: 1-hydroxybenzotriazole rt: room temperature DMSO: dimethyl sulfoxide

MODE OF CARRYING OUT THE INVENTION

The embodiments of the present invention are described in detail below by way of specific examples, but in any case they cannot be construed as limiting the present invention.

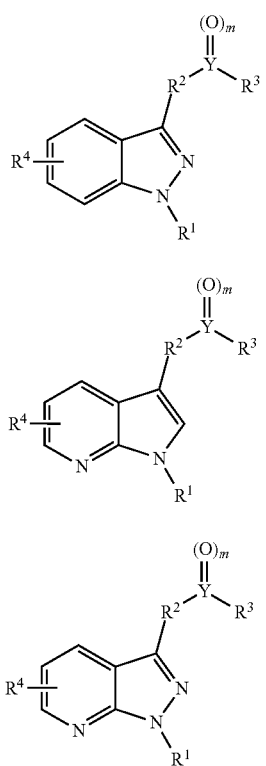
The above compound of formula was divided into several types for preparation.
The compounds of formula I:
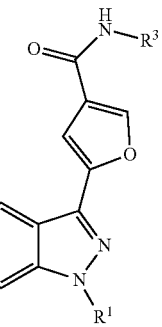
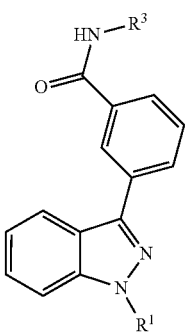
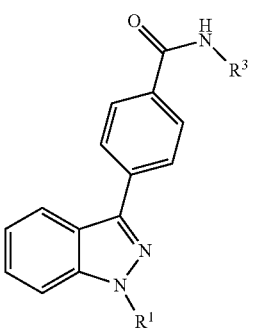
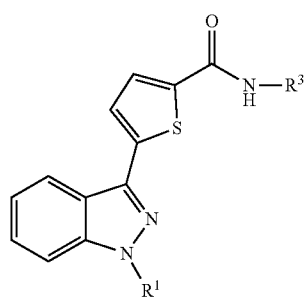
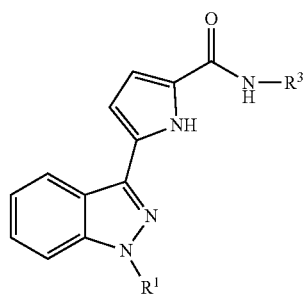

Synthetic Scheme of Compound I-a:

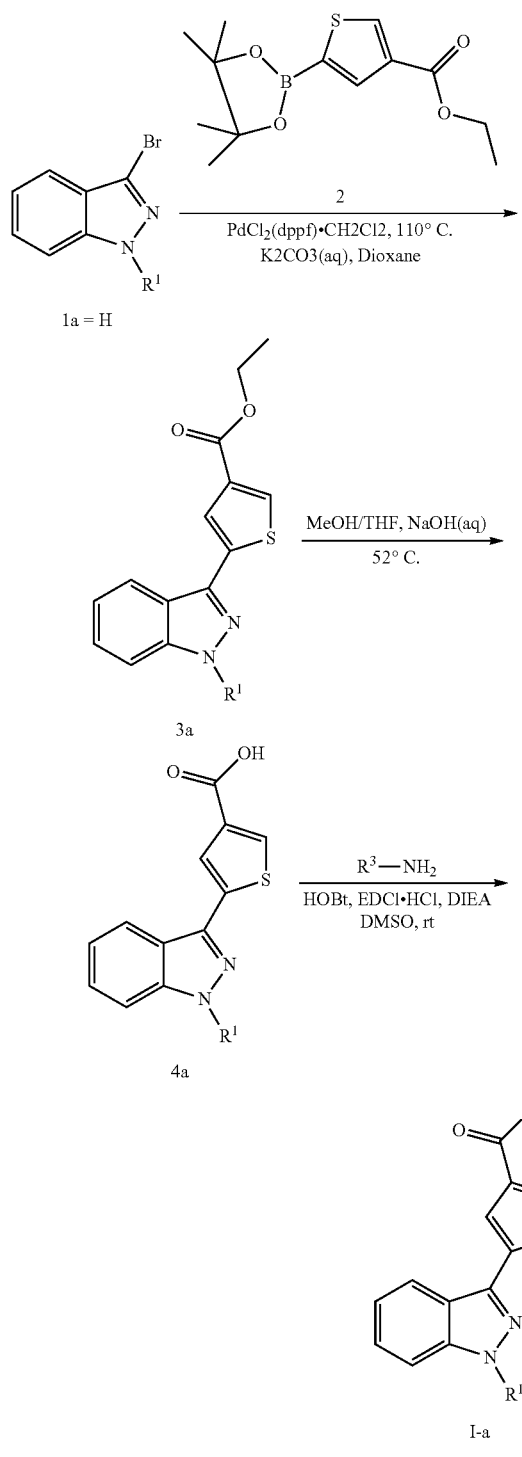

Preparation of Compound 3a

Compound 1a (1 mmol), compound 2 (1.5 mmol), PdCl$_2$(dppf).CH$_2$Cl$_2$ (20% m %), K$_2$CO$_3$ (4 mmol) were added to 10 mL of 1,4-dioxane and 3.3 mL of H$_2$O, the system was purged with nitrogen, and placed in an oil bath preheated to 110° C. and stirred with heating overnight. The reaction system was filtered to remove solids and concentrated, followed by separation with silica gel column chromatography to obtain compound 3a. (white solid, 83 mg, 30.5%). MS (ESI) m/z 273 [M+H]+.

Preparation of Compound 4a

Compound 3a (0.3 mmol) was dissolved in MeOH (0.3 mL)/THF (0.3 mL), to which was added 0.3 mL of 1N NaOH aqueous solution, followed by heating to 52° C. and stirring overnight. The organic solvent was removed under reduced pressure, the reaction system was adjusted with dilute hydrochloric acid to pH=6, to precipitate out a solid, then the solid was washed with water, and dried to obtain compound 4a. (beige solid, 72 mg, 96.7%). MS (ESI) m/z 245 [M+H]+.

Preparation of Compound I-a

Method A:
Compound 4a (0.14 mmol) was dissolved in dimethyl sulfoxide, to which were added HOBt (0.35 mmol), EDCl.HCl (0.35 mmol), DIEA (0.56 mmol). After stirring at room temperature for 15 minutes, arylamine (0.14 mmol) was added. The reaction was carried out at room temperature for 5 hours. The reaction system was extracted with water/ethyl acetate (3×15 mL), then the organic phase was washed with saturated sodium chloride solution, dried with anhydrous sodium sulfate, concentrated, and separated by silica gel column chromatography (dichloromethane/methanol) to obtain compound I-a.

Method B:
Compound 4a (0.14 mmol) was dissolved in dimethyl sulfoxide, to which were added HOBt (0.35 mmol), EDCl.HCl (0.35 mmol), DIEA (0.56 mmol). After stirring at room temperature for 15 minutes, arylamine (0.14 mmol) was added. The reaction was carried out at room temperature for 5 hours. The reaction system was extracted with water/ethyl acetate (3×15 mL), then the organic phase was washed with saturated sodium chloride solution, dried with anhydrous sodium sulfate, concentrated, purified by reverse phase preparative HPLC (using 0.35% trifluoroacetic acid-containing aqueous solution and methanol as mobile phase), and vacuum concentrated to obtain compound I-a.

Compounds I-b, I-c, I-d, I-e, I-f, I-g all could be synthesized by a similar method.

The table below lists the specific compounds and structure identification data.

The synthesis of the compounds of examples is described in detail below. R$^3$—NH$^2$:

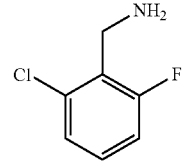

(CAS: 68220-26-8, Bide, Shanghai)

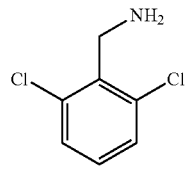

| 63 | 64 |
|---|---|
| (CAS: 6575-27-5, Energy, Shanghai) | (CAS: 140-75-0, Energy, Shanghai) |
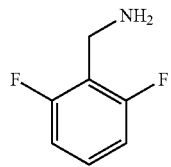
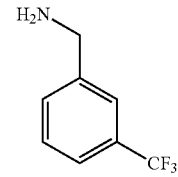
(CAS: 69385-30-4, Energy, Shanghai)
(CAS: 2740-83-2, Energy, Shanghai)
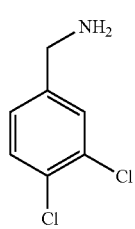
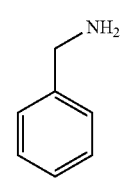
(CAS: 102-49-8, Energy, Shanghai)
(CAS: 199296-61-2, Aikon, Suzhou)
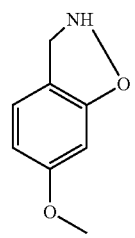
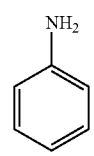
(CAS: 20781-20-8, Energy, Shanghai)
(CAS: 100-46-9, Energy, Shanghai)
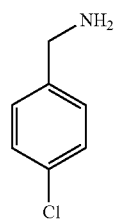
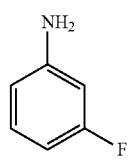
(CAS: 104-86-9, Energy, Shanghai)
(CAS: 62-53-3, Energy, Shanghai)
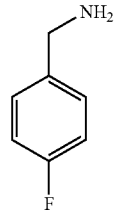
(CAS: 372-19-0, Energy, Shanghai)
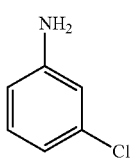

| 65 | 66 |
|---|---|
| (CAS: 108-42-9, Energy, Shanghai) | (CAS: 371404, Energy, Shanghai) |
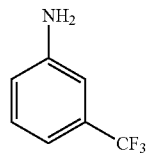
(CAS: 98-16-8, Energy, Shanghai)
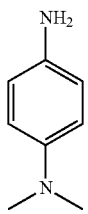
(CAS: 99-98-9, Energy, Shanghai)
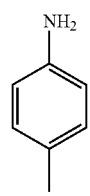
(CAS: 106-49-0, Energy, Shanghai)
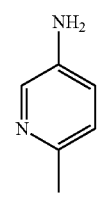
(CAS: 3430-14-6, Energy, Shanghai)
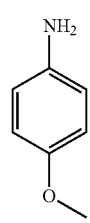
(CAS: 104-94-9, Energy, Shanghai)
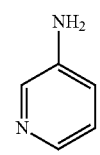
(CAS: 462-08-8, Energy, Shanghai)
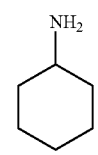
(CAS: 108-91-8, Energy, Shanghai)
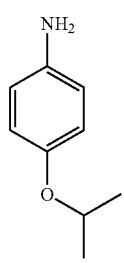
(CAS: 7664-66-6, Energy, Shanghai)
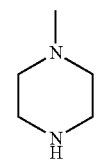
(CAS: 109-01-3, Energy, Shanghai)
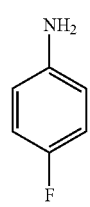
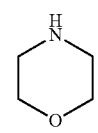

| 67 | 68 |
|---|---|
| (CAS: 110-91-8, Energy, Shanghai) | (CAS: 156-41-2, Energy, Shanghai) |
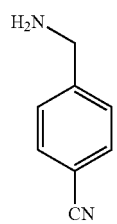
(CAS: 765-30-0, Energy, Shanghai)
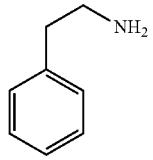
(CAS: 10406-25-4, Energy, Shanghai)
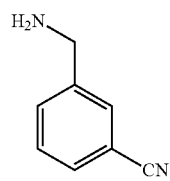
(CAS: 64-04-0, Energy, Shanghai)
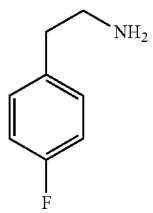
(CAS: 10406-24-3, Energy, Shanghai)
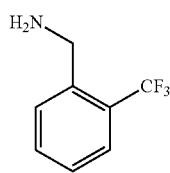
(CAS: 1583-88-6, Energy, Shanghai)
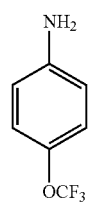
(CAS: 3048-01-9, Energy, Shanghai)
(CAS: 461-82-5, Energy, Shanghai)
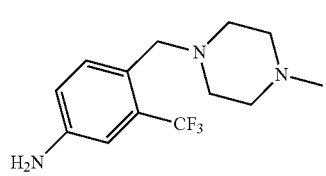 [SMILES: CN1CCN(Cc2ccc(N)cc2C(F)(F)F)CC1]
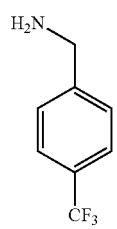
(CAS: 694499-26-8, Sundia, Shanghai)
(CAS: 3300-51-4, Energy, Shanghai)
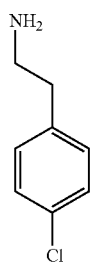
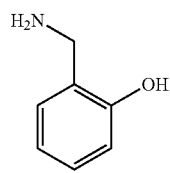

(CAS: 932-30-9, Energy, Shanghai)
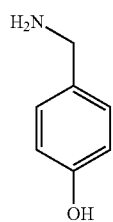
(CAS: 696-60-6, Energy, Shanghai)
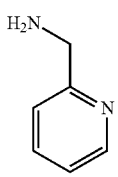
(CAS: 3731-51-9, Energy, Shanghai)
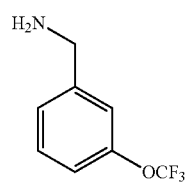
(CAS: 93071-75-1, Energy, Shanghai)
(CAS: 175205-64-8, Energy, Shanghai)
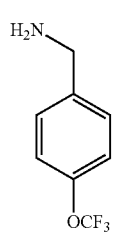
(CAS: 93919-56-3, Energy, Shanghai)
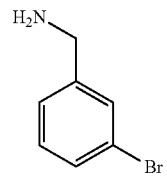
(CAS: 10269-01-9, Energy, Shanghai)
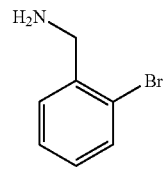
(CAS: 3959-05-5, Energy, Shanghai)
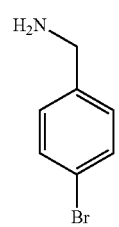
(CAS: 3959-07-7, Energy, Shanghai)
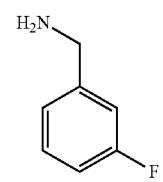
(CAS: 100-82-3, Energy, Shanghai)
(CAS: 89-99-6, Energy, Shanghai)
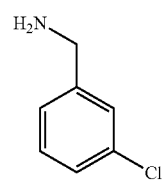

71
(CAS: 4152-90-3, Energy, Shanghai)
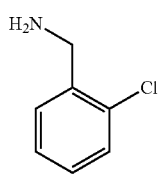
(CAS: 89-97-4, Energy, Shanghai)
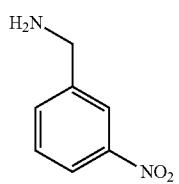
(CAS: 7409-18-9, Energy, Shanghai)
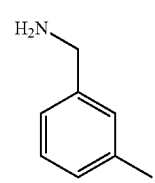
(CAS: 100-81-2, Energy, Shanghai)
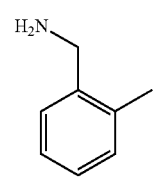
(CAS: 89-93-0, Energy, Shanghai)
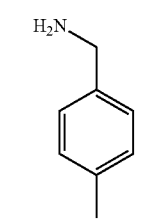
(CAS: 104-847, Energy, Shanghai)
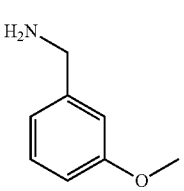
72
(CAS: 5071-96-5, Energy, Shanghai)
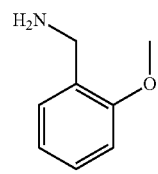
(CAS: 6850-57-3, Energy, Shanghai)
(CAS: 2393-23-9, Energy, Shanghai)
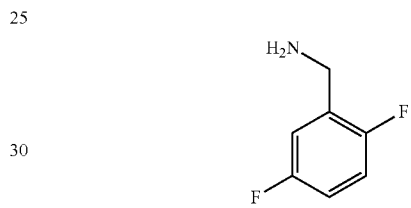
(CAS: 85118-06-5, Energy, Shanghai)
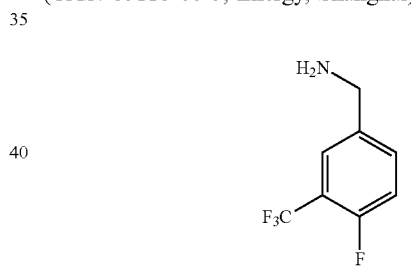
(CAS: 67515-74-6, Energy, Shanghai)
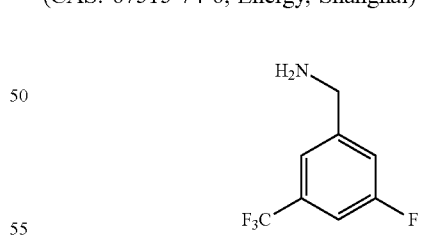
(CAS: 150517-77-4, Energy, Shanghai)
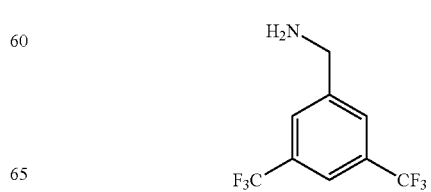

(CAS: 85068-29-7, Energy, Shanghai)

(CAS: 239135-49-0, Energy, Shanghai)

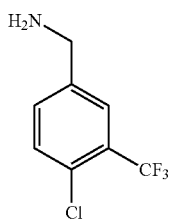

(CAS: 62039-92-3, Energy, Shanghai)
1. Compound I-a-1:
Synthesis of Intermediate:

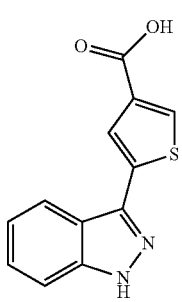 [SMILES: O=C(O)c1csc(-c2n[nH]c3ccccc23)c1]

Compound

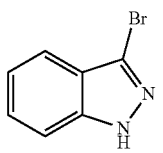

(1 mmol, 197.0 mg) (CAS: 40598-94-5, Bide, Shanghai), compound

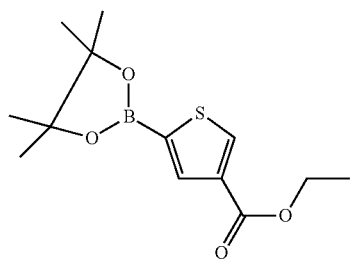 [SMILES: CCOC(=O)c1csc(B2OC(C)(C)C(C)(C)O2)c1]

(1.5 mmol, 282.16 mg) (CAS: 960116-27-2, Efe, Shanghai), PdCl$_2$(dppf).CH$_2$Cl$_2$ (20% m %, 39.4 mg) (CAS: 95464-05-4, Energy, Shanghai), K$_2$CO$_3$ (4 mmol, 552.08 mg) were added to 10 mL of 1,4-dioxane and 3.3 mL of H$_2$O, the system was purged with nitrogen, and placed in an oil bath preheated to 110° C. and stirred with heating overnight. The reaction system was filtered to remove solids and concentrated, followed by separation with silica gel column chromatography to obtain 83 mg of compound, ethyl 5-(1H-indazol-3-yl)thiophene-3-carboxylate.

Ethyl 5-(1H-indazol-3-yl)thiophene-3-carboxylate (0.3 mmol, 83 mg) was dissolved in MeOH (0.3 mL)/THF (0.3 mL), then 0.3 mL of 1N NaOH aqueous solution was added, heated to 52° C., and stirred overnight. The organic solvent was removed under reduced pressure, the reaction system was adjusted with dilute hydrochloric acid to pH=6, to precipitate out a solid, then the solid was washed with water, and dried to obtain 72 mg of 5-(1H-indazol-3-yl)thiophene-3-carboxylic acid.

The above intermediate

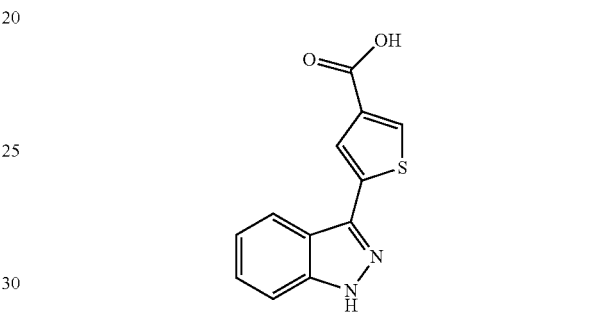

(0.14 mmol, 35 mg) was dissolved in dimethyl sulfoxide (DMSO), to which were added HOBt (0.35 mmol, 49.43 mg), EDCl. HCl (0.35 mmol, 68.42 mg), DIEA (0.56 mmol, 73.79 mg). After stirring at room temperature for 15 minutes,

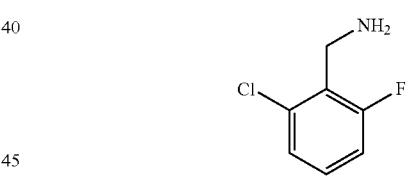

(0.14 mmol, 22.82 mg) (CAS: 68220-26-8, Bide, Shanghai) was added. The reaction was carried out at room temperature for 5 hours. The reaction system was extracted with water/ethyl acetate (3×15 mL), then the organic phase was washed with saturated sodium chloride solution, dried with anhydrous sodium sulfate, concentrated, purified by reverse phase preparative HPLC (using 0.35% trifluoroacetic acid-containing aqueous solution and methanol as mobile phase), and vacuum concentrated to obtain compound I-a-1 (12.1 mg, 22%).

2. Using compound

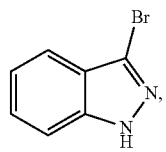

compound

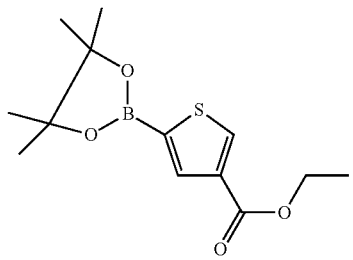 [SMILES: CCOC(=O)c1csc(B2OC(C)(C)C(C)(C)O2)c1]

and the corresponding R³—NH² as raw materials, compounds I-a-2~I-a-27 were obtained with a reference to the preparation method of compound I-a-1.

3. Using compound

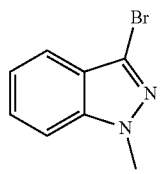

(CAS: 326474-67-3, Bide, Shanghai), compound

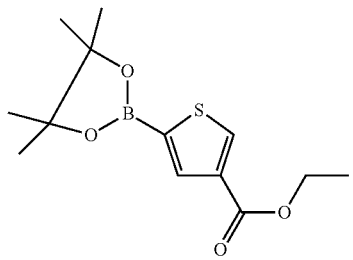 [SMILES: CCOC(=O)c1csc(B2OC(C)(C)C(C)(C)O2)c1]

and the corresponding R³—NH² as raw materials, compound I-a-28 was obtained by silica gel column chromatography (dichloromethane/methanol).

4. Using compound

(CAS: 885521-40-4, Bide, Shanghai), compound

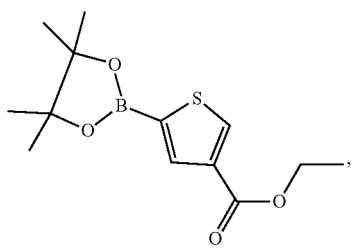

and the corresponding R³—NH² as raw materials, compound I-a-29 was obtained with a reference to the preparation method of compound I-a-1.

5. Compound I-a-30:

Synthesis of Intermediate:

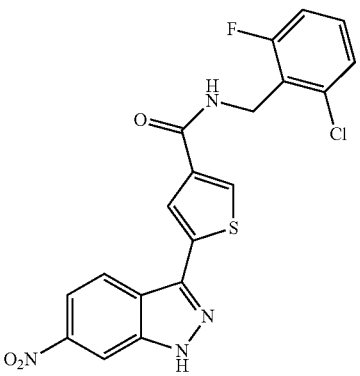 [SMILES: O=C(NCc1c(F)cccc1Cl)c1csc(-c2n[nH]c3cc([N+](=O)[O-])ccc23)c1]

Using compound

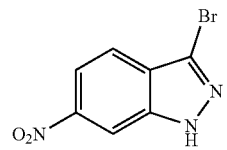 [SMILES: O=[N+]([O-])c1ccc2c(Br)n[nH]c2c1]

(CAS: 70315-68-3, Bide, Shanghai), compound and the corresponding R³—NH² as raw materials, compound

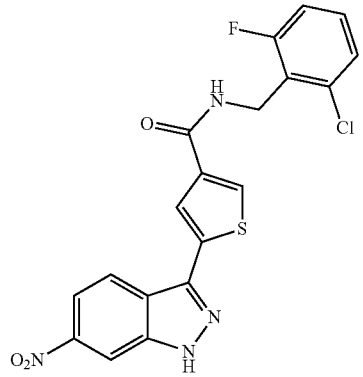 [SMILES: O=C(NCc1c(F)cccc1Cl)c1csc(-c2n[nH]c3cc([N+](=O)[O-])ccc23)c1]

was obtained with a reference to the preparation method of compound I-a-1.

Compound

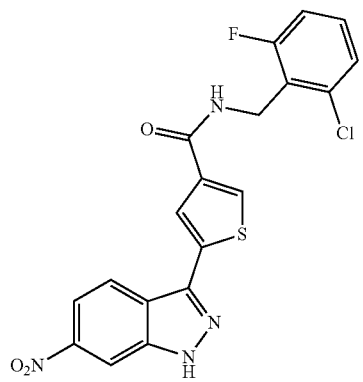 [SMILES: O=C(NCc1c(F)cccc1Cl)c1csc(-c2n[nH]c3cc([N+](=O)[O-])ccc23)c1]

(0.1 mmol, 43 mg), Fe powder (5 mmol, 28 mg) were dissolved in 1 mL of EtOH, to which was then added dropwise 0.2 mL of NH₄Cl (0.4 mmol, 21.3 mg) aqueous solution, followed by heating to 50° C., overnight. The reaction system was filtered through silica gel, and extracted with water/ethyl acetate, then the organic phase was washed with saturated sodium chloride solution, dried with anhydrous sodium sulfate, concentrated, and separated by silica gel column chromatography (dichloromethane/methanol) to obtain compound I-a-30 (21 mg, 52.5%).

6. Using compound

compound

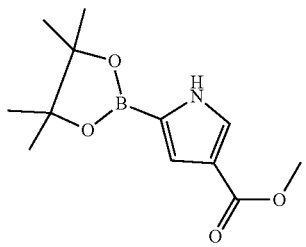

(CAS: 1268619-58-4, Efe, Shanghai) and the corresponding R³—NH² as raw materials, compounds I-b-1~I-b-2 were obtained with a reference to the preparation method of compound I-a-1.

7. Using compound

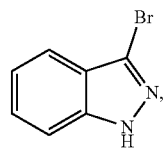

compound

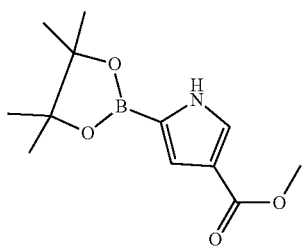

(CAS: 1111096-29-7, Efe, Shanghai) and the corresponding R³—NH² as raw materials, compounds I-c-1~I-c-2 were obtained with a reference to the preparation method of compound I-a-1.

8. Using compound

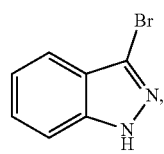

compound

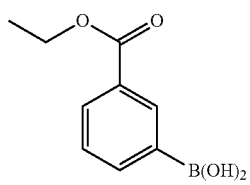

(CAS: 4334-87-6, Energy, Shanghai) and the corresponding R³—NH² as raw materials, compounds I-d-1~I-d-2 were obtained with a reference to the preparation method of compound I-a-28.

9. Using compound

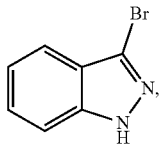

compound

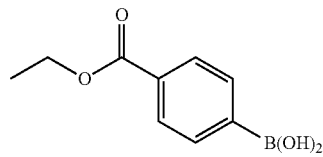

(CAS: 4334-88-7, Energy, Shanghai) and the corresponding R³—NH² as raw materials, compounds I-e-1~I-e-2 were obtained with a reference to the preparation method of compound I-a-1.

10. Using compound

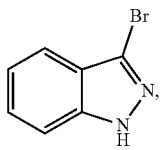

compound

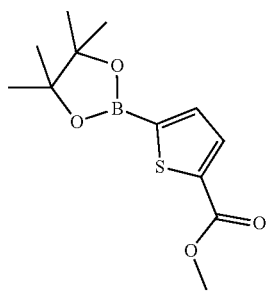 [SMILES: COC(=O)c1ccc(B2OC(C)(C)C(C)(C)O2)s1]

(CAS: 916138-13-1, Efe, Shanghai) and the corresponding R³—NH² as raw materials, compounds I-f-1~I-f-3 were obtained with a reference to the preparation method of compound compound 1-a-28.

11. Compound I-g-1:

Synthesis of Intermediate:

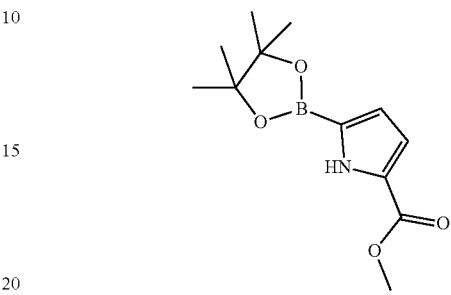

Compound methyl 5-bromo-1H-pyrrole-2-carboxylate (0.5 mmol, 102 mg) (CAS: 934-07-6, Accela ChemBio, Shanghai), bis(pinacolato)diboron (0.55 mmol, 139.6 mg) (CAS: 73183-34-3, Energy, Shanghai), palladium [1,1'-bis (diphenylphosphino)ferrocene]dichloride (10.2 mg) (CAS: 72287-26-4, Energy, Shanghai) and potassium acetate (1 mmol, 98.1 mg) were dissolved in 3 mL of anhydrous 1,4-dioxane. The system was purged with nitrogen, and placed in an oil bath preheated to 105° C. and stirred with heating overnight. The reaction system was filtered to remove solids and concentrated to obtain a crude product of methyl 5-(4,4,5,5-tetramethyl-1,3,2-dioxaborolan-2-yl)-1H-pyrrole-2-carboxylate.

Using compound

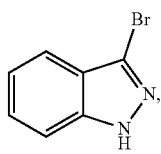

the intermediate

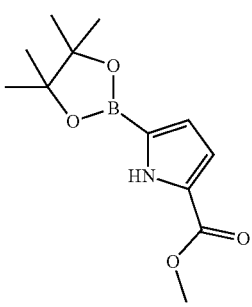 [SMILES: COC(=O)c1ccc(B2OC(C)(C)C(C)(C)O2)[nH]1]

and the corresponding R³—NH² as raw materials, compound I-g-1 was obtained with a reference to the preparation method of compound I-a-1.

TABLE 1

| | Structure and characterization of compounds I | |
|---|---|---|
| No. | Structure | 1H NMR and/or MS data |
| I-a-1 | (structure: N-(2-chloro-6-fluorobenzyl) 5-(1H-indazol-3-yl)thiophene-3-carboxamide) TFA salt | $^1$H NMR (600 MHz, Methanol-d$_4$) δ 8.10 (dd, J = 8.3, 1.0 Hz, 1H), 8.08 (d, J = 2.0 Hz, 2H), 7.56 (dt, J = 8.5, 0.9 Hz, 1H), 7.44 (ddd, J = 8.3, 6.9, 1.0 Hz, 1H), 7.34 (dd, J = 8.2, 5.8 Hz, 1H), 7.30 (dt, J = 8.2, 1.1 Hz, 1H), 7.25 (ddd, J = 8.0, 6.8, 0.9 Hz, 1H), 7.14 (ddd, J = 9.6, 8.2, 1.3 Hz, 1H), 4.77 (d, J = 1.6 Hz, 2H). MS (ESI) m/z: 386 [M + H]$^+$. |
| I-a-2 | (structure: N-(2,6-dichlorobenzyl) 5-(1H-indazol-3-yl)thiophene-3-carboxamide) | MS (ESI) m/z: 403 [M + H]$^+$. |
| I-a-3 | (structure: N-(2,6-difluorobenzyl) 5-(1H-indazol-3-yl)thiophene-3-carboxamide) | MS (ESI) m/z: 370 [M + H]$^+$. |

TABLE 1-continued

Structure and characterization of compounds I

| No. | Structure | 1H NMR and/or MS data |
|---|---|---|
| I-a-4 | 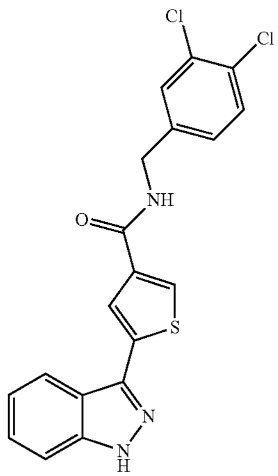 [SMILES: O=C(NCc1ccc(Cl)c(Cl)c1)c1csc(-c2n[nH]c3ccccc23)c1] | MS (ESI) m/z: 403 [M + H]+. |
| I-a-5 | 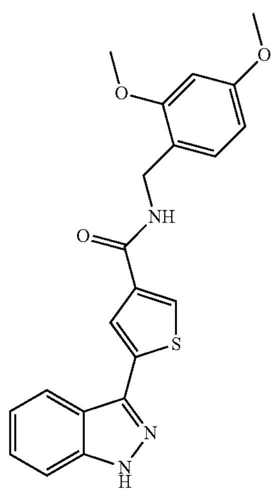 [SMILES: COc1ccc(CNC(=O)c2csc(-c3n[nH]c4ccccc34)c2)c(OC)c1] | MS (ESI) m/z: 394 [M + H]+. |
| I-a-6 | 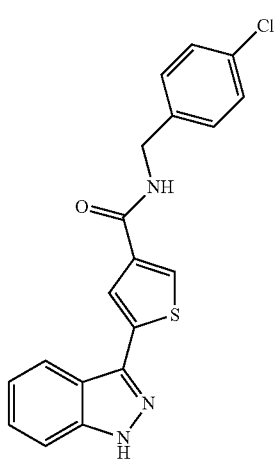 [SMILES: O=C(NCc1ccc(Cl)cc1)c1csc(-c2n[nH]c3ccccc23)c1] | MS (ESI) m/z: 368 [M + H]+. |

TABLE 1-continued

Structure and characterization of compounds I

| No. | Structure | 1H NMR and/or MS data |
|---|---|---|
| I-a-7 | 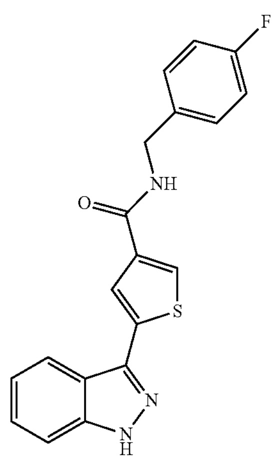 [SMILES: O=C(NCc1ccc(F)cc1)c1csc(-c2n[nH]c3ccccc23)c1] | MS (ESI) m/z: 352 [M + H]⁺. |
| I-a-8 | 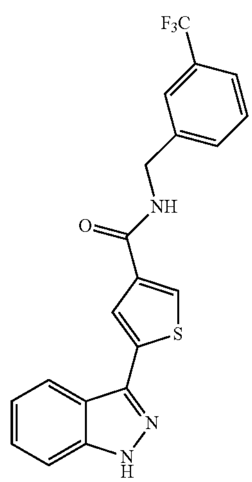 [SMILES: O=C(NCc1cccc(C(F)(F)F)c1)c1csc(-c2n[nH]c3ccccc23)c1] | ¹H NMR (600 MHz, DMSO-d$_6$) δ 9.12 (t, J = 6.0 Hz, 1H), 8.17 (dd, J = 4.9, 1.4 Hz, 3H), 7.71 (d, J = 2.1 Hz, 1H), 7.67 (d, J = 7.4 Hz, 1H), 7.65-7.57 (m, 3H), 7.44 (ddd, J = 8.2, 6.9, 1.0 Hz, 1H), 7.27 (ddd, J = 7.9, 6.8, 0.9 Hz, 1H), 4.60 (d, J = 5.9 Hz, 2H). MS (ESI) m/z 402 [M + H]⁺. |
| I-a-9 (TFA salt) | | ¹H NMR (600 MHz, DMSO-d6) δ 9.08 (t, J = 5.8 Hz, 1H), 8.19-8.10 (m, 3H), 7.79 (dd, J = 6.8, 2.4 Hz, 1H), 7.77-7.72 (m, 1H), 7.61 (dt, J = 8.4, 0.9 Hz, 1H), 7.51-7.40 (m, 2H), 7.27 (ddd, J = 7.9, 6.8, 0.9 Hz, 1H), 4.60 (d, J = 5.7 Hz, 2H). MS (ESI) m/z: 420 [M + H]⁺. |

TABLE 1-continued

Structure and characterization of compounds I

| No. | Structure | 1H NMR and/or MS data |
| --- | --- | --- |
| I-a-10 | (structure: N-benzyl 5-(1H-indazol-3-yl)thiophene-3-carboxamide) | (ESI) m/z: 334 [M + H]$^+$. |
| I-a-11 | (structure: N-phenyl 5-(1H-indazol-3-yl)thiophene-3-carboxamide) TFA salt | $^1$H NMR (600 MHz, Methanol-d$_4$) δ 8.25 (d, J = 1.4 Hz, 1H), 8.21 (d, J = 1.4 Hz, 1H), 8.20-8.17 (m, 1H), 7.79-7.69 (m, 2H), 7.59 (dt, J = 8.4, 0.9 Hz, 1H), 7.47 (ddd, J = 8.2, 6.8, 1.0 Hz, 1H), 7.39 (dd, J = 8.5, 7.4 Hz, 2H), 7.30 (ddd, J = 7.9, 6.8, 0.9 Hz, 1H), 7.21-7.13 (m, 1H). MS (ESI) m/z: 320 [M + H]$^+$. |
| I-a-12 | (structure: N-(3-fluorophenyl) 5-(1H-indazol-3-yl)thiophene-3-carboxamide) | MS (ESI) m/z: 338 [M + H]$^+$. |
| I-a-13 | (structure: N-(3-chlorophenyl) 5-(1H-indazol-3-yl)thiophene-3-carboxamide) | MS (ESI) m/z: 354 [M + H]$^+$. |

TABLE 1-continued

Structure and characterization of compounds I

| No. | Structure | 1H NMR and/or MS data |
|---|---|---|
| I-a-14 | 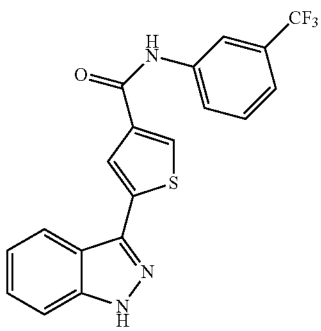 [SMILES: O=C(Nc1cccc(C(F)(F)F)c1)c1csc(-c2n[nH]c3ccccc23)c1] | MS (ESI) m/z: 388 [M + H]+. |
| I-a-15 | 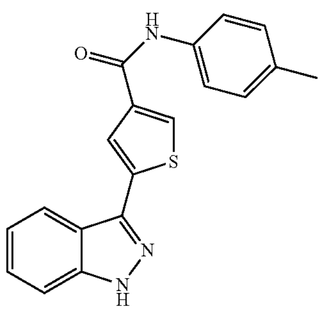 [SMILES: Cc1ccc(NC(=O)c2csc(-c3n[nH]c4ccccc34)c2)cc1] | MS (ESI) m/z: 334 [M + H]+. |
| I-a-16 | 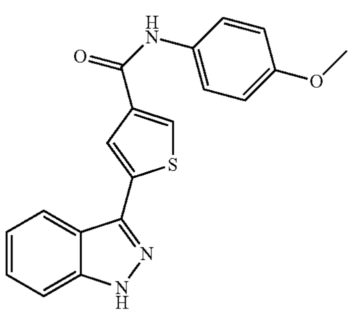 [SMILES: COc1ccc(NC(=O)c2csc(-c3n[nH]c4ccccc34)c2)cc1] | MS (ESI) m/z: 350 [M + H]+. |
| I-a-17 | 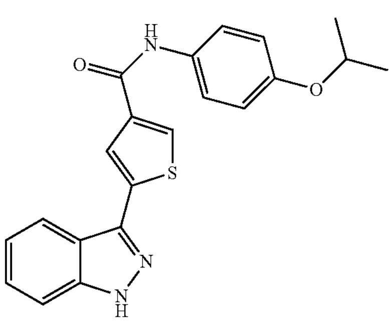 [SMILES: CC(C)Oc1ccc(NC(=O)c2csc(-c3n[nH]c4ccccc34)c2)cc1] | MS (ESI) m/z: 378 [M + H]+. |

TABLE 1-continued

Structure and characterization of compounds I

| No. | Structure | 1H NMR and/or MS data |
|---|---|---|
| I-a-18 | 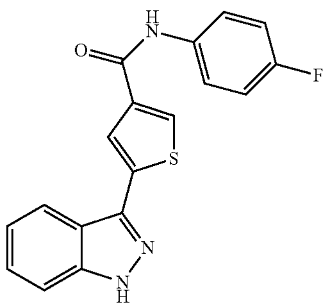 [SMILES: O=C(Nc1ccc(F)cc1)c1csc(-c2n[nH]c3ccccc23)c1] | MS (ESI) m/z: 338 [M + H]$^+$. |
| I-a-19 | 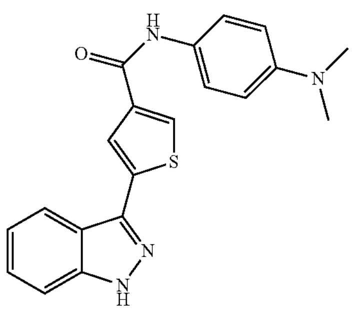 [SMILES: CN(C)c1ccc(NC(=O)c2csc(-c3n[nH]c4ccccc34)c2)cc1] | MS (ESI) m/z: 363 [M + H]$^+$. |
| I-a-20 | 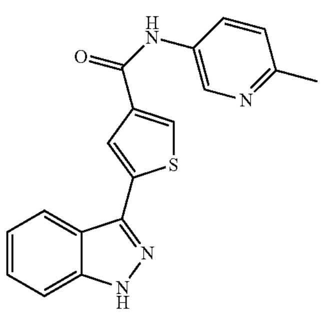 [SMILES: Cc1ccc(NC(=O)c2csc(-c3n[nH]c4ccccc34)c2)cn1] | MS (ESI) m/z: 335 [M + H]$^+$. |
| I-a-21 | 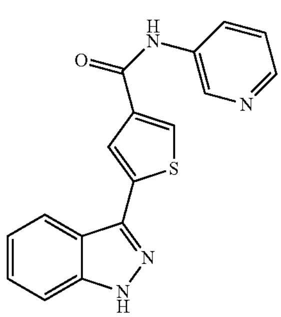 [SMILES: O=C(Nc1cccnc1)c1csc(-c2n[nH]c3ccccc23)c1] | MS (ESI) m/z: 321 [M + H]$^+$. |

TABLE 1-continued

Structure and characterization of compounds I

| No. | Structure | 1H NMR and/or MS data |
|---|---|---|
| I-a-22 | 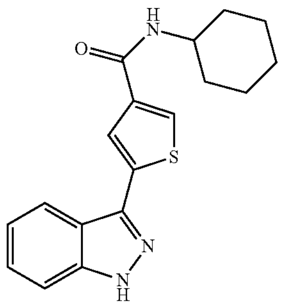 [SMILES: O=C(NC1CCCCC1)c1csc(-c2n[nH]c3ccccc23)c1] | MS (ESI) m/z: 326 [M + H]+. |
| I-a-23 | 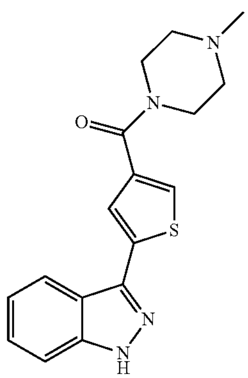 [SMILES: CN1CCN(C(=O)c2csc(-c3n[nH]c4ccccc34)c2)CC1] | MS (ESI) m/z: 327 [M + H]+. |
| I-a-24 | 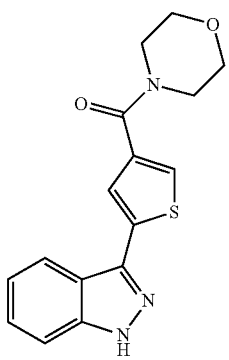 [SMILES: O=C(c1csc(-c2n[nH]c3ccccc23)c1)N1CCOCC1] | MS (ESI) m/z: 314 [M + H]+. |
| I-a-25 | 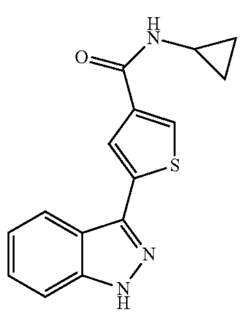 [SMILES: O=C(NC1CC1)c1csc(-c2n[nH]c3ccccc23)c1] | MS (ESI) m/z: 284 [M + H]+. |

TABLE 1-continued

Structure and characterization of compounds I

| No. | Structure | 1H NMR and/or MS data |
|---|---|---|
| I-a-26 | 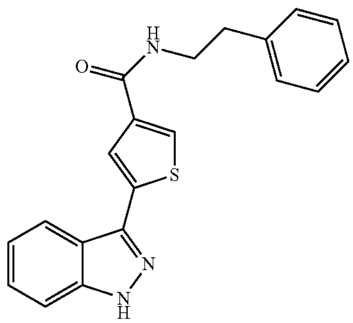 [SMILES: O=C(NCCc1ccccc1)c1csc(-c2n[nH]c3ccccc23)c1] | MS (ESI) m/z: 348 [M + H]+. |
| I-a-27 | 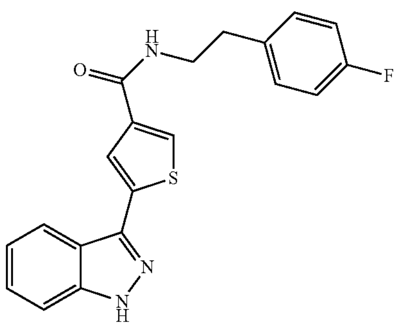 [SMILES: O=C(NCCc1ccc(F)cc1)c1csc(-c2n[nH]c3ccccc23)c1] | MS (ESI) m/z: 366 [M + H]+. |
| I-a-28 | 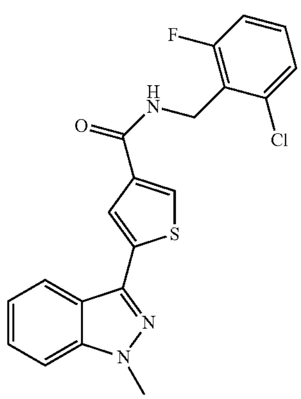 [SMILES: Cn1nc(-c2cc(C(=O)NCc3c(F)cccc3Cl)cs2)c2ccccc21] | $^1$H NMR (600 MHz, DMSO-d$_6$) δ 8.74 (t, J = 4.9 Hz, 1H), 8.19-8.07 (m, 3H), 7.70 (dt, J = 8.5, 0.9 Hz, 1H), 7.48 (ddd, J = 8.3, 6.9, 1.0 Hz, 1H), 7.41 (td, J = 8.2, 6.0 Hz, 1H), 7.36 (dt, J = 8.1, 1.0 Hz, 1H), 7.31-7.23 (m, 2H), 4.61 (d, J = 1.5 Hz, 2H), 4.08 (s, 3H). MS (ESI) m/z 400 [M + H]+. |
| I-a-29 | TFA salt | $^1$H NMR (600 MHz, Methanol-d$_4$) δ 8.12 (d, J = 1.4 Hz, 1H), 7.91 (d, J = 1.4 Hz, 1H), 7.51 (d, J = 8.4 Hz, 1H), 7.39-7.30 (m, 2H), 7.30-7.27 (m, 1H), 7.19 (d, J = 7.3 Hz, 1H), 7.12 (ddd, J = 9.5, 8.2, 1.3 Hz, 1H), 4.73 (d, J = 1.6 Hz, 2H). MS (ESI) m/z: 421 [M + H]+. |

TABLE 1-continued

Structure and characterization of compounds I

| No. | Structure | 1H NMR and/or MS data |
|---|---|---|
| I-a-30 | TFA salt | ¹H NMR (600 MHz, DMSO-d₆) δ 12.85 (s, 1H), 8.71 (t, J = 5.0 Hz, 1H), 8.11 (d, J = 1.3 Hz, 1H), 8.03 (d, J = 1.3 Hz, 1H), 7.91 (d, J = 8.6 Hz, 1H), 7.44-7.38 (m, 1H), 7.37-7.34 (m, 1H), 7.30-7.19 (m, 1H), 6.91 (s, 1H), 6.83 (dd, J = 8.7, 1.9 Hz, 1H), 4.61 (dd, J = 4.9, 1.4 Hz, 2H). MS (ESI) m/z: 401 [M + H]⁺. |
| I-b-1 | TFA salt | ¹H NMR (600 MHz, DMSO-d₆) δ 11.72 (s, 1H), 8.12 (t, J = 5.0 Hz, 1H), 8.01 (d, J = 8.2 Hz, 1H), 7.53 (d, J = 8.4 Hz, 1H), 7.42-7.31 (m, 4H), 7.27-7.15 (m, 3H), 4.56 (d, J = 4.8 Hz, 2H). MS (ESI) m/z: 369 [M + H]⁺. |
| I-b-2 | TFA salt | ¹H NMR (600 MHz, DMSO-d₆) δ 11.92 (s, 1H), 9.62 (s, 1H), 8.11 (d, J = 8.2 Hz, 1H), 7.82-7.72 (m, 2H), 7.62-7.53 (m, 2H), 7.42 (ddd, J = 8.1, 6.7, 1.0 Hz, 1H), 7.39-7.29 (m, 4H), 7.23 (ddd, J = 7.9, 6.8, 0.9 Hz, 1H), 7.09-7.00 (m, 1H). MS (ESI) m/z: 303 [M + H]⁺. |

TABLE 1-continued

Structure and characterization of compounds I

| No. | Structure | 1H NMR and/or MS data |
|---|---|---|
| I-c-1 | (TFA salt) | $^1$H NMR (600 MHz, Methanol-$d_4$) δ 8.64 (s, 1H), 8.22 (s, 1H), 8.09 (d, J = 8.3 Hz, 1H), 7.60-7.54 (m, 1H), 7.46 (ddd, J = 8.3, 6.9, 1.0 Hz, 1H), 7.39-7.33 (m, 3H), 7.33-7.29 (m, 1H), 7.26 (ddd, J = 8.0, 6.8, 0.9 Hz, 1H), 7.15 (ddd, J = 9.5, 8.2, 1.2 Hz, 1H), 4.76 (d, J = 1.5 Hz, 2H). MS (ESI) m/z: 370 [M + H]$^+$. |
| I-c-2 | (TFA salt) | $^1$H NMR (600 MHz, Methanol-$d_4$) δ 8.38 (s, 1H), 8.15 (dt, J = 8.2, 1.0 Hz, 1H), 7.76-7.69 (m, 2H), 7.60 (dt, J = 8.3, 0.9 Hz, 1H), 7.53-7.44 (m, 2H), 7.39 (dd, J = 8.5, 7.3 Hz, 2H), 7.30 (ddd, J = 8.0, 6.8, 0.9 Hz, 1H), 7.21-7.11 (m, 1H). MS (ESI) m/z: 304 [M + H]$^+$. |
| I-d-1 | 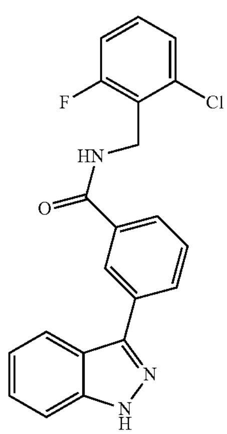 [SMILES: O=C(NCc1c(F)cccc1Cl)c1cccc(-c2n[nH]c3ccccc23)c1] | $^1$H NMR (600 MHz, Methanol-$d_4$) δ 8.40 (d, J = 1.9 Hz, 1H), 8.12 (dt, J = 7.8, 1.5 Hz, 1H), 8.08 (d, J = 8.2 Hz, 1H), 7.85 (dt, J = 7.8, 1.5 Hz, 1H), 7.68-7.55 (m, 2H), 7.45 (ddd, J = 8.3, 6.8, 0.9 Hz, 1H), 7.35 (td, J = 8.2, 5.8 Hz, 1H), 7.31 (d, J = 8.0 Hz, 1H), 7.25 (dd, J = 8.1, 6.9 Hz, 1H), 7.14 (td, J = 8.7, 8.0, 1.3 Hz, 1H), 4.80 (d, J = 1.5 Hz, 2H). MS (ESI) m/z: 380 [M + H]$^+$. |

TABLE 1-continued

Structure and characterization of compounds I

| No. | Structure | 1H NMR and/or MS data |
|---|---|---|
| I-d-2 | 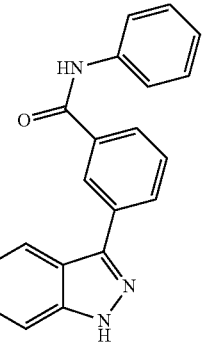 | ¹H NMR (600 MHz, Methanol-d₄) δ 8.54 (t, J = 1.8 Hz, 1H), 8.20 (dt, J = 7.7, 1.3 Hz, 1H), 8.13 (dd, J = 8.2, 1.0 Hz, 1H), 7.99 (ddd, J = 7.8, 1.9, 1.1 Hz, 1H), 7.78-7.73 (m, 2H), 7.69 (t, J = 7.7 Hz, 1H), 7.61 (dt, J = 8.4, 1.0 Hz, 1H), 7.49-7.44 (m, 1H), 7.42-7.38 (m, 2H), 7.28 (ddd, J = 8.0, 6.8, 0.9 Hz, 1H), 7.18 (tt, J = 7.5, 1.1 Hz, 1H). MS (ESI) m/z: 316 [M + H]⁺. |
| I-e-1 | 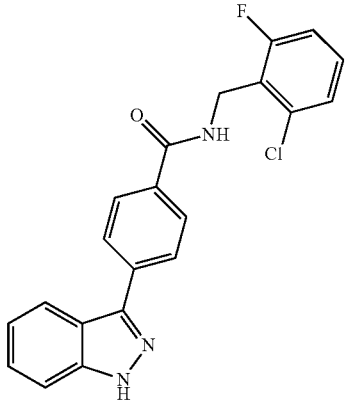<br>TFA salt | ¹H NMR (600 MHz, Methanol-d₄) δ 8.10-8.04 (m, 3H), 8.01-7.93 (m, 2H), 7.60 (dt, J = 8.4, 0.9 Hz, 1H), 7.45 (ddd, J = 8.5, 6.8, 1.0 Hz, 1H), 7.36 (td, J = 8.2, 5.8 Hz, 1H), 7.32 (dt, J = 8.2, 1.1 Hz, 1H), 7.27 (ddd, J = 7.9, 6.9, 0.9 Hz, 1H), 7.15 (ddd, J = 9.5, 8.2, 1.3 Hz, 1H), 4.80 (d, J= 1.5 Hz, 2H). MS (ESI) m/z: 380 [M + H]⁺. |
| I-e-2 | 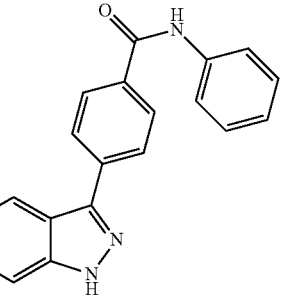<br>TFA salt | ¹H NMR (600 MHz, Methanol-d₄) δ 8.17-8.03 (m, 5H), 7.77-7.69 (m, 2H), 7.61 (dt, J = 8.4, 0.9 Hz, 1H), 7.48-7.44 (m, 1H), 7.42-7.35 (m, 2H), 7.27 (ddd, J = 7.9, 6.8, 0.9 Hz, 1H), 7.18 (tt, J = 7.5, 1.1 Hz, 1H). MS (ESI) m/z: 314 [M + H]⁺. |
| I-f-1 | 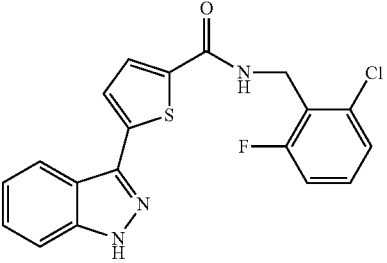 [SMILES: O=C(NCc1c(F)cccc1Cl)c1ccc(-c2n[nH]c3ccccc23)s1] | ¹H NMR (600 MHz, DMSO-d₆) δ 8.84 (t, J = 4.9 Hz, 1H), 8.12 (d, J = 8.2 Hz, 1H), 7.85 (d, J = 3.9 Hz, 1H), 7.74 (d, J = 4.0 Hz, 1H), 7.60 (d, J = 8.4 Hz, 1H), 7.46-7.38 (m, 2H), 7.36 (d, J = 8.0 Hz, 1H), 7.29-7.22 (m, 2H), 4.59 (dd, J = 4.9, 1.4 Hz, 2H). MS (ESI) m/z: 386 [M + H]⁺. |

TABLE 1-continued

Structure and characterization of compounds I

| No. | Structure | 1H NMR and/or MS data |
|---|---|---|
| I-f-2 | 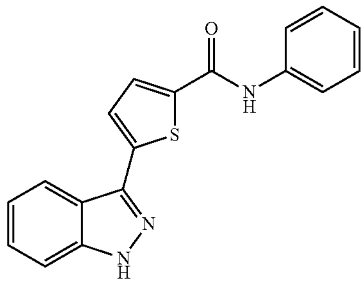 [SMILES: O=C(Nc1ccccc1)c1ccc(-c2n[nH]c3ccccc23)s1] | $^1$H NMR (600 MHz, DMSO-d$_6$) δ 10.27 (s, 1H), 8.17 (d, J = 8.1 Hz, 1H), 8.11 (d, J = 3.9 Hz, 1H), 7.86 (d, J = 4.0 Hz, 1H), 7.76 (d, J = 8.0 Hz, 2H), 7.62 (d, J = 8.4 Hz, 1H), 7.45 (t, J = 7.6 Hz, 1H), 7.37 (t, J = 7.7 Hz, 2H), 7.28 (t, J = 7.5 Hz, 1H), 7.12 (t, J = 7.4 Hz, 1H). MS (ESI) m/z: 320 [M + H]$^+$. |
| I-f-3 | 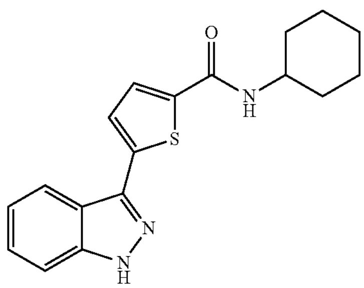 [SMILES: O=C(NC1CCCCC1)c1ccc(-c2n[nH]c3ccccc23)s1] | $^1$H NMR (600 MHz, DMSO-d$_6$) δ 8.28 (d, J = 8.0 Hz, 1H), 8.13 (d, J = 8.3 Hz, 1H), 7.87 (d, J = 3.8 Hz, 1H), 7.76 (d, J = 3.9 Hz, 1H), 7.61 (d, J = 8.4 Hz, 1H), 7.44 (ddd, J = 8.1, 6.8, 0.9 Hz, 1H), 7.26 (ddd, J = 7.9, 6.8, 0.8 Hz, 1H), 3.84-3.65 (m, 1H), 1.85 (dt, J = 7.3, 3.6 Hz, 2H), 1.78-1.64 (m, 2H), 1.66-1.55 (m, 1H), 1.32 (ddt, J = 14.3, 12.0, 7.9 Hz, 4H), 1.23-1.00 (m, 1H). MS (ESI) m/z: 326 [M + H]$^+$. |
| I-g-1 | TFA salt | $^1$H NMR (600 MHz, DMSO-d$_6$) δ 11.58 (t, J = 2.6 Hz, 1H), 8.44 (t, J = 4.8 Hz, 1H), 8.01 (d, J = 8.2 Hz, 1H), 7.56 (dd, J = 8.4, 0.9 Hz, 1H), 7.45-7.34 (m, 3H), 7.27 (dd, J = 9.6, 8.1, 1.3 Hz, 1H), 7.19 (ddd, J = 7.9, 6.8, 0.9 Hz, 1H), 6.90 (dd, J = 3.7, 2.5 Hz, 1H), 6.78 (dd, J = 3.8, 2.3 Hz, 1H), 4.59 (d, J = 4.9 Hz, 2H). MS (ESI) m/z: 369 [M + H]$^+$ |

The compounds of formula

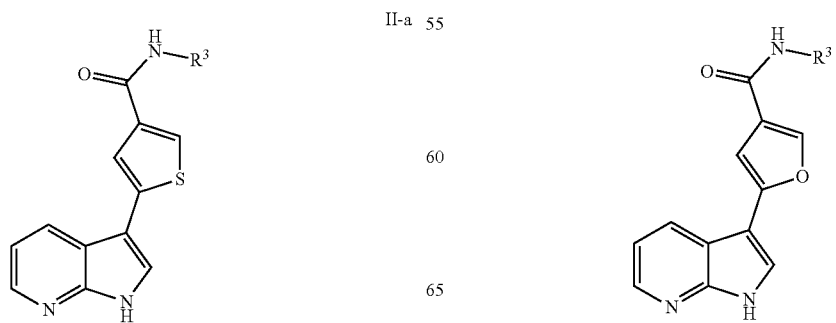

-continued

II-c

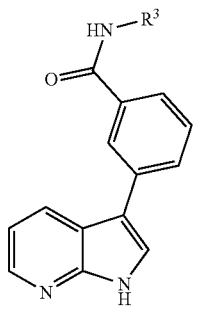

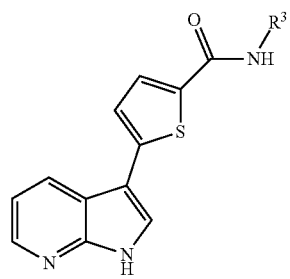

Compound II was synthesized by a method similar to that for the synthesis of compound I.

The synthesis of the compounds of examples is described in detail below.

Using compound

II-d

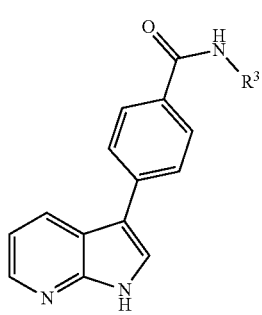

(CAS: 74420-15-8, PharmaBlock, Nanjing), the above-mentioned boric acid or borate and the corresponding $R^3$—$NH^2$ as raw materials, compounds II-a-1~II-e-2 were obtained with a reference to the preparation method of compound I-a-1 or I-a-28.

The table below lists the specific compounds and structure identification data.

TABLE 2

Structure and characterization of compounds II

| No. | Structure | $^1$H NMR and/or MS data |
|---|---|---|
| II-a-1 | 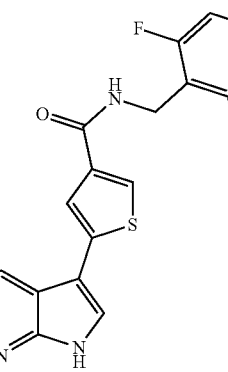<br>TFA Salt | $^1$H NMR (600 MHz, Methanol-$d_4$) δ 8.58 (dd, J = 8.0, 1.4 Hz, 1H), 8.36 (d, J = 5.1 Hz, 1H), 8.00 (d, J = 1.4 Hz, 1H), 7.81 (s, 1H), 7.75 (d, J = 1.4 Hz, 1H), 7.39-7.35 (m, 2H), 7.33-7.30 (m, 1H), 7.15 (ddd, J = 9.5, 8.2, 1.3 Hz, 1H), 4.77 (d, J = 1.6 Hz, 2H). MS (ESI) m/z: 386[M + H]$^+$. |
| II-a-2 | 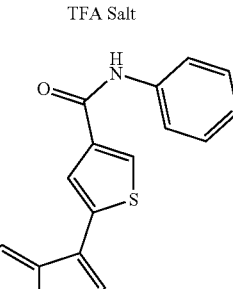<br>TFA Salt | $^1$H NMR (600 MHz, DMSO-$d_6$) δ 12.08 (s, 1H), 10.08 (s, 1H), 8.36 (d, J = 7.9 Hz, 1H), 8.33 (d, J = 4.5 Hz, 1H), 8.21 (d, J = 1.4 Hz, 1H), 7.97 (d, J = 2.5 Hz, 1H), 7.88 (d, J = 1.3 Hz, 1H), 7.78 (d, J = 8.1 Hz, 2H), 7.38 (t, J = 7.7 Hz, 2H), 7.24 (dd, J = 8.0, 4.7 Hz, 1H), 7.12 (t, J = 7.4 Hz, 1H). MS (ESI) m/z: 320[M + H]$^+$. |

TABLE 2-continued

Structure and characterization of compounds II

| No. | Structure | ¹H NMR and/or MS data |
| --- | --- | --- |
| II-a-3 | 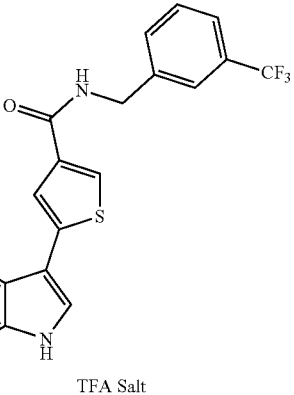 TFA Salt | ¹H NMR (600 MHz, DMSO-$d_6$) δ 12.33-11.88 (m, 1H), 9.02 (t, J = 6.0 Hz, 1H), 8.35-8.28 (m, 2H), 8.04 (d, J = 1.4 Hz, 1H), 7.91 (d, J = 2.4 Hz, 1H), 7.79 (d, J = 1.4 Hz, 1H), 7.69 (d, J = 2.1 Hz, 1H), 7.68-7.57 (m, 3H), 7.21 (dd, J = 7.7, 4.8 Hz, 1H), 4.58 (d, J = 5.9 Hz, 2H). MS (ESI) m/z: 402[M + H]⁺. |
| II-b-1 | 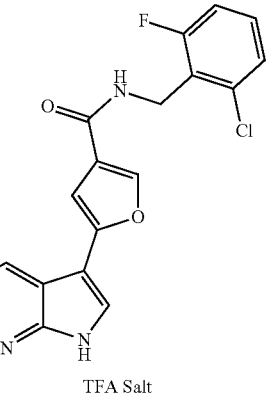 TFA Salt | ¹H NMR (600 MHz, Methanol-$d_4$) δ 8.75-8.69 (m, 1H), 8.42 (dd, J = 5.4, 1.4 Hz, 1H), 8.13 (d, J = 0.8 Hz, 1H), 7.94 (s, 1H), 7.50 (dd, J = 7.9, 5.5 Hz, 1H), 7.37 (td, J = 8.2, 5.9 Hz, 1H), 7.32 (dt, J = 8.2, 1.1 Hz, 1H), 7.16 (ddd, J = 9.5, 8.2, 1.2 Hz, 1H), 7.11 (d, J = 0.9 Hz, 1H), 4.75 (d, J = 1.5 Hz, 2H). MS (ESI) m/z: 370[M + H]⁺. |
| II-b-2 | 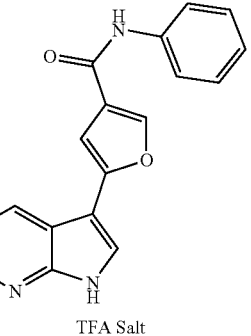 TFA Salt | ¹H NMR (600 MHz, Methanol-$d_4$) δ 8.74 (dd, J = 8.0, 1.4 Hz, 1H), 8.43 (dd, J = 5.3, 1.4 Hz, 1H), 8.29 (s, 1H), 7.97 (s, 1H), 7.76-7.65 (m, 2H), 7.50 (dd, J = 8.0, 5.3 Hz, 1H), 7.44-7.33 (m, 2H), 7.24 (s, 1H), 7.18 (tt, J = 7.4, 1.2 Hz, 1H). MS (ESI) m/z: 304[M + H]⁺. |

TABLE 2-continued

Structure and characterization of compounds II

| No. | Structure | ¹H NMR and/or MS data |
|---|---|---|
| II-c-1 | (structure: N-(2-chloro-6-fluorobenzyl)-3-(1H-pyrrolo[2,3-b]pyridin-3-yl)benzamide, TFA Salt) | ¹H NMR (600 MHz, Methanol-$d_4$) δ 8.41 (dd, J = 7.9, 1.4 Hz, 1H), 8.28 (d, J = 4.7 Hz, 1H), 8.14 (d, J = 1.9 Hz, 1H), 7.87 (d, J = 7.9 Hz, 1H), 7.75 (s, 1H), 7.72 (d, J = 7.8 Hz, 1H), 7.54 (t, J = 7.7 Hz, 1H), 7.35 (dd, J = 8.2, 5.8 Hz, 1H), 7.32 (s, 1H), 7.23 (dd, J = 8.0, 4.7 Hz, 1H), 7.19-7.11 (m, 1H), 4.80 (s, J = 1.5 Hz, 2H). MS(ESI) m/z: 380[M + H]⁺. |
| II-c-2 | (structure: N-phenyl-3-(1H-pyrazolo[3,4-b]pyridin-3-yl)benzamide, TFA Salt) | ¹¹H NMR (600 MHz, DMSO-$d_6$) δ 7.92 (s, 1H), 7.52-7.46 (m, 2H), 7.13 (s, 4H), 6.92-6.81 (m, 2H), 6.61-6.58 (m, 4H), 6.38 (s, 1H). MS (ESI) m/z: 314 [M + H]⁺. |
| II-d-1 | (structure: N-(2-chloro-6-fluorobenzyl)-4-(1H-pyrazolo[3,4-b]pyridin-3-yl)benzamide, TFA Salt) | ¹H NMR (600 MHz, Methanol-$d_4$) δ 8.61 (dd, J = 8.0, 1.3 Hz, 1H), 8.37 (s, 1H), 7.95-7.91 (m, 2H), 7.90 (s, 1H), 7.84-7.76 (m, 2H), 7.43-7.34 (m, 2H), 7.32 (dt, J = 8.1, 1.1 Hz, 1H), 7.15 (ddd, J = 9.6, 8.2, 1.3 Hz, 1H), 4.79 ((d, J = 1.5 Hz, 2H). MS (ESI) m/z: 380 [M + H]⁺. |

TABLE 2-continued

Structure and characterization of compounds II

| No. | Structure | $^1$H NMR and/or MS data |
| --- | --- | --- |
| II-d-2 | 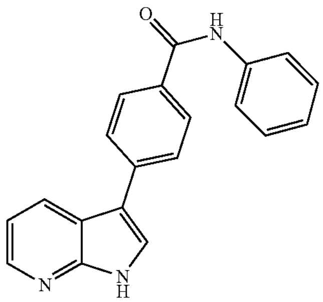 [SMILES: O=C(Nc1ccccc1)c1ccc(-c2c[nH]c3ncccc23)cc1] | $^1$H NMR (600 MHz, DMSO-$d_6$) δ 12.09 (s, 1H), 10.23 (s, 1H), 8.39 (dd, J = 8.2, 1.4 Hz, 1H), 8.31 (dd, J = 4.6, 1.5 Hz, 1H), 8.08 (d, J = 2.7 Hz, 1H), 8.07-8.04 (m, 2H), 7.93-7.87 (m, 2H), 7.84-7.78 (m, 2H), 7.41-7.32 (m, 2H), 7.21 (dd, J = 7.9, 4.6 Hz, 1H), 7.14-7.06 (m, 1H). MS (ESI) m/z: 314[M + H]$^+$. |
| II-e-1 | 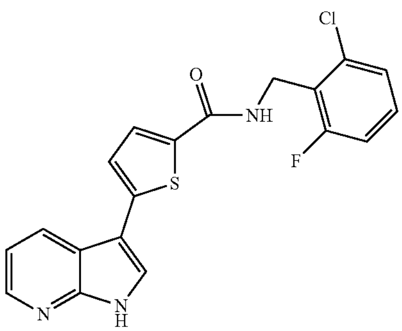 [SMILES: O=C(NCc1c(F)cccc1Cl)c1ccc(-c2c[nH]c3ncccc23)s1] | $^1$H NMR (600 MHz, DMSO-$d_6$) δ 12.15-11.90 (m, 1H), 8.71 (t, J = 5.0 Hz, 1H), 8.37-8.22 (m, 2H), 8.00 (d, J = 2.7 Hz, 1H), 7.79 (d, J = 3.9 Hz, 1H), 7.45-7.38 (m, 2H), 7.36 (dt, J = 8.2, 1.0 Hz, 1H), 7.26 (ddd, J = 9.6, 8.2, 1.3 Hz, 1H), 7.21 (dd, J = 8.0, 4.7 Hz, 1H), 4.59 (dd, J = 4.9, 1.5 Hz, 2H). MS (ESI) m/z: 386[M + H]$^+$. |
| II-e-2 | 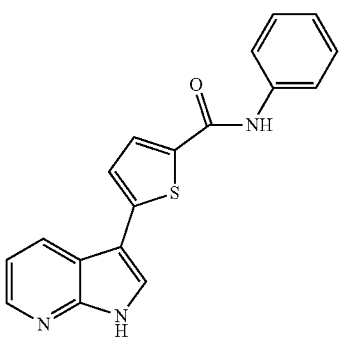 [SMILES: O=C(Nc1ccccc1)c1ccc(-c2c[nH]c3ncccc23)s1] | $^1$H NMR (600 MHz, DMSO-$d_6$) δ 12.17 (d, J = 2.5 Hz, 1H), 10.18 (s, 1H), 8.41-8.27 (m, 2H), 8.06 (dd, J = 13.2, 3.3 Hz, 2H), 7.80-7.70 (m, 2H), 7.52 (d, J = 4.0 Hz, 1H), 7.37 (dd, J = 8.5, 7.3 Hz, 2H), 7.24 (dd, J = 7.9, 4.6 Hz, 1H), 7.16-7.00 (m, 1H). MS (ESI) m/z: 320[M + H]$^+$. |

The compounds of formula III:

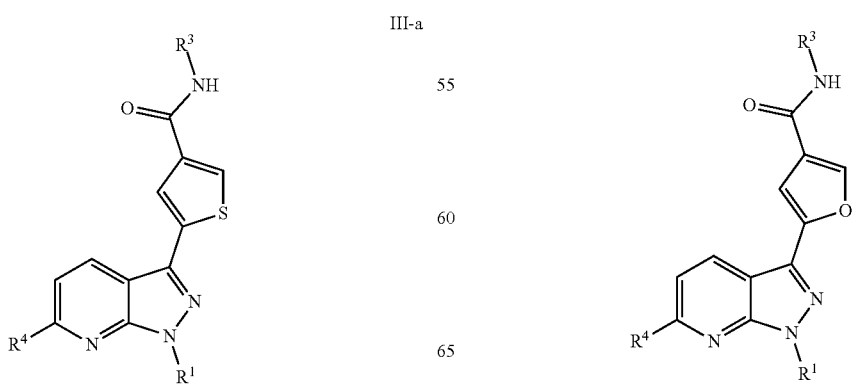

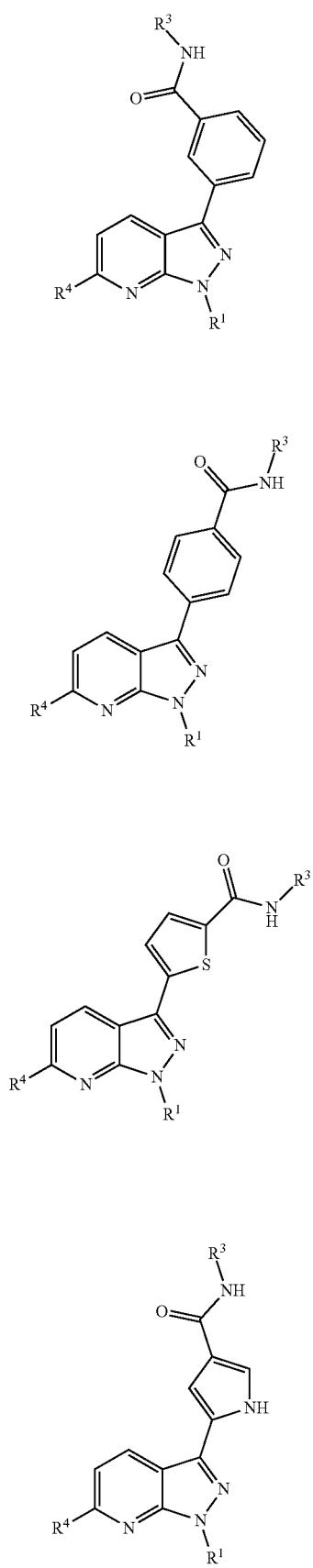
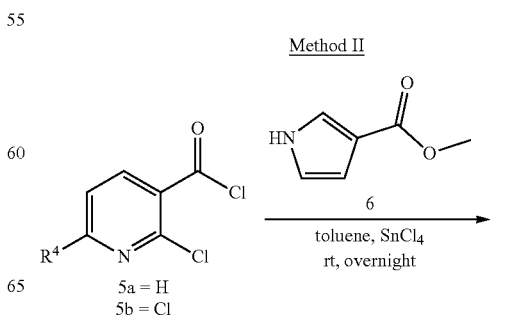
wherein,
Compounds III-a, III-b, III-c, III-d, III-e, III-i were synthesized by a method similar to that for the synthesis of compound I.
Synthetic Scheme of Compound III-f:
Method I: Similar to that of Compound I.
Method II

115

-continued

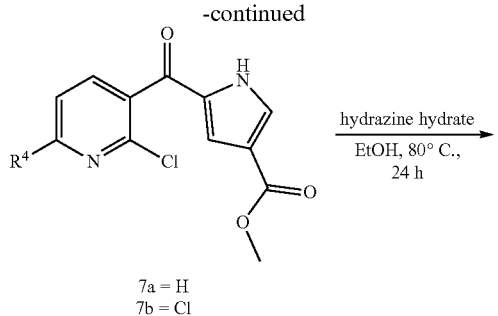

7a = H
7b = Cl

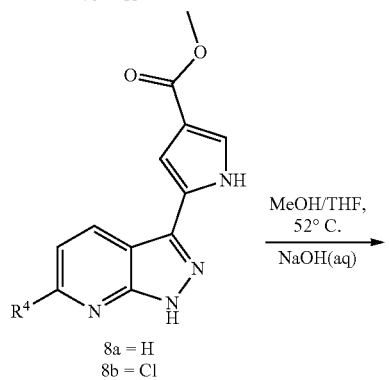

8a = H
8b = Cl

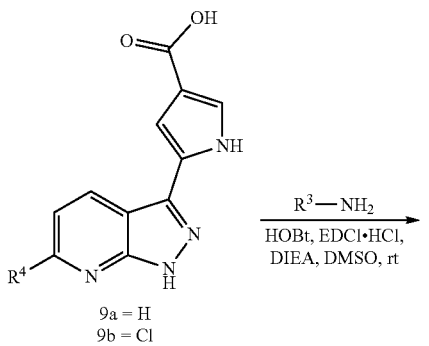

9a = H
9b = Cl

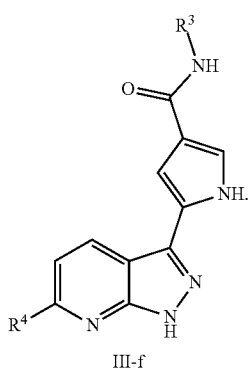

III-f

Preparation of Compound 7

A solution of compound 5 (20 mmol) in toluene (30 mL) was slowly added dropwise at 0° C. to a mixed solution of compound 6 (30 mmol) and tin tetrachloride (20 mmol) in toluene (20 mL), and the mixture was allowed to react for 1 h after returning to room temperature. The reaction system was extracted with water/ethyl acetate three times, then the organic phase was washed with saturated sodium chloride solution, dried with anhydrous sodium sulfate, concentrated, and separated by silica gel column chromatography (ethyl acetate/petroleum ether) to obtain compound 7.

Preparation of Compound 8

Compound 7 (8 mmol) was dissolved in ethanol (25 mL), to which was added hydrazine hydrate (7.76 mL). The system was allowed to react at 80° C. for 24 h. The organic solvent was removed under reduced pressure, water was added to precipitate out a solid, then the solid was washed with water, and dried to obtain compound 8.

Preparation of Compound 9

Compound 8 (6 mmol) was dissolved in MeOH (6 mL)/THF (6 mL), to which was added 6 mL of 1N NaOH aqueous solution, followed by heating to 52V, and stirring overnight. The organic solvent was removed under reduced pressure, the reaction system was adjusted with dilute hydrochloric acid to pH=6, to precipitate out a solid, then the solid was washed with water, and dried to obtain compound 9.

Preparation of Compound III-f

The preparation method was the same as that of compound I-a.

Synthetic Scheme of Compound III-g:

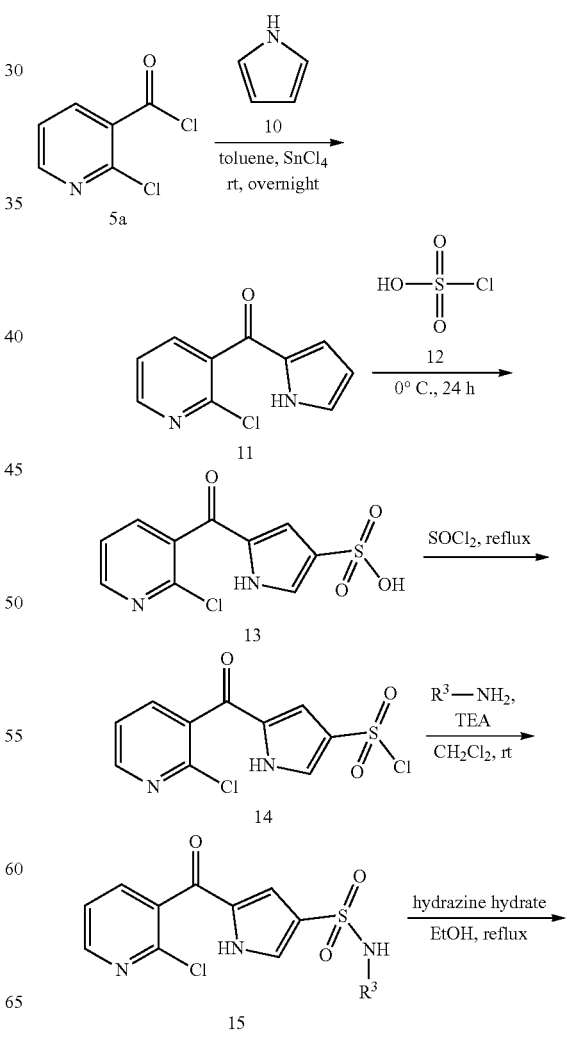

117
-continued

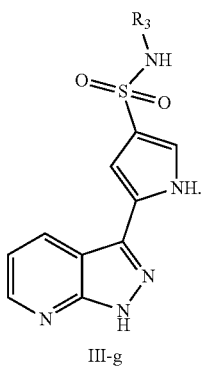

III-g

Preparation of Compound 11

The preparation method was the same as that of compound 7.

Preparation of Compound 13

Compound 12 (6.6 mL, 100 mmol) was slowly added dropwise at 0° C. to compound 11 (2.06 g, 10 mmol), and the mixture was allowed to react at 0° C. for 24 h. The reaction system was poured into ice water, to precipitate out a solid, then the solid was washed with water, and dried to obtain compound 13. (brown solid, 2.67 g, 93.4%), MS (ESI) m/z 287 [M+H]+.

Preparation of Compound 14

Thionyl chloride (0.871 mL, 12 mmol) was slowly added dropwise at 0° C. to compound 13 (2.29 g, 8 mmol), followed by returning to room temperature. After refluxing for 30 min, unreacted thionyl chloride was removed under reduced pressure to obtain compound 14 (white solid, 1.95 g, 79.8%). MS (ESI) m/z 306 [M+H]+.

Preparation of Compound 15

Arylamine (0.35 mmol), triethylamine (1.4 mmol) were dissolved in dichloromethane (1.5 mL), and a solution of compound 14 (035 mmol) in dichloromethane (1.5 mL) was slowly added dropwise to the mixed solution at 0° C. The mixture was allowed to react for 4 h after returning to room temperature, and extracted with water/dichloromethane three times, then the organic phase was washed with saturated sodium chloride solution, dried with anhydrous sodium sulfate, concentrated, and separated by silica gel column chromatography (ammonia in methanol/dichloromethane) to obtain compound 15.

Preparation of Compound III-g

Compound 15 (0.12 mmol) was dissolved in ethanol (2.5 mL), to which was added hydrazine hydrate (0.073 mL), followed by reacting at 80° C. for 24 h. The reaction system was concentrated, purified by reverse phase preparative HPLC (using 0.035% trifluoroacetic acid-containing aqueous solution and methanol as mobile phase), and vacuum concentrated to obtain compound III-g.

118
Synthetic Scheme of Compound III-h:

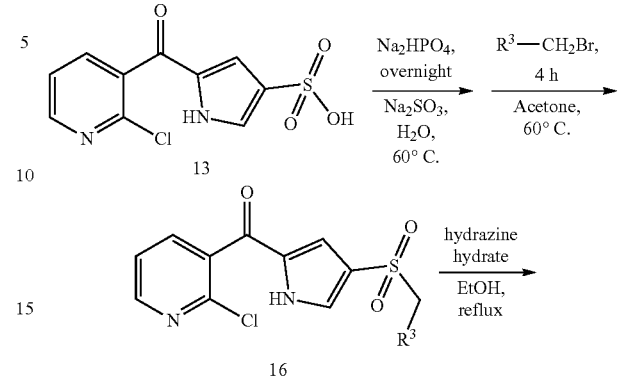

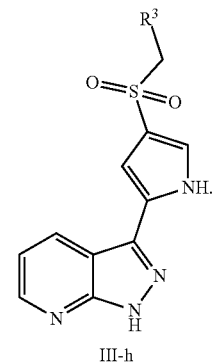

III-h

Preparation of Compound 16

Compound 13 (0.2 mmol), $Na_2SO_3$ (0.4 mmol), $NaHPO_4$ (0.2 mmol) were mixed in 1 mL of water. The mixture was heated to react at 60° C. for 16 h, during which the reaction system changed from turbid to clear and then became turbid. A solution of arylbenzyl bromide (0.15 mmol) in acetone (1 mL) was slowly added dropwise to the above system, followed by reacting at 60° C. for 4 h. The reaction system was cooled to room temperature, then the organic solvent was removed under reduced pressure, and the precipitate was washed with a mixture of methanol and water. The precipitate was collected, and dried to obtain compound 16.

Preparation of Compound III-h

The preparation method was the same as that of compound III-g.

The synthesis of the compounds of examples is described in detail below.
1. Using compound

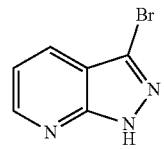

(CAS: 68618-36-0, PharmaBlock, Nanjing), the above-mentioned boric acid or borate and the corresponding $R^3$—$NH^2$ as raw materials, compounds III-a-1~III-e-2 were obtained with a reference to the preparation method of compound I-a-1 or I-a-28.

2. Compound III-f-1:
Synthesis of Intermediate:

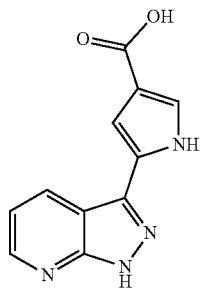 [SMILES: O=C(O)c1c[nH]c(-c2n[nH]c3ncccc23)c1]

A solution of compound 2-chloronicotinyl chloride (20 mmol, 3.52 g) (CAS: 49609-84-9, PharmaBlock, Nanjing) in toluene (30 mL), at 0° C., was slowly added dropwise to a mixed solution of compound methyl 1H-pyrrole-3-carboxylate (30 mmol, 3.75 g) (CAS: 2703-17-5, PharmaBlock, Nanjing) and tin tetrachloride (20 mmol, 2.34 mL) (CAS: 7646-78-8, Bide, Shanghai) in toluene (20 mL), and the mixture was allowed to react for 1 h after returning to room temperature. The reaction system was extracted with water/ethyl acetate three times, then the organic phase was washed with saturated sodium chloride solution, dried with anhydrous sodium sulfate, concentrated, and separated by silica gel column chromatography (ethyl acetate/petroleum ether) to obtain 2.11 g of methyl 5-(2-chloronicotinyl)-1H-pyrrole-3-carboxylate.

Methyl 5-(2-chloronicotinyl)-1H-pyrrole-3-carboxylate (7.97 mmol, 2.11 g) was dissolved in ethanol (25 mL), to which was added hydrazine hydrate (7.76 mL). The mixture was allowed to react at 80° C. for 24 h. The organic solvent was removed under reduced pressure, water was added to precipitate out a solid, then the solid was washed with water, and dried to obtain 1.8 g of methyl 5-(1H-pyrazolo[3,4-b]pyrid-3-yl)-1H-pyrrole-3-carboxylate.

Methyl 5-(1H-pyrazolo[3,4-b]pyrid-3-yl)-1H-pyrrole-3-carboxylate (6 mmol, 1.45 g) was dissolved in MeOH (6 mL)/THF (6 mL), to which was added 6 mL of 1N NaOH aqueous solution, followed by heating to 52° C., and stirring overnight. The organic solvent was removed under reduced pressure, the reaction system was adjusted with dilute hydrochloric acid to pH=6, to precipitate out a solid, then the solid was washed with water, and dried to obtain 1.1 g of 5-(1H-pyrazolo[3,4-b]pyrid-3-yl)-1H-pyrrole-3-carboxylic acid.

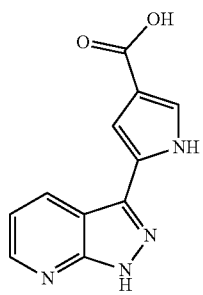 [SMILES: O=C(O)c1c[nH]c(-c2n[nH]c3ncccc23)c1]

(0.14 mmol, 31.9 mg) was dissolved in 1 mL of dimethyl sulfoxide (DMSO), to which were added HOBt (0.35 mmol, 49.43 mg), EDCl.HCl (0.35 mmol, 68.42 mg), DIEA (0.56 mmol, 73.79 mg). After stirring at room temperature for 15 minutes,

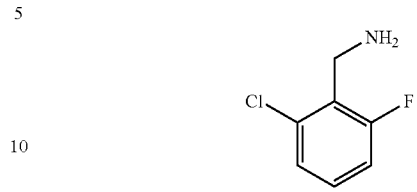

(0.14 mmol, 22.82 mg) was added. The reaction was carried out at room temperature for 5 hours. The reaction system was extracted with water/ethyl acetate (3×15 mL), then the organic phase was washed with saturated sodium chloride solution, dried with anhydrous sodium sulfate, concentrated, purified by reverse phase preparative HPLC (using 0.35% trifluoroacetic acid-containing aqueous solution and methanol as mobile phase), and vacuum concentrated to obtain compound III-f-1 (15.3 mg, 29.6%).

3. Using the intermediate

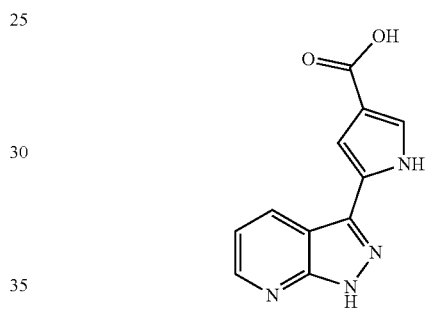

and the corresponding $R^3$—$NH^2$ as raw materials, compounds III-f-2~III-f-62, III-i-1 were obtained with a reference to the preparation method of compound III-f-1.

4. Compound III-g-1:
Synthesis of Intermediate:

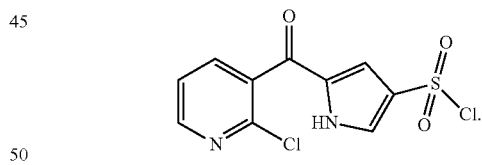

A solution of compound 2-chloronicotinyl chloride (20 mmol, 3.52 g) (CAS: 49609-84-9, PharmaBlock, Nanjing) in toluene (30 mL), at 0° C., was slowly added dropwise to a mixed solution of compound pyrrole (20 mmol, 1.34 g) (CAS: 109-97-7, Macklin) and tin tetrachloride (20 mmol, 2.34 mL) (CAS: 7646-78-8, Bide, Shanghai) in toluene (20 mL), and the mixture was allowed to react for 1 h after returning to room temperature. The reaction system was extracted with water/ethyl acetate three times, then the organic phase was washed with saturated sodium chloride solution, dried with anhydrous sodium sulfate, concentrated, and separated by silica gel column chromatography (ethyl acetate/petroleum ether) to obtain 2.06 g of (2-chloropyrid-3-yl) (1H-pyrrol-2-yl)methanone.

Chlorosulfonic acid (6.6 mL, 100 mmol) (CAS: 7790-94-5, Energy, Shanghai), at 0° C., was slowly added dropwise to (2-chloropyrid-3-yl) (1H-pyrrole-2-yl)methanone (10 mmol, 2.06 g), followed by reacting at 0° C. for 24 h. The reaction system was poured into ice water, to precipitate out a solid, then the solid was washed with water, and dried to obtain 2.67 g of

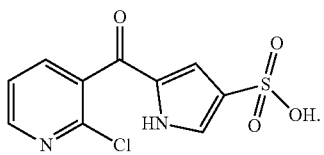 [SMILES: O=C(c1cc(S(=O)(=O)O)c[nH]1)c1cccnc1Cl]

Thionyl chloride (0.871 mL, 12 mmol) (CAS: 7719-09-7, Aladdin), at 0° C., was slowly added dropwise to compound

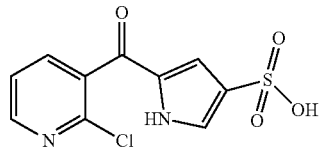 [SMILES: O=C(c1cc(S(=O)(=O)O)c[nH]1)c1cccnc1Cl]

(2.29 g, 8 mmol), followed by returning to room temperature. After refluxing for 30 min, unreacted thionyl chloride was removed under reduced pressure to obtain 1.95 g of

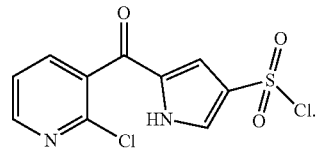 [SMILES: O=C(c1cc(S(=O)(=O)Cl)c[nH]1)c1cccnc1Cl]

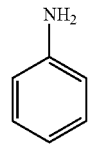

(0.35 mmol, 32.6 mg), triethylamine (1.4 mmol, 141.4 mg) were dissolved in dichloromethane (1.5 mL), at 0° C., to which was slowly added dropwise a solution of

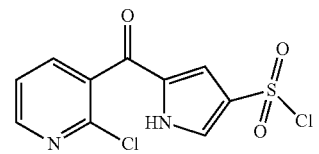 [SMILES: O=C(c1cc(S(=O)(=O)Cl)c[nH]1)c1cccnc1Cl]

(0.35 mmol, 106.8 mg) in dichloromethane (1.5 mL). The mixture was allowed to react for 4 h after returning to room temperature. The system was extracted with water/dichloromethane three times, then the organic phase was washed with saturated sodium chloride solution, dried with anhydrous sodium sulfate, concentrated, and separated by silica gel column chromatography (ammonia in methanol/dichloromethane) to obtain 44.4 mg of 5-(2-chloronicotinyl)-N-phenyl-1H-pyrrole-3-sulfonamide.

The compound, 5-(2-chloronicotinyl)-N-phenyl-1H-pyrrole-3-sulfonamide (0.12 mmol, 43.4 mg) was dissolved in ethanol (2.5 mL), to which was added hydrazine hydrate (0.073 mL), followed by reacting at 80° C. for 24 h. The reaction system was concentrated, purified by reverse phase preparative HPLC (using 0.35% trifluoroacetic acid-containing aqueous solution and methanol as mobile phase), and vacuum concentrated to obtain compound III-g-1 (20.2 mg, 49.6%).

5. Using the intermediate

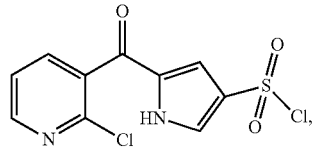 [SMILES: O=C(c1cc(S(=O)(=O)Cl)c[nH]1)c1cccnc1Cl]

the corresponding $R^3$—$NH^2$ and hydrazine hydrate as raw materials, compounds III-g-2~III-g-4 were obtained with a reference to the preparation method of compound III-g-1.

6. Compound III-h-1:

The intermediate

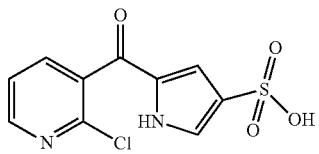 [SMILES: O=C(c1cc(S(=O)(=O)O)c[nH]1)c1cccnc1Cl]

(0.2 mmol, 57.2 mg), $Na_2SO_3$ (0.4 mmol), $NaHPO_4$ (0.2 mmol) were mixed in 1 mL of water. The mixture was allowed to react at 60° C. for 16 h, during which the reaction system changed from turbid to clear and then became turbid. Then, a solution of

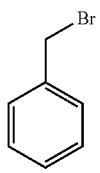

(0.15 mmol, 25.65 mg) (CAS: 100-39-0, Admas) in acetone (1 mL) was slowly added dropwise to the above system, followed by reacting at 60° C. for 4 h. The reaction system was cooled to room temperature, then the organic solvent was removed under reduced pressure, and the precipitate was washed with a mixture of methanol and water. The precipitate was collected, and dried to obtain 30.4 mg of (4-(benzylsulfonyl)-1H-pyrrol-2-yl) (2-chloropyrid-3-yl)methanone.

The compound, (4-(benzylsulfonyl)-1H-pyrrol-2-yl) (2-chloropyrid-3-yl)methanone (0.08 mmol, 30.4 mg) was dissolved in ethanol (2 mL), to which was added hydrazine hydrate (0.073 mL), followed by reacting at 80° C. for 24 h. The reaction system was concentrated, purified by reverse phase preparative HPLC (using 0.35% trifluoroacetic acid-containing aqueous solution and methanol as mobile phase), and vacuum concentrated to obtain compound III-h-1 (25.2 mg, 93%).

7. Using the intermediate

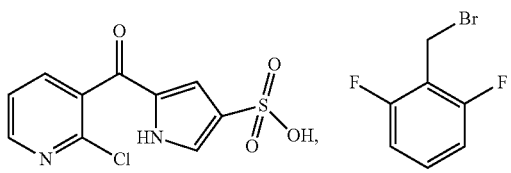 [SMILES: O=C(c1cc(S(=O)(=O)O)c[nH]1)c1cccnc1Cl ; Fc1cccc(F)c1CBr]

(CAS: 85118-00-9, Energy, Shanghai) and hydrazine hydrate as raw materials, compound III-h-2 was obtained with a reference to the preparation method of compound III-h-1.

8. Using the intermediate

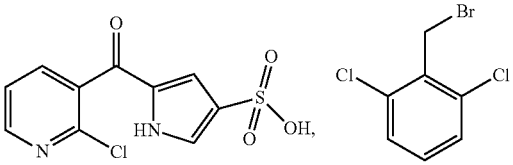 [SMILES: O=C(c1cc(S(=O)(=O)O)c[nH]1)c1cccnc1Cl ; Clc1cccc(Cl)c1CBr]

(CAS: 20443-98-5, Energy, Shanghai) and hydrazine hydrate as raw materials, compound ill-h-3 was obtained with a reference to the preparation method of compound III-h-1.

9. Using the intermediate

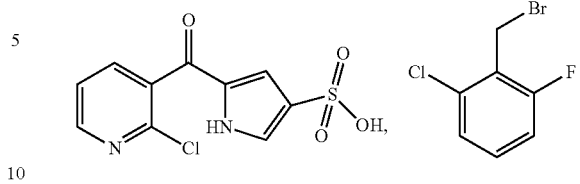

(CAS: 68220-26-8, Energy, Shanghai) and hydrazine hydrate as raw materials, compound III-h-4 was obtained with a reference to the preparation method of compound III-h-1.

10. Using the intermediate

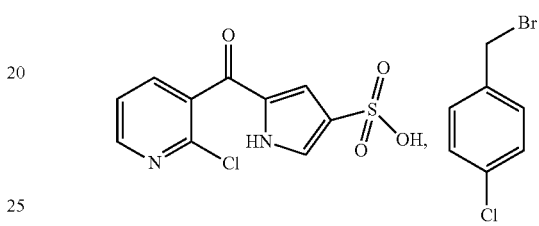

(CAS: 622-95-7, Energy, Shanghai) and hydrazine hydrate as raw materials, compound III-h-5 was obtained with a reference to the preparation method of compound III-h-1.

The table below lists the specific compounds and structure identification data.

TABLE 3

Structure and characterization of compounds III

| No. | Structure | $^1$H NMR and/or MS data |
|---|---|---|
| III-a-1 | 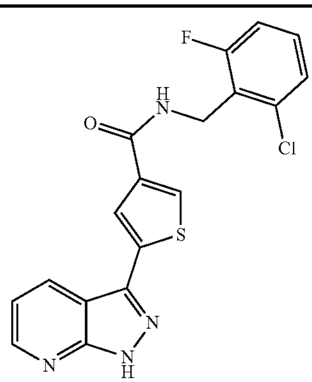 | $^1$H NMR (600 MHz, DMSO-$d_6$) δ 8.71 (t, J = 4.9 Hz, 1H), 8.63-8.56 (m, 2H), 8.17 (dd, J = 15.2, 1.3 Hz, 2H), 7.42 (td, J = 8.1, 5.9 Hz, 1H), 7.38-7.31 (m, 2H), 7.27 (ddd, J = 9.5, 8.2, 1.3 Hz, 1H), 4.63 (d, J = 1.4 Hz, 2H). MS (ESI) m/z: 387[M + H]$^+$. |
| III-a-2 TFA Salt | | $^1$H NMR (600 MHz, DMSO-$d_6$) δ 10.15 (s, 1H), 8.69 (dd, J = 8.2, 1.6 Hz, 1H), 8.63 (dd, J = 4.4, 1.5 Hz, 1H), 8.36 (d, J = 1.4 Hz, 1H), 8.29 (d, J = 1.5 Hz, 1H), 7.85-7.72 (m, 2H), 7.45-7.33 (m, 3H), 7.18-7.05 (m, 1H). MS (ESI) m/z: 321[M + H]$^+$. |

TABLE 3-continued

Structure and characterization of compounds III

| No. | Structure | $^1$H NMR and/or MS data |
|---|---|---|
| III-a-3 | (TFA Salt) | $^1$H NMR (600 MHz, DMSO-$d_6$) δ 9.10 (t, J = 6.0 Hz, 1H), 8.63 (d, J = 8.2 Hz, 1H), 8.61 (d, J = 4.3 Hz, 1H), 8.20 (d, J = 4.9 Hz, 2H), 7.70 (s, 1H), 7.58-7.55 (m, 1H), 7.52-7.43 (m, 2H), 7.34 (dd, J = 8.1, 4.4 Hz, 1H), 4.60 (d, J = 5.9 Hz, 2H). MS (ESI) m/z: 403[M + H]$^+$. |
| III-a-4 | (TFA Salt) | $^1$H NMR (600 MHz, DMSO-$d_6$) δ 9.05 (t, J = 5.8 Hz, 1H), 8.66-8.57 (m, 2H), 8.24-8.13 (m, 2H), 7.79 (dd, J = 6.8, 2.4 Hz, 1H), 7.76-7.71 (m, 1H), 7.47 (t, J = 9.1 Hz, 1H), 7.34 (dd, J = 8.1, 4.5 Hz, 1H), 4.60 (d, J = 5.7 Hz, 2H). MS (ESI) m/z: 421[M + H]$^+$. |
| III-b-1 | (TFA Salt) | $^1$H NMR (600 MHz, DMSO-$d_6$) δ 8.60 (dd, J = 4.5, 1.5 Hz, 1H), 8.55 (t, J = 4.9 Hz, 1H), 8.48 (dd, J = 8.2, 1.5 Hz, 1H), 8.36 (d, J = 0.8 Hz, 1H), 7.49 (d, J = 0.8 Hz, 1H), 7.42 (td, J = 8.2, 6.0 Hz, 1H), 7.37 (dt, J = 8.0, 0.9 Hz, 1H), 7.31 (dd, J = 8.1, 4.5 Hz, 1H), 7.27 (ddd, J = 9.5, 8.2, 1.2 Hz, 1H), 4.60 (d, J = 4.9, 1.5 Hz, 2H). MS (ESI) m/z: 371[M + H]$^+$. |
| III-b-2 | (TFA Salt) | $^1$H NMR (600 MHz, DMSO-$d_6$) δ 10.04 (s, 1H), 8.62 (dd, J = 4.4, 1.5 Hz, 1H), 8.58-8.53 (m, 2H), 7.81-7.74 (m, 2H), 7.63 (d, J = 0.9 Hz, 1H), 7.38 (dd, J = 8.5, 7.4 Hz, 2H), 7.12 (td, J = 7.3, 1.2 Hz, 1H). MS (ESI) m/z: 305[M + H]$^+$. |

TABLE 3-continued

Structure and characterization of compounds III

| No. | Structure | ¹H NMR and/or MS data |
|---|---|---|
| III-c-1 | (structure shown) TFA Salt | ¹H NMR (600 MHz, DMSO-$d_6$) δ 7.87-7.66 (m, 2H), 7.63 (s, 1H), 7.37 (d, J = 7.6 Hz, 1H), 7.07 (d, J = 7.7 Hz, 1H), 6.82 (t, J = 7.7 Hz, 1H), 6.58-6.45 (m, 3H), 6.34 (t, J = 8.8 Hz, 1H), 4.00 (d, J = 1.5 Hz, 2H). MS (ESI) m/z: 381[M + H]⁺. |
| III-c-2 | (structure shown) TFA Salt | ¹H NMR (600 MHz, DMSO-$d_6$) δ 7.86 (d, J = 8.2 Hz, 1H), 7.82-7.72 (m, 2H), 7.44 (d, J = 7.8 Hz, 1H), 7.22 (d, J = 7.8 Hz, 1H), 6.98-6.85 (m, 3H), 6.60 (t, J = 7.9 Hz, 2H), 6.55 (dd, J = 8.3, 4.5 Hz, 1H), 6.38 (t, J = 7.5 Hz, 1H), 3.80 (s, 2H). MS (ESI) m/z: 315[M + H]⁺. |
| III-c-3 | (structure shown) | ¹H NMR (600 MHz, DMSO-$d_6$) δ 10.39 (s, 1H), 8.65 (d, J = 8.0 Hz, 1H), 8.62-8.58 (m, 2H), 8.29 (dd, J = 7.7, 1.6 Hz, 1H), 8.04 (d, J = 7.8 Hz, 1H), 7.72 (t, J = 7.7 Hz, 1H), 7.49-7.42 (m, 2H), 7.40-7.36 (m, 1H), 7.34 (dd, J = 8.2, 4.5 Hz, 1H). MS (ESI) m/z: 367[M + H]⁺. |

TABLE 3-continued

Structure and characterization of compounds III

| No. | Structure | ¹H NMR and/or MS data |
|---|---|---|
| III-d-1 | 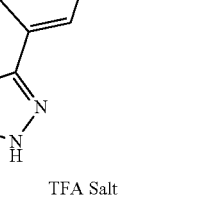 TFA Salt | ¹H NMR (600 MHz, Methanol-d₄) δ 8.65-8.55 (m, 2H), 8.16-8.07 (m, 2H), 8.02-7.94 (m, 2H), 7.40-7.29 (m, 3H), 7.16 (ddd, J = 9.6, 8.2, 1.3 Hz, 1H), 4.80 (d, J = 1.4 Hz, 2H). MS (ESI) m/z: 381[M + H]⁺. |
| III-d-2 | 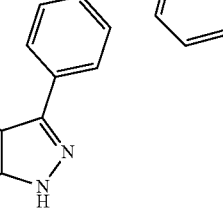 TFA Salt | ¹H NMR (600 MHz, Methanol-d₄) δ 8.63 (dd, J = 8.2, 1.5 Hz, 1H), 8.60 (dd, J = 4.6, 1.5 Hz, 1H), 8.21-8.17 (m, 2H), 8.15-8.11 (m, 2H), 7.78-7.72 (m, 2H), 7.44-7.35 (m, 3H), 7.25-7.12 (m, 1H), 4.61 (s, 2H). MS (ESI) m/z: 315[M + H]⁺. |
| III-d-3 | 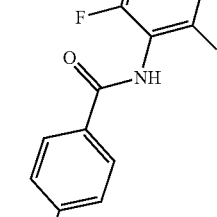 | ¹H NMR (600 MHz, DMSO-d₆) δ 10.28 (s, 1H), 8.68 (dd, J = 8.2, 1.5 Hz, 1H), 8.61 (dd, J = 4.5, 1.5 Hz, 1H), 8.26-8.21 (m, 2H), 8.19-8.13 (m, 2H), 7.48-7.41 (m, 2H), 7.37 (ddd, J = 9.7, 8.2, 1.6 Hz, 1H), 7.33 (dd, J = 8.1, 4.4 Hz, 1H). MS (ESI)m/z: 367[M + H]⁺. |
| III-e-1 | 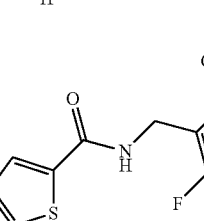 | ¹H NMR (600 MHz, DMSO-d₆) δ 8.87 (t, J = 5.0 Hz, 1H), 8.64-8.58 (m, 2H), 7.87 (d, J = 4.0 Hz, 1H), 7.81 (d, J = 4.0 Hz, 1H), 7.42 (td, J = 8.2, 6.0 Hz, 1H), 7.37 (dt, J = 8.1, 1.0 Hz, 1H), 7.32 (dd, J = 8.1, 4.5 Hz, 1H), 7.27 (ddd, J = 9.6, 8.2, 1.2 Hz, 1H), 4.60 (dd, J = 4.9, 1.5 Hz, 2H). MS (ESI)m/z: 387[M + H]⁺. |

TABLE 3-continued

Structure and characterization of compounds III

| No. | Structure | ¹H NMR and/or MS data |
|---|---|---|
| III-e-2 | 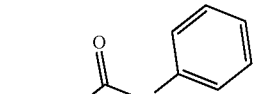 | ¹H NMR (600 MHz, DMSO-d$_6$) δ 10.30 (s, 1H), 8.68 (dd, J = 8.1, 1.5 Hz, 1H), 8.62 (dd, J = 4.5, 1.5 Hz, 1H), 8.12 (d, J = 4.0 Hz, 1H), 7.92 (d, J = 4.0 Hz, 1H), 7.78-7.73 (m, 2H), 7.40-7.36 (m, 2H), 7.40-7.33 (m, 1H), 7.15-7.10 (m, 1H). MS (ESI)m/z: 321[M + H]⁺. |
| III-f-1 | 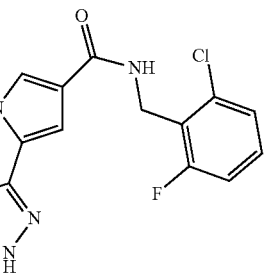<br>TFA salt | ¹H NMR (600 MHz, DMSO-d$_6$) δ 11.84 (t, J = 2.9 Hz, 1H), 8.55 (dd, J = 4.5, 1.6 Hz, 1H), 8.47 (dd, J = 8.1, 1.6 Hz, 1H), 8.10 (t, J = 5.0 Hz, 1H), 7.42 (dd, J = 3.0, 1.6 Hz, 1H), 7.41-7.37 (m, 1H), 7.35 (d, J = 8.0 Hz, 1H), 7.28-7.22 (m, 3H), 4.57 (d, J = 1.5 Hz, 2H). MS (ESI) m/z: 370 [M + H]⁺. |
| III-f-2 | 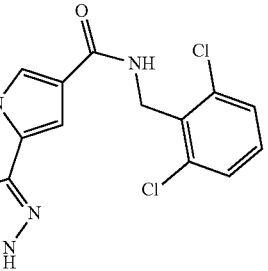<br>TFA salt | ¹H NMR (600 MHz, Methanol-d$_4$) δ 8.58-8.48 (m, 2H), 7.53 (d, J = 1.6 Hz, 2H), 7.44 (d, J = 8.1 Hz, 2H), 7.34-7.28 (m, 2H), 7.28-7.25 (m, 2H), 4.87 (d, J = 1.4 Hz, 2H). MS (ESI) m/z: 387 [M + H]⁺. |
| III-f-3 | 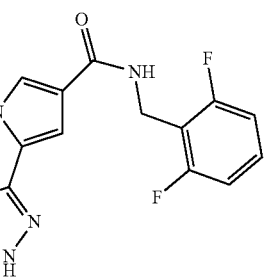<br>TFA salt | ¹H NMR (600 MHz, Methanol-d$_4$) δ 8.53 (s, 1H), 8.54-8.50 (m, 1H), 7.51 (d, J = 1.5 Hz, 1H), 7.39-7.31 (m, 1H), 7.28 (dd, J = 7.9, 4.8 Hz, 1H), 7.24 (d, J = 1.7 Hz, 1H), 7.05 (s, 1H), 6.99 (t, J = 8.0 Hz, 2H), 4.85(d, J = 1.5 Hz, 2H). MS (ESI) m/z: 354 [M + H]⁺. |
| III-f-4 | 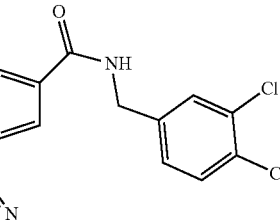<br>TFA salt | ¹H NMR (600 MHz, DMSO-d$_6$) δ 8.60-8.54 (m, 2H), 8.50 (d, J = 8.1 Hz, 1H), 7.61 (d, J = 8.3 Hz, 1H), 7.57 (d, J = 2.0 Hz, 1H), 7.45 (d, J = 1.8 Hz, 1H), 7.33 (dd, J = 8.5, 1.9 Hz, 1H), 7.28 (q, J = 5.1 Hz, 2H), 4.46 (d, J = 5.9 Hz, 2H). MS (ESI) m/z: 387[M + H]+. |

TABLE 3-continued

Structure and characterization of compounds III

| No. | Structure | ¹H NMR and/or MS data |
|---|---|---|
| III-f-5 | 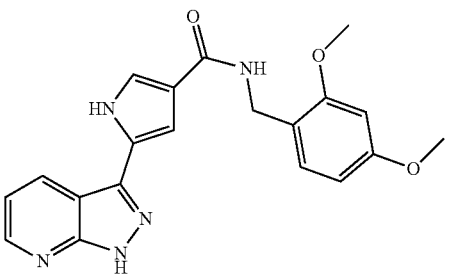<br>TFA salt | ¹H NMR (600 MHz, DMSO-d$_6$) δ 11.88 (s, 1H), 8.58-8.53 (m, 1H), 8.51 (d, J = 8.3 Hz, 1H), 8.19 (d, J = 6.3 Hz, 1H), 7.43 (s, 1H), 7.31 (s, 1H), 7.30-7.23 (m, 1H), 7.13 (d, J = 8.5 Hz, 1H), 6.59-6.53 (m, 1H), 6.49 (d, J = 8.5 Hz, 1H), 4.35 (d, J = 5.7 Hz, 2H), 3.81 (s, 3H), 3.74 (s, 3H). MS (ESI) m/z: 378[M + H]⁺. |
| III-f-6 | 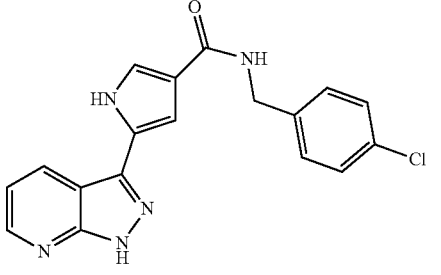 [SMILES: O=C(NCc1cccc(C(F)(F)F)c1)c1c[nH]c(-c2n[nH]c3ncccc23)c1]<br>TFA salt | ¹H NMR (600 MHz, DMSO-d$_6$) δ 11.92 (s, 1H), 8.56 (dd, J = 4.6, 1.5 Hz, 1H), 8.53-8.47 (m, 2H), 7.44 (dd, J = 3.0, 1.6 Hz, 1H), 7.40 (d, J = 8.4 Hz, 2H), 7.35 (d, J = 8.5 Hz, 2H), 7.31-7.25 (m, 2H), 4.45 (d, J = 6.0 Hz, 2H). MS (ESI) m/z: 352[M + H]⁺. |
| III-f-7 | 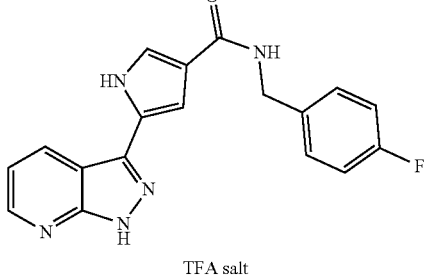<br>TFA salt | ¹H NMR (600 MHz, Methanol-d$_4$) δ 8.61-8.49 (m, 2H), 7.55 (d, J = 1.6 Hz, 1H), 7.41 (dd, J = 8.6, 5.5 Hz, 2H), 7.30 (dd, J = 8.1, 4.6 Hz, 1H), 7.27 (d, J = 1.6 Hz, 1H), 7.08 (t, J = 8.8 Hz, 2H), 4.57 (s, 2H). MS (ESI) m/z: 336[M + H]⁺. |
| III-f-8 | 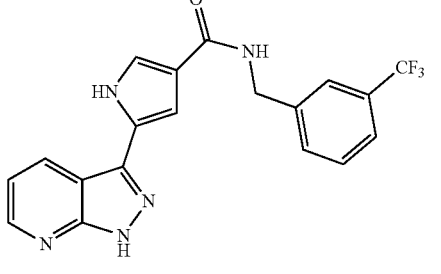 | ¹H NMR (600 MHz, Methanol-d$_4$) δ 8.52(dd, J = 4.6, 1.5 Hz, 1H), 8.48 (dd, J = 8.1, 1.6 Hz, 1H), 7.69 (s, 1H), 7.64 (d, J = 7.6 Hz, 1H), 7.57 (d, J = 1.6 Hz, 1H), 7.54 (dt, J = 15.2, 7.9 Hz, 2H), 7.28-7.26 (m, 1H), 7.26-7.24 (m, 1H), 4.65 (s, 2H). MS (ESI) m/z: 386[M + H]⁺. |
| III-f-9 | 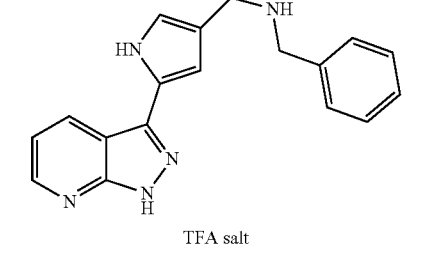<br>TFA salt | ¹H NMR (600 MHz, Methanol-d$_4$) δ 8.56-8.48 (m, 2H), 7.54 (d, J = 1.6 Hz, 1H), 7.37 (d, J = 8.3 Hz, 2H), 7.33 (t, J = 7.6 Hz, 2H), 7.31-7.27 (m, 1H), 7.27-7.22 (m, 2H), 4.58 (s, 2H). MS (ESI) m/z: 318 [M + H]⁺. |

TABLE 3-continued

Structure and characterization of compounds III

| No. | Structure | ¹H NMR and/or MS data |
|---|---|---|
| III-f-10 | 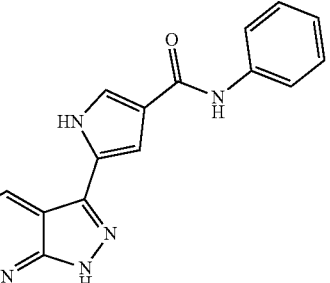<br>TFA salt | ¹H NMR (600 MHz, Methanol-d₄) δ 8.59-8.57 (m, 1H), 8.57-8.53 (m, 1H), 7.71 (d, J = 1.1 Hz, 1H), 7.70 (d, J = 1.1 Hz, 1H), 7.67 (d, J = 1.7 Hz, 1H), 7.41 (d, J = 1.6 Hz, 1H), 7.35 (m, 2H), 7.33-7.29 (m, 1H), 7.12 (tt, J = 7.4, 1.1 Hz, 1H). MS (ESI) m/z: 304[M + H]⁺. |
| III-f-11 | 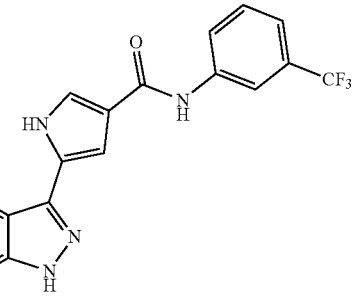<br>TFA salt | ¹H NMR (600 MHz, Methanol-d₄) δ 8.59 (dd, J = 8.1, 1.5 Hz, 1H), 8.58-8.56 (m, 1H), 8.21 (d, J = 2.0 Hz, 1H), 8.01-7.96 (m, 1H), 7.72 (d, J = 1.6 Hz, 1H), 7.56 (t, J = 8.0 Hz, 1H), 7.44 (d, J = 1.7 Hz, 1H), 7.42 (d, J = 7.8 Hz, 1H), 7.34 (dd, J = 8.1, 4.6 Hz, 1H). MS (ESI) m/z: 372 [M + H]⁺. |
| III-f-12 | 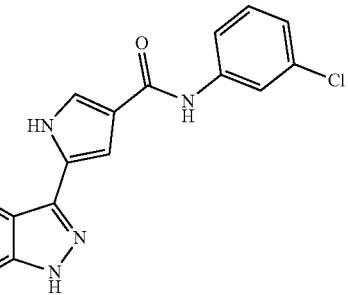<br>TFA salt | ¹H NMR (600 MHz, Methanol-d₄) δ 8.60 (dd, J = 8.1, 1.5 Hz, 1H), 8.57 (dd, J = 4.7, 1.4 Hz, 1H), 7.92 (s, 1H), 7.70 (d, J = 1.7 Hz, 1H), 7.63 (dd, J = 8.2, 2.0 Hz, 1H), 7.42 (d, J = 1.8 Hz, 1H), 7.34 (ddd, J = 8.3, 6.4, 1.9 Hz, 2H), 7.13 (dd, J = 8.1, 2.0 Hz, 1H). MS (ESI) m/z: 338[M + H]⁺. |
| III-f-13 | 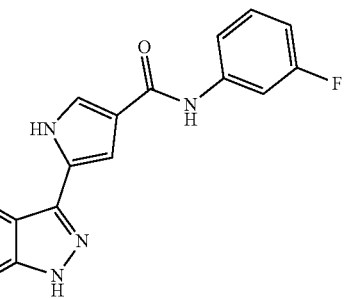<br>TFA salt | ¹H NMR (600 MHz, DMSO-d₆) δ 12.12 (s, 1H), 9.82 (s, 1H), 8.59-8.56 (m, 2H), 7.96 (s, 1H), 7.80-7.78 (m, 1H), 7.67 (s, 1H), 7.54 (d, J = 8.4 Hz, 1H), 7.38 (d, J = 7.4 Hz, 2H), 7.34-7.28 (m, 1H), 6.88 (s, 1H). MS (ESI) m/z: 322[M + H]⁺. |

TABLE 3-continued

Structure and characterization of compounds III

| No. | Structure | ¹H NMR and/or MS data |
|---|---|---|
| III-f-14 | 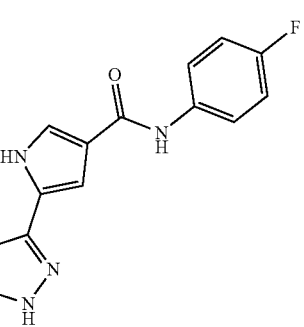 TFA salt | ¹H NMR (600 MHz, Methanol-d₄) δ 8.61-8.53 (m, 2H), 7.76-7.69 (m, 2H), 7.68 (d, J = 1.6 Hz, 1H), 7.40 (d, J = 1.7 Hz, 1H), 7.32 (dd, J = 8.0, 4.6 Hz, 1H), 7.11 (t, J = 8.8 Hz, 2H). MS (ESI) m/z: 322[M + H]⁺. |
| III-f-15 | 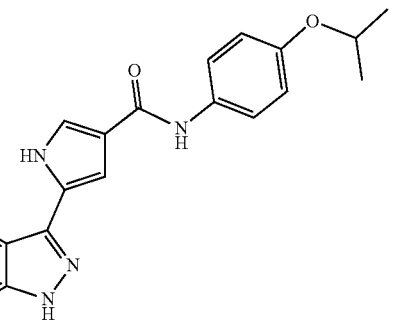 TFA salt | ¹H NMR (600 MHz, DMSO-d₆) δ 12.02 (d, J = 2.9 Hz, 1H), 9.52(s, 1H), 8.59-8.54 (m, 2H), 7.66-7.61 (m, 2H), 7.60 (dd, J = 3.0, 1.6 Hz, 1H), 7.38 (t, J = 2.1 Hz, 1H), 7.30 (dd, J = 8.1, 4.5 Hz, 1H), 6.93-6.84 (m, 2H), 4.56 (p, J = 6.0 Hz, 1H), 1.26 (d, J = 6.0 Hz, 6H). MS (ESI) m/z: 362[M + H]⁺. |
| III-f-16 | 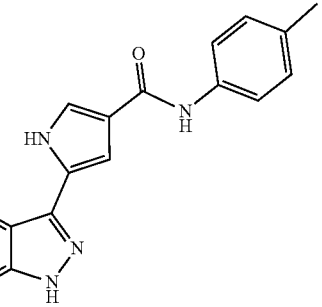 | ¹H NMR (600 MHz, DMSO-d₆) δ 12.04 (s, 1H), 9.57 (s, 1H), 8.64-8.52(m, 2H), 7.66 (dd, J = 8.4, 3.7 Hz, 2H), 7.61 (d, J = 1.8 Hz, 1H), 7.40 (dd, J = 2.6, 1.6 Hz, 1H), 7.30 (dd, J = 8.0, 4.5 Hz, 1H), 7.14 (dd, J = 7.9, 1.2 Hz, 2H), 2.28 (s, 3H). MS (ESI) m/z: 318[M + H]⁺. |
| III-f-17 | 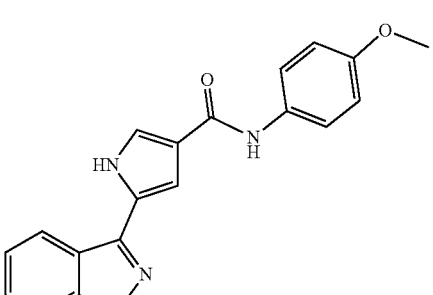 | ¹H NMR (600 MHz, DMSO-d₆) δ 12.11-11.95 (m, 1H), 9.53 (s, 1H), 8.62-8.49 (m, 2H), 7.69-7.63 (m, 2H), 7.59 (dd, J = 3.1, 1.6 Hz, 1H), 7.38 (dd, J = 2.5, 1.6 Hz, 1H), 7.30 (dd, J = 8.0, 4.5 Hz, 1H), 7.01-6.81 (m, 2H), 3.75 (s, 3H). MS (ESI) m/z: 334[M + H]⁺. |

TABLE 3-continued

Structure and characterization of compounds III

| No. | Structure | ¹H NMR and/or MS data |
|---|---|---|
| III-f-18 | 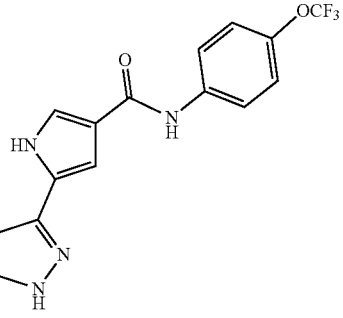 TFA salt | ¹H NMR (600 MHz, DMSO-d₆) δ 12.10 (s, 1H), 9.83 (s, 1H), 8.65-8.40 (m, 2H), 7.91-7.87 (m, 2H), 7.67 (dd, J = 3.1, 1.6 Hz, 1H), 7.38 (dd, J = 2.6, 1.7 Hz, 1H), 7.36 (d, J = 8.6 Hz, 2H), 7.31 (dd, J = 8.0, 4.5 Hz, 1H). MS (ESI) m/z: 388[M + H]⁺. |
| III-f-19 | 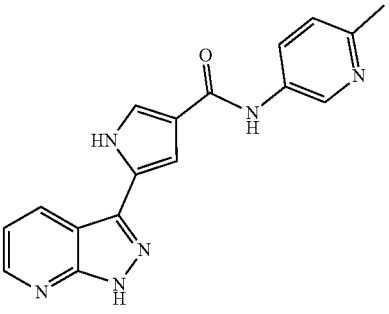 [SMILES: Cc1ccc(NC(=O)c2c[nH]c(-c3n[nH]c4ncccc34)c2)cn1] | ¹H NMR (600 MHz, DMSO-d₆) δ 12.08 (s, 1H), 9.78 (s, 1H), 8.80 (d, J = 2.6 Hz, 1H), 8.59 (dd, J = 4.5, 1.6 Hz, 1H), 8.56 (dd, J = 8.0, 1.5 Hz, 1H), 8.09 (dd, J = 8.3, 2.7 Hz, 1H), 7.65 (dd, J = 3.0, 1.7 Hz, 1H), 7.38 (dd, J = 2.6, 1.7 Hz, 1H), 7.31 (dd, J = 8.1, 4.5 Hz, 1H), 7.26 (d, J = 8.3 Hz, 1H), 2.45 (s, 3H). MS (ESI) m/z: 319[M + H]⁺. |
| III-f-20 | 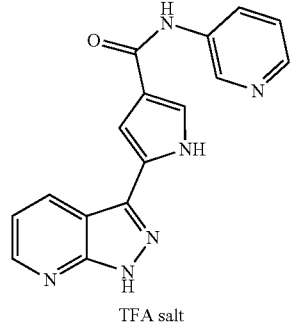 [SMILES: O=C(Nc1cccnc1)c1c[nH]c(-c2n[nH]c3ncccc23)c1] TFA salt | ¹H NMR (600 MHz, DMSO-d₆) δ 12.17 (s, 1H), 10.12 (s, 1H), 9.14 (s, 1H), 8.59 (dd, J = 4.5, 1.5 Hz, 1H), 8.56 (dd, J = 8.1, 1.6 Hz, 1H), 8.42-8.40 (m, 2H), 7.72 (dd, J = 3.1, 1.6 Hz, 1H), 7.69-7.62 (m, 1H), 7.39 (dd, J = 2.6, 1.7 Hz, 1H), 7.31 (dd, J = 8.0, 4.5 Hz, 1H). MS (ESI) m/z: 305[M + H]⁺. |
| III-f-21 | 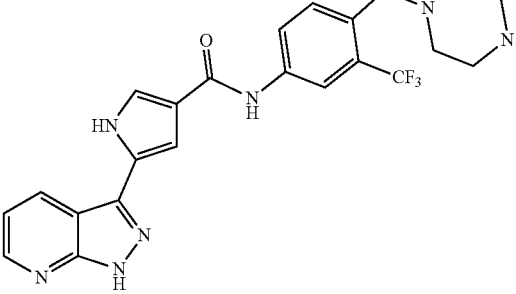 | ¹H NMR (600 MHz, DMSO-d₆) δ 12.10 (s, 1H), 9.90 (s, 1H), 8.60-8.54 (m, 1H), 8.20 (d, J = 2.3 Hz, 1H), 8.05 (dd, J = 8.5, 2.2 Hz, 1H), 7.71-7.63 (m, 2H), 7.39 (d, J = 2.3 Hz, 1H), 7.31 (dd, J = 8.1, 4.5 Hz, 1H), 3.57 (s, 2H), 2.20 (s, 3H). MS (ESI) m/z: 484[M + H]⁺. |

TABLE 3-continued

Structure and characterization of compounds III

| No. | Structure | ¹H NMR and/or MS data |
|---|---|---|
| III-f-22 | 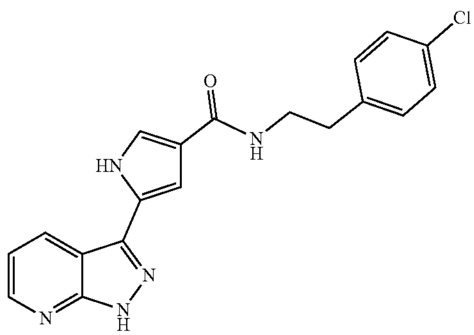 [SMILES: O=C(NCCc1ccc(Cl)cc1)c1c[nH]c(-c2n[nH]c3ncccc23)c1] | ¹H NMR (600 MHz, Methanol-d₄) δ 8.55 (dd, J = 4.5, 1.5 Hz, 1H), 8.51 (dd, J = 8.1, 1.5 Hz, 1H), 7.49 (d, J = 1.7 Hz, 1H), 7.33-7.25 (m, 5H), 7.19 (d, J = 1.6 Hz, 1H), 3.59 (t 2H), 2.93 (t, J = 7.4 Hz, 2H). MS (ESI) m/z: 366 [M + H]⁺. |
| III-f-23 | TFA salt | ¹H NMR (600 MHz, Methanol-d₄) δ 8.59-8.50 (m, 2H), 7.51 (d, J = 1.6 Hz, 1H), 7.31 (dd, J = 8.0, 4.7 Hz, 1H), 7.29-7.26 (m, 2H), 7.21 (d, J = 1.6 Hz, 1H), 7.02 (t, J = 8.8 Hz, 2H), 3.58 t, J = 7.4 Hz, 2H), 2.92 (t, J = 7.4 Hz, 2H). MS (ESI) m/z: 350[M + H]⁺. |
| III-f-24 | TFA salt | ¹H NMR (600 MHz, Methanol-d₄) δ 8.64-8.47 (m, 2H), 7.51 (d, J = 1.8 Hz, 1H), 7.35-7.25 (m, 5H), 7.23-7.17 (m, 2H), 3.60 (dd, J = 8.4, 6.7 Hz, 2H), 2.94 (t, J = 7.5 Hz, 2H). MS (ESI) m/z: 332[M + H]⁺. |
| III-f-25 | 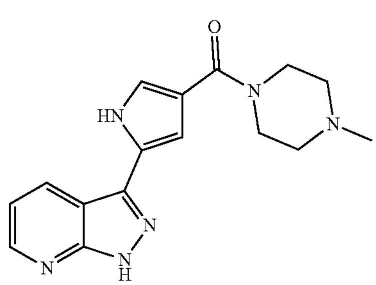 [SMILES: CN1CCN(C(=O)c2c[nH]c(-c3n[nH]c4ncccc34)c2)CC1] | ¹H NMR (600 MHz, DMSO-d₆) δ 11.92 (t, J = 2.8 Hz, 1H), 8.56-8.51 (m, 2H), 7.24 (dd, J = 8.1, 4.5 Hz, 1H), 7.18 (dd, J = 2.9, 1.6 Hz, 1H), 6.92 (dd, J = 2.6, 1.6 Hz, 1H), 3.68 (s, 4H), 2.38 (d, J = 5.2 Hz, 4H), 2.23 (s, 3H). MS (ESI) m/z: 311[M + H]⁺ |

TABLE 3-continued

Structure and characterization of compounds III

| No. | Structure | $^1$H NMR and/or MS data |
|---|---|---|
| III-f-26 | 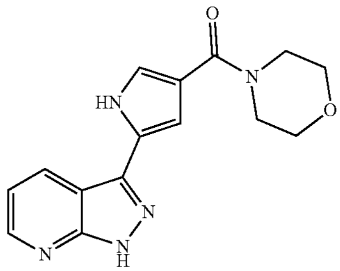 [SMILES: O=C(c1c[nH]c(-c2n[nH]c3ncccc23)c1)N1CCOCC1] | $^1$H NMR (600 MHz, DMSO-d$_6$) δ 11.95 (s, 1H), 8.67-8.40 (m, 2H), 7.27-7.24 (m, 1H), 7.22-7.19 (m, 1H), 7.00-6.84 (m, 1H), (s, 4H), 2.73 (s, 4H). MS (ESI) m/z: 298 [M + H]$^+$. |
| III-f-27 | TFA Salt | $^1$H NMR (600 MHz, Methanol-d$_4$) δ 8.59 (dd, J = 8.1, 1.5 Hz, 1H), 8.56 (d, J = 4.6 Hz, 1H), 7.54 (d, J = 1.6 Hz, 1H), 7.32 (dd, J = 8.1, 4.6 Hz, 1H), 7.29 (d, J = 1.6 Hz, 1H), 3.88 (m, 1H), 2.06-1.93 (m, 2H), 1.88-1.76 (m, 2H), 1.74-1.69 (m, 2H), 1.43-1.38 (m, 2H). MS (ESI) m/z: 310[M + H]$^+$. |
| III-f-28 | 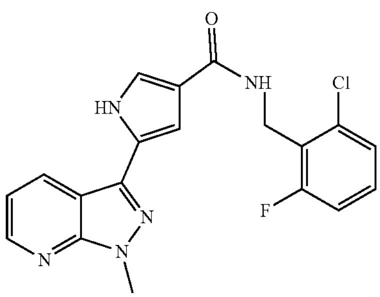 [SMILES: Cn1nc(-c2cc(C(=O)NCc3c(F)cccc3Cl)c[nH]2)c2cccnc21] | $^1$H NMR (600 MHz, Methanol-d$_4$) δ 8.50 (dd, J = 4.6, 1.5 Hz, 1H), 8.38 (dd, J = 8.1, 1.5 Hz, 1H), 7.52 (d, J = 1.7 Hz, 1H), 7.32 (td, J = 8.2, 5.8 Hz, 1H), 7.27 (dt, J = 8.2, 1.1 Hz, 1H), 7.23-7.19 (m, 2H), 7.11 (ddd, J = 9.6, 8.2, 1.3 Hz, 1H), 4.74 (d, J = 1.5 Hz, 2H), 4.08 (s, 3H). MS (ESI) m/z: 384[M + H]$^+$. |
| III-f-29 | TFA salt | $^1$H NMR (600 MHz, DMSO-d$_6$) δ 11.89 (t, J = 2.8 Hz, 1H), 8.50 (d, J = 8.3 Hz, 1H), 8.09 (t, J = 4.9 Hz, 1H), 7.44-7.37 (m, 2H), 7.36-7.31 (m, 2H), 7.28-7.22 (m, 2H), 4.57 (d, J = 4.9, 1.5 Hz, 2H). MS (ESI) m/z: 405[M + H]$^+$. |
| III-f-30 | TFA salt | $^1$H NMR (600 MHz, DMSO-d$_6$) δ 12.07 (s, 1H), 9.62 (s, 1H), 8.61 (d, J = 8.4 Hz, 1H), 7.76 (d, J = 8.0 Hz, 2H), 7.65 (dd, J = 2.9, 1.5 Hz, 1H), 7.41 (t, J = 2.1 Hz, 1H), 7.39-7.30 (m, 3H), 7.05 (t, J = 7.4 Hz, 1H). MS (ESI) m/z: 338[M + H]$^+$. |

TABLE 3-continued

Structure and characterization of compounds III

| No. | Structure | ¹H NMR and/or MS data |
|---|---|---|
| III-f-31 | 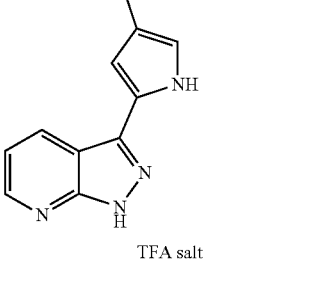 TFA salt | ¹H NMR (600 MHz, DMSO-d₆) δ 11.92 (t, J = 2.8 Hz, 1H), 8.58 (t, J = 6.1 Hz, 1H), 8.56 (dd, J = 4.5, 1.5 Hz, 1H), 8.49 (ddd, J = 8.2, 1.6, 0.7 Hz, 1H), 7.86-7.77 (m, 2H), 7.53-7.50 (m, 2H), 7.45 (dd, J = 3.1, 1.6 Hz, 1H), 7.29-7.25 (m, 2H), 4.54 (d, J = 6.0 Hz, 2H). MS (ESI) m/z: 343[M + H]⁺. |
| III-f-32 | 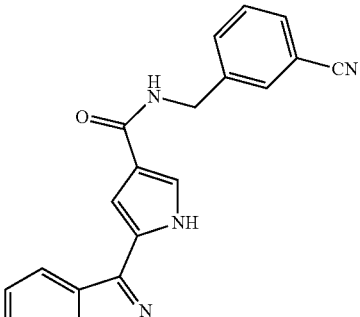 TFA salt | ¹H NMR (600 MHz, DMSO-d₆) δ 11.92 (d, J = 3.5 Hz, 1H), 8.60-8.52(m, 2H), 8.49 (dd, J = 8.1, 1.5 Hz, 1H), 7.76-7.74 (m, 1H), 7.73-7.65 (m, 2H), 7.56 (t, J = 7.7 Hz, 1H), 7.45 (dd, J = 3.0, 1.6 Hz, 1H), 7.30-7.21 (m, 2H), 4.51 (d, J = 6.0 Hz, 2H). MS (ESI) m/z: 343[M + H]⁺ |
| III-f-33 | 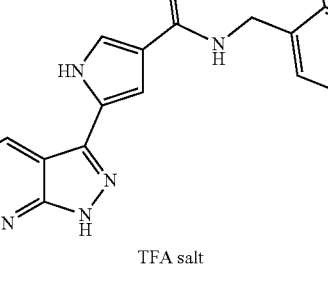 TFA salt | ¹H NMR (600 MHz, DMSO-d₆) δ 11.94 (s, 1H), 8.57-8.52(m, 2H), 8.50 (dd, J = 8.1, 1.6 Hz, 1H), 7.73 (dd, J = 7.9, 1.2 Hz, 1H), 7.67 (t, J = 7.6 Hz, 1H), 7.56 (d, J = 7.8 Hz, 1H), 7.50-7.42 (m, 2H), 7.32 (dd, J = 2.6, 1.6 Hz, 1H), 7.29-7.25 (m, 1H), 4.65 (d, J = 5.8 Hz, 2H). MS (ESI) m/z: 386[M + H]⁺. |
| III-f-34 | 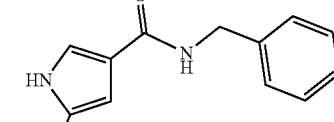 TFA salt | ¹H NMR (600 MHz, DMSO-d₆) δ 11.91 (s, 1H), 8.59 -8.54 (m, 2H), 8.49 (ddd, J = 8.1, 1.6, 0.7 Hz, 1H), 7.70 (d, J = 8.1 Hz, 2H), 7.55 (d, J = 8.0 Hz, 2H), 7.45 (dd, J = 3.0, 1.6 Hz, 1H), 7.30-7.23 (m, 2H), 4.54 (d, J = 6.0 Hz, 2H). MS(ESI) m/z: 386[M + H]⁺. |

TABLE 3-continued

Structure and characterization of compounds III

| No. | Structure | ¹H NMR and/or MS data |
|---|---|---|
| III-f-35 | 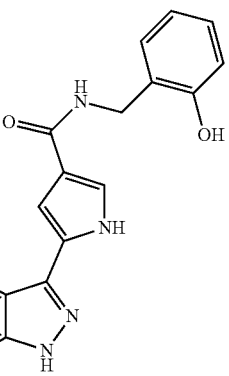 TFA salt | ¹H NMR (600 MHz, DMSO-d$_6$) δ 11.92 (t, J = 2.9 Hz, 1H), 9.82 (s, 1H), 8.56 (dd, J = 4.5, 1.5 Hz, 1H), 8.54-8.47 (m, 2H), 7.46 (dd, J = 3.1, 1.6 Hz, 1H), 7.31 (dd, J = 2.6, 1.6 Hz, 1H), 7.27 (dd, J = 8.1, 4.5 Hz, 1H), 7.17 (dd, J = 7.6, 1.7 Hz, 1H), 7.12-7.05 (m, 1H), 6.81 (dd, J = 8.0, 1.2 Hz, 1H), 6.77 (td, J = 7.4, 1.2 Hz, 1H), 4.39 (d, J = 6.0 Hz, 2H). MS (ESI) m/z: 334[M + H]⁺. |
| III-f-36 | 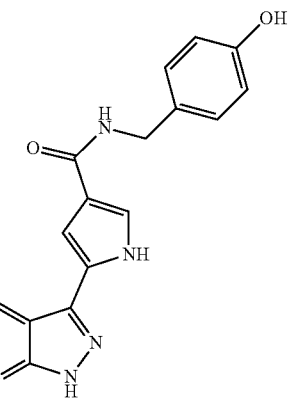 TFA salt | ¹H NMR (600 MHz, DMSO-d$_6$) δ 11.85 (t, J = 2.8 Hz, 1H), 9.25 (s, 1H), 8.55 (dd, J = 4.5, 1.5 Hz, 1H), 8.49 (dd, J = 8.0, 1.5 Hz, 1H), 8.31 (t, J = 6.0 Hz, 1H), 7.41 (dd, J = 3.1, 1.6 Hz, 1H), 7.28 (dd, J = 2.6, 1.6 Hz, 1H), 7.26 (dd, J = 8.1, 4.5 Hz, 1H), 7.16-7.10 (m, 2H), 6.75-6.68 (m, 2H), 4.34 (d, J = 6.0 Hz, 2H). MS (ESI) m/z: 334[M + H]⁺. |
| III-f-37 | 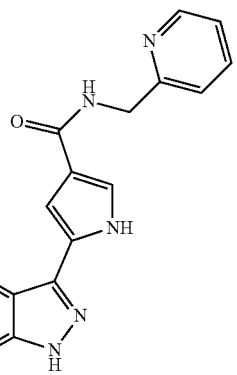 TFA salt | ¹H NMR (600 MHz, DMSO-d$_6$) δ 11.90 (d, J = 3.4 Hz, 1H), 8.56 (dt, J = 5.6, 2.6 Hz, 2H), 8.54-8.48 (m, 2H), 7.76 (td, J = 7.7, 1.8 Hz, 1H), 7.46 (dd, J = 3.0, 1.6 Hz, 1H), 7.34 (dt, J = 7.9, 1.0 Hz, 1H), 7.32 (s, 1H), 7.26 (ddd, J = 7.4, 6.0, 4.1 Hz, 2H), 4.55 (d, J = 6.0 Hz, 2H). MS (ESI) m/z: 319[M + H]⁺. |
| III-f-38 | 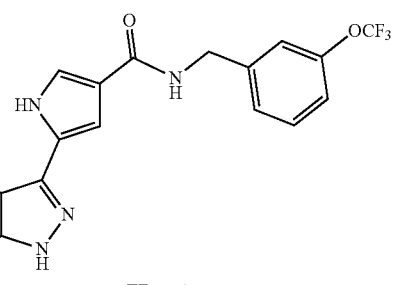 TFA salt | ¹H NMR (600 MHz, DMSO-d$_6$) δ 11.91 (s, 1H), 8.58-8.53 (m, 2H), 8.49 (dd, J = 8.1, 1.5 Hz, 1H), 7.47 (t, J = 7.9 Hz, 1H), 7.45 (dd, J = 3.1, 1.6 Hz, 1H), 7.39-7.35 (m, 1H), 7.31-7.25 (m, 3H), 7.25-7.22 (m, 1H), 4.51 (d, J = 6.0 Hz, 2H). MS (ESI) m/z: 402[M + H]⁺. |

TABLE 3-continued

Structure and characterization of compounds III

| No. | Structure | $^1$H NMR and/or MS data |
|---|---|---|
| III-f-39 | (structure) TFA salt | $^1$H NMR (600 MHz, DMSO-$d_6$) δ 11.92 (s, 1H), 8.56 (dd, J = 4.5, 1.5 Hz, 1H), 8.52-8.43 (m, 2H), 7.47 (ddd, J = 4.6, 3.3, 1.8 Hz, 2H), 7.43-7.34 (m, 3H), 7.30 (dd, J = 2.6, 1.6 Hz, 1H), 7.27 (dd, J = 8.1, 4.5 Hz, 1H), 4.53 (d, J = 5.8 Hz, 2H). MS (ESI) m/z: 402[M + H]$^+$. |
| III-f-40 | (structure) TFA salt | $^1$H NMR (600 MHz, DMSO-$d_6$) δ 11.90 (s, 1H), 8.56 (dd, J = 4.5, 1.5 Hz, 1H), 8.51 (t, J = 6.1 Hz, 1H), 8.49 (dd, J = 8.1, 1.5 Hz, 1H), 7.48-7.41 (m, 3H), 7.33 (dt, J = 7.5, 1.1 Hz, 2H), 7.29-7.23 (m, 2H), 4.48 (d, J = 6.0 Hz, 2H). MS (ESI) m/z: 402[M + H]$^+$. |
| III-f-41 | (structure) TFA salt | $^1$H NMR (600 MHz, DMSO-$d_6$) δ 11.90 (s, 1H), 8.56 (dd, J = 4.5, 1.5 Hz, 1H), 8.52-8.48 (m, 2H), 7.51 (t, J = 1.8 Hz, 1H), 7.46-7.41 (m, 2H), 7.35-7.32 (m, 1H), 7.31 (d, J = 7.7 Hz, 1H), 7.28-7.25 (m, 2H), 4.46 (d, J = 6.0 Hz, 2H). MS (ESI) m/z: 397[M + H]$^+$. |
| III-f-42 | (structure) TFA salt | $^1$H NMR (600 MHz, DMSO-$d_6$) δ 11.92 (s, 1H), 8.56 (dd, J = 4.5, 1.5 Hz, 1H), 8.53-8.46 (m, 2H), 7.62 (dd, J = 7.8, 1.0 Hz, 1H), 7.47 (dd, J = 3.1, 1.6 Hz, 1H), 7.41-7.32 (m, 2H), 7.31 (dd, J = 2.6, 1.7 Hz, 1H), 7.30-7.25 (m, 1H), 7.24-7.18 (m, 1H), 4.49 (d, J = 5.9 Hz, 2H). MS (ESI) m/z: 397[M + H]$^+$. |
| III-f-43 | (structure) TFA salt | $^1$H NMR (600 MHz, DMSO-$d_6$) δ 11.91 (s, 1H), 8.56 (dd, J = 4.5, 1.5 Hz, 1H), 8.53-8.45 (m, 2H), 7.57-7.50 (m, 2H), 7.43 (dd, J = 3.0, 1.6 Hz, 1H), 7.32-7.24 (m, 4H), 4.42 (d, J = 6.0 Hz, 2H). MS (ESI) m/z: 397[M + H]$^+$. |

TABLE 3-continued

Structure and characterization of compounds III

| No. | Structure | ¹H NMR and/or MS data |
|---|---|---|
| III-f-44 | 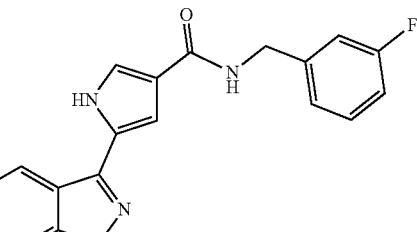 TFA salt | ¹H NMR (600 MHz, DMSO-d$_6$) δ 11.90 (s, 1H), 8.56 (dd, J = 4.5, 1.5 Hz, 1H), 8.52-8.46 (m, 2H), 7.45 (dd, J = 3.0, 1.6 Hz, 1H), 7.38 (td, J = 7.9, 6.1 Hz, 1H), 7.31-7.23 (m, 2H), 7.20-7.15 (m, 1H), 7.15-7.09 (m, 1H), 7.06 (td, J = 8.7, 2.5 Hz, 1H), 4.48 (d, J = 6.0 Hz, 2H). MS (ESI) m/z: 336[M + H]⁺. |
| III-f-45 | 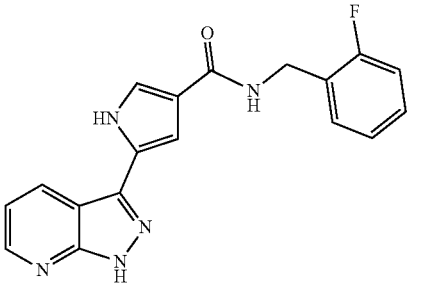 TFA salt | ¹H NMR (600 MHz, DMSO-d$_6$) δ 11.91 (s, 1H), 8.56 (dd, J = 4.5, 1.5 Hz, 1H), 8.50 (dd, J = 8.1, 1.5 Hz, 1H), 8.45 (t, J = 6.0 Hz, 1H), 7.44 (dd, J = 3.0, 1.6 Hz, 1H), 7.39 (td, J = 7.7, 1.7 Hz, 1H), 7.34-7.25 (m, 3H), 7.22-7.12 (m, 2H), 4.50 (d, J = 5.8 Hz, 2H). MS (ESI) m/z: 336[M + H]⁺. |
| III-f-46 | 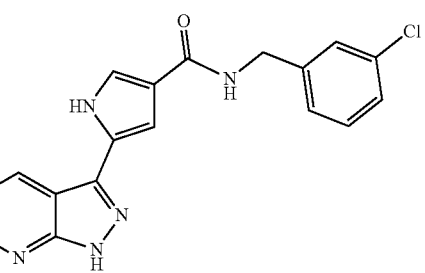 TFA salt | ¹H NMR (600 MHz, DMSO-d$_6$) δ 11.91 (s, 1H), 8.56 (dd, J = 4.5, 1.5 Hz, 1H), 8.53-8.47 (m, 2H), 7.46 (dd, J = 3.0, 1.6 Hz, 1H), 7.40-7.35 (m, 2H), 7.33-7.25 (m, 4H), 4.47 (d, J = 6.0 Hz, 2H). MS (ESI) m/z: 352[M + H]⁺. |
| III-f-47 | 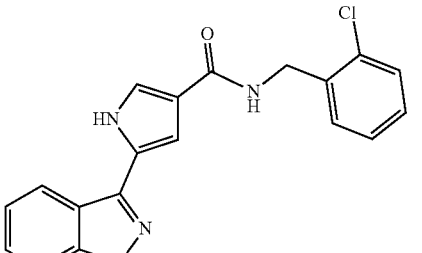 TFA salt | ¹H NMR (600 MHz, DMSO-d$_6$) δ 11.94 (s, 1H), 8.56 (dd, J = 4.5, 1.5 Hz, 1H), 8.53-8.45 (m, 2H), 7.53-7.43 (m, 2H), 7.39 (dd, J = 7.6, 1.8 Hz, 1H), 7.36-7.28 (m, 4H), 4.52 (d, J = 5.9 Hz, 2H). MS (ESI) m/z: 352[M + H]⁺. |

TABLE 3-continued

Structure and characterization of compounds III

| No. | Structure | ¹H NMR and/or MS data |
|---|---|---|
| III-f-48 | 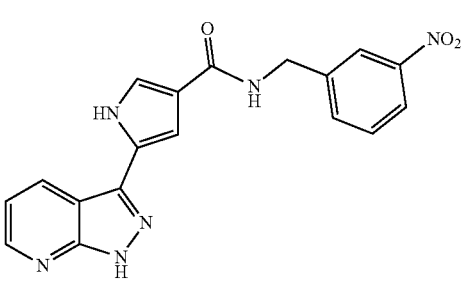 TFA salt | ¹H NMR (600 MHz, DMSO-d₆) δ 11.92 (s, 1H), 8.65 (t, J = 6.1 Hz, 1H), 8.55 (dd, J = 4.5, 1.5 Hz, 1H), 8.48 (dd, J = 8.0, 1.5 Hz, 1H), 8.18 (t, J = 2.0 Hz, 1H), 8.12 (ddd, J = 8.2, 2.5, 1.0 Hz, 1H), 7.80 (dt, J = 7.8, 1.2 Hz, 1H), 7.64 (t, J = 7.9 Hz, 1H), 7.46 (dd, J = 3.1, 1.6 Hz, 1H), 7.33-7.23 (m, 2H), 4.58 (d, J = 6.0 Hz, 2H). MS (ESI) m/z: 363[M + H]⁺. |
| III-f-49 | 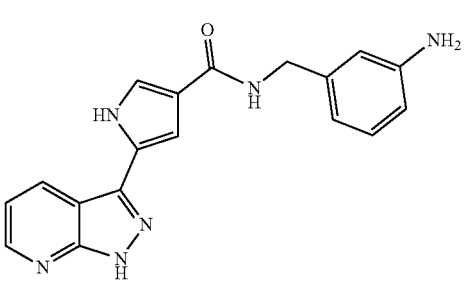 TFA salt | ¹H NMR (600 MHz, DMSO-d₆) δ 11.85 (s, 1H), 8.55 (dd, J = 4.5, 1.5 Hz, 1H), 8.50 (dd, J = 8.1, 1.5 Hz, 1H), 8.32 (t, J = 6.1 Hz, 1H), 7.43 (dd, J = 3.1, 1.6 Hz, 1H), 7.32-7.28 (m, 1H), 7.26 (dd, J = 8.1, 4.5 Hz, 1H), 6.95 (t, J = 7.7 Hz, 1H), 6.53 (d, J = 1.9 Hz, 1H), 6.50-6.41 (m, 2H), 5.01 (s, 2H), 4.33 (d, J = 6.0 Hz, 2H). MS (ESI) m/z: 333[M + H]⁺. |
| III-f-50 | 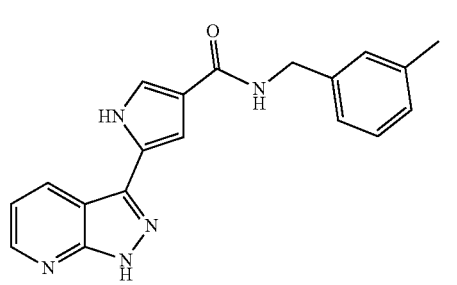 TFA salt | ¹H NMR (600 MHz, DMSO-d₆) δ 11.87 (s, 1H), 8.55 (dd, J = 4.5, 1.5 Hz, 1H), 8.49 (dd, J = 8.1, 1.5 Hz, 1H), 8.41 (t, J = 6.1 Hz, 1H), 7.43 (dd, J = 3.0, 1.6 Hz, 1H), 7.29 (dd, J = 2.6, 1.6 Hz, 1H), 7.26 (dd, J = 8.1, 4.5 Hz, 1H), 7.21 (t, J = 7.5 Hz, 1H), 7.15-7.10 (m, 2H), 7.05 (d, J = 7.4 Hz, 1H), 4.43 (d, J = 6.1 Hz, 2H), 2.29 (s, 3H). MS (ESI) m/z: 332[M + H]⁺. |
| III-f-51 | 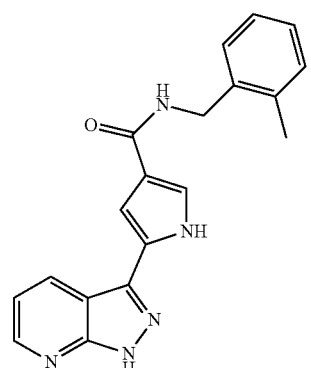 TFA salt | ¹H NMR (600 MHz, DMSO-d₆) δ 11.88 (s, 1H), 8.55 (dd, J = 4.5, 1.6 Hz, 1H), 8.50 (dd, J = 8.1, 1.6 Hz, 1H), 8.29 (t, J = 5.8 Hz, 1H), 7.45 (dd, J = 3.0, 1.6 Hz, 1H), 7.31 (dd, J = 2.6, 1.6 Hz, 1H), 7.29-7.25 (m, 2H), 7.19-7.136 (m, 3H), 4.44 (d, J = 5.7 Hz, 2H), 2.29 (s, 3H). MS (ESI) m/z: 332[M + H]⁺. |

TABLE 3-continued

Structure and characterization of compounds III

| No. | Structure | ¹H NMR and/or MS data |
|---|---|---|
| III-f-52 | 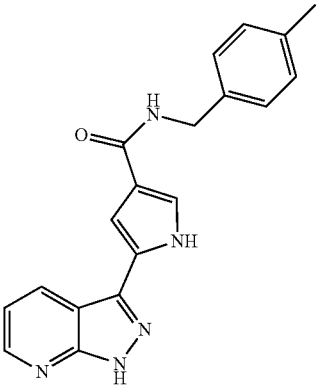 TFA salt | ¹H NMR (600 MHz, DMSO-d$_6$) δ 11.88 (t, J = 2.9 Hz, 1H), 8.55 (dd, J = 4.5, 1.6 Hz, 1H), 8.51-8.47 (m, 1H), 8.40 (t, J = 6.1 Hz, 1H), 7.43 (dd, J = 3.0, 1.6 Hz, 1H), 7.30 (dd, J = 2.6, 1.6 Hz, 1H), 7.26 (dd, J = 8.1, 4.5 Hz, 1H), 7.23-7.19 (m, 2H), 7.13 (d, J = 7.8 Hz, 2H), 4.42 (d, J = 6.0 Hz, 2H), 2.27 (s, 3H). MS (ESI) m/z: 332[M + H]⁺. |
| III-f-53 | 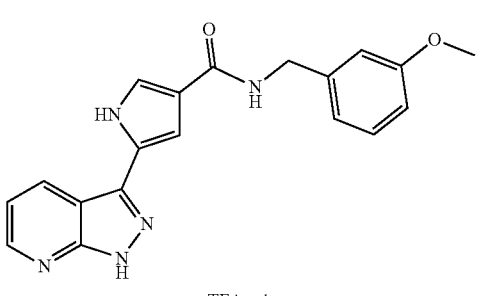 TFA salt | ¹H NMR (600 MHz, DMSO-d$_6$) δ 11.87 (s, 1H), 8.55 (dd, J = 4.5, 1.5 Hz, 1H), 8.49 (dd, J = 8.1, 1.5 Hz, 1H), 8.42 (t, J = 6.1 Hz, 1H), 7.43 (dd, J = 3.0, 1.6 Hz, 1H), 7.29 (dd, J = 2.6, 1.6 Hz, 1H), 7.28-7.22 (m, 2H), 6.92-6.88 (m, 2H), 6.81 (ddd, J = 8.2, 2.6, 0.9 Hz, 1H), 4.43 (d, J = 6.0 Hz, 2H), 3.73 (s, 3H). MS (ESI) m/z: 348[M + H]⁺. |
| III-f-54 | 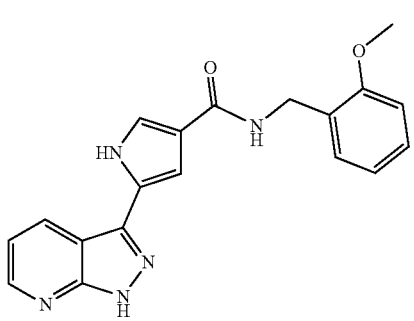 TFA salt | ¹H NMR (600 MHz, DMSO-d$_6$) δ 11.89 (s, 1H), 8.56 (dd, J = 4.5, 1.5 Hz, 1H), 8.51 (ddd, J = 8.1, 1.6, 0.7 Hz, 1H), 8.28 (t, J = 6.0 Hz, 1H), 7.44 (dd, J = 3.0, 1.6 Hz, 1H), 7.32 (dd, J = 2.6, 1.6 Hz, 1H), 7.27 (dd, J = 8.1, 4.5 Hz, 1H), 7.25-7.18 (m, 2H), 6.99 (dd, J = 8.2, 1.1 Hz, 1H), 6.91 (td, J = 7.4, 1.1 Hz, 1H), 4.42 (d, J = 5.9 Hz, 2H), 3.83 (s, 3H). MS (ESI) m/z: 348[M + H]⁺. |
| III-f-55 | 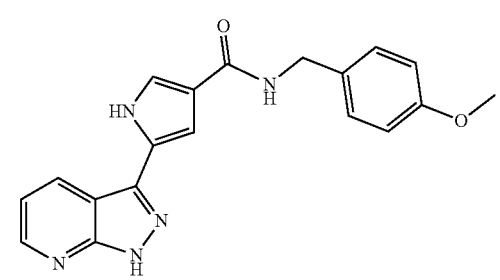 TFA salt | ¹H NMR (600 MHz, DMSO-d$_6$) δ 11.88 (s, 1H), 8.55 (dd, J = 4.5, 1.5 Hz, 1H), 8.49 (ddd, J = 8.1, 1.6, 0.8 Hz, 1H), 8.39 (t, J = 6.0 Hz, 1H), 7.42 (dd, J = 3.0, 1.6 Hz, 1H), 7.29-7.24 (m, 4H), 6.98-6.84 (m, 2H), 4.39 (d, J = 6.0 Hz, 2H), 3.72 (s, 3H). MS (ESI) m/z: 348[M + H]⁺. |

TABLE 3-continued

Structure and characterization of compounds III

| No. | Structure | ¹H NMR and/or MS data |
|---|---|---|
| III-f-56 | 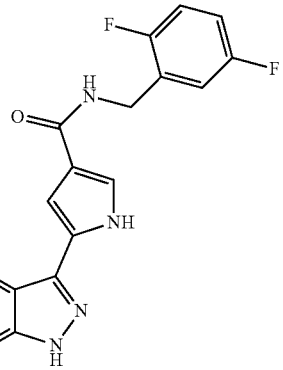 TFA salt | ¹H NMR (600 MHz, DMSO-$d_6$) δ 11.93 (d, J = 3.5 Hz, 1H), 8.56 (dd, J = 4.5, 1.6 Hz, 1H), 8.52-8.45 (m, 2H), 7.46 (dd, J = 3.0, 1.6 Hz, 1H), 7.29 (dd, J = 2.6, 1.6 Hz, 1H), 7.28-7.23 (m, 2H), 7.20-7.10 (m, 2H), 4.48 (d, J = 5.8 Hz, 2H). MS (ESI) m/z: 354[M + H]⁺. |
| III-f-57 | 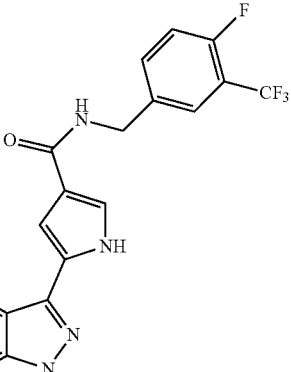 TFA salt | ¹H NMR (600 MHz, DMSO-$d_6$) δ 11.92 (s, 1H), 8.57-8.53 (m, 2H), 8.49 (dd, J = 8.1, 1.5 Hz, 1H), 7.75-7.66 (m, 2H), 7.52-7.46 (m, 1H), 7.44 (dd, J = 3.0, 1.6 Hz, 1H), 7.29-7.23 (m, 2H), 4.50 (d, J = 6.0 Hz, 2H). MS (ESI) m/z: 404[M + H]⁺. |
| III-f-58 | 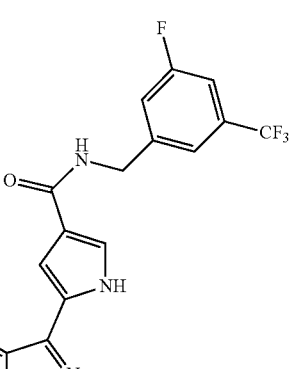 TFA salt | ¹H NMR (600 MHz, DMSO-$d_6$) δ 11.92 (s, 1H), 8.59 (t, J = 6.1 Hz, 1H), 8.55 (dd, J = 4.5, 1.5 Hz, 1H), 8.49 (dd, J = 8.1, 1.5 Hz, 1H), 7.57-7.53 (m, 2H), 7.51-7.44 (m, 2H), 7.31-7.22 (m, 2H), 4.55 (d, J = 6.0 Hz, 2H). MS (ESI) m/z: 404[M + H]⁺. |

TABLE 3-continued

Structure and characterization of compounds III

| No. | Structure | ¹H NMR and/or MS data |
|---|---|---|
| III-f-59 | 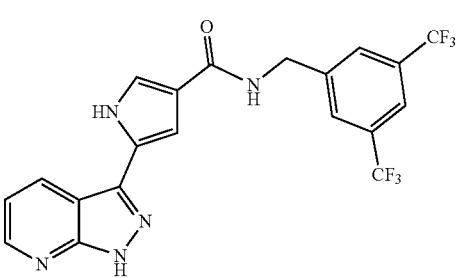<br>TFA salt | ¹H NMR (600 MHz, DMSO-d₆) δ 11.94 (s, 1H), 8.65 (t, J = 6.1 Hz, 1H), 8.56 (dd, J = 4.5, 1.6 Hz, 1H), 8.49 (ddd, J = 8.2, 1.6, 0.7 Hz, 1H), 8.02 (d, J = 1.4 Hz, 2H), 8.00 (s, 1H), 7.46 (dd, J = 3.0, 1.6 Hz, 1H), 7.28-7.26 (m, 1H), 7.26-7.24 (m, 1H), 4.63 (d, J = 6.0 Hz, 2H). MS (ESI) m/z: 454[M + H]⁺. |
| III-f-60 | 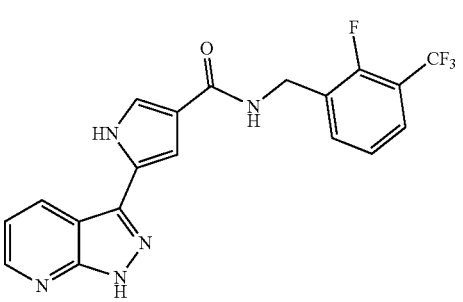<br>TFA salt | ¹H NMR (600 MHz, DMSO-d₆) δ 11.92 (t, J = 2.9 Hz, 1H), 8.57-8.53 (m, 2H), 8.49 (dd, J = 8.1, 1.5 Hz, 1H), 7.76-7.65 (m, 2H), 7.45 (dd, J = 3.0, 1.6 Hz, 1H), 7.40 (t, J = 7.8 Hz, 1H), 7.27 (dd, J = 8.2, 4.0 Hz, 2H), 4.55 (d, J = 5.8 Hz, 2H). MS (ESI) m/z: 404[M + H]⁺. |
| III-f-61 | 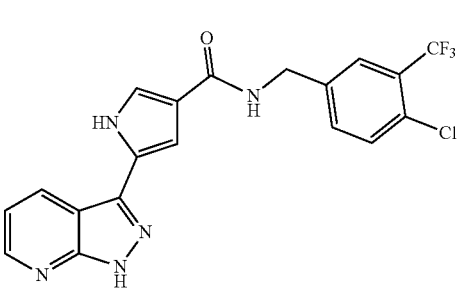<br>TFA salt | ¹H NMR (600 MHz, DMSO-d₆) δ 11.93 (s, 1H), 8.60 (t, J = 6.1 Hz, 1H), 8.57-8.54 (m, 1H), 8.49 (dd, J = 8.1, 1.5 Hz, 1H), 7.84 (d, J = 8.2 Hz, 1H), 7.64 (s, 1H), 7.49 (d, J = 8.1 Hz, 1H), 7.45 (dd, J = 3.1, 1.6 Hz, 1H), 7.29-7.25 (m, 2H), 4.53 (d, J = 6.0 Hz, 2H). MS (ESI) m/z: 420[M + H]⁺. |
| III-f-62 | 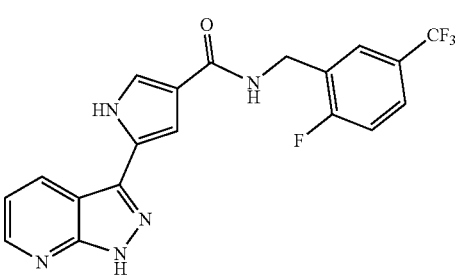<br>TFA salt | ¹H NMR (600 MHz, DMSO-d₆) δ 11.93 (d, J = 3.1 Hz, 1H), 8.59-8.51 (m, 2H), 8.49 (dd, J = 8.1, 1.6 Hz, 1H), 7.73 (ddd, J = 11.4, 6.0, 2.2 Hz, 2H), 7.50-7.43 (m, 2H), 7.31-7.22 (m, 2H), 4.55 (d, J = 5.8 Hz, 2H). MS (ESI) m/z: 404[M + H]⁺. |

TABLE 3-continued

Structure and characterization of compounds III

| No. | Structure | ¹H NMR and/or MS data |
| --- | --- | --- |
| III-g-1 | 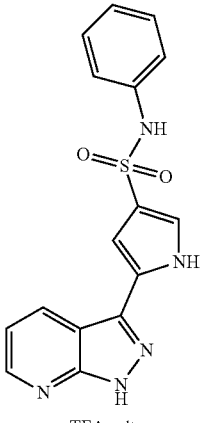<br>TFA salt | ¹H NMR (600 MHz, DMSO-$d_6$) δ 12.25 (s, 1H), 9.89 (s, 1H), 8.57 (dd, J = 4.5, 1.4 Hz, 1H), 8.44-8.29 (m, 1H), 7.31-7.29 (m, 1H), 7.29-7.26 (m, 1H), 7.24 (t, J = 7.8 Hz, 2H), 7.21-7.17 (m, 2H), 7.00 (t, J = 7.3 Hz, 1H), 6.90 (t, J = 2.1 Hz, 1H). MS (ESI) m/z: 340[M + H]$^+$. |
| III-g-2 | 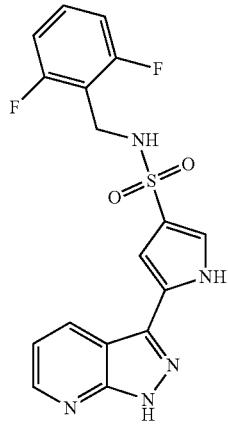<br>TFA salt | ¹H NMR (600 MHz, DMSO-$d_6$) δ 12.25 (s, 1H), 8.59 (dd, J = 4.5, 1.4 Hz, 1H), 8.48-8.43 (m, 1H), 7.46 (t, J = 5.5 Hz, 1H), 7.43 (d, J = 8.0 Hz, 2H), 7.37 (dd, J = 3.1, 1.6 Hz, 1H), 7.34-7.28 (m, 2H), 7.04 (t, J = 2.2 Hz, 1H), 4.26 (d, J = 5.5 Hz, 2H). MS (ESI) m/z: 390[M + H]$^+$. |
| III-g-3 | 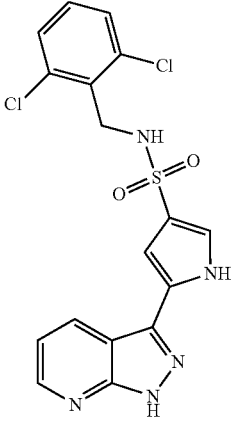 [SMILES: O=S(=O)(NCc1c(F)cccc1Cl)c1c[nH]c(-c2n[nH]c3ncccc23)c1]<br>TFA salt | ¹H NMR (600 MHz, DMSO-$d_6$) δ 12.25 (s, 1H), 8.59 (dd, J = 4.5, 1.5 Hz, 1H), 8.46 (dd, J = 7.9, 1.4 Hz, 1H), 7.46 (t, J = 5.5 Hz, 1H), 7.43 (d, J = 8.0 Hz, 2H), 7.37 (dd, J = 3.0, 1.6 Hz, 1H), 7.34-7.28 (m, 2H), 7.04 (t, J = 2.2 Hz, 1H), 4.26 (d, J = 5.5 Hz, 2H). MS (ESI) m/z: 423[M + H]$^+$. |

TABLE 3-continued

Structure and characterization of compounds III

| No. | Structure | ¹H NMR and/or MS data |
|---|---|---|
| III-g-4 | 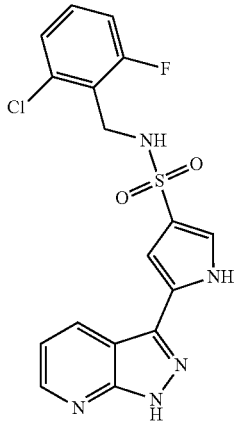 | ¹H NMR (600 MHz, DMSO-$d_6$) δ 12.26 (s, 1H), 8.59 (dd, J = 4.5, 1.6 Hz, 1H), 8.45 (dd, J = 8.1, 1.5 Hz, 1H), 7.56 (t, J = 5.7 Hz, 1H), 7.35 (t, J = 1.6 Hz, 1H), 7.32-7.27 (m, 2H), 7.18 (ddd, J = 9.3, 8.1, 1.2 Hz, 1H), 7.01 (dd, J = 2.6, 1.6 Hz, 1H), 4.14 (dd, J = 5.7, 1.6 Hz, 2H). MS (ESI) m/z: 406[M + H]⁺. |
| III-h-1 | 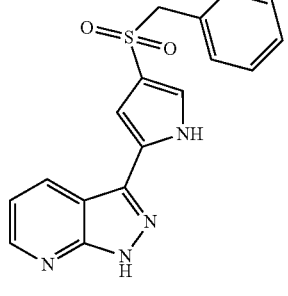<br>TFA salt | ¹H NMR (600 MHz, DMSO-$d_6$) δ 12.39 (s, 1H), 8.59 (dd, J = 4.5, 1.5 Hz, 1H), 8.49 (dd, J = 8.1, 1.5 Hz, 1H), 7.32 (dd, J = 5.1, 2.0 Hz, 3H), 7.29 (dd, J = 8.1, 4.4 Hz, 1H), 7.27-7.23 (m, 2H), 7.20-7.18 (m, 1H), 7.01 (dd, J = 2.6, 1.6 Hz, 1H), 4.59 (s, 2H). MS (ESI) m/z: 339[M + H]⁺. |
| III-h-2 | 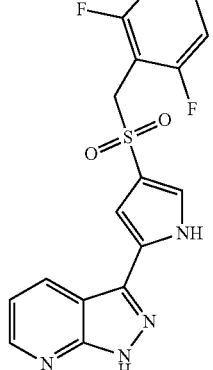<br>TFA salt | ¹H NMR (600 MHz, DMSO-$d_6$) δ 12.48 (s, 1H), 8.58 (dd, J = 4.5, 1.5 Hz, 1H), 8.54-8.45 (m, 1H), 7.50-7.45 (m, 1H), 7.32 (dd, J = 3.4, 1.6 Hz, 1H), 7.28 (dd, J = 8.1, 4.4 Hz, 1H), 7.11 (t, J = 8.0 Hz, 2H), 7.02 (t, J = 2.1 Hz, 1H), 4.63 (s, 2H). MS (ESI) m/z: 375[M + H]⁺. |

TABLE 3-continued

Structure and characterization of compounds III

| No. | Structure | ¹H NMR and/or MS data |
|---|---|---|
| III-h-3 | 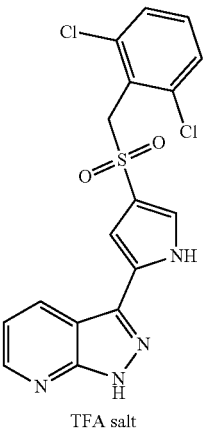 [SMILES: O=S(=O)(Cc1c(Cl)cccc1Cl)c1c[nH]c(-c2n[nH]c3ncccc23)c1] TFA salt | ¹H NMR (600 MHz, DMSO-$d_6$) δ 12.50 (s, 1H), 8.58 (dd, J = 4.5, 1.5 Hz, 1H), 8.48 (dd, J = 8.1, 1.4 Hz, 1H), 7.50 (d, J = 8.0 Hz, 2H), 7.40 (dd, J = 8.6, 7.5 Hz, 1H), 7.31 (dd, J = 3.1, 1.6 Hz, 1H), 7.28 (dd, J = 8.1, 4.5 Hz, 1H), 6.97 (t, J = 2.0 Hz, 1H), 4.89 (s, 2H). MS (ESI) m/z: 408[M + H]⁺. |
| III-h-4 | 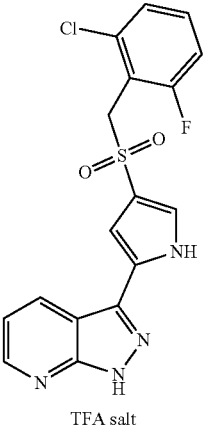 [SMILES: O=S(=O)(Cc1c(F)cccc1Cl)c1c[nH]c(-c2n[nH]c3ncccc23)c1] TFA salt | ¹H NMR (600 MHz, DMSO-$d_6$) δ 12.49 (s, 1H), 8.58 (dd, J = 4.5, 1.5 Hz, 1H), 8.48 (dd, J = 8.1, 1.4 Hz, 1H), 7.45 (td, J = 8.3, 6.0 Hz, 1H), 7.35 (d, J = 8.1 Hz, 1H), 7.30 (dd, J = 3.2, 1.6 Hz, 1H), 7.29-7.24 (m, 2H), 6.97 (t, J = 2.1 Hz, 1H), 4.73 (s, 2H). MS (ESI) m/z: 391[M + H]⁺. |
| III-h-5 | 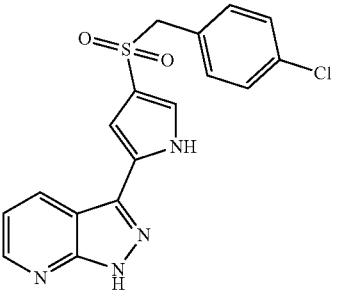 TFA salt | ¹H NMR (600 MHz, DMSO-$d_6$) δ 12.41 (s, 1H), 8.59 (dd, J = 4.5, 1.5 Hz, 1H), 8.50-8.45 (m, 1H), 7.42-7.38 (m, 2H), 7.29 (dd, J = 8.1, 4.5 Hz, 1H), 7.27-7.24 (m, 2H), 7.20 (dd, J = 3.2, 1.6 Hz, 1H), 6.99 (t, J = 2.1 Hz, 1H), 4.62 (s, 2H). MS (ESI) m/z: 373[M + H]⁺. |
| III-i-1 | 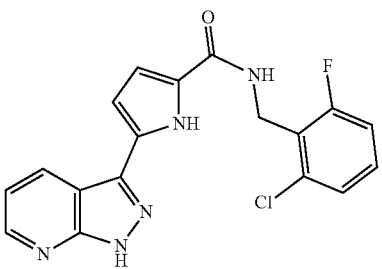 TFA salt | ¹H NMR (600 MHz, DMSO-$d_6$) δ 11.71 (s, 1H), 8.55 (dd, J = 4.5, 1.5 Hz, 1H), 8.51 (dd, J = 8.1, 1.5 Hz, 1H), 8.45 (t, J = 4.9 Hz, 1H), 7.45-7.39 (m, 1H), 7.39-7.34 (m, 1H), 7.29-7.23 (m, 2H), 6.90 (dd, J = 3.8, 2.5 Hz, 1H), 6.84 (dd, J = 3.8, 2.3 Hz, 1H), 4.59 (d, J = 4.8 Hz, 2H). MS (ESI) m/z: 370[M + H]⁺ |

The compounds of formula IV:

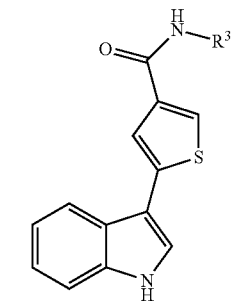
IV-a

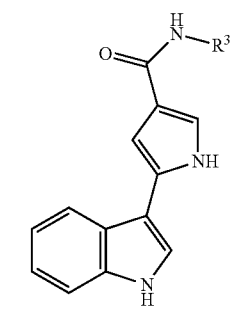
IV-b

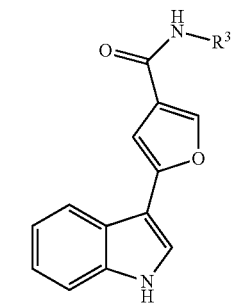
IV-c

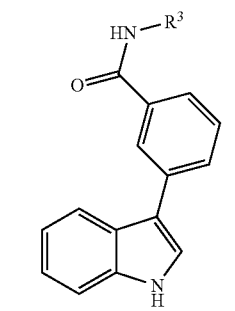
IV-d

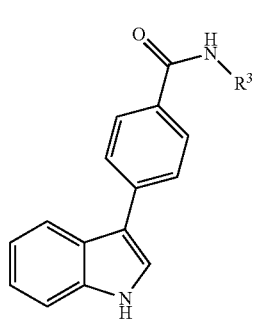
IV-e

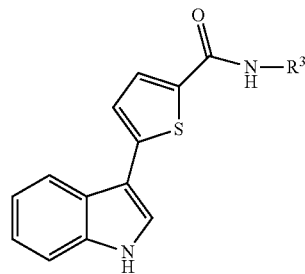
IV-f

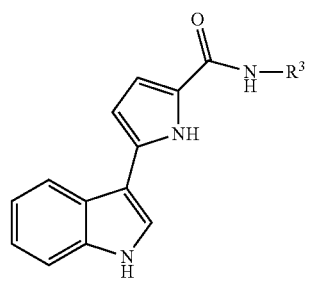
IV-g

Compound IV was synthesized by a method similar to that for the synthesis of compound I.

The synthesis of the compounds of examples is described in detail below.

Synthesis of Intermediate:

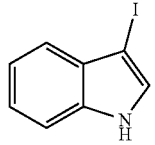

1H-indole (5 mmol, 585.75 mg) (CAS: 120-72-9, Bide, Shanghai) was dissolved in 5 mL of N,N-dimethylformamide (DMF), to which was added potassium hydroxide (12.5 mmol, 1725 mg), followed by stirring at room temperature for 30 min;

$I_2$ (5 mmol, 1269 mg) was dissolved in 2.5 mL of N,N-dimethylformamide (DMF), and then added dropwise to a solution of 1H-indole in DMF, followed by reacting at room temperature for 1 h. The reaction system was poured into 100 mL of ice water, to precipitate out a solid. After centrifugation, the obtained solid was washed with water, and collected to obtain 840 mg of 3-iodo-1H-indole.

Using the intermediate

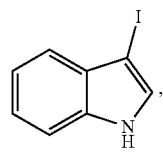

boric acid or borate and the corresponding $R^3$—$NH^2$ as raw materials, compounds IV-a-1~IV-g-1 were obtained with a reference to the preparation method of compound I-a-1.

The table below lists the specific compounds and structure identification data.

TABLE 4

| No. | Structure | ¹H NMR and/or MS data |
|---|---|---|
| IV-a-1 | (structure) | ¹H NMR (600 MHz, DMSO-d₆) δ 11.47 (d, J = 2.7 Hz, 1H), 8.62 (t, J = 4.9 Hz, 1H), 7.98 (d, J = 1.3 Hz, 1H), 7.89 (d, J = 7.7 Hz, 1H), 7.74 (d, J = 2.6 Hz, 1H), 7.71 (d, J = 1.4 Hz, 1H), 7.46 (d, J = 7.9 Hz, 1H), 7.41 (td, J = 8.2, 5.9 Hz, 1H), 7.36 (d, J = 8.0 Hz, 1H), 7.26 (ddd, J = 9.5, 8.2, 1.2 Hz, 1H), 7.21-7.17 (m, 1H), 7.17-7.11 (m, 1H), 4.60 (dd, J = 4.9, 1.4 Hz, 2H). MS (ESI) m/z: 385 [M + H]⁺. |
| IV-a-2 | (structure) TFA salt | ¹H NMR (600 MHz, DMSO-d₆) δ 11.53 (d, J = 2.5 Hz, 1H), 10.10 (s, 1H), 8.19 (d, J = 1.4 Hz, 1H), 7.99-7.93 (m, 1H), 7.85 (d, J = 1.5 Hz, 1H), 7.82 (d, J = 2.6 Hz, 1H), 7.81-7.77 (m, 2H), 7.49 (dt, J = 8.2, 0.9 Hz, 1H), 7.40-7.34 (m, 2H), 7.20 (dddd, J = 19.1, 8.1, 7.0, 1.3 Hz, 2H), 7.12 (ddt, J = 8.5, 7.3, 1.2 Hz, 1H). MS (ESI) m/z: 319 [M + H]⁺. |
| IV-a-3 | (structure) TFA salt | ¹H NMR (600 MHz, DMSO-d₆) δ 11.47 (d, J = 2.5 Hz, 1H), 8.05 (d, J = 8.0 Hz, 1H), 7.94 (d, J = 1.3 Hz, 1H), 7.93-7.90 (m, 1H), 7.75 (d, J = 2.6 Hz, 1H), 7.71 (d, J = 1.4 Hz, 1H), 7.49-7.43 (m, 1H), 7.18 (dddd, J = 20.9, 8.1, 7.0, 1.2 Hz, 2H), 3.81-3.69 (m, 1H), 1.90-1.80 (m, 2H), 1.79-1.70 (m, 2H), 1.67-1.57 (m, 1H), 1.35-1.29 (m, 4H), 1.20-1.08 (m, 1H). MS (ESI) m/z: 325 [M + H]⁺. |
| IV-b-1 | (structure) | MS (ESI) m/z: 368 [M + H]⁺. |

Structure and characterization of compounds IV

TABLE 4-continued

Structure and characterization of compounds IV

| No. | Structure | ¹H NMR and/or MS data |
|---|---|---|
| IV-b-2 | 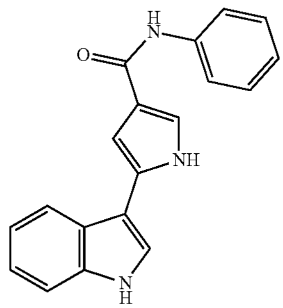 [SMILES: O=C(Nc1ccccc1)c1c[nH]c(-c2c[nH]c3ccccc23)c1] | MS (ESI) m/z: 302 [M + H]⁺. |
| IV-b-3 | 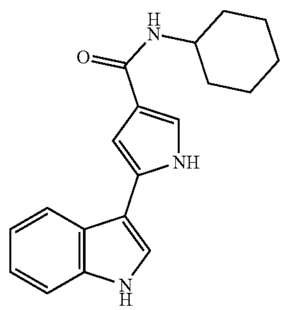 [SMILES: O=C(NC1CCCCC1)c1c[nH]c(-c2c[nH]c3ccccc23)c1] | MS (ESI) m/z: 308 [M + H]⁺. |
| IV-c-1 | 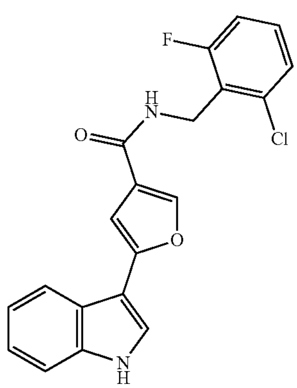 [SMILES: O=C(NCc1c(F)cccc1Cl)c1coc(-c2c[nH]c3ccccc23)c1] | ¹H NMR (600 MHz, Methanol-$d_4$) δ 8.03 (d, J = 0.8 Hz, 1H), 7.88 (dt, J = 8.0, 1.0 Hz, 1H), 7.60 (s, 1H), 7.43 (dt, J = 8.1, 0.9 Hz, 1H), 7.33 (td, J = 8.1, 5.8 Hz, 1H), 7.29 (dt, J = 8.2, 1.1 Hz, 1H), 7.19 (ddd, J = 8.2, 7.0, 1.2 Hz, 1H), 7.16-7.09 (m, 2H), 6.96 (d, J = 0.9 Hz, 1H), 4.74 (d, J = 1.5 Hz, 2H). MS (ESI) m/z: 369 [M + H]⁺. |
| IV-c-2 | 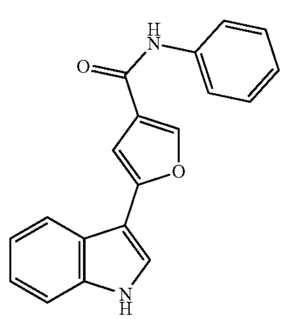 [SMILES: O=C(Nc1ccccc1)c1coc(-c2c[nH]c3ccccc23)c1] | ¹H NMR (600 MHz, DMSO-$d_6$) δ 11.53 (s, 1H), 9.93 (s, 1H), 8.34 (d, J = 0.8 Hz, 1H), 7.98-7.90 (m, 1H), 7.81 (d, J = 2.6 Hz, 1H), 7.78-7.73 (m, 2H), 7.49 (dt, J = 8.0, 1.0 Hz, 1H), 7.41-7.33 (m, 2H), 7.24-7.16 (m, 3H), 7.11 (tt, J = 7.4, 1.2 Hz, 1H). MS (ESI) m/z: 303 [M + H]⁺. |

TABLE 4-continued

Structure and characterization of compounds IV

| No. | Structure | ¹H NMR and/or MS data |
|---|---|---|
| IV-c-3 | 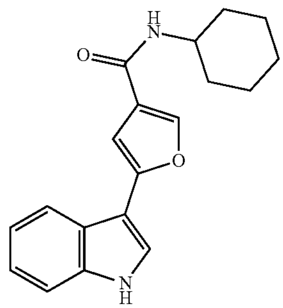 [SMILES: O=C(NC1CCCCC1)c1coc(-c2c[nH]c3ccccc23)c1] | MS (ESI) m/z: 309 [M + H]⁺. |
| IV-d-1 | 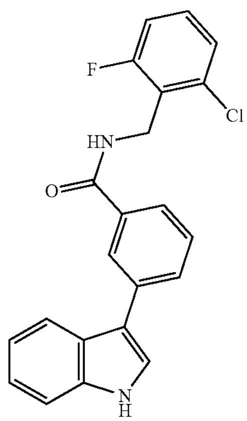 [SMILES: O=C(NCc1c(F)cccc1Cl)c1cccc(-c2c[nH]c3ccccc23)c1] | ¹H NMR (600 MHz, DMSO-d₆) δ 11.52-11.26 (m, 1H), 8.85 (t, J = 4.9 Hz, 1H), 8.15 (t, J = 1.8 Hz, 1H), 7.90-7.85 (m, 1H), 7.85-7.81 (m, 1H), 7.75 (d, J = 2.6 Hz, 1H), 7.70 (ddd, J = 7.7, 1.7, 1.1 Hz, 1H), 7.52-7.45 (m, 2H), 7.43-7.36 (m, 1H), 7.37-7.33 (m, 1H), 7.25 (ddd, J = 9.5, 8.2, 1.2 Hz, 1H), 7.17 (ddd, J = 8.1, 7.0, 1.2 Hz, 1H), 7.12 (ddd, J = 8.0, 6.9, 1.1 Hz, 1H), 4.37 (dd, J = 4.2 Hz, 2H). MS (ESI) m/z: 379 [M + H]⁺. |
| IV-d-2 | 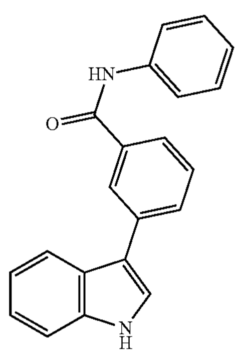 [SMILES: O=C(Nc1ccccc1)c1cccc(-c2c[nH]c3ccccc23)c1] | ¹H NMR (600 MHz, DMSO-d₆) δ 11.46 (s, 1H), 10.31 (s, 1H), 8.24 (t, J = 1.8 Hz, 1H), 7.96-7.90 (m, 2H), 7.83 (d, J = 2.6 Hz, 1H), 7.82-7.78 (m, 3H), 7.59 (t, J = 7.7 Hz, 1H), 7.49 (dt, J = 8.2, 1.0 Hz, 1H), 7.40-7.34 (m, 2H), 7.19 (ddd, J = 8.1, 6.9, 1.2 Hz, 1H), 7.16-7.08 (m, 2H). MS (ESI) m/z: 313 [M + H]⁺. |
| IV-d-3 | 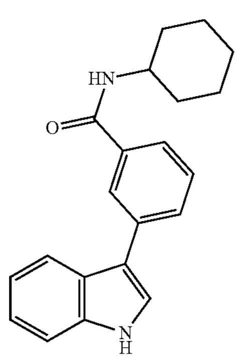 [SMILES: O=C(NC1CCCCC1)c1cccc(-c2c[nH]c3ccccc23)c1] | MS (ESI) m/z: 319 [M + H]⁺. |

TABLE 4-continued

Structure and characterization of compounds IV

| No. | Structure | ¹H NMR and/or MS data |
|---|---|---|
| IV-e-1 | 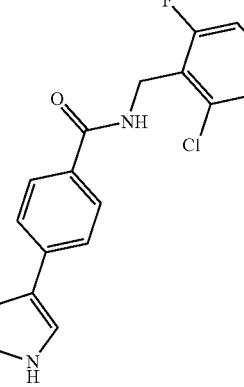 | ¹H NMR (600 MHz, DMSO-$d_6$) δ 11.49 (s, 1H), 8.74 (t, J = 4.9 Hz, 1H), 7.95-7.89 (m, 3H), 7.83 (d, J = 2.7 Hz, 1H), 7.80-7.75 (m, 2H), 7.47 (dt, J = 8.1, 1.0 Hz, 1H), 7.40 (td, J = 8.2, 5.9 Hz, 1H), 7.35 (dt, J = 8.1, 1.0 Hz, 1H), 7.25 (ddd, J = 9.6, 8.2, 1.3 Hz, 1H), 7.18 (ddd, J = 8.1, 7.0, 1.2 Hz, 1H), 7.13 (ddd, J = 8.1, 7.0, 1.1 Hz, 1H), 4.62 (dd, J = 4.9, 1.4 Hz, 2H). MS (ESI) m/z: 379 [M + H]⁺. |
| IV-e-2 | 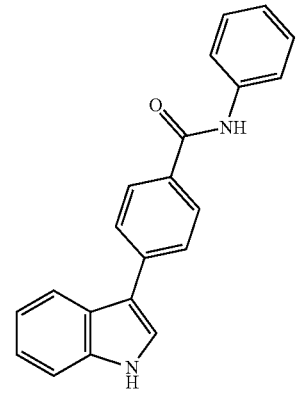 [SMILES: O=C(Nc1ccccc1)c1ccc(-c2c[nH]c3ccccc23)cc1] | ¹H NMR (600 MHz, DMSO-$d_6$) δ 11.56 (d, J = 2.6 Hz, 1H), 10.23 (s, 1H), 8.09-8.01 (m, 2H), 7.97 (d, J = 7.9 Hz, 1H), 7.90-7.86 (m, 3H), 7.83 (ddd, J = 8.4, 4.0, 1.3 Hz, 2H), 7.52-7.48 (m, 1H), 7.37 (dd, J = 8.5, 7.3 Hz, 2H), 7.20 (ddd, J = 8.1, 6.9, 1.2 Hz, 1H), 7.16 (ddd, J = 8.0, 7.0, 1.1 Hz, 1H), 7.11 (tt, J = 7.3, 1.2 Hz, 1H). MS (ESI) m/z: 313 [M + H]⁺. |
| IV-e-3 | 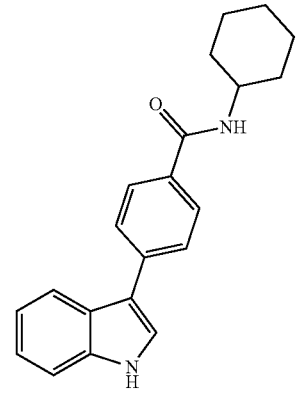 [SMILES: O=C(NC1CCCCC1)c1ccc(-c2c[nH]c3ccccc23)cc1] | ¹H NMR (600 MHz, DMSO-$d_6$) δ 11.49 (d, J = 2.6 Hz, 1H), 8.16 (d, J = 8.0 Hz, 1H), 7.96-7.87 (m, 3H), 7.82 (d, J = 2.7 Hz, 1H), 7.80-7.75 (m, 2H), 7.48 (dt, J = 8.1, 1.0 Hz, 1H), 7.18 (ddd, J = 8.2, 7.0, 1.2 Hz, 1H), 7.13 (ddd, J = 8.0, 7.0, 1.1 Hz, 1H), 3.83-3.72 (m, 1H), 1.90-1.80 (m, 2H), 1.79-1.68 (m, 2H), 1.67-1.57 (m, 1H), 1.41-1.23 (m, 5H), 1.20-1.05 (m, 1H). MS (ESI) m/z: 319 [M + H]⁺. |
| IV-f-1 | 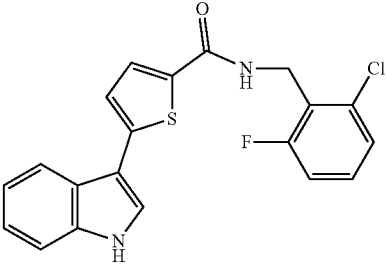 [SMILES: O=C(NCc1c(F)cccc1Cl)c1ccc(-c2c[nH]c3ccccc23)s1] | ¹H NMR (600 MHz, DMSO-$d_6$) δ 11.57 (d, J = 3.3 Hz, 1H), 8.69 (d, J = 4.4 Hz, 1H), 7.90 (d, J = 7.9 Hz, 1H), 7.86 (d, J = 2.5 Hz, 1H), 7.78 (d, J = 3.9 Hz, 1H), 7.47 (d, J = 8.0 Hz, 1H), 7.41 (td, J = 8.1, 6.0 Hz, 1H), 7.37-7.33 (m, 2H), 7.26 (t, J = 8.7 Hz, 1H), 7.22-7.12 (m, 2H), 4.59 (d, J = 3 Hz, 2H). MS (ESI) m/z: 385 [M + H]⁺. |

TABLE 4-continued
Structure and characterization of compounds IV
| No. | Structure | ¹H NMR and/or MS data |
|---|---|---|
| IV-f-2 | 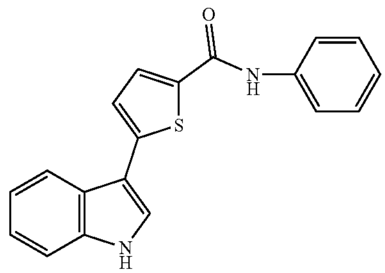 [SMILES: O=C(Nc1ccccc1)c1ccc(-c2c[nH]c3ccccc23)s1] | MS (ESI) m/z: 319 [M + H]⁺. |
| IV-f-3 | 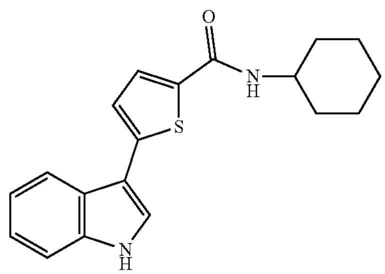 [SMILES: O=C(NC1CCCCC1)c1ccc(-c2c[nH]c3ccccc23)s1] | MS (ESI) m/z: 325 [M + H]⁺. |
| IV-g-1 | 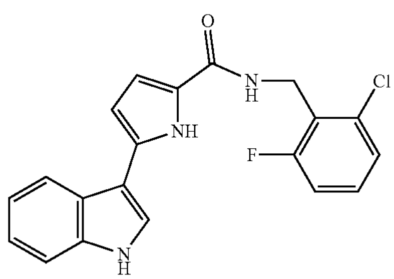 [SMILES: O=C(NCc1c(F)cccc1Cl)c1ccc(-c2c[nH]c3ccccc23)[nH]1] | MS (ESI) m/z: 368 [M + H]⁺. |
The compounds of formula VI
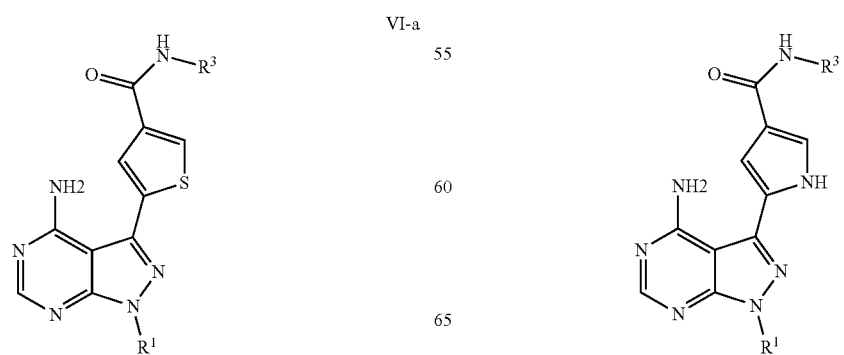

VI-c

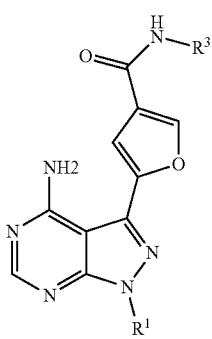

VI-d

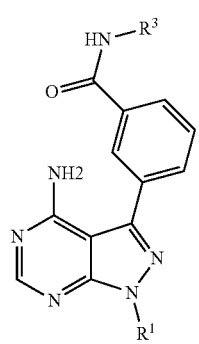

VI-e

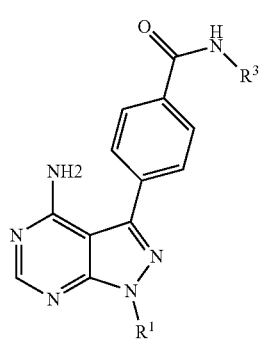

VI-f

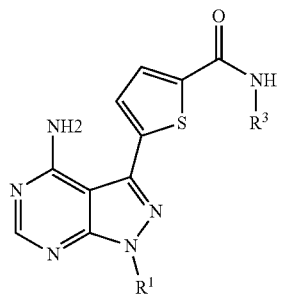

Compound VI was synthesized by a method similar to that for the synthesis of compound I.

The synthesis of the compounds of examples is described in detail below.

Synthesis of Intermediate:

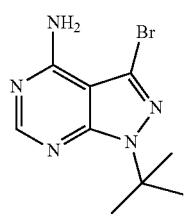

3-Bromo-1H-pyrazolo[3,4-d]pyrimidine-4-amine (5 mmol, 1.35 g) (CAS: 83255-86-1, Energy, Shanghai) was dissolved in 5 mL of N,N-dimethylformamide. Iodoisopropane (5 mmol, 920.1 mg) was added dropwise in an ice bath, followed by returning to room temperature, and standing by overnight. The reaction system was extracted with water/ethyl acetate, then the organic phase was washed with saturated sodium chloride solution, dried with anhydrous sodium sulfate, concentrated, to obtain 1.05 g of 3-bromo-1-(t-butyl)-1H-pyrazolo[3,4-d]pyrimidine-4-amine.

Using the intermediate

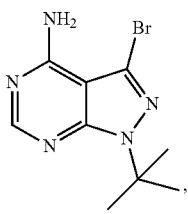

boric acid or borate and the corresponding $R^3$—$NH^2$ as raw materials, compounds VI-a-1~VI-f-2 were obtained with a reference to the preparation method of compound I-a-1.

The table below lists the specific compounds and structure identification data.

TABLE 5
Structure and characterization of compounds VI
| No. | Structure | ¹H NMR and/or MS data |
|---|---|---|
| VI-a-1 | 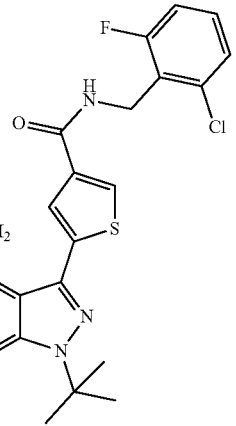 | ¹H NMR (600 MHz, Methanol-$d_4$) δ 8.22 (s, 1H), 8.16 (d, J = 1.4 Hz, 1H), 7.76 (d, J = 1.4 Hz, 1H), 7.35 (td, J = 8.2, 5.8 Hz, 1H), 7.32-7.28 (m, 1H), 7.14 (ddd, J = 9.4, 8.1, 1.2 Hz, 1H), 4.75 (d, J = 1.6 Hz, 2H), 1.80 (s, 9H). MS (ESI) m/z: 360 [M + H]⁺. |
| VI-a-2 | 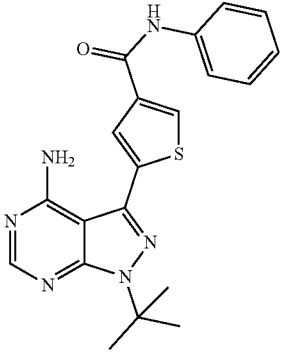 | ¹H NMR (600 MHz, DMSO-$d_6$) δ 10.13 (s, 1H), 8.41 (d, J = 1.4 Hz, 1H), 8.28 (s, 1H), 7.89 (d, J = 1.4 Hz, 1H), 7.82-7.70 (m, 2H), 7.37 (dd, J = 8.5, 7.3 Hz, 2H), 7.21-7.02 (m, 1H), 1.76 (s, 9H). MS (ESI) m/z: 393 [M + H]⁺. |
| VI-a-3 | 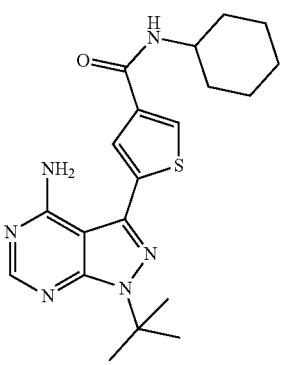<br>TFA salt | ¹H NMR (600 MHz, DMSO-$d_6$) δ 8.39 (s, 1H), 8.25 (d, J = 1.3 Hz, 1H), 8.12 (d, J = 7.9 Hz, 1H), 7.77 (d, J = 1.4 Hz, 1H), 3.84-3.65 (m, 1H), 1.88-1.81 (m, 2H), 1.75 (s, 9H), 1.75-1.71 (m, 2H), 1.65-1.59 (m, 1H), 1.37-1.24 (m, 4H), 1.19-1.09 (m, 1H). MS (ESI) m/z: 399 [M + H]⁺. |

TABLE 5-continued

Structure and characterization of compounds VI

| No. | Structure | ¹H NMR and/or MS data |
|---|---|---|
| VI-b-1 | 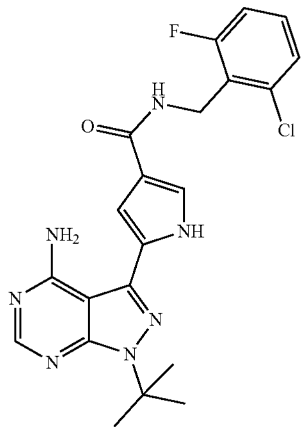 [SMILES: CC(C)(C)n1nc(-c2cc(C(=O)NCc3c(F)cccc3Cl)c[nH]2)c2c(N)ncnc21] | MS (ESI) m/z: 443 [M + H]⁺. |
| VI-b-2 | 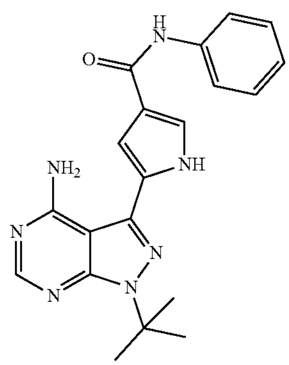 [SMILES: CC(C)(C)n1nc(-c2cc(C(=O)Nc3ccccc3)c[nH]2)c2c(N)ncnc21] | MS (ESI) m/z: 376 [M + H]⁺. |
| VI-c-1 | 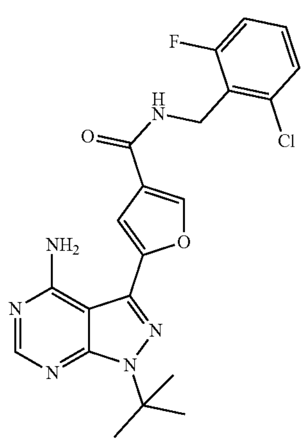 [SMILES: CC(C)(C)n1nc(-c2cc(C(=O)NCc3c(F)cccc3Cl)co2)c2c(N)ncnc21] | MS (ESI) m/z: 443 [M + H]⁺. |

TABLE 5-continued
Structure and characterization of compounds VI
| No. | Structure | ¹H NMR and/or MS data |
| --- | --- | --- |
| VI-c-2 | 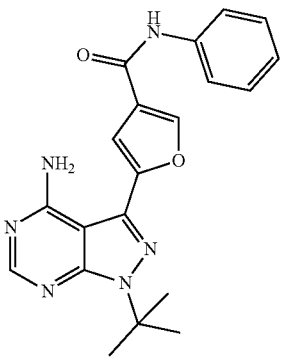 [SMILES: CC(C)(C)n1nc(-c2cc(C(=O)Nc3ccccc3)co2)c2c(N)ncnc21] | MS (ESI) m/z: 377 [M + H]⁺. |
| VI-d-1 | 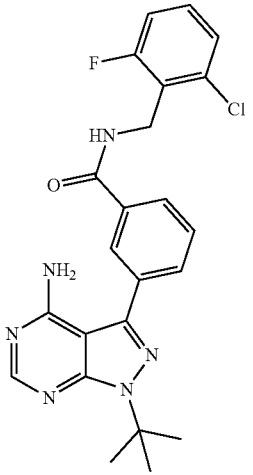 [SMILES: CC(C)(C)n1nc(-c2cccc(C(=O)NCc3c(F)cccc3Cl)c2)c2c(N)ncnc21] | ¹H NMR (600 MHz, DMSO-d$_6$) δ 8.89 (t, J = 4.9 Hz, 1H), 8.39 (s, 1H), 8.13 (t, J = 1.8 Hz, 1H), 7.98 (dt, J = 8.0, 1.4 Hz, 1H), 7.78 (dt, J = 7.6, 1.4 Hz, 1H), 7.62 (t, J = 7.7 Hz, 1H), 7.40 (td, J = 8.2, 5.9 Hz, 1H), 7.34 (d, J = 8.0 Hz, 1H), 7.24 (ddd, J = 9.5, 8.2, 1.2 Hz, 1H), 4.62 (dd, J = 4.9, 1.3 Hz, 2H), 1.77 (s, 9H). MS (ESI) m/z: 454 [M + H]⁺. |
| VI-d-2 | 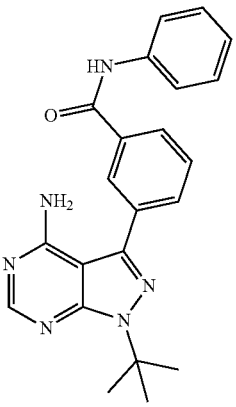 [SMILES: CC(C)(C)n1nc(-c2cccc(C(=O)Nc3ccccc3)c2)c2c(N)ncnc21] | ¹H NMR (600 MHz, DMSO-d$_6$) δ 10.34 (s, 1H), 8.40 (s, 1H), 8.23 (t, J = 1.8 Hz, 1H), 8.10 (ddd, J = 7.8, 1.8, 1.1 Hz, 1H), 7.88 (ddd, J = 7.6, 1.8, 1.1 Hz, 1H), 7.83-7.76 (m, 2H), 7.72 (t, J = 7.7 Hz, 1H), 7.37 (dd, J = 8.5, 7.4 Hz, 2H), 7.12 (tt, J = 7.4, 1.2 Hz, 1H), 1.79 (s, 9H). MS (ESI) m/z: 387 [M + H]⁺. |

TABLE 5-continued

Structure and characterization of compounds VI

| No. | Structure | ¹H NMR and/or MS data |
|---|---|---|
| VI-e-1 | 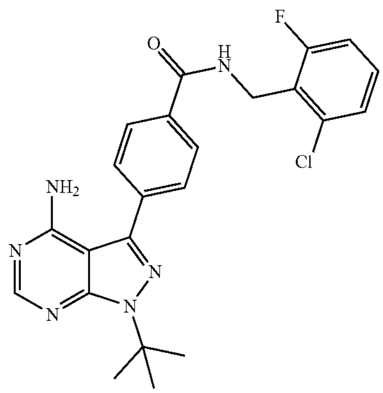 [SMILES: CC(C)(C)n1nc(-c2ccc(C(=O)NCc3c(F)cccc3Cl)cc2)c2c(N)ncnc21] | MS (ESI) m/z: 454 [M + H]⁺. |
| VI-e-2 | 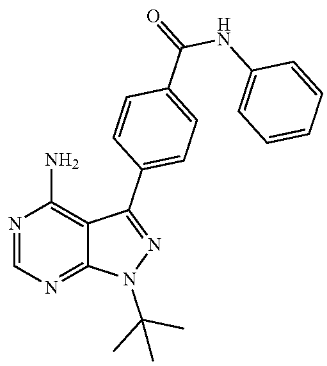 [SMILES: CC(C)(C)n1nc(-c2ccc(C(=O)Nc3ccccc3)cc2)c2c(N)ncnc21] | MS (ESI) m/z: 387 [M + H]⁺. |
| VI-f-1 | 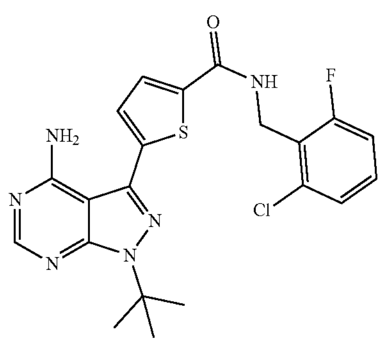 [SMILES: CC(C)(C)n1nc(-c2ccc(C(=O)NCc3c(F)cccc3Cl)s2)c2c(N)ncnc21] | MS (ESI) m/z: 500 [M + H]⁺. |
| VI-f-2 | 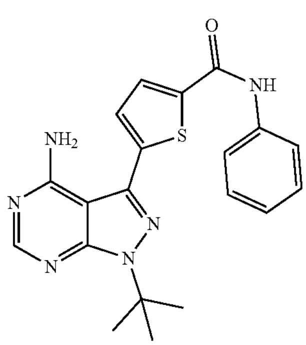 [SMILES: CC(C)(C)n1nc(-c2ccc(C(=O)Nc3ccccc3)s2)c2c(N)ncnc21] | MS (ESI) m/z: 393 [M + H]⁺. |

The compounds of formula VII:

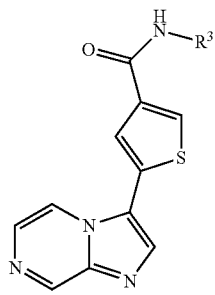
VII-a

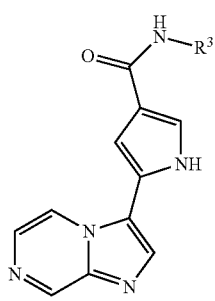
VII-b

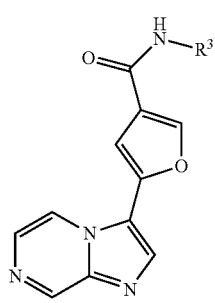
VII-c

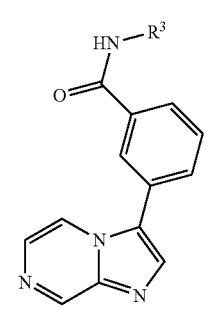
VII-d

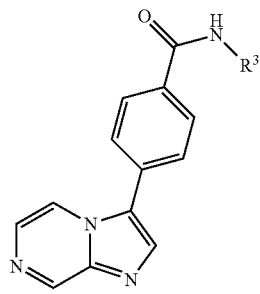
VII-e

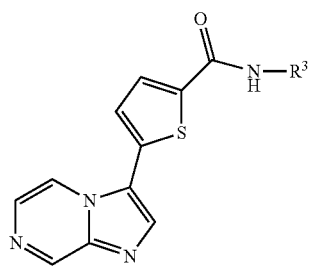
VII-f

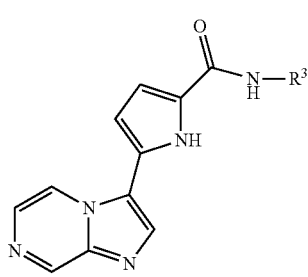
VII-g

Compound VII was synthesized by a method similar to that for the synthesis of compound I.

The synthesis of the compounds of examples is described in detail below.

Using compound

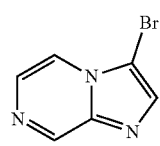

(CAS: 57948-41-1, Bide, Shanghai), boric acid or borate and the corresponding $R^3$—$NH_2$ as raw materials, compounds VII-a-1~VII-g-1 were obtained with a reference to the preparation method of compound I-a-1.

The table below lists the specific compounds and structure identification data.

TABLE 6

Structure and characterization of compounds VII

| No. | Structure | ¹H NMR and/or MS data |
|---|---|---|
| VII-a-1 | 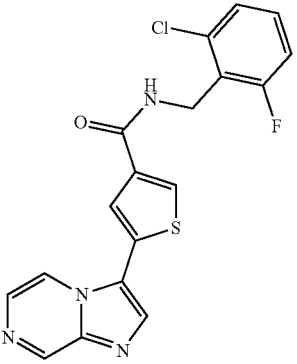 [SMILES: O=C(NCc1c(F)cccc1Cl)c1csc(-c2cnc3cnccn23)c1] | ¹H NMR (600 MHz, Methanol-$d_4$) δ 9.08 (d, J = 1.5 Hz, 1H), 8.64 (dd, J = 4.7, 1.5 Hz, 1H), 8.26 (d, J = 1.4 Hz, 1H), 8.04 (s, 1H), 8.01 (d, J = 4.8 Hz, 1H), 7.90 (d, J = 1.4 Hz, 1H), 7.40-7.32 (m, 1H), 7.32-7.28 (m, 1H), 7.14 (ddd, J = 9.5, 8.2, 1.2 Hz, 1H), 4.76 (d, J = 1.6 Hz, 2H). MS (ESI) m/z: 387 [M + H]⁺. |
| VII-a-2 | 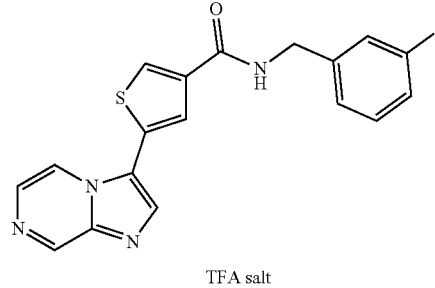<br>TFA salt | ¹H NMR (600 MHz, DMSO-$d_6$) δ 9.20-9.15 (m, 1H), 9.11 (t, J = 6.0 Hz, 1H), 8.69 (dd, J = 4.7, 1.5 Hz, 1H), 8.36 (d, J = 1.4 Hz, 1H), 8.15 (s, 1H), 8.06 (d, J = 4.7 Hz, 1H), 7.99 (d, J = 1.4 Hz, 1H), 7.70 (s, 1H), 7.69-7.54 (m, 3H), 4.59 (d, J = 6.0 Hz, 2H). MS (ESI) m/z: 403 [M + H]⁺. |
| VII-a-3 | 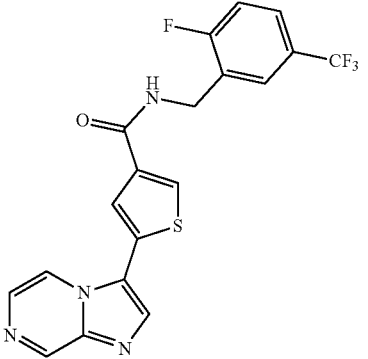 [SMILES: O=C(NCc1cc(C(F)(F)F)ccc1F)c1csc(-c2cnc3cnccn23)c1] | ¹H NMR (600 MHz, DMSO-$d_6$) δ 9.14 (d, J = 1.5 Hz, 1H), 9.05 (t, J = 5.8 Hz, 1H), 8.66 (dd, J = 4.7, 1.5 Hz, 1H), 8.34 (d, J = 1.4 Hz, 1H), 8.11 (s, 1H), 8.03 (d, J = 4.7 Hz, 1H), 7.96 (d, J = 1.5 Hz, 1H), 7.77 (dd, J = 6.8, 2.4 Hz, 1H), 7.75-7.67 (m, 1H), 7.44 (t, J = 9.1 Hz, 1H), 4.57 (d, J = 5.7 Hz, 2H). MS (ESI) m/z: 421 [M + H]⁺. |
| VII-b-1 | 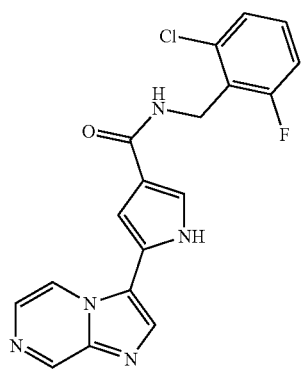 [SMILES: O=C(NCc1c(F)cccc1Cl)c1c[nH]c(-c2cnc3cnccn23)c1] | ¹H NMR (600 MHz, DMSO-$d_6$) δ 11.99 (s, 1H), 9.12 (s, 1H), 8.56 (dd, J = 4.7, 1.5 Hz, 1H), 8.13 (t, J = 5.0 Hz, 1H), 8.06 (s, 1H), 8.01 (d, J = 4.7 Hz, 1H), 7.60 (dd, J = 3.0, 1.5 Hz, 1H), 7.44-7.38 (m, 1H), 7.37-7.33 (m, 1H), 7.26 (ddd, J = 9.5, 8.2, 1.3 Hz, 1H), 7.15 (dd, J = 2.6, 1.5 Hz, 1H), 4.59 (dd, J = 4.9, 1.5 Hz, 2H). MS (ESI) m/z: 370 [M + H]⁺. |

TABLE 6-continued

Structure and characterization of compounds VII

| No. | Structure | ¹H NMR and/or MS data |
|---|---|---|
| VII-b-2 | 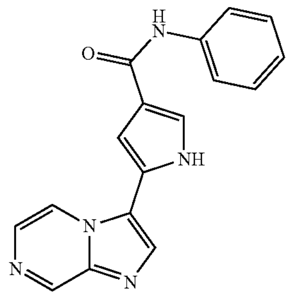 [SMILES: O=C(Nc1ccccc1)c1c[nH]c(-c2cnc3cnccn23)c1] | ¹H NMR (600 MHz, DMSO-d$_6$) δ 12.17 (s, 1H), 9.16 (s, 1H), 8.67 (d, J = 4.7 Hz, 1H), 8.12 (s, 1H), 8.05 (d, J = 4.5 Hz, 1H), 7.90-7.88 (m, 1H), 7.85-7.84 (m, 1H), 7.80 (dd, J = 3.0, 1.5 Hz, 1H), 7.79-7.72 (m, 2H), 7.38-7.32 (m, 2H), 7.07 (t, J = 7.4 Hz, 1H). MS (ESI) m/z: 304 [M + H]⁺. |
| VII-b-3 | 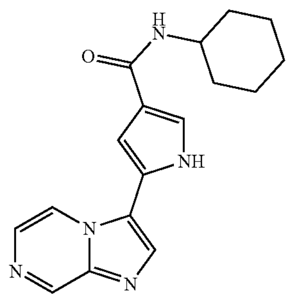 [SMILES: O=C(NC1CCCCC1)c1c[nH]c(-c2cnc3cnccn23)c1] | ¹H NMR (600 MHz, DMSO-d6) δ 11.95 (s, 1H), 9.12 (d, J = 1.4 Hz, 1H), 8.60 (dd, J = 4.7, 1.5 Hz, 1H), 8.07 (s, 1H), 8.03 (d, J = 4.7 Hz, 1H), 7.61 (d, J = 8.0 Hz, 1H), 7.57 (dd, J = 3.0, 1.5 Hz, 1H), 7.15 (dd, J = 2.6, 1.6 Hz, 1H), 3.85-3.65 (m, 1H), 1.87-1.82 (m, 2H), 1.77-1.72 (m, 2H), 1.67-1.59 (m, 1H), 1.37-1.25 (m, 4H), 1.19-1.08 (m, 1H). MS (ESI) m/z: 310 [M + H]⁺. |
| VII-c-1 | 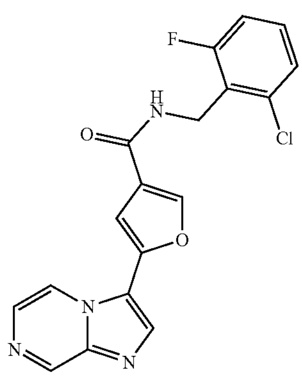 [SMILES: O=C(NCc1c(F)cccc1Cl)c1coc(-c2cnc3cnccn23)c1] | ¹H NMR (600 MHz, DMSO-d$_6$) δ 9.18 (d, J = 1.5 Hz, 1H), 8.70 (dd, J = 4.7, 1.5 Hz, 1H), 8.56 (t, J = 4.9 Hz, 1H), 8.42 (d, J = 0.7 Hz, 1H), 8.21 (s, 1H), 8.06 (d, J = 4.7 Hz, 1H), 7.48 (d, J = 0.8 Hz, 1H), 7.45-7.40 (m, 1H), 7.37 (dt, J = 8.1, 0.9 Hz, 1H), 7.27 (ddd, J = 9.4, 8.2, 1.2 Hz, 1H), 4.61 (dd, J = 5.0, 1.6 Hz, 2H). MS (ESI) m/z: 371 [M + H]⁺. |
| VII-c-2 | 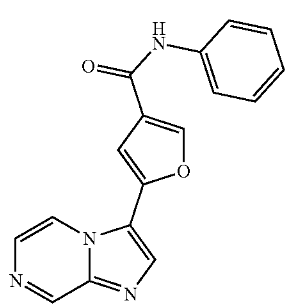 [SMILES: O=C(Nc1ccccc1)c1coc(-c2cnc3cnccn23)c1] | ¹H NMR (600 MHz, DMSO-d$_6$) δ 10.08 (s, 1H), 9.21 (d, J = 1.5 Hz, 1H), 8.80 (dd, J = 4.6, 1.5 Hz, 1H), 8.61 (d, J = 0.8 Hz, 1H), 8.28 (s, 1H), 8.10 (d, J = 4.7 Hz, 1H), 7.81-7.62 (m, 2H), 7.60 (d, J = 0.8 Hz, 1H), 7.38 (dd, J = 8.5, 7.3 Hz, 2H), 7.13 (tt, J = 7.4, 1.2 Hz, 1H). MS (ESI) m/z: 305 [M + H]⁺. |

TABLE 6-continued

Structure and characterization of compounds VII

| No. | Structure | ¹H NMR and/or MS data |
|---|---|---|
| VII-c-3 | 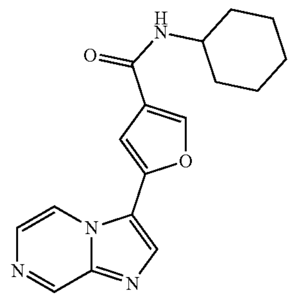 [SMILES: O=C(NC1CCCCC1)c1coc(-c2cnc3cnccn23)c1] | MS (ESI) m/z: 311 [M + H]⁺. |
| VII-d-1 | 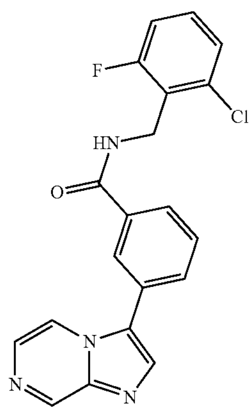 [SMILES: O=C(NCc1c(F)cccc1Cl)c1cccc(-c2cnc3cnccn23)c1] | ¹H NMR (600 MHz, DMSO-d$_6$) δ 9.16 (d, J = 1.5 Hz, 1H), 8.91 (t, J = 4.9 Hz, 1H), 8.63 (dd, J = 4.7, 1.5 Hz, 1H), 8.16 (t, J = 1.8 Hz, 1H), 8.10 (s, 1H), 7.98-7.95 (m, 2H), 7.90 (ddd, J = 7.7, 1.7, 1.1 Hz, 1H), 7.67 (t, J = 7.8 Hz, 1H), 7.40 (td, J = 8.1, 5.9 Hz, 1H), 7.35 (dt, J = 8.2, 1.0 Hz, 1H), 7.25 (ddd, J = 9.6, 8.2, 1.3 Hz, 1H), 4.64 (dd, J = 5.0, 1.5 Hz, 2H). MS (ESI) m/z: 381 [M + H]⁺. |
| VII-d-2 | 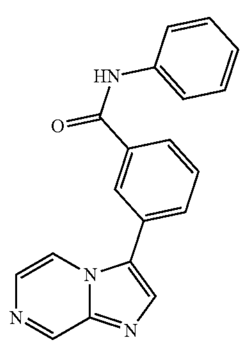 [SMILES: O=C(Nc1ccccc1)c1cccc(-c2cnc3cnccn23)c1] | ¹H NMR (600 MHz, DMSO-d$_6$) δ 10.36 (s, 1H), 9.18 (d, J = 1.4 Hz, 1H), 8.75 (dd, J = 4.7, 1.5 Hz, 1H), 8.28 (t, J = 1.8 Hz, 1H), 8.17 (s, 1H), 8.05 (dt, J = 7.8, 1.4 Hz, 1H), 7.99 (d, J = 4.7 Hz, 1H), 7.97 (dt, J = 7.7, 1.3 Hz, 1H), 7.82-7.78 (m, 2H), 7.75 (t, J = 7.7 Hz, 1H), 7.38 (dd, J = 8.5, 7.3 Hz, 2H), 7.13 (tt, J = 7.3, 1.2 Hz, 1H). MS (ESI) m/z: 315 [M + H]⁺. |
| VII-d-3 | 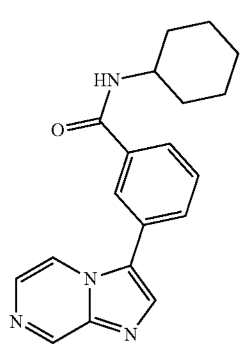 [SMILES: O=C(NC1CCCCC1)c1cccc(-c2cnc3cnccn23)c1] | MS (ESI) m/z: 321 [M + H]⁺. |

TABLE 6-continued

Structure and characterization of compounds VII

| No. | Structure | $^1$H NMR and/or MS data |
|---|---|---|
| VII-e-1 | 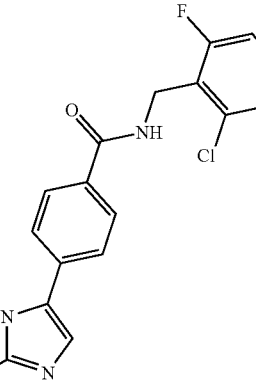 | $^1$H NMR (600 MHz, Methanol-$d_4$) δ 9.29-9.16 (m, 1H), 8.71 (s, 1H), 8.20 (s, 1H), 8.12-8.06 (m, 1H), 8.07-7.99 (m, 2H), 7.87-7.77 (m, 2H), 7.35 (td, J = 8.2, 5.9 Hz, 1H), 7.30 (dt, J = 8.2, 1.1 Hz, 1H), 7.14 (ddd, J = 9.6, 8.2, 1.2 Hz, 1H), 4.79 (d, J = 1.4 Hz, 2H). MS (ESI) m/z: 381 [M + H]$^+$. |
| VII-e-2 | 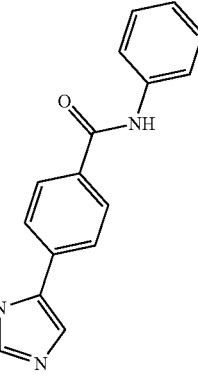 | $^1$H NMR (600 MHz, DMSO-$d_6$) δ 10.38 (s, 1H), 9.19 (d, J = 1.4 Hz, 1H), 8.71 (dd, J = 4.7, 1.5 Hz, 1H), 8.21 (s, 1H), 8.17 (d, J = 8.4 Hz, 2H), 8.01 (d, J = 4.7 Hz, 1H), 7.97-7.90 (m, 2H), 7.85-7.79 (m, 2H), 7.38 (dd, J = 8.5, 7.3 Hz, 2H), 7.15-7.08 (m, 1H). MS (ESI) m/z: 315 [M + H]$^+$. |
| VII-e-3 | 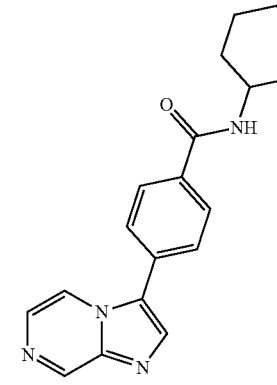 | $^1$H NMR (600 MHz, DMSO-$d_6$) δ 9.17 (d, J = 1.5 Hz, 1H), 8.67 (dd, J = 4.7, 1.5 Hz, 1H), 8.34 (d, J = 7.9 Hz, 1H), 8.16 (s, 1H), 8.08-8.02 (m, 2H), 7.99 (d, J = 4.7 Hz, 1H), 7.88-7.81 (m, 2H), 3.87-3.71 (m, 1H), 1.89-1.83 (m, 2H), 1.66-1.56 (m, 1H), 1.79-1.72 (m, 2H), 1.67-1.58 (m, 1H), 1.39-1.28 (m, 4H), 1.20-1.08 (m, 1H). MS (ESI) m/z: 321 [M + H]$^+$. |
| VII-f-1 | 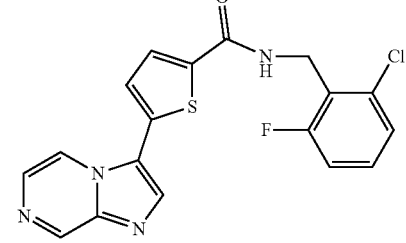 | $^1$H NMR (600 MHz, DMSO-$d_6$) δ 9.18 (d, J = 1.5 Hz, 1H), 8.93 (t, J = 4.9 Hz, 1H), 8.72 (dd, J = 4.8, 1.5 Hz, 1H), 8.21 (s, 1H), 8.05 (d, J = 4.7 Hz, 1H), 7.94 (d, J = 3.9 Hz, 1H), 7.66 (d, J = 4.0 Hz, 1H), 7.43 (td, J = 8.2, 6.0 Hz, 1H), 7.37 (dt, J = 8.1, 1.0 Hz, 1H), 7.27 (ddd, J = 9.6, 8.3, 1.2 Hz, 1H), 4.62 (dd, J = 5.0, 1.5 Hz, 2H). MS (ESI) m/z: 387 [M + H]$^+$. |

TABLE 6-continued

Structure and characterization of compounds VII

| No. | Structure | $^1$H NMR and/or MS data |
|---|---|---|
| VII-f-2 | 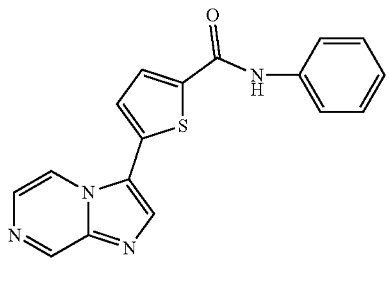 [SMILES: O=C(Nc1ccccc1)c1ccc(-c2cnc3cnccn23)s1] | $^1$H NMR (600 MHz, DMSO-$d_6$) δ 10.37 (s, 1H), 9.21 (d, J = 1.4 Hz, 1H), 8.78 (dd, J = 4.8, 1.4 Hz, 1H), 8.28 (s, 1H), 8.19 (d, J = 4.0 Hz, 1H), 8.09 (d, J = 4.6 Hz, 1H), 7.78 (d, J = 4.0 Hz, 1H), 7.77-7.74 (m, 2H), 7.38 (dd, J = 8.5, 7.4 Hz, 2H), 7.21-7.08 (m, 1H). MS (ESI) m/z: 321 [M + H]$^+$. |
| VII-f-3 | 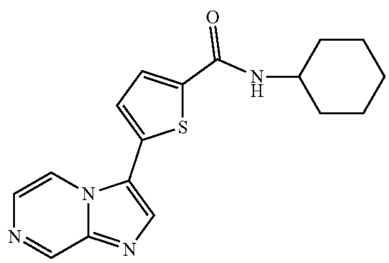 [SMILES: O=C(NC1CCCCC1)c1ccc(-c2cnc3cnccn23)s1] | $^1$H NMR (600 MHz, DMSO-$d_6$) δ 9.19 (d, J = 1.4 Hz, 1H), 8.74 (dd, J = 4.8, 1.4 Hz, 1H), 8.38 (d, J = 8.0 Hz, 1H), 8.23 (s, 1H), 8.06 (d, J = 4.7 Hz, 1H), 7.94 (d, J = 3.9 Hz, 1H), 7.68 (d, J = 4.0 Hz, 1H), 3.81-3.71 (m, 1H), 1.89-1.80 (m, 2H), 1.80-1.70 (m, 2H), 1.63 (dd, J = 13.6, 3.5 Hz, 1H), 1.39-1.23 (m, 4H), 1.20-1.09 (m, 1H). MS (ESI) m/z: 327 [M + H]$^+$. |
| VII-g-1 | TFA salt | $^1$H NMR (600 MHz, DMSO-$d_6$) δ 12.14 (s, 1H), 9.11 (s, 1H), 8.67-8.51 (m, 1H), 8.45 (t, J = 5.0 Hz, 1H), 8.24 (s, 1H), 7.96 (d, J = 4.7 Hz, 1H), 7.43-7.37 (m, 1H), 7.35 (d, J = 8.0 Hz, 1H), 7.29-7.17 (m, 1H), 7.04 (dd, J = 3.8, 2.4 Hz, 1H), 6.72 (dd, J = 3.9, 2.5 Hz, 1H), 4.60 (d, J = 5.1 Hz, 2H). MS (ESI) m/z: 370 [M + H]$^+$. |

The compounds of formula VIII

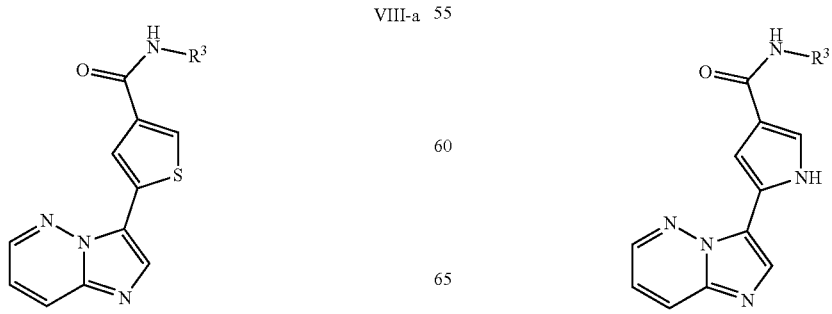

VIII-c

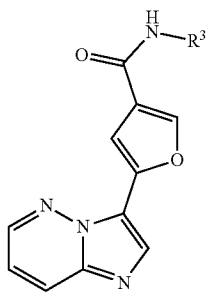

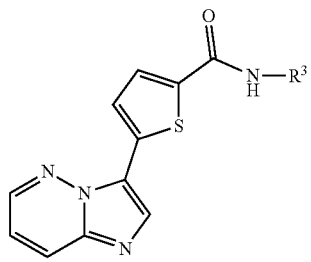
VIII-f

VIII-d

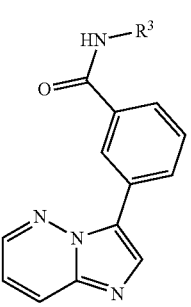

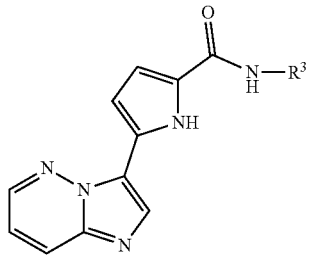
VIII-g

VIII-e

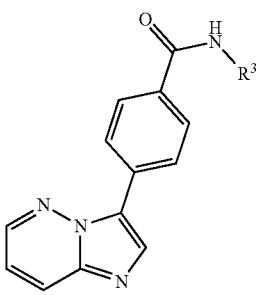

Compound VIII was synthesized by a method similar to that for the synthesis of compound I.

The synthesis of the compounds of examples is described in detail below.

Using compound

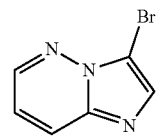

(CAS: 18087-73-5, Shuya, Shanghai), boric acid or borate and the corresponding $R^3$—$NH^2$ as raw materials, compounds VIII-a-1~VIII-g-1 were obtained with a reference to the preparation method of compound I-a-1.

The table below lists the specific compounds and structure identification data.

TABLE 7

| | Structure and characterization of compounds VIII | |
|---|---|---|
| No. | Structure | $^1$H NMR and/or MS data |
| VIII-a-1 | | $^1$H NMR (600 MHz, DMSO-$d_6$) δ 8.73 (dd, J = 4.5, 1.6 Hz, 1H), 8.69 (t, J = 4.9 Hz, 1H), 8.32 (s, 1H), 8.26-8.23 (m, 2H), 8.21 (d, J = 1.4 Hz, 1H), 7.44-7.38 (m, 1H), 7.36 (dt, J = 8.1, 1.0 Hz, 1H), 7.32 (dd, J = 9.2, 4.5 Hz, 1H), 7.26 (ddd, J = 9.6, 8.3, 1.3 Hz, 1H), 4.60 (dd, J = 4.9, 1.5 Hz, 2H). MS (ESI) m/z: 387 [M + H]$^+$. |

TABLE 7-continued

Structure and characterization of compounds VIII

| No. | Structure | ¹H NMR and/or MS data |
|---|---|---|
| VIII-a-2 | (structure: N-(3-trifluoromethylbenzyl) thiophene-carboxamide linked to imidazo[1,2-b]pyridazine; TFA salt) | ¹H NMR (600 MHz, DMSO-d₆) δ 9.09 (t, J = 6.0 Hz, 1H), 8.76 (dd, J = 4.5, 1.5 Hz, 1H), 8.37 (s, 1H), 8.31-8.21 (m, 3H), 7.71-7.56 (m, 4H), 7.36 (dd, J = 9.2, 4.5 Hz, 1H), 4.57 (d, J = 5.9 Hz, 2H). MS (ESI) m/z: 403 [M + H]⁺. |
| VIII-a-3 | (structure: N-(2-fluoro-5-trifluoromethylbenzyl) thiophene-carboxamide linked to imidazo[1,2-b]pyridazine) | ¹H NMR (600 MHz, DMSO-d₆) δ 9.04 (t, J = 5.8 Hz, 1H), 8.74 (dd, J = 4.5, 1.6 Hz, 1H), 8.34 (s, 1H), 8.27-8.24 (m, 2H), 8.23 (d, J = 1.4 Hz, 1H), 7.78 (dd, J = 6.8, 2.4 Hz, 1H), 7.77-7.71 (m, 1H), 7.46 (t, J = 9.1 Hz, 1H), 7.33 (dd, J = 9.2, 4.5 Hz, 1H), 4.58 (d, J = 5.7 Hz, 2H). MS (ESI) m/z: 421 [M + H]⁺. |
| VIII-b-1 | (structure: N-(2-chloro-6-fluorobenzyl) pyrrole-carboxamide linked to imidazo[1,2-b]pyridazine; TFA salt) | ¹H NMR (600 MHz, Methanol-d₄) δ 8.82 (d, J = 4.5 Hz, 1H), 8.27 (d, J = 9.2 Hz, 1H), 8.21 (s, 1H), 7.63-7.54 (m, 2H), 7.43 (d, J = 1.6 Hz, 1H), 7.32 (td, J = 8.2, 5.7 Hz, 1H), 7.27 (dd, J = 8.3, 1.1 Hz, 1H), 7.15-7.05 (m, 1H), 4.72 (d, J = 1.4 Hz, 2H). MS (ESI) m/z: 370 [M + H]⁺. |
| VIII-b-2 | (structure: N-phenyl pyrrole-carboxamide linked to imidazo[1,2-b]pyridazine) | ¹H NMR (600 MHz, DMSO-d₆) δ 12.02 (s, 1H), 9.73 (s, 1H), 8.71 (dd, J = 4.4, 1.6 Hz, 1H), 8.22-8.18 (m, 2H), 7.79 (dt, J = 6.2, 1.3 Hz, 3H), 7.53 (dd, J = 2.6, 1.7 Hz, 1H), 7.36-7.30 (m, 2H), 7.28 (dd, J = 9.1, 4.4 Hz, 1H), 7.09-7.01 (m, 1H). MS (ESI) m/z: 304 [M + H]⁺. |

TABLE 7-continued

Structure and characterization of compounds VIII

| No. | Structure | ¹H NMR and/or MS data |
|---|---|---|
| VIII-b-3 | (structure) | ¹H NMR (600 MHz, DMSO-$d_6$) δ 11.81 (d, J = 3.5 Hz, 1H), 8.68 (dd, J = 4.5, 1.6 Hz, 1H), 8.24-8.08 (m, 2H), 7.67 (d, J = 8.1 Hz, 1H), 7.54 (dd, J = 3.0, 1.7 Hz, 1H), 7.36 (t, J = 2.1 Hz, 1H), 7.25 (dd, J = 9.2, 4.4 Hz, 1H), 3.85-3.66 (m, 1H), 1.87-1.67 (m, 4H), 1.68-1.55 (m, 1H), 1.38-1.19 (m, 5H), 1.13 (td, J = 12.2, 3.5 Hz, 1H). MS (ESI) m/z: 310 [M + H]⁺. |
| VIII-c-1 | (structure) TFA salt | ¹H NMR (600 MHz, DMSO-$d_6$) δ 8.77 (dd, J = 4.5, 1.6 Hz, 1H), 8.68 (t, J = 4.9 Hz, 1H), 8.36 (d, J = 0.8 Hz, 1H), 8.30 (dd, J = 9.2, 1.6 Hz, 1H), 8.23 (s, 1H), 7.63 (d, J = 0.8 Hz, 1H), 7.46-7.34 (m, 3H), 7.27 (ddd, J = 9.5, 8.2, 1.2 Hz, 1H), 4.59 (dd, J = 4.9, 1.5 Hz, 2H). MS (ESI) m/z: 371 [M + H]⁺. |
| VIII-c-2 | (structure) | ¹H NMR (600 MHz, DMSO-$d_6$) δ 10.15 (s, 1H), 8.79 (dd, J = 4.5, 1.6 Hz, 1H), 8.55 (d, J = 1.0 Hz, 1H), 8.30 (dd, J = 9.2, 1.6 Hz, 1H), 8.24 (s, 1H), 7.81-7.71 (m, 3H), 7.45-7.28 (m, 3H), 7.12 (tt, J = 7.3, 1.2 Hz, 1H). MS (ESI) m/z: 305 [M + H]⁺. |
| VIII-c-3 | (structure) | ¹H NMR (600 MHz, DMSO-$d_6$) δ 8.75 (dd, J = 4.4, 1.5 Hz, 1H), 8.32 (d, J = 0.9 Hz, 1H), 8.28 (dd, J = 9.2, 1.6 Hz, 1H), 8.19 (s, 1H), 8.15 (d, J = 7.9 Hz, 1H), 7.61 (d, J = 0.9 Hz, 1H), 7.36 (dd, J = 9.2, 4.5 Hz, 1H), 3.85-3.67 (m, 1H), 1.89-1.69 (m, 5H), 1.67-1.57 (m, 1H), 1.31 (q, J = 9.8 Hz, 4H), 1.13 (dq, J = 8.1, 3.7 Hz, 1H). MS (ESI) m/z: 311 [M + H]⁺. |

TABLE 7-continued

Structure and characterization of compounds VIII

| No. | Structure | $^1$H NMR and/or MS data |
| --- | --- | --- |
| VIII-d-1 | (TFA salt) | $^1$H NMR (600 MHz, DMSO-$d_6$) δ 8.90 (t, J = 4.9 Hz, 1H), 8.79 (dd, J = 4.4, 1.6 Hz, 1H), 8.56 (t, J = 1.8 Hz, 1H), 8.44 (s, 1H), 8.33 (dd, J = 9.2, 1.6 Hz, 1H), 8.28 (dt, J = 7.8, 1.3 Hz, 1H), 7.90 (dt, J = 7.8, 1.4 Hz, 1H), 7.62 (t, J = 7.8 Hz, 1H), 7.48 (dd, J = 9.2, 4.4 Hz, 1H), 7.40 (td, J = 8.2, 5.9 Hz, 1H), 7.35 (dt, J = 8.0, 1.0 Hz, 1H), 7.25 (ddd, J = 9.6, 8.2, 1.3 Hz, 1H), 4.64 (dd, J = 4.9, 1.4 Hz, 2H). MS (ESI) m/z: 381 [M + H]$^+$. |
| VIII-d-2 | 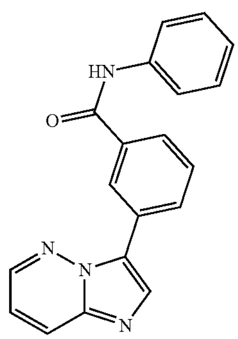 [SMILES: O=C(Nc1ccccc1)c1cccc(-c2cnc3cccnn23)c1] | $^1$H NMR (600 MHz, DMSO-$d_6$) δ 10.36 (s, 1H), 8.70 (dt, J = 4.0, 1.9 Hz, 2H), 8.44-8.34 (m, 2H), 8.26 (dd, J = 9.2, 1.7 Hz, 1H), 7.96 (dt, J = 7.8, 1.4 Hz, 1H), 7.81 (d, J = 7.9 Hz, 2H), 7.69 (t, J = 7.8 Hz, 1H), 7.44-7.27 (m, 3H), 7.13 (t, J = 7.3 Hz, 1H). MS (ESI) m/z: 315 [M + H]$^+$. |
| VIII-d-3 | 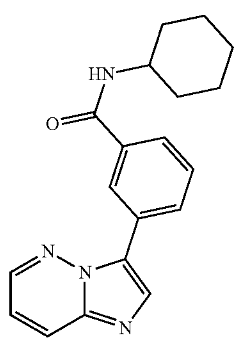 [SMILES: O=C(NC1CCCCC1)c1cccc(-c2cnc3cccnn23)c1] | $^1$H NMR (600 MHz, DMSO-$d_6$) δ 8.72 (dd, J = 4.4, 1.6 Hz, 1H), 8.53 (t, J = 1.8 Hz, 1H), 8.38 (s, 1H), 8.33-8.25 (m, 3H), 7.86 (dt, J = 7.8, 1.3 Hz, 1H), 7.62 (t, J = 7.8 Hz, 1H), 7.39 (dd, J = 9.2, 4.4 Hz, 1H), 3.87-3.72 (m, 1H), 1.87 (d, J = 9.1 Hz, 2H), 1.76 (d, J = 9.0 Hz, 2H), 1.63 (d, J = 13.0 Hz, 1H), 1.43-1.27 (m, 4H), 1.27-1.21 (m, 1H), 1.20-1.09 (m, 1H). MS (ESI) m/z: 321 [M + H]$^+$. |
| VIII-e-1 | (TFA salt) | $^1$H NMR (600 MHz, DMSO-$d_6$) δ 8.86 (t, J = 4.9 Hz, 1H), 8.72 (dd, J = 4.4, 1.6 Hz, 1H), 8.42 (s, 1H), 8.32-8.23 (m, 3H), 8.04-7.96 (m, 2H), 7.44-7.32 (m, 3H), 7.25 (ddd, J = 9.5, 8.2, 1.2 Hz, 1H), 4.63 (dd, J = 4.9, 1.4 Hz, 2H). MS (ESI) m/z: 381 [M + H]$^+$. |

TABLE 7-continued

Structure and characterization of compounds VIII

| No. | Structure | ¹H NMR and/or MS data |
|---|---|---|
| VIII-e-2 | 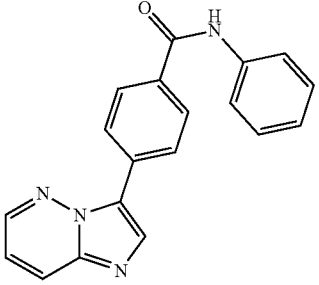<br>TFA salt | ¹H NMR (600 MHz, DMSO-d$_6$) δ 10.33 (s, 1H), 8.79 (dd, J = 4.4, 1.6 Hz, 1H), 8.53 (s, 1H), 8.42-8.28 (m, 3H), 8.17-8.06 (m, 2H), 7.85-7.74 (m, 2H), 7.46 (dd, J = 9.2, 4.4 Hz, 1H), 7.41-7.34 (m, 2H), 7.12 (tt, J = 7.3, 1.2 Hz, 1H). MS (ESI) m/z: 315 [M + H]$^+$. |
| VIII-e-3 | 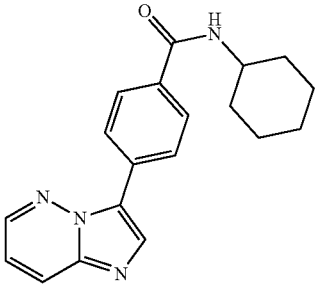<br>TFA salt | ¹H NMR (600 MHz, DMSO-d$_6$) δ 8.77 (dd, J = 4.4, 1.6 Hz, 1H), 8.48 (s, 1H), 8.32 (dd, J = 9.2, 1.6 Hz, 1H), 8.29-8.24 (m, 3H), 8.08-7.91 (m, 2H), 7.44 (dd, J = 9.2, 4.5 Hz, 1H), 3.80 (dt, J = 7.3, 3.7 Hz, 1H), 1.85 (dt, J = 7.9, 3.5 Hz, 2H), 1.81-1.69 (m, 2H), 1.63 (dd, J = 12.3, 4.0 Hz, 1H), 1.39-1.27 (m, 4H), 1.25-1.05 (m, 1H). MS (ESI) m/z: 321 [M + H]$^+$. |
| VIII-f-1 | 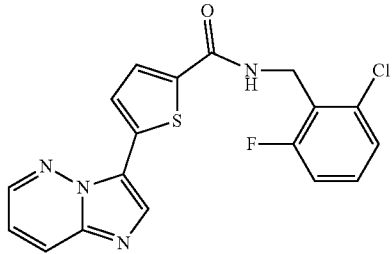<br>TFA salt | ¹H NMR (600 MHz, DMSO-d$_6$) δ 8.83 (t, J = 4.9 Hz, 1H), 8.79 (dd, J = 4.5, 1.5 Hz, 1H), 8.46 (s, 1H), 8.28 (dd, J = 9.1, 1.6 Hz, 1H), 7.90-7.84 (m, 2H), 7.44-7.33 (m, 3H), 7.27 (ddd, J = 9.6, 8.3, 1.3 Hz, 1H), 4.61 (dd, J = 5.0, 1.5 Hz, 2H). MS (ESI) m/z: 387 [M + H]$^+$. |
| VIII-f-2 | 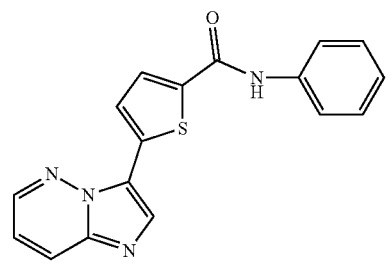<br>TFA salt | ¹H NMR (600 MHz, DMSO-d$_6$) δ 10.28 (s, 1H), 8.81 (dd, J = 4.5, 1.6 Hz, 1H), 8.50 (s, 1H), 8.30 (dd, J = 9.2, 1.6 Hz, 1H), 8.13 (d, J = 4.0 Hz, 1H), 7.96 (d, J = 4.0 Hz, 1H), 7.76 (dd, J = 8.6, 1.2 Hz, 2H), 7.46-7.31 (m, 3H), 7.12 (t, J = 7.3 Hz, 1H). MS (ESI) m/z: 321 [M + H]$^+$. |
| VIII-f-3 | 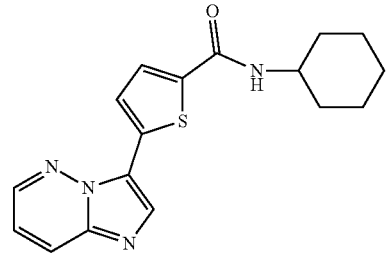 [SMILES: O=C(NC1CCCCC1)c1ccc(-c2cnc3cccnn23)s1] | ¹H NMR (600 MHz, DMSO-d$_6$) δ 8.78 (dd, J = 4.5, 1.6 Hz, 1H), 8.43 (s, 1H), 8.33-8.20 (m, 2H), 7.87 (q, J = 4.0 Hz, 2H), 7.36 (dd, J = 9.2, 4.5 Hz, 1H), 3.74 (d, J = 10.1 Hz, 1H), 1.85 (d, J = 7.3 Hz, 2H), 1.75 (s, 2H), 1.62 (d, J = 12.9 Hz, 1H), 1.38-1.24 (m, 4H), 1.14 (t, J = 6.5 Hz, 1H). MS (ESI) m/z: 327 [M + H]$^+$. |

TABLE 7-continued
Structure and characterization of compounds VIII
| No. | Structure | ¹H NMR and/or MS data |
|---|---|---|
| VIII-g-1 | 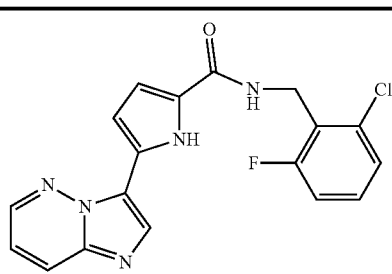<br>TFA salt | ¹H NMR (600 MHz, DMSO-$d_6$) δ 11.85 (s, 1H), 8.66 (dd, J = 4.5, 1.6 Hz, 1H), 8.45 (t, J = 5.1 Hz, 1H), 8.43 (s, 1H), 8.18 (dd, J = 9.2, 1.6 Hz, 1H), 7.43-7.36 (m, 1H), 7.36-7.32 (m, 1H), 7.27-7.23 (m, 2H), 7.11-6.90 (m, 2H), 4.60 (d, J = 5.1 Hz, 2H). MS (ESI) m/z: 370 [M + H]⁺. |
The compounds of formula IX:
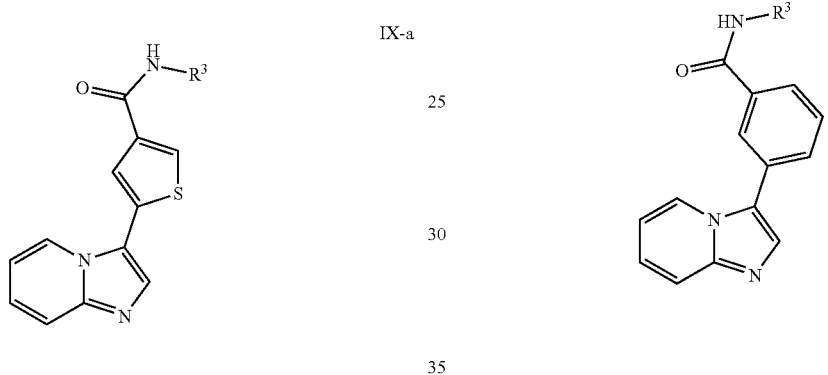
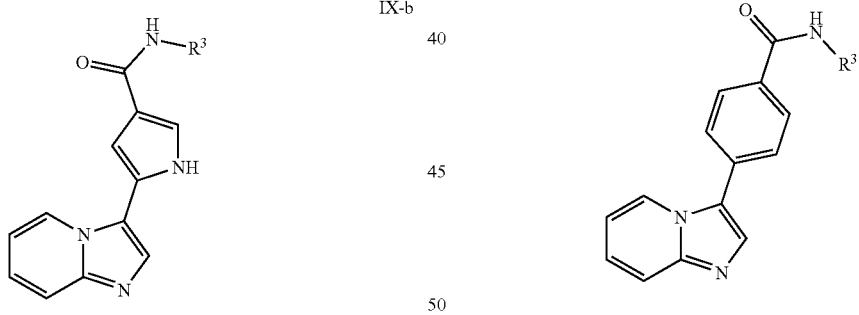
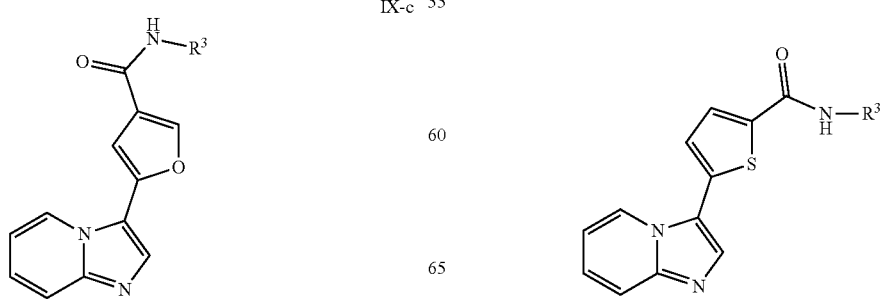

-continued

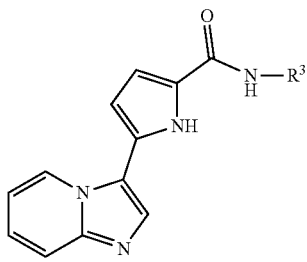

Compound IX was synthesized by a method similar to that for the synthesis of compound I.

The synthesis of the compounds of examples is described in detail below.

Using compound IX-g

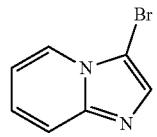

(CAS: 4926-47-0, Bide, Shanghai), boric acid or borate and the corresponding R³—NH² as raw materials, compounds IX-a-1~IX-g-1 were obtained with a reference to the preparation method of compound I-a-1.

The table below lists the specific compounds and structure identification data.

TABLE 8

Structure and characterization of compounds IX

| No. | Structure | ¹H NMR and/or MS data |
|---|---|---|
| IX-a-1 | 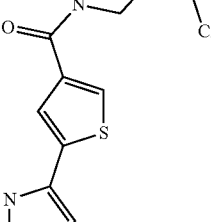<br>TFA salt | ¹H NMR (600 MHz, DMSO-d6) δ 8.78-8.69 (m, 1H), 8.43-8.34 (m, 1H), 8.25 (s, 1H), 8.19 (s, 1H), 7.93 (d, J = 1.4 Hz, 1H), 7.87 (d, J = 9.1 Hz, 1H), 7.68 (d, J = 8.4 Hz, 1H). 7.42-7.41 (m, 1H), 7.37-7.37 (m, 2H), 7.28-7.26 (m, 1H), 4.61 (dd, J = 4.8, 1.4 Hz, 2H). MS (ESI) m/z: 386[M + H]⁺. |
| IX-a-2 | 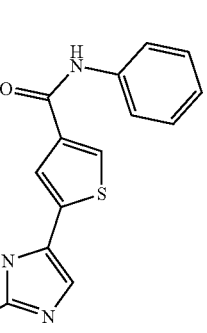 | ¹H NMR (600 MHz, DMSO-d₆) δ 10.24 (s, 1H), 8.87 (d, J = 6.8 Hz, 1H), 8.60 (d, J = 1.4 Hz, 1H), 8 40 (s, 1H), 8.10 (d, J = 1.4 Hz, 1H), 7.98 (d, J = 9.0 Hz, 1H), 7.85 (ddd, J = 9.1, 6.8, 1.1 Hz, 1H), 7.79-7.75 (m, 2H), 7.45 (td, J = 6.9, 0.9 Hz, 1H), 7.41-7.34 (m, 2H), 7.13 (tt, J = 7.4, 1.2 Hz, 1H). MS (ESI) m/z: 320[M + H]⁺. |
| IX-b-1 | 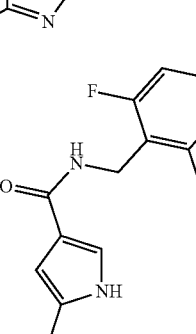 | ¹H NMR (600 MHz, DMSO-d6) δ 12.00 (s, 1H), 8 73 (d, J = 6.9 Hz, 1H), 8.18 (t, J = 5.0 Hz, 1H), 8.15 (s, 1H), 7.92 (d, J = 9.1 Hz, 1H), 7.78 (dd, J = 9.0, 6.9 Hz, 1H), 7.67-7.61 (m, 1H), 7.43-7.38 (m, 2H), 7.37-7.34 (m, 1H), 7.25 (t, J = 8 8 Hz, 1H), 7.12 (t, J = 2.2 Hz, 1H), 4.58 (d, J = 4.8 Hz, 2H). MS (ESI) m/z: 369[M + H]⁺. |

TABLE 8-continued

Structure and characterization of compounds IX

| No. | Structure | ¹H NMR and/or MS data |
|---|---|---|
| IX-b-2 | 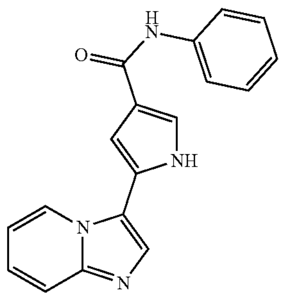 [SMILES: O=C(Nc1ccccc1)c1c[nH]c(-c2cnc3ccccn23)c1] | MS (ESI) m/z: 303[M + H]⁺. |
| IX-c-1 | 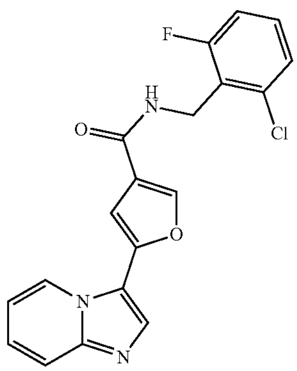 [SMILES: O=C(NCc1c(F)cccc1Cl)c1coc(-c2cnc3ccccn23)c1] | ¹H NMR (600 MHz, DMSO-d6) δ 8.66 (dt, J = 6.9, 1.2 Hz, 1H), 8.53 (t, J = 4.9 Hz, 1H), 8.36 (d, J = 0.8 Hz, 1H), 7.97 (s, 1H), 7.71 (dt, J = 9.1, 1.2 Hz, 1H), 7.45-7.36 (m, 3H), 7.33 (d, J = 0.8 Hz, 1H), 7.28 (ddd, J = 9.6, 8.2, 1.3 Hz, 1H), 7.10 (td, J = 6.9, 1.3 Hz, 1H), 4.60 (dd, J = 5.0, 1.5 Hz, 2H). MS (ESI) m/z: 370[M + H]⁺. |
| IX-c-2 | 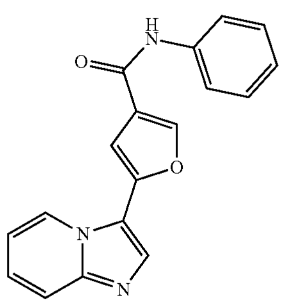 [SMILES: O=C(Nc1ccccc1)c1coc(-c2cnc3ccccn23)c1] | ¹H NMR (600 MHz, DMSO-d6) δ 10.04 (s, 1H), 8.75 (dt, J = 6.8, 1.2 Hz, 1H), 8.55 (d, J = 0.8 Hz, 1H), 8.04 (s, 1H), 7.78-7.70 (m, 3H), 7.46 (d, J = 0.8 Hz, 1H), 7.43-7.34 (m, 3H), 7.19-7.05 (m, 2H). MS (ESI) m/z: 304[M + H]⁺. |
| IX-d-1 | 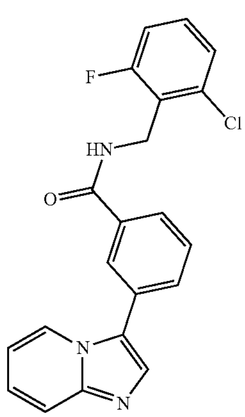 [SMILES: O=C(NCc1c(F)cccc1Cl)c1cccc(-c2cnc3ccccn23)c1] | ¹H NMR (600 MHz, DMSO-d6) δ 8.85 (t, J = 4.9 Hz, 1H), 8.59 (dt, J = 7.0, 1.2 Hz, 1H), 8.02-7.94 (m, 2H), 7.83 (s, 1H), 7.76-7.68 (m, 2H), 7.64 (dt, J = 9.0, 1.2 Hz, 1H), 7.39-7.33 (m, 1H), 7.32-7.27 (m, 2H), 7.21 (ddd, J = 9.6, 8.2, 1.3 Hz, 1H), 6.96 (td, J = 6.8, 1.3 Hz, 1H), 4.58 (dd, J = 4.9, 1.4 Hz, 2H). MS (ESI) m/z: 380[M + H]⁺. |

TABLE 8-continued

Structure and characterization of compounds IX

| No. | Structure | ¹H NMR and/or MS data |
| --- | --- | --- |
| IX-d-2 | 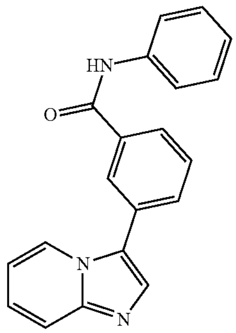 [SMILES: O=C(Nc1ccccc1)c1cccc(-c2cnc3ccccn23)c1] | MS (ESI) m/z: 314[M + H]⁺. |
| IX-e-1 | 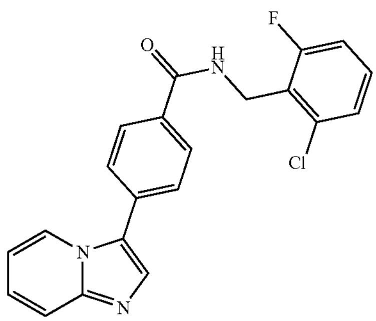 [SMILES: O=C(NCc1c(F)cccc1Cl)c1ccc(-c2cnc3ccccn23)cc1] | ¹H NMR (600 MHz, DMSO-d6) δ 8.90 (t, J = 4.9 Hz, 1H), 8.58 (dt, J = 6.9, 1.2 Hz, 1H), 8.11 (t, J = 1.8 Hz, 1H), 7.93-7.88 (m, 1H), 7.85-7.78 (m, 2H), 7.70-7.58 (m, 2H), 7.40 (td, J = 8.2, 6.0 Hz, 1H), 7.36-7.30 (m, 2H), 7.25 (ddd, J = 9.6, 8.2, 1.2 Hz, 1H), 6.99 (td, J = 6.8, 1.2 Hz, 1H), 4.63 (dd, J = 4 9, 1.4 Hz, 2H). MS (ESI) m/z: 380[M + H]⁺. |
| IX-e-2 | 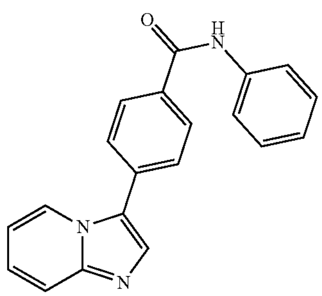 [SMILES: O=C(Nc1ccccc1)c1ccc(-c2cnc3ccccn23)cc1] | ¹H NMR (600 MHz, DMSO-d6) δ 10.34 (s, 1H), 8.68 (dt, J = 6.9, 1.2 Hz, 1H), 8.23 (t, J = 1.8 Hz, 1H), 8.00 (dt, J = 7.8, 1.4 Hz, 1H), 7.91-7.88 (m, 2H), 7.82-7.78 (m, 2H), 7.74-7.66 (m, 2H), 7.41-7.30 (m, 3H), 7.16-7.06 (m, 1H), 7.01 (td, J = 6.8, 1.3 Hz, 1H). MS (ESI) m/z: 314[M + H]⁺. |
| IX-f-1 | 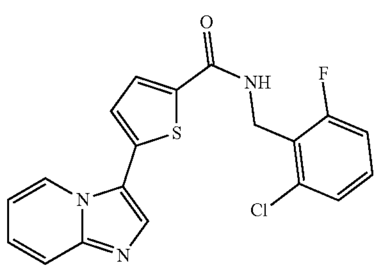 [SMILES: O=C(NCc1c(F)cccc1Cl)c1ccc(-c2cnc3ccccn23)s1] | ¹H NMR (600 MHz, DMSO-d6) δ 8.94 (d, J = 4.9 Hz, 1H), 8.76 (d, J = 7.0 Hz, 1H), 8 13 (d, J = 5.1 Hz, 1H), 7.92 (d, J = 3.9 Hz, 1H), 7.81 (d, J = 9.1 Hz, 1H), 7.60-7.54 (m, 2H), 7.42 (dd, J = 8.3, 6.1 Hz, 1H), 7.36 (m, 1H), 7.30-7.20 (m, 2H), 4.61 (d, J = 4.9 Hz, 2H). MS (ESI) m/z: 386[M + H]⁺. |
| IX-f-2 | 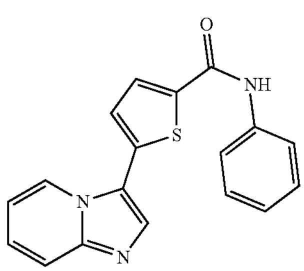 [SMILES: O=C(Nc1ccccc1)c1ccc(-c2cnc3ccccn23)s1] | MS (ESI) m/z: 320[M + H]⁺. |

TABLE 8-continued
Structure and characterization of compounds IX
| No. | Structure | ¹H NMR and/or MS data |
|---|---|---|
| IX-g-1 | 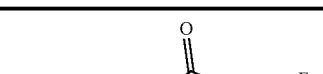 | MS (ESI) m/z: 369[M + H]⁺. |
The compounds of formula X:
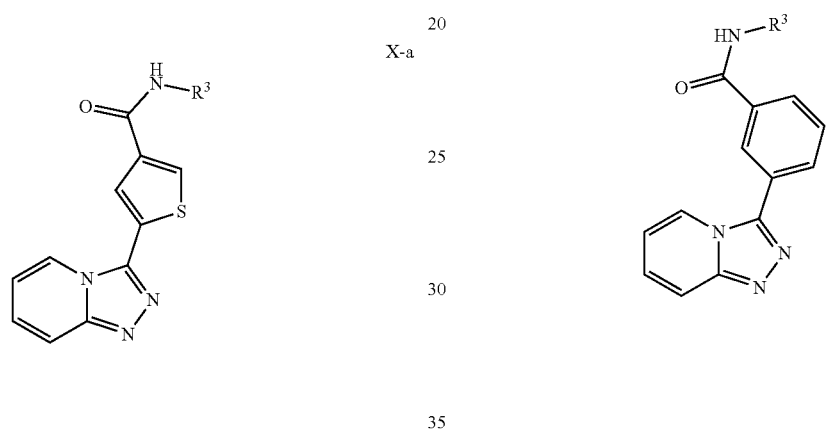
X-a
X-b
X-d
X-e
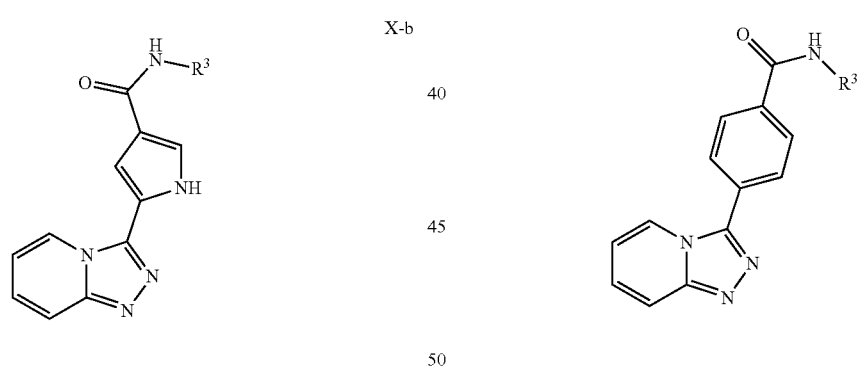
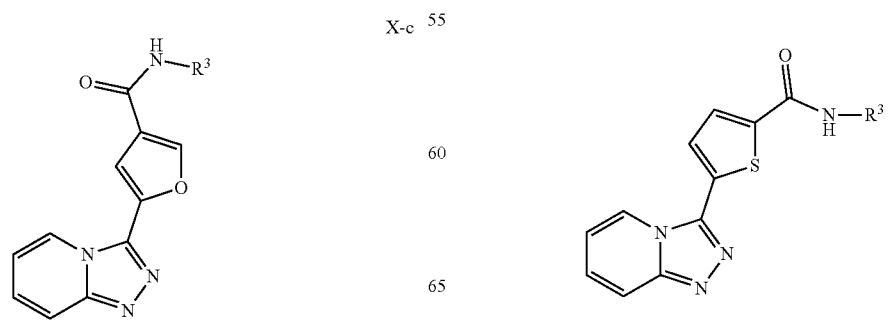
X-c
X-f

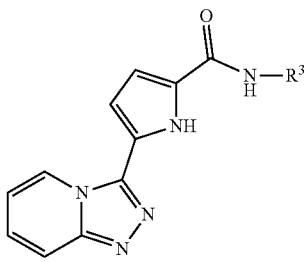

Compound X was synthesized by a method similar to that for the synthesis of compound I.

The synthesis of the compounds of examples is described in detail below.

Using compound X-g

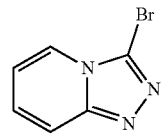

(CAS: 4922-68-3, Sundia, Shanghai), boric acid or borate and the corresponding $R^3$—$NH^2$ as raw materials, compounds X-a-1~X-g-1 were obtained with a reference to the preparation method of compound I-a-1.

The table below lists the specific compounds and structure identification data.

TABLE 9

Structure and characterization of compounds X

| No. | Structure | $^1$H NMR and/or MS data |
|---|---|---|
| X-a-1 | 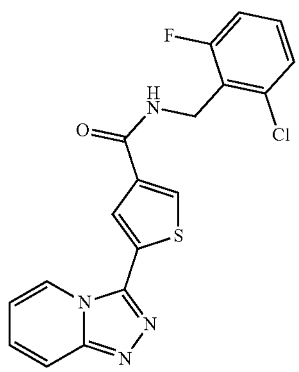 [SMILES: O=C(NCc1c(F)cccc1Cl)c1csc(-c2nnc3ccccn23)c1] | $^1$H NMR (600 MHz, Methanol-$d_4$) δ 8.72 (dd, J = 7.1, 1.1 Hz, 1H), 8.35 (d, J = 1.3 Hz, 1H), 8.17 (d, J = 1.3 Hz, 1H), 7.85 (dt, J = 9.3, 1.1 Hz. 1H), 7.56 (ddd, J = 9.3, 6.6, 1.0 Hz, 1H), 7.40-7.35 (m, 1H), 7.34-7.32 (m, 1H), 7.20-7.15 (m, 2H), 4.79 (dd, J = 1.6 Hz, 2H). MS (ESI) m/z: 387[M + H]$^+$. |
| X-a-2 | 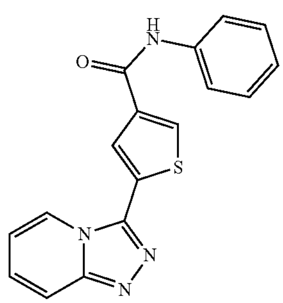 [SMILES: O=C(Nc1ccccc1)c1csc(-c2nnc3ccccn23)c1] | MS (ESI) m/z: 321[M + H]$^+$. |
| X-b-1 | 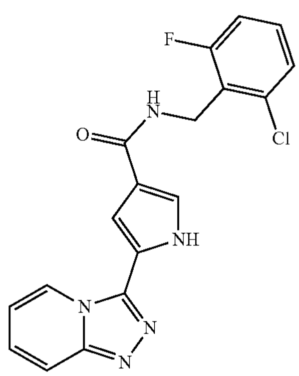 [SMILES: O=C(NCc1c(F)cccc1Cl)c1c[nH]c(-c2nnc3ccccn23)c1] | MS (ESI) m/z: 370[M + H]$^+$. |

TABLE 9-continued

Structure and characterization of compounds X

| No. | Structure | ¹H NMR and/or MS data |
|---|---|---|
| X-b-2 | 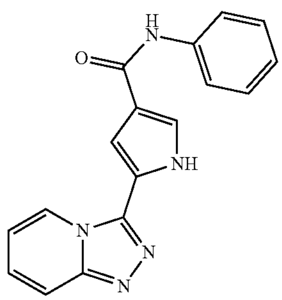 [SMILES: O=C(Nc1ccccc1)c1c[nH]c(-c2nnc3ccccn23)c1] | MS (ESI) m/z: 304[M + H]⁺. |
| X-c-1 | 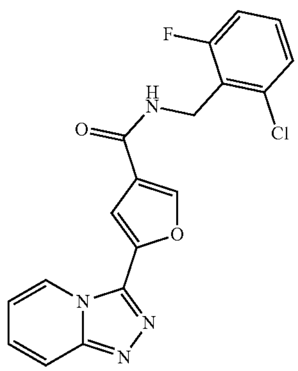 [SMILES: O=C(NCc1c(F)cccc1Cl)c1coc(-c2nnc3ccccn23)c1] | ¹H NMR (600 MHz, DMSO-d6) δ 8.73 (dt, J = 6.9, 1.2 Hz, 1H), 8.66 (t, J = 4.9 Hz, 1H), 8.50 (d, J = 0.8 Hz, 1H), 7.90 (dt, J = 9.2, 1.1 Hz, 1H), 7.68 (d, J = 0.8 Hz, 1H), 7.49 (ddd, J = 9.2, 6.6, 1.1 Hz, 1H), 7.43 (td, J = 8.2, 6.0 Hz, 1H), 7.39-7.36 (m, 1H), 7.28 (ddd, J = 9.5, 8.2, 1.2 Hz, 1H), 7.15 (td, J = 6.8, 1.1 Hz, 1H), 4.61 (dd, J = 4.9, 1.5 Hz, 2H). MS (ESI) m/z: 371 [M + H]⁺. |
| X-c-2 | 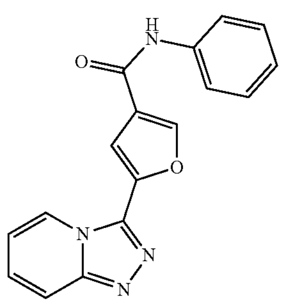 [SMILES: O=C(Nc1ccccc1)c1coc(-c2nnc3ccccn23)c1] | MS (ESI) m/z: 305[M + H]⁺. |
| X-d-1 | 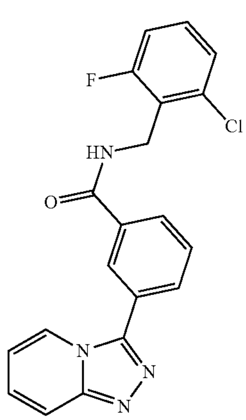 [SMILES: O=C(NCc1c(F)cccc1Cl)c1cccc(-c2nnc3ccccn23)c1] | ¹H NMR (600 MHz, DMSO-d₆) δ 8.99 (t, J = 4.9 Hz, 1H), 8.59 (dt, J = 7.1, 1.1 Hz, 1H), 8.35 (t, J = 1.8 Hz, 1H), 8.06 (dp, J = 7.8, 1.3 Hz, 2H), 7.88 (dt, J = 9.3, 1.2 Hz, 1H), 7.72 (t, J = 7.8 Hz, 1H), 7.45 (ddd, J = 9.3, 6.5, 11 Hz, 1H), 7.40 (td, J = 8.2, 6.0 Hz, 1H), 7.35 (dt, J = 8.1, 1.0 Hz, 1H), 7.25 (ddd, J = 9.5, 8.2, 1.2 Hz, 1H), 7.06 (td, J = 6.8, 1.1 Hz, 1H), 4.64 (dd, J = 3.9, 1.4 Hz, 2H). MS (ESI) m/z: 381[M + H]⁺. |

TABLE 9-continued

Structure and characterization of compounds X

| No. | Structure | ¹H NMR and/or MS data |
|---|---|---|
| X-d-2 | 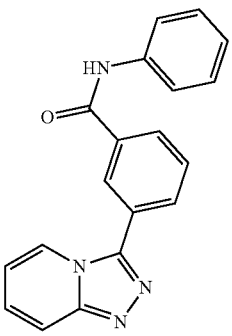 [SMILES: O=C(Nc1ccccc1)c1cccc(-c2nnc3ccccn23)c1] | ¹H NMR (600 MHz, DMSO-d₆) δ 10.43 (s, 1H), 8.70 (dt, J = 7.1, 1.2 Hz, 1H), 8.47 (t, J = 1.8 Hz, 1H), 8.15 (ddt, J = 16.1, 7.7, 1.4 Hz, 2H), 7.90 (dt, J = 9.2, 1.2 Hz, 1H), 7.83-7.78 (m, 3H), 7.48 (ddd, J = 9.2, 6.5, 1.1 Hz, 1H), 7.41-7.35 (m, 2H), 7.16-7.11 (m, 1H), 7.08 (td, J = 6.8, 1.1 Hz, 1H). MS (ESI) m/z: 315[M + H]⁺. |
| X-d-3 | 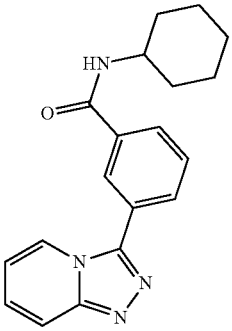<br>TFA salt | ¹H NMR (600 MHz, DMSO-d₆) δ 8.68 (dt, J = 6.9, 1.1 Hz, 1H), 8.45-8.41 (m, 1H), 8.34 (t, J = 1.8 Hz, 1H), 8.08 (dt, J = 7.9, 1.4 Hz, 1H), 8.05 (dt, J = 7.7, 1.4 Hz, 1H), 7.96 (dt, J = 9.2, 1.1 Hz, 1H), 7.74 (t, J = 7.8 Hz, 1H), 7.62 (ddd, J = 9.3, 6.6, 1.1 Hz, 1H), 7.18 (td, J = 6.8, 1.1 Hz, 1H), 3.91-3.72 (m, 1H), 1.92-1.83 (m, 2H), 1.79-1.71 (m, 2H), 1.67-1.57 (m, 1H), 1.41-1.24 (m, 4H), 1.20-1.05 (m, 1H). MS (ESI) m/z: 321[M + H]⁺. |
| X-e-1 | 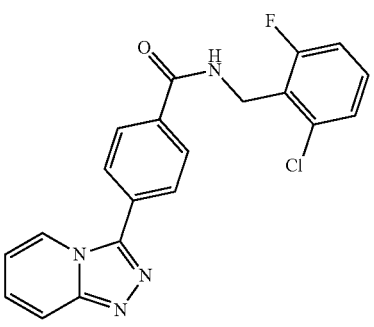 [SMILES: O=C(NCc1c(F)cccc1Cl)c1ccc(-c2nnc3ccccn23)cc1] | ¹H NMR (600 MHz, DMSO-d6) δ 8.99 (t, J = 4.9 Hz, 1H), 8.63 (dt, J = 7.1, 1.2 Hz, 1H), 8.09 (d, J = 8.5 Hz, 2H), 8.04-7.98 (m, 2H), 7.89 (d, J = 9.2 Hz, 1H), 7.46 (ddd, J = 9.3, 6.6, 1.1 Hz, 1H), 7.42 (td, J = 8.2, 6.0 Hz, 1H), 7.36 (dt, J = 8.1, 1.0 Hz, 1H), 7.27 (ddd, J = 9.5, 8.2, 1.3 Hz, 1H), 7.07 (td, J = 6.8, 1.1 Hz. 1H), 4.65 (dd, J = 4.9, 1.5 Hz, 2H). MS (ESI) m/z: 381[M + H]⁺. |
| X-e-2 | 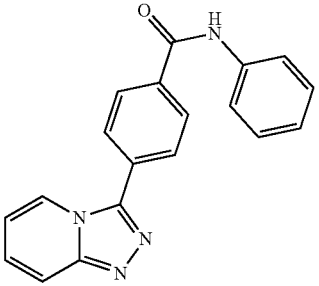 [SMILES: O=C(Nc1ccccc1)c1ccc(-c2nnc3ccccn23)cc1] | MS (ESI) m/z: 315[M + H]⁺. |

TABLE 9-continued

Structure and characterization of compounds X

| No. | Structure | $^1$H NMR and/or MS data |
|---|---|---|
| X-f-1 | (structure) | $^1$H NMR (600 MHz, DMSO-d6) δ 8.99 (t, J = 5.0 Hz, 1H), 8.78 (d, J = 7.0 Hz, 1H), 7.97-7.95 (m, 1H), 7.92 (s, 1H), 7.91-7.89 (m, 1H), 7.53-7.47 (m, 1H), 7.43 (td, J = 8.2, 5.9 Hz, 1H), 7.38 (d, J = 8.0 Hz, 1H), 7.28 (t, J = 8.9 Hz, 1H), 7.15 (t, J = 6.8 Hz, 1H), 4.62 (dd, J = 4.1 Hz, 2H). MS (ESI) m/z: 387[M + H]$^+$. |
| X-f-2 | (structure) | MS (ESI) m/z: 321[M + H]$^+$. |
| X-g-1 | (structure) | MS (ESI) m/z: 370[M + H]$^+$. |

Test Example

Biological Activity Assay:

I. Inhibitory Activity of Compounds on K-RAS

Figure 1:
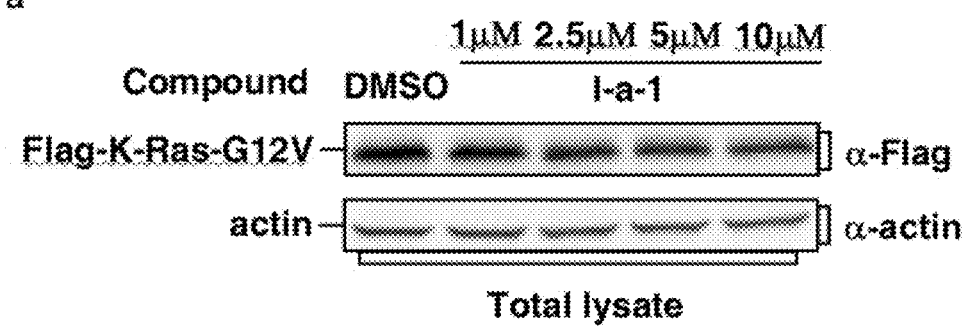
FIG. 1 shows that compound I-a-1 is effective in lowering K-RAS protein levels in cells.
Figure 1:
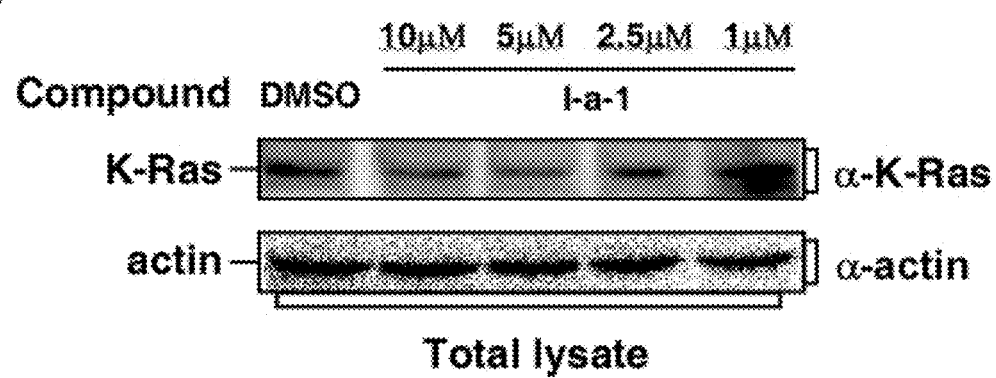

Inhibitory activity of compounds on K-RAS was evaluated by the degradation rate of protein level of administration group relative to control group (Cell Rep 2014, 7, 871-882). Specifically, the Western blot method was used for activity test, the activity data were as shown in Table 6, and the results of representative compounds were as shown in FIG. 1.

The specific method was as follows:

1. Cell plating: SW-620 cells in logarithmic growth phase were inoculated into a 24-well plate at $2\times10^4$/well, and cultured in a 37° C., 5% $CO_2$ incubator.

2. Administering drug to cells: after 24 h of culture, various drug stocks were diluted with RPM1640 medium containing 10% FBS to obtain a drug solution having a final concentration of 10 mM; the original solution in the 24-well plate was discarded, to which was added the obtained drug solution, with the DMSO group as the blank control; after the drug solution was added, the 24-well plate was transferred to the 37° C. $CO_2$ incubator to continue the culture.

3. Detection of K-Ras protein level: after 24 h of administration and culture, the liquid in the well was discarded, the cells were routinely collected, and rinsed twice with 1×PBS, a cell lysate was added to extract the total cellular protein, and the protein concentration was determined by BCA method. 30 μg of the protein sample was taken for SDS-polyacrylamide gel electrophoretic transmembrane, the membrane was blocked sequentially, incubated with K-Ras antibody (1:1000) and internal reference antibody β-actin (1:2000) respectively overnight at 4° C., rinsed with TBST for 5 min×3 times, then incubated with the addition of the corresponding horseradish peroxidase-labeled secondary antibody (1:5000) for 1-2 h, and rinsed with TBST for 5 min×3 times. Finally, chemiluminescence image was acquired using Image Lab software.

4. Calculation of single-point K-Ras protein degradation rate: quantitative and calibration analysis of K-Ras and β-actin were conducted using Image-Lab software, and then the intracellular K-Ras degradation rate was calculated according to the following formula: single-point K-Ras protein degradation rate (%)=(control group−administration group)/control group×100%. The drug with degradation rate ≥20% was selected for soft agar experiment.

The reagents used were formulated as follows:

RPM1640 Medium:

10.4 g of RPM1640 powder and 2.0 g of $NaHCO_3$ were weighed in a 1 L Solvent reservoir, an appropriate amount of ultrapure water was added, then the system was stirred with a magnetic stirrer until completely dissolved, adjusted to pH=7.2-7.4 with 1 mol/L HCl, and finally made up to 1 L with ultrapure water. Then, the obtained solution was sterilized by a 0.22 μm pore size filter, and stored in a refrigerator at 4° C. 10% fetal bovine serum was added to the solution before use.

1×PBS:
8 g of NaCl, 0.2 g of KCl, 1.44 g of $Na_2HPO_4$ and 0.24 g of $KH_2PO_4$ were weighed in a 1 L Solvent reservoir, an appropriate amount of ultrapure water was added, then the system was stirred with a magnetic stirrer until completely dissolved, adjusted to pH=7.2 with 1 mol/L HCl, and finally made up to 1 L with ultrapure water. After autoclaving, the obtained solution was stored at room temperature.

1× Trypsin:
A digestive solution of 0.02% ethylenediaminetetraacetic acid (EDTA) containing 0.25% trypsin was prepared in phosphate buffer, sterilized by a 0.22 μm pore size filter and stored in a refrigerator at 4° C.

Cell Lysate:
50 mL of 1 mol/L Tris-HCl (pH 7.4), 37.5 mL of 4 mol/L NaCl, 2 mL of 0.5 mol/L EDTA and 5 mL of Triton X-100 were pipette in a 1 L Solvent reservoir, which was made up to 1 L with ultrapure water. The obtained solution was taken out in a required buffer amount, and 1 mmol/L PMSF was added therein before use.

4× Loading Buffer:
4 g of SDS, 0.04 g of bromo phenol blue, 6.16 g of DTT were weighed, and 20 mL of 1 mol/L Tris-HCl (pH 6.8), 20 mL of glycerol were pipette in a 100 mL tube, which was made up to 100 mL with ultrapure water. The obtained solution was sub-packed in small tubes and stored at −20° C.

4× Separating Buffer:
84.5 g of Tris and 1.25 g of SDS were weighed in a 500 mL Solvent reservoir, an appropriate amount of ultrapure water was added for complete dissolution, then the obtained solution was adjusted to pH=8.8, finally made up to 500 mL and stored at 4° C.

4× Stacking Buffer:
6.06 g of Tris was weighed, and 4 mL of 10% SDS was pipette in a 100 mL Solvent reservoir, an appropriate amount of ultrapure water was added for complete dissolution, then the obtained solution was adjusted to pH=6.8, finally made up to 100 mL and stored at 4° C.

10× Running Buffer:
30.3 g of Tris, 10 g of SDS and 144 g of glycine were weighed in a 1 L Solvent reservoir, and ultrapure water was added to make up to 1 L.

10× Transfer Buffer:
30.3 g of Tris and 144 g of glycine were weighed in a 1 L Solvent reservoir, and ultrapure water was added to make up to 1 L.

10×TBST:
24.2 g of Tris, 80 g of NaCl were weighed, and 10 mL of Tween-20 was measured in a 1 L Solvent reservoir, an appropriate amount of ultrapure water was added for complete dissolution, then the obtained solution was adjusted to pH=7.6, and finally made up to 1 L.

Blocking Solution:
50 g of BSA was weighed, and 10 mL of 1% $NaN_3$ was pipette in a 1 L Solvent reservoir, TBST was added to make up to 1 L, and the obtained solution was stored at 4° C.

II. In soft agar colony formation experiment, representative compounds could effectively inhibit the growth of cancer cells with RAS positive genetic background while had no significant effect on the growth of cancer cells with RAF mutation genetic background downstream of RAS (FIG. 2).

The specific method was as follows:
1. Bottom Agar
1) 1% agar was formulated, and autoclaved. 1% agar was heated and melted in a boiling water bath before use, and then cooled in a 40° C. water bath (by holding in the bath for at least 30 minutes, the agar was cooled to a temperature of 40° C.); at the same time, 2×DMEM/FBS was placed in a warm bath.
2) A bottom agar with 0.5% agar was prepared by mixing 1% agar with 2×DMEM/FBS in a sterile tube at a volume ratio of 1:1. The mixed solution was added to a 6-well plate rapidly at 1.5 ml per well, shaked slightly, and placed at room temperature for solidification (after solidification, the bottom agar could be stored at 4° C. for 1 week. Before use, it was placed at room temperature for at least 30 minutes to return to room temperature).

2. Upper Agar
1) A mixed solution with a final concentration of 0.3% agar+1×DMEM/FBS was formulated in a sterile tube using 1% agar, 2×DMEM/FBS and sterile water at a temperature of 40° C. The prepared mixed solution was placed in a 40° C. water bath for use.
2) The cells were trypsinized and counted. The cell density was adjusted according to the needs of the experiment.
3) The formulated mixed solution of 0.3% agar+1×DMEM/FBS was taken out of the 40° C. water bath, and the cells were added in the corresponding number, and blown gently till uniform with a gun; then the solution was added onto the solidified bottom agar, 1.5 ml per well.
4) The 6-well plate was placed in a 37° C., 5% $CO_2$ incubator to conduct the culture for 10-30 days, while replenishing fresh medium every 3-6 days, 200 μl per well.

The reagents used were formulated as follows:
1% Agar:
1 g of agar powder was dissolved in 100 ml of sterile water and sterilized for use.

2×DMEM:
13.4 g of DMEM powder and 3.7 g of $NaHCO_3$ were weighed in a 500 ml Solvent reservoir, an appropriate amount of ultrapure water was added, then the system was stirred with a magnetic stirrer until completely dissolved, adjusted to pH=7.2-7.4 with 1 mol/L HCl, and finally made up to 500 ml with ultrapure water. Then, the obtained solution was sterilized by a 0.22 μm pore size filter, and stored in a refrigerator at 4° C. 20% fetal bovine serum was added to the solution before use.

Phosphate Buffer Solution (PBS):
8 g of NaCl, 0.2 g of KCl, 1.44 g of $Na_2HPO_4$ and 0.24 g of $KH_2PO_4$ were weighed in a 1 L Solvent reservoir, an appropriate amount of ultrapure water was added, then the system was stirred with a magnetic stirrer until completely dissolved, adjusted to pH=7.2 with 1 mol/L HCl, and finally made up to 1 L with ultrapure water. After autoclaving, the obtained solution was stored at room temperature.

Trypsin:
A digestive solution of 0.02% ethylenediaminetetraacetic acid (EDTA) containing 0.25% trypsin was prepared in phosphate buffer, sterilized by a 0.22 μm pore size filter and stored in a refrigerator at 4° C.

III. In a nude mouse xenograft tumor experiment, compound I-a-1 could effectively inhibit the growth of cancer cells with RAS positive genetic background in nude mice, and had a good dose-dependence (FIG. 3, N=10/group).

The specific method was as follows:
1. 4-5 weeks old nude mice were subcutaneously injected with a SW620 cell suspension with a cell number controlled at about $5\times10^6$.
2. The tumor-bearing condition was observed after two to three days, and the mice were administered when the tumor volume was about 150 $mm^3$.
3. The initial volume of tumor was recorded, the mice were randomly divided into three groups: the control group, the drug-administered group of 40 mg/kg once a day, and the drug-administered group of 40 mg/kg twice a day, and it was ensured that the initial tumor volume did not differ greatly.

4. The mice were injected intravenously regularly with drug or control solvent every day, and the daily tumor volume was recorded.

5. The mice were continuously administered for 10 days, and the changes in tumor volume of the drug-administered group and the control group were observed.

6. 10 days later, eyeball blood was taken from all mice, and blood samples were kept for subsequent testing. After the mice were killed, the subcutaneously growing tumors were completely taken out, the tumor weights were recorded, and the tumors were stored in liquid nitrogen for subsequent testing.

TABLE 10

Degradation rate of compounds on Ras protein

| No. | Degradation rate of compounds at 10 μM on Ras protein (%) |
|---|---|
| I-a-1 | 52% |
| I-a-8 | 20% |
| I-a-9 | 30% |
| I-a-11 | 30% |
| I-b-1 | 50% |
| I-b-2 | 56% |
| I-c-1 | 11% |
| I-d-1 | 2% |
| I-e-2 | 12% |
| I-f-1 | 20% |
| I-f-2 | 25% |
| I-g-1 | 30% |
| II-b-1 | 52% |
| II-b-2 | 50% |
| II-d-1 | 2% |
| II-e-1 | 15% |
| III-a-1 | 21% |
| III-a-2 | 9% |
| III-a-3 | 60% |
| III-a-4 | 60% |
| III-b-1 | 35% |
| III-c-3 | 16% |
| III-d-2 | 18% |
| III-d-3 | 27% |
| III-e-1 | 40% |
| III-e-2 | 40% |
| III-e-7 | 38% |
| III-e-8 | 44% |
| III-e-12 | 29% |
| III-e-14 | 27% |
| III-e-19 | 32% |
| III-e-22 | 31% |
| III-e-23 | 39% |
| III-e-26 | 26% |
| III-e-29 | 30% |
| III-f-1 | 60% |
| III-f-3 | 6% |
| III-f-4 | 19% |
| III-f-6 | 15% |
| III-f-10 | 18% |
| III-f-11 | 13% |
| III-f-13 | 16% |
| III-f-15 | 14% |
| III-f-16 | 15% |
| III-f-17 | 19% |
| III-f-18 | 15% |
| III-f-24 | 13% |
| III-f-27 | 14% |
| III-f-31 | 45% |
| III-f-32 | 60% |
| III-f-34 | 60% |
| III-f-35 | 50% |
| III-f-37 | 35% |
| III-f-38 | 50% |
| III-f-39 | 60% |
| III-f-40 | 30% |
| III-f-41 | 60% |
| III-f-42 | 70% |
| III-f-43 | 40% |
| III-f-44 | 70% |
| III-f-45 | 50% |
| III-f-46 | 60% |
| III-f-47 | 50% |
| III-f-48 | 60% |
| III-f-49 | 50% |
| III-f-50 | 40% |
| III-f-51 | 70% |
| III-f-52 | 35% |
| III-f-53 | 50% |
| III-f-54 | 50% |
| III-f-55 | 25% |
| III-f-56 | 70% |
| III-f-57 | 70% |
| III-f-58 | 75% |
| III-f-59 | 60% |
| III-f-60 | 65% |
| III-f-61 | 50% |
| III-f-62 | 70% |
| III-g-4 | 12% |
| III-h-1 | 14% |
| III-h-3 | 18% |
| III-h-4 | 41% |
| III-h-5 | 16% |
| IV-a-1 | 10% |
| IV-a-2 | 50% |
| IV-a-3 | 35% |
| IV-c-1 | 30% |
| IV-c-2 | 50% |
| IV-e-1 | 30% |
| IV-e-2 | 20% |
| IV-e-3 | 40% |
| IV-f-1 | 10% |
| VI-a-1 | 20% |
| VI-a-2 | 30% |
| VI-d-1 | 30% |
| VI-d-2 | 30% |
| VII-a-1 | 5% |
| VII-a-2 | 60% |
| VII-a-3 | 30% |
| VII-b-1 | 20% |
| VII-b-2 | 20% |
| VII-b-3 | 10% |
| VII-e-1 | 30% |
| VII-e-2 | 20% |
| VII-e-3 | 30% |
| VII-f-1 | 25% |
| VII-f-2 | 30% |
| VII-f-3 | 20% |
| VIII-a-1 | 40% |
| VIII-a-2 | 60% |
| VIII-a-3 | 50% |
| VIII-b-1 | 20% |
| VIII-b-2 | 10% |
| VIII-b-3 | 2% |
| VIII-c-1 | 12% |
| VIII-c-2 | 10% |
| VIII-d-1 | 2% |
| VIII-e-3 | 20% |
| VIII-f-3 | 15% |
| IX-c-1 | 40% |
| IX-c-2 | 40% |
| IX-d-1 | 30% |
| IX-e-1 | 40% |
| IX-e-2 | 50% |
| IX-f-1 | 50% |
| X-c-1 | 10% |
| X-e-1 | 10% |
| X-f-1 | 20% |

The invention claimed is:

1. A compound, which is:

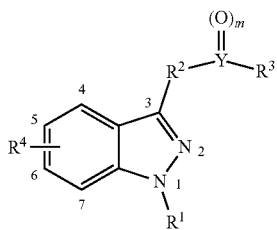

wherein, $R^1$ is selected from H or unsubstituted methyl;
$R^2$ is selected from:
1) formula 1,

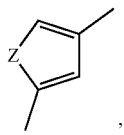

wherein Z is selected from S, O or NH;
2) formula 2,

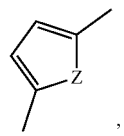

wherein Z is selected from S or NH;
3) formula 3,

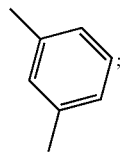

or
4) formula 4,

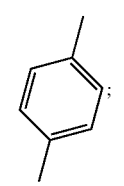

Y is C;
m=1;
$R^3$ is selected from:
1) formula (a),

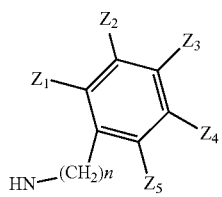

wherein, n=0 or 1,
when n=0,
$Z_2$ is selected from either chloro or trifluoromethyl, and $Z_1$, $Z_3$, $Z_4$ and $Z_5$ are H; or,
$Z_3$ is selected from methyl, methoxy, isopropoxy, fluoro or dimethylamino, and $Z_1$, $Z_2$, $Z_4$ and $Z_5$ are H; or
$Z_1$, $Z_2$, $Z_3$, $Z_4$ and $Z_5$ are all H;
when n=1,
$Z_1$ and $Z_5$ each are independently selected from fluoro or chloro, and $Z_2$, $Z_3$ and $Z_4$ are H; or,
both of $Z_2$ and $Z_3$ are chloro, and $Z_1$, $Z_4$ and $Z_5$ are H; or,
both of $Z_1$ and $Z_3$ are methoxy, and $Z_2$, $Z_4$ and $Z_5$ are H; or,
$Z_1$ and $Z_4$ each are independently selected from fluoro or trifluoromethyl, and $Z_2$, $Z_3$ and $Z_5$ are H; or,
$Z_3$ is selected front chloro or fluoro, and $Z_1$, $Z_3$, $Z_4$, and $Z_5$ are H; or,
$Z_2$ is Selected from trifluoromethyl, and $Z_1$, $Z_3$, $Z_4$ and $Z_5$ are H; or,
$Z_1$, $Z_2$, $Z_3$, $Z_4$ and $Z_5$ are all H;
2) formula (b),

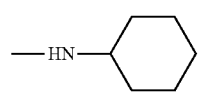

or —NH-cyclopropyl;
3) HN-heteroaryl, wherein said heteroaryl is selected from 2-methyl-pyrid-5-yl or pyrid-3-yl;
4) heterocyclyl, wherein said heterocyclyl is selected from unsubstituted 4-methylpiperazin-1-yl or unsubstituted morpholin-4-yl, or
5) —NH—$C_2H_4$—$R_6$, wherein $R_6$ is selected from phenyl or 4-fluorophenyl; and $R^4$ is selected from H, fluoro, chloro, bromo or unsubstituted amino, and wherein:
when Z is NH then $R^4$ is not fluoro, chloro, or bromo.

2. A compound according to claim 1, which is selected from:
| No. | Structure |
|---|---|
| I-a-1 | 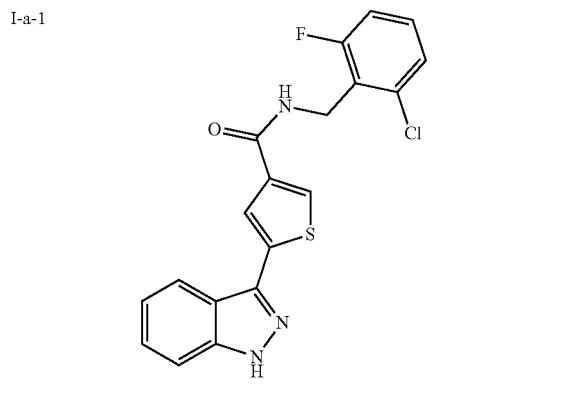 |
| I-a-2 | 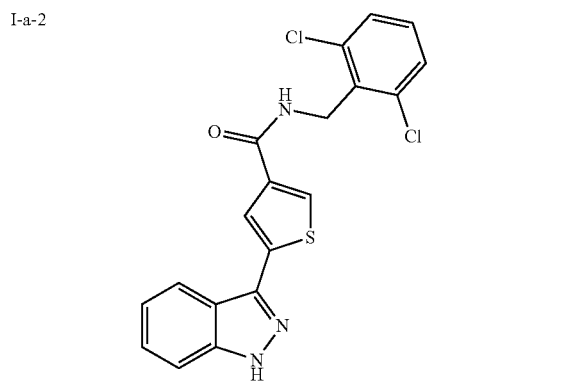 |
| I-a-3 | 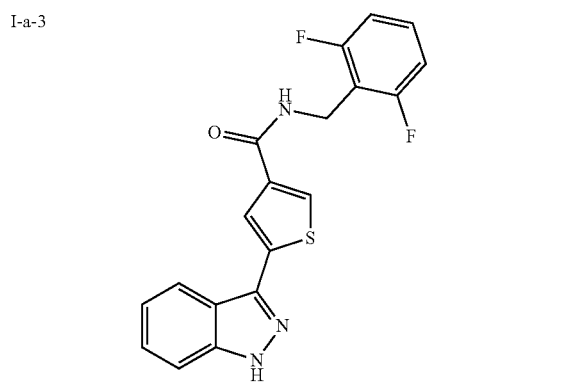 |
-continued
| No. | Structure |
|---|---|
| I-a-4 | 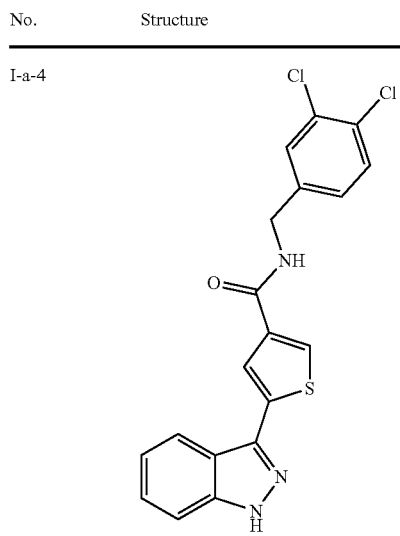 |
| I-a-5 | 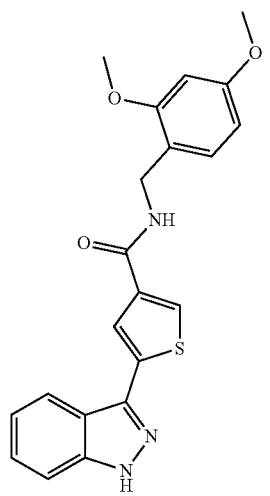 [SMILES: COc1ccc(CNC(=O)c2csc(-c3n[nH]c4ccccc34)c2)c(OC)c1] |
| I-a-6 | 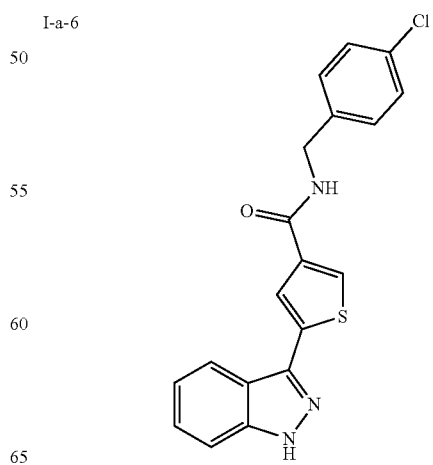 |

| No. | Structure |
|---|---|
| I-a-7 | 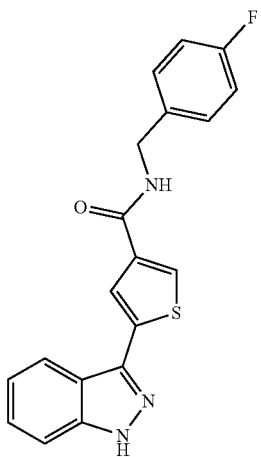 [SMILES: O=C(NCc1ccc(F)cc1)c1csc(-c2n[nH]c3ccccc23)c1] |
| I-a-8 | 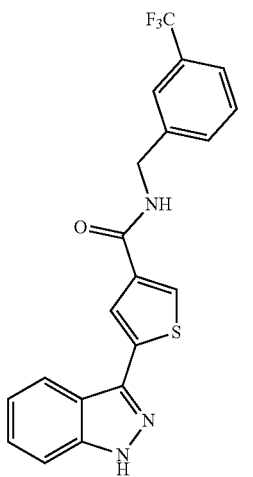 [SMILES: O=C(NCc1cccc(C(F)(F)F)c1)c1csc(-c2n[nH]c3ccccc23)c1] |
| I-a-9 | 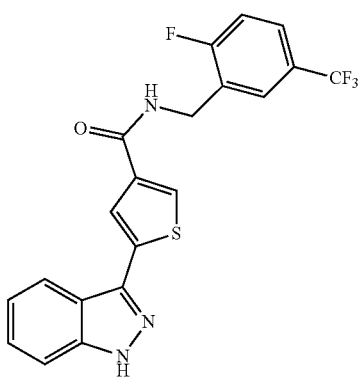 [SMILES: O=C(NCc1cc(C(F)(F)F)ccc1F)c1csc(-c2n[nH]c3ccccc23)c1] |
| No. | Structure |
|---|---|
| I-a-10 | 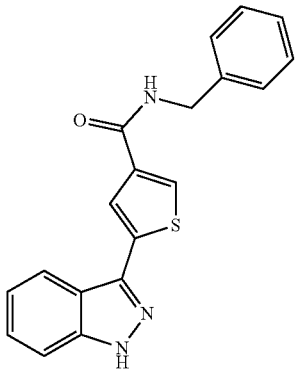 [SMILES: O=C(NCc1ccccc1)c1csc(-c2n[nH]c3ccccc23)c1] |
| I-a-11 | 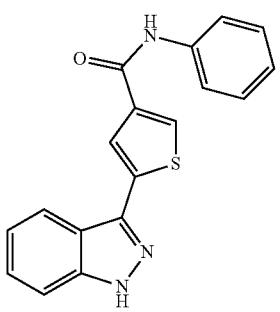 [SMILES: O=C(Nc1ccccc1)c1csc(-c2n[nH]c3ccccc23)c1] |
| I-a-12 | 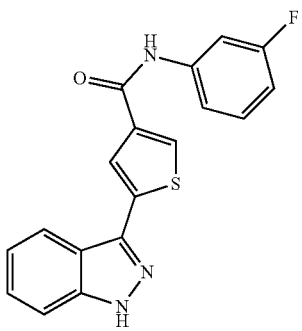 [SMILES: O=C(Nc1cccc(F)c1)c1csc(-c2n[nH]c3ccccc23)c1] |
| I-a-13 | 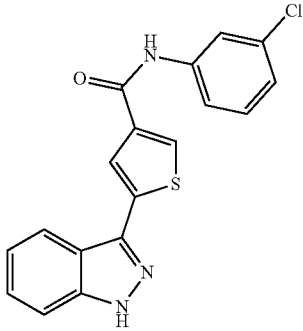 [SMILES: O=C(Nc1cccc(Cl)c1)c1csc(-c2n[nH]c3ccccc23)c1] |

| No. | Structure |
|---|---|
| I-a-14 | 3-(5-(1H-indazol-3-yl)thiophene-2-carboxamide) N-(3-(trifluoromethyl)phenyl) |
| I-a-15 | N-(p-tolyl) 5-(1H-indazol-3-yl)thiophene-2-carboxamide |
| I-a-16 | N-(4-methoxyphenyl) 5-(1H-indazol-3-yl)thiophene-2-carboxamide |
| I-a-17 | N-(4-isopropoxyphenyl) 5-(1H-indazol-3-yl)thiophene-2-carboxamide |
| I-a-18 | N-(4-fluorophenyl) 5-(1H-indazol-3-yl)thiophene-2-carboxamide |

| No. | Structure |
|---|---|
| I-a-19 | N-(4-(dimethylamino)phenyl) 5-(1H-indazol-3-yl)thiophene-2-carboxamide |
| I-a-20 | N-(6-methylpyridin-3-yl) 5-(1H-indazol-3-yl)thiophene-2-carboxamide |
| I-a-21 | N-(pyridin-3-yl) 5-(1H-indazol-3-yl)thiophene-2-carboxamide |
| I-a-22 | N-cyclohexyl 5-(1H-indazol-3-yl)thiophene-2-carboxamide |

| No. | Structure |
|---|---|
| I-a-23 | 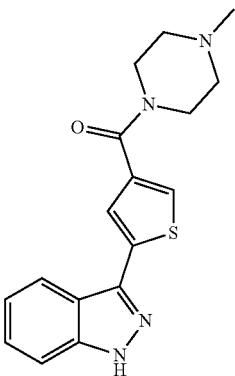 [SMILES: CN1CCN(C(=O)c2csc(-c3n[nH]c4ccccc34)c2)CC1] |
| I-a-24 | 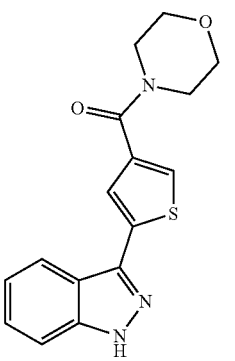 [SMILES: O=C(c1csc(-c2n[nH]c3ccccc23)c1)N1CCOCC1] |
| I-a-25 | 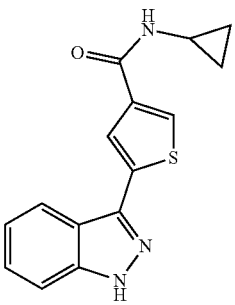 [SMILES: O=C(NC1CC1)c1csc(-c2n[nH]c3ccccc23)c1] |
| I-a-26 | 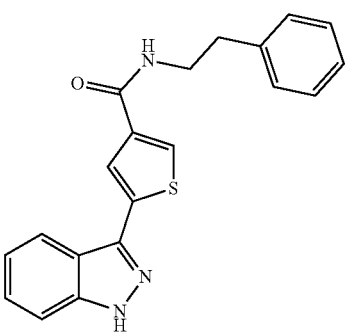 [SMILES: O=C(NCCc1ccccc1)c1csc(-c2n[nH]c3ccccc23)c1] |
| I-a-27 | 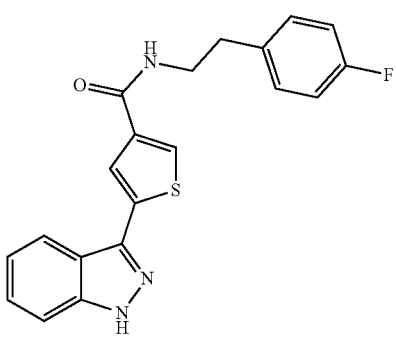 [SMILES: O=C(NCCc1ccc(F)cc1)c1csc(-c2n[nH]c3ccccc23)c1] |
| I-a-28 | 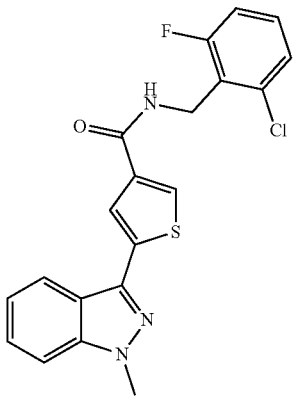 [SMILES: Cn1nc(-c2cc(C(=O)NCc3c(F)cccc3Cl)cs2)c2ccccc21] |
| I-a-29 | 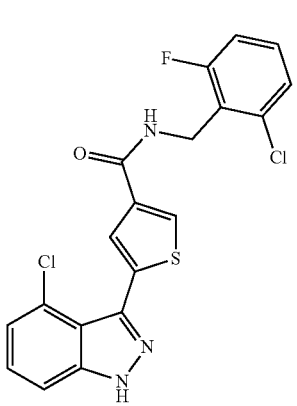 [SMILES: O=C(NCc1c(F)cccc1Cl)c1csc(-c2n[nH]c3cccc(Cl)c23)c1] |
| I-a-30 | 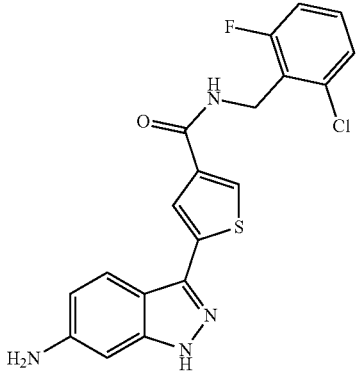 [SMILES: Nc1ccc2c(-c3cc(C(=O)NCc4c(F)cccc4Cl)cs3)n[nH]c2c1] |

| No. | Structure |
|---|---|
| I-b-1 | 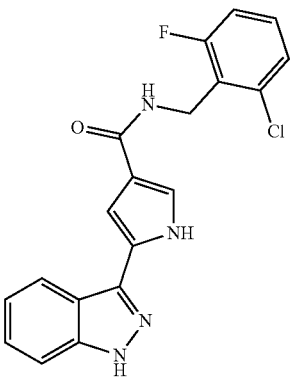 [SMILES: O=C(NCc1c(F)cccc1Cl)c1c[nH]c(-c2n[nH]c3ccccc23)c1] |
| I-b-2 | 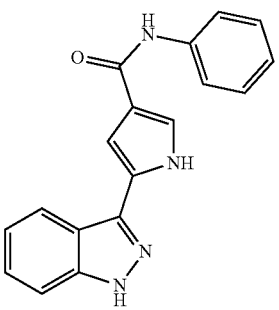 [SMILES: O=C(Nc1ccccc1)c1c[nH]c(-c2n[nH]c3ccccc23)c1] |
| I-c-1 | 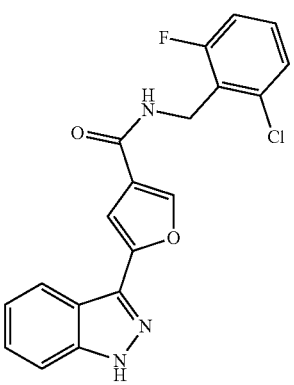 [SMILES: O=C(NCc1c(F)cccc1Cl)c1coc(-c2n[nH]c3ccccc23)c1] |
| I-c-2 | 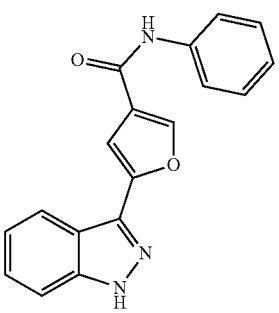 [SMILES: O=C(Nc1ccccc1)c1coc(-c2n[nH]c3ccccc23)c1] |
| I-d-1 | 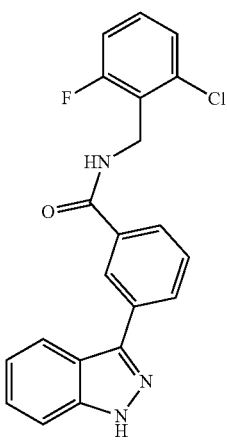 [SMILES: O=C(NCc1c(F)cccc1Cl)c1cccc(-c2n[nH]c3ccccc23)c1] |
| I-d-2 | 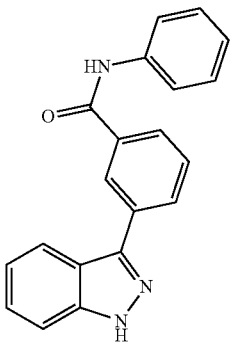 [SMILES: O=C(Nc1ccccc1)c1cccc(-c2n[nH]c3ccccc23)c1] |
| I-e-1 | 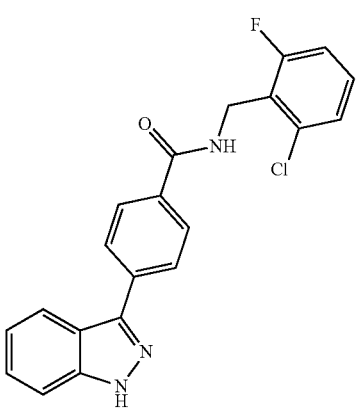 [SMILES: O=C(NCc1c(F)cccc1Cl)c1ccc(-c2n[nH]c3ccccc23)cc1] |
| I-e-2 | 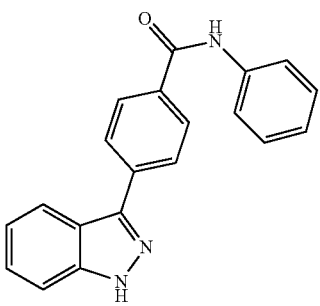 [SMILES: O=C(Nc1ccccc1)c1ccc(-c2n[nH]c3ccccc23)cc1] |

245
-continued

| No. | Structure |
|---|---|
| I-f-1 | 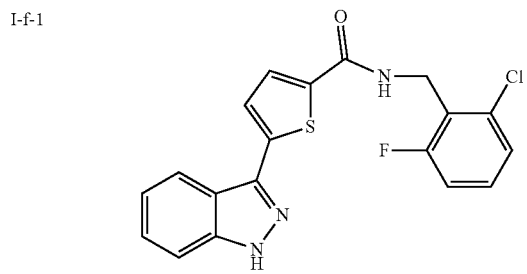 |
| I-f-2 | 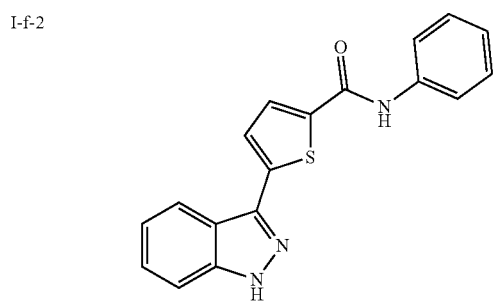 |
| I-f-3 | 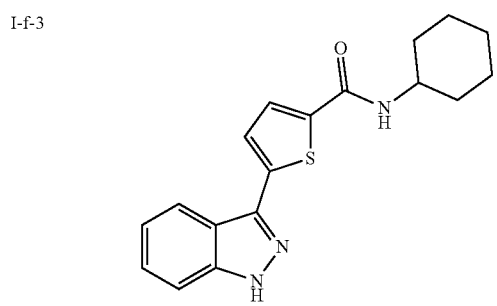 |
| I-g-1 | 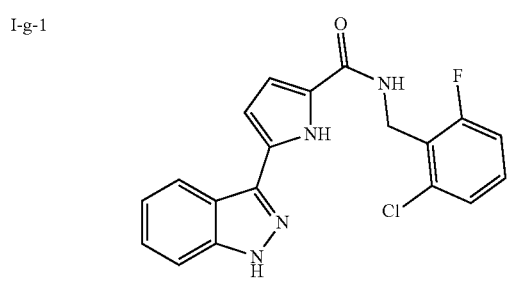 | or a stereoisomer thereof, a pharmaceutically acceptable salt thereof or a pharmaceutically acceptable solvate thereof.

3. A pharmaceutical composition comprising the compound according to claim 1 or a stereoisomer thereof, a pharmaceutically acceptable salt thereof or a pharmaceutically acceptable solvate thereof and optionally a pharmaceutically acceptable excipient.

4. A preparation method for the compound according to claim 1, comprising the following steps:

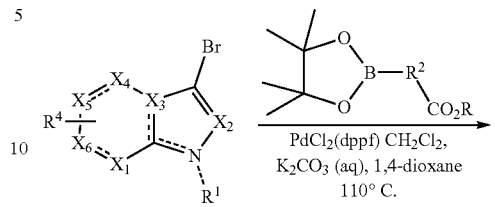

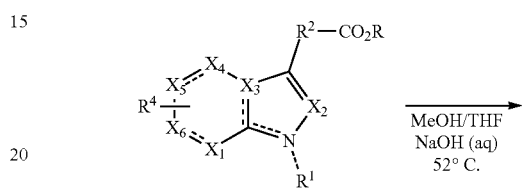

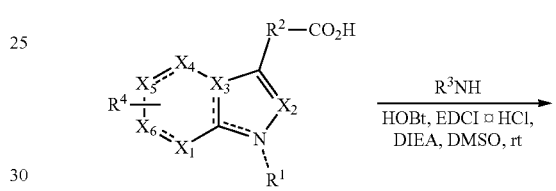

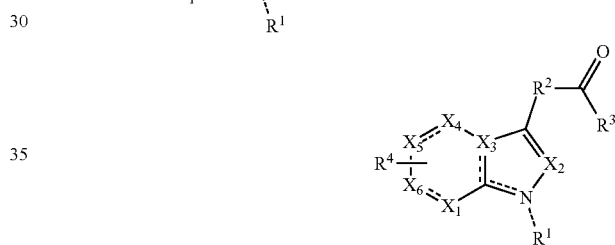

wherein,

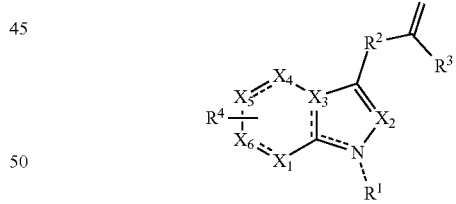

is selected from:

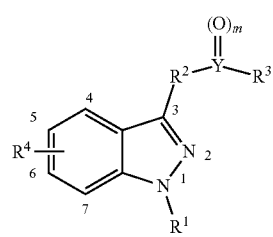

I and wherein

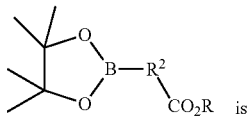
is

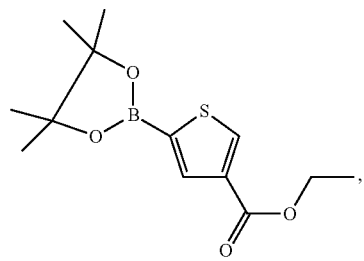

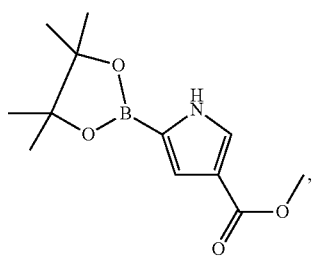

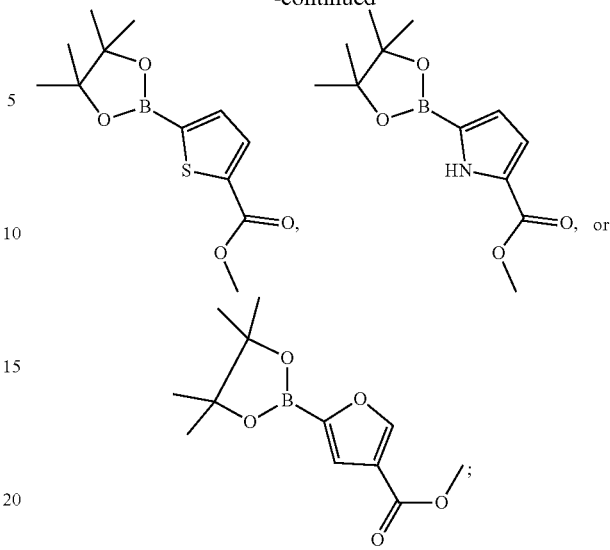

under the following reaction conditions:
(a) coupling reaction of carbon-carbon bond formation catalyzed by metal palladium: $PdCl_2(dppf) \cdot CH_2Cl_2$, $K_2CO_3$ (aq), 1,4-dioxane, and 110° C.:
(b) ester hydrolysis under alkaline condition: selected from LiOH or NaOH (aq): MeOH/THF and 52° C.;
(c) amide condensation reaction under alkaline condition: selected from HOBT or HATU; triethylamine or diisopropylethylamine: EDCl.HCl, DMSO, and rt.

\* \* \* \* \*